(12) United States Patent
Albitov et al.

(10) Patent No.: US 12,357,459 B2
(45) Date of Patent: Jul. 15, 2025

(54) TRANSLUMINAL DELIVERY SYSTEM

(71) Applicant: CARDIOVALVE LTD., Or Yehuda (IL)

(72) Inventors: Michael Albitov, Kfar Saba (IL); Maxim Karalnik, Karmiel (IL); Meni Iamberger, Kfar Saba (IL); Ilia Hariton, Zichron Yaackov (IL); Tal Hammer, Ramat Gan (IL)

(73) Assignee: CARDIOVALVE LTD., Or Yehuda (IL)

( * ) Notice: Subject to any disclaimer, the term of this patent is extended or adjusted under 35 U.S.C. 154(b) by 803 days.

(21) Appl. No.: 17/399,594

(22) Filed: Aug. 11, 2021

(65) Prior Publication Data

US 2022/0175526 A1 Jun. 9, 2022

Related U.S. Application Data

(60) Provisional application No. 63/120,808, filed on Dec. 3, 2020.

(51) Int. Cl.
*A61F 2/24* (2006.01)
*A61F 2/95* (2013.01)

(52) U.S. Cl.
CPC .......... *A61F 2/2436* (2013.01); *A61F 2/2439* (2013.01); *A61F 2/9524* (2020.05); *A61F 2220/0033* (2013.01)

(58) Field of Classification Search
None
See application file for complete search history.

(56) References Cited

U.S. PATENT DOCUMENTS 3,604,488 A 9/1971 Wishart et al.
3,656,185 A 4/1972 Carpentier
(Continued)

FOREIGN PATENT DOCUMENTS

CA 2822801 8/2006
CA 2671966 6/2008
(Continued)

OTHER PUBLICATIONS

An International Search Report and a Written Opinion both dated May 3, 2022, which issued during the prosecution of Applicant's PCT/IL2021/051433.

(Continued)

*Primary Examiner* — Shaun L David
(74) *Attorney, Agent, or Firm* — Sughrue Mion, PLLC

(57) ABSTRACT

A delivery tool including a shaft and a proximal capsule and a distal capsule is dimensioned for percutaneous delivery to the heart. An open end of the proximal capsule faces the open end of the distal capsule. The capsules are coupled to the shaft in a manner that allows axial movement of the capsule with respect to the shaft. A prosthetic heart valve includes a tubular portion that defines a lumen and prosthetic leaflets disposed within the lumen. The prosthetic heart valve is restrainable in a compressed state by the delivery tool, such that a downstream end of the tubular portion is disposed within the distal capsule. The distal capsule is shaped so as to define an opening for visualizing ensheathing of at least a portion of the downstream end of the tubular portion within the distal capsule. Other embodiments are also described.

18 Claims, 47 Drawing Sheets

(56) References Cited

U.S. PATENT DOCUMENTS

| | | |
|---|---|---|
| 3,840,018 A | 10/1974 | Heifetz |
| 3,874,388 A | 4/1975 | King et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,222,126 A | 9/1980 | Boretos et al. |
| 4,261,342 A | 4/1981 | Aranguren |
| 4,275,469 A | 6/1981 | Gabbay |
| 4,340,091 A | 7/1982 | Skelton et al. |
| 4,423,525 A | 1/1984 | Vallana et al. |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,853,986 A | 8/1989 | Allen |
| 4,892,541 A | 1/1990 | Alonso |
| 4,917,698 A | 4/1990 | Carpenter et al. |
| 4,961,738 A | 10/1990 | Mackin |
| 4,972,494 A | 11/1990 | White et al. |
| 4,994,077 A | 2/1991 | Dobben |
| 5,061,277 A | 10/1991 | Carpentier et al. |
| 5,078,739 A | 1/1992 | Martin |
| 5,104,407 A | 4/1992 | Lam et al. |
| 5,108,420 A | 4/1992 | Marks |
| 5,201,757 A | 4/1993 | Heyn et al. |
| 5,201,880 A | 4/1993 | Wright |
| 5,258,008 A | 11/1993 | Wilk |
| 5,275,622 A * | 1/1994 | Lazarus ............ A61F 2/958 623/1.14 |
| 5,300,034 A | 4/1994 | Behnke |
| 5,306,296 A | 4/1994 | Wright et al. |
| 5,314,473 A | 5/1994 | Godin |
| 5,325,845 A | 7/1994 | Adair |
| 5,332,402 A | 7/1994 | Teitelbaum |
| 5,397,351 A | 3/1995 | Pavcnik et al. |
| 5,405,378 A | 4/1995 | Strecker |
| 5,443,500 A | 8/1995 | Sigwart |
| 5,450,860 A | 9/1995 | O'Connor |
| 5,473,812 A | 12/1995 | Morris et al. |
| 5,477,856 A | 12/1995 | Lundquist |
| 5,593,424 A | 1/1997 | Northrup III |
| 5,601,572 A | 2/1997 | Middleman et al. |
| 5,607,444 A | 3/1997 | Lam |
| 5,607,470 A | 3/1997 | Milo |
| 5,626,609 A | 5/1997 | Zvenyatsky et al. |
| 5,647,857 A | 7/1997 | Anderson et al. |
| 5,669,919 A | 9/1997 | Sanders et al. |
| 5,674,279 A | 10/1997 | Wright et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,713,948 A | 2/1998 | Uflacker |
| 5,716,370 A | 2/1998 | Williamson et al. |
| 5,716,397 A | 2/1998 | Myers |
| 5,716,417 A | 2/1998 | Girard et al. |
| 5,728,116 A | 3/1998 | Rosenman |
| 5,730,150 A | 3/1998 | Peppel et al. |
| 5,741,297 A | 4/1998 | Simon |
| 5,749,371 A | 5/1998 | Zadini et al. |
| 5,765,682 A | 6/1998 | Bley et al. |
| 5,776,140 A | 7/1998 | Cottone |
| 5,810,882 A | 9/1998 | Bolduc |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,868,777 A | 2/1999 | Lam |
| 5,873,906 A | 2/1999 | Lau et al. |
| 5,876,373 A | 3/1999 | Giba et al. |
| 5,935,098 A | 8/1999 | Blaisdell et al. |
| 5,954,766 A | 9/1999 | Zadno-Azizi et al. |
| 5,957,949 A | 9/1999 | Leonhardt et al. |
| 5,957,953 A | 9/1999 | DiPoto et al. |
| 5,961,440 A | 10/1999 | Schweich et al. |
| 5,961,539 A | 10/1999 | Northrup, III et al. |
| 5,980,565 A | 11/1999 | Jayaraman |
| 5,984,959 A | 11/1999 | Robertson |
| 6,010,530 A | 1/2000 | Goicoechea |
| 6,019,787 A | 2/2000 | Richard et al. |
| 6,042,554 A | 3/2000 | Rosenman |
| 6,042,607 A | 3/2000 | Williamson, IV |
| 6,045,497 A | 4/2000 | Schweich et al. |
| 6,050,936 A | 4/2000 | Schweich et al. |
| 6,059,715 A | 5/2000 | Schweich et al. |
| 6,059,827 A | 5/2000 | Fenton |
| 6,074,401 A | 6/2000 | Gardiner et al. |
| 6,074,417 A | 6/2000 | Peredo |
| 6,102,945 A | 8/2000 | Campbell |
| 6,106,550 A | 8/2000 | Magovern |
| 6,110,200 A | 8/2000 | Hinnenkamp |
| 6,113,612 A | 9/2000 | Swanson et al. |
| 6,120,534 A | 9/2000 | Ruiz |
| 6,126,686 A | 10/2000 | Badylak et al. |
| 6,143,024 A | 11/2000 | Campbell et al. |
| 6,152,937 A | 11/2000 | Peterson et al. |
| 6,159,240 A | 12/2000 | Sparer |
| 6,165,119 A | 12/2000 | Schweich et al. |
| 6,165,183 A | 12/2000 | Kuehn et al. |
| 6,165,210 A | 12/2000 | Lau et al. |
| 6,174,332 B1 | 1/2001 | Loch |
| 6,183,411 B1 | 2/2001 | Mortier et al. |
| 6,187,020 B1 | 2/2001 | Zegdi et al. |
| 6,187,040 B1 | 2/2001 | Wright |
| 6,193,686 B1 | 2/2001 | Estrada et al. |
| 6,193,745 B1 | 2/2001 | Fogarty et al. |
| 6,315,784 B1 | 2/2001 | Djurovic |
| 6,217,610 B1 | 4/2001 | Carpentier et al. |
| 6,221,102 B1 * | 4/2001 | Baker ............ A61F 2/07 623/1.36 |
| 6,231,602 B1 | 5/2001 | Carpentier et al. |
| 6,251,092 B1 | 6/2001 | Qin et al. |
| 6,254,609 B1 | 7/2001 | Vrba et al. |
| 6,264,700 B1 | 7/2001 | Kilcoyne et al. |
| 6,287,339 B1 | 9/2001 | Vasquez et al. |
| 6,296,656 B1 | 10/2001 | Bodluc et al. |
| 6,312,465 B1 | 11/2001 | Griffin et al. |
| 6,319,281 B1 | 11/2001 | Patel |
| 6,332,893 B1 | 12/2001 | Mortier et al. |
| 6,334,873 B1 | 1/2002 | Lane et al. |
| 6,346,074 B1 | 2/2002 | Roth |
| 6,350,278 B1 | 2/2002 | Lenker et al. |
| 6,352,561 B1 | 3/2002 | Leopold et al. |
| 6,391,036 B1 | 5/2002 | Berg et al. |
| 6,402,780 B2 | 6/2002 | Williamson, IV |
| 6,406,420 B1 | 6/2002 | McCarthy et al. |
| 6,406,493 B1 | 6/2002 | Tu et al. |
| 6,409,755 B1 | 6/2002 | Vrba |
| 6,419,696 B1 | 7/2002 | Ortiz et al. |
| 6,428,550 B1 | 8/2002 | Vargas et al. |
| 6,440,164 B1 | 8/2002 | Dimatteo et al. |
| 6,451,054 B1 | 9/2002 | Stevens |
| 6,454,799 B1 | 9/2002 | Schreck |
| 6,458,153 B1 | 10/2002 | Bailey et al. |
| 6,461,366 B1 | 10/2002 | Seguin |
| 6,470,892 B1 | 10/2002 | Forsell |
| 6,478,807 B1 | 11/2002 | Foreman et al. |
| 6,482,228 B1 | 11/2002 | Norred |
| 6,491,711 B1 | 12/2002 | Durcan |
| 6,503,274 B1 | 1/2003 | Howanec et al. |
| 6,511,491 B2 | 1/2003 | Grudem et al. |
| 6,524,338 B1 | 2/2003 | Gundry |
| 6,530,952 B2 | 3/2003 | Vesely |
| 6,533,772 B1 | 3/2003 | Sherts et al. |
| 6,537,314 B2 | 3/2003 | Langberg et al. |
| 6,540,782 B1 | 4/2003 | Snyders |
| 6,547,801 B1 | 4/2003 | Dargent et al. |
| 6,551,350 B1 | 4/2003 | Thornton et al. |
| 6,554,845 B1 | 4/2003 | Fleenor et al. |
| 6,558,396 B1 | 5/2003 | Inoue |
| 6,558,418 B2 | 5/2003 | Carpentier et al. |

(56) References Cited

U.S. PATENT DOCUMENTS

| | | |
|---|---|---|
| 6,564,805 B2 | 5/2003 | Garrison et al. |
| 6,565,603 B2 | 5/2003 | Cox |
| 6,569,196 B1 | 5/2003 | Vesely |
| 6,569,198 B1 | 5/2003 | Wilson et al. |
| 6,579,297 B2 | 6/2003 | Bicek et al. |
| 6,582,464 B2 | 6/2003 | Gabbay |
| 6,589,160 B2 | 7/2003 | Schweich et al. |
| 6,602,263 B1 | 8/2003 | Swanson et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,616,675 B1 | 9/2003 | Evard et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich et al. |
| 6,651,671 B1 | 11/2003 | Donlon et al. |
| 6,652,556 B1 | 11/2003 | VanTassel et al. |
| 6,669,724 B2 | 12/2003 | Park et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,699,256 B1 | 3/2004 | Logan et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,456 B2 | 3/2004 | Langberg et al. |
| 6,711,444 B2 | 3/2004 | Koblish |
| 6,716,244 B2 | 4/2004 | Klaco |
| 6,718,985 B2 | 4/2004 | Hlavka et al. |
| 6,719,781 B1 | 4/2004 | Kim |
| 6,719,786 B2 | 4/2004 | Ryan et al. |
| 6,719,788 B2 | 4/2004 | Cox |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,514 B1 | 7/2004 | Li et al. |
| 6,764,518 B2 | 7/2004 | Godin |
| 6,767,362 B2 | 7/2004 | Schreck |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,821,297 B2 | 11/2004 | Snyders |
| 6,830,585 B1 | 12/2004 | Artof et al. |
| 6,830,638 B2 | 12/2004 | Boylan et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,884,257 B1 | 4/2005 | Cox |
| 6,893,459 B1 | 5/2005 | Macoviak |
| 6,893,460 B2 | 5/2005 | Spenser et al. |
| 6,908,482 B2 | 6/2005 | McCarthy et al. |
| 6,918,917 B1 | 7/2005 | Nguyen et al. |
| 6,926,715 B1 | 8/2005 | Hauck et al. |
| 6,926,730 B1 | 8/2005 | Nguyen et al. |
| 6,951,571 B1 | 10/2005 | Srivastava |
| 6,960,217 B2 | 11/2005 | Bolduc |
| 6,964,684 B2 | 11/2005 | Ortiz et al. |
| 6,964,686 B2 | 11/2005 | Gordon |
| 6,974,476 B2 | 12/2005 | McGuckin et al. |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,918 B2 | 2/2006 | Soltesz et al. |
| 6,997,951 B2 | 2/2006 | Solem et al. |
| 7,004,176 B2 | 2/2006 | Lau |
| 7,011,669 B2 | 3/2006 | Kimblad |
| 7,011,681 B2 | 3/2006 | Vesely |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,041,132 B2 | 5/2006 | Quijano et al. |
| 7,074,236 B2 | 7/2006 | Rabkin et al. |
| 7,077,850 B2 | 7/2006 | Kortenbach |
| 7,077,861 B2 | 7/2006 | Spence |
| 7,077,862 B2 | 7/2006 | Vidlund et al. |
| 7,087,064 B1 | 8/2006 | Hyde |
| 7,101,336 B2 | 9/2006 | Miller |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,137,184 B2 | 11/2006 | Schreck |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,656 B2 | 2/2007 | Khairkhahan |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,198,646 B2 | 4/2007 | Figulla et al. |
| 7,201,772 B2 | 4/2007 | Schwammenthal |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,261,686 B2 | 8/2007 | Couvillon, Jr. |
| 7,288,097 B2 | 10/2007 | Seguin |
| 7,288,111 B1 | 10/2007 | Holloway et al. |
| 7,294,148 B2 | 11/2007 | McCarthy |
| 7,297,150 B2 | 11/2007 | Cartledge et al. |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,316,716 B2 | 1/2008 | Egan |
| 7,329,279 B2 | 2/2008 | Haug et al. |
| 7,329,280 B2 | 2/2008 | Bolling et al. |
| 7,335,213 B1 | 2/2008 | Hyde et al. |
| 7,351,256 B2 | 4/2008 | Hojeibane et al. |
| 7,361,190 B2 | 4/2008 | Shoulian et al. |
| 7,364,588 B2 | 4/2008 | Mathis et al. |
| 7,374,571 B2 | 5/2008 | Pease et al. |
| 7,374,573 B2 | 5/2008 | Gabbay |
| 7,377,938 B2 | 5/2008 | Sarac et al. |
| 7,377,941 B2 | 5/2008 | Rhee et al. |
| 7,381,218 B2 | 6/2008 | Schreck |
| 7,381,219 B2 | 6/2008 | Salahieh et al. |
| 7,390,329 B2 | 6/2008 | Westra et al. |
| 7,404,824 B1 | 7/2008 | Webler et al. |
| 7,422,603 B2 | 9/2008 | Lane |
| 7,429,269 B2 | 9/2008 | Schwammenthal |
| 7,431,692 B2 | 10/2008 | Zollinger et al. |
| 7,442,204 B2 | 10/2008 | Schwammenthal |
| 7,442,207 B2 | 10/2008 | Rafiee |
| 7,445,630 B2 | 11/2008 | Lashinski et al. |
| 7,452,376 B2 | 11/2008 | Lim et al. |
| 7,455,677 B2 | 11/2008 | Vargas et al. |
| 7,455,688 B2 | 11/2008 | Furst et al. |
| 7,455,690 B2 | 11/2008 | Cartledge et al. |

(56) References Cited

U.S. PATENT DOCUMENTS

| | | | |
|---|---|---|---|
| 7,462,162 | B2 | 12/2008 | Phan et al. |
| 7,481,838 | B2 | 1/2009 | Carpentier et al. |
| 7,485,142 | B2 | 2/2009 | Milo |
| 7,500,989 | B2 | 3/2009 | Solem et al. |
| 7,507,252 | B2 | 3/2009 | Lashinski et al. |
| 7,510,575 | B2 | 3/2009 | Spenser et al. |
| 7,510,577 | B2 | 3/2009 | Moaddeb et al. |
| 7,513,909 | B2 | 4/2009 | Lane et al. |
| 7,524,331 | B2 | 4/2009 | Birdsall |
| 7,527,646 | B2 | 5/2009 | Rahdert et al. |
| 7,527,647 | B2 | 5/2009 | Spence |
| 7,530,995 | B2 | 5/2009 | Quijano et al. |
| 7,549,983 | B2 | 6/2009 | Roue et al. |
| 7,556,632 | B2 | 7/2009 | Zadno |
| 7,556,646 | B2 | 7/2009 | Yang et al. |
| 7,559,936 | B2 | 7/2009 | Levine |
| 7,562,660 | B2 | 7/2009 | Saadat |
| 7,563,267 | B2 | 7/2009 | Goldfarb et al. |
| 7,563,273 | B2 | 7/2009 | Goldfarb et al. |
| 7,569,062 | B1 | 8/2009 | Kuehn et al. |
| 7,582,111 | B2 | 9/2009 | Krolik et al. |
| 7,585,321 | B2 | 9/2009 | Cribier |
| 7,588,582 | B2 | 9/2009 | Starksen et al. |
| 7,591,826 | B2 | 9/2009 | Alferness et al. |
| 7,597,711 | B2 | 10/2009 | Drews et al. |
| 7,604,646 | B2 | 10/2009 | Goldfarb et al. |
| 7,608,091 | B2 | 10/2009 | Goldfarb et al. |
| 7,608,103 | B2 | 10/2009 | McCarthy |
| 7,611,534 | B2 | 11/2009 | Kapadia et al. |
| 7,618,449 | B2 | 11/2009 | Tremulis et al. |
| 7,621,948 | B2 | 11/2009 | Hermann et al. |
| 7,625,403 | B2 | 12/2009 | Krivoruchko |
| 7,632,302 | B2 | 12/2009 | Vreeman et al. |
| 7,632,303 | B1 | 12/2009 | Stalker et al. |
| 7,635,329 | B2 | 12/2009 | Goldfarb et al. |
| 7,635,386 | B1 | 12/2009 | Gammie |
| 7,648,528 | B2 | 1/2010 | Styrc |
| 7,655,015 | B2 | 2/2010 | Goldfarb et al. |
| 7,666,204 | B2 | 2/2010 | Thornton et al. |
| 7,682,319 | B2 | 3/2010 | Martin |
| 7,682,369 | B2 | 3/2010 | Seguin |
| 7,682,380 | B2 | 3/2010 | Thornton et al. |
| 7,686,822 | B2 | 3/2010 | Shayani |
| 7,699,892 | B2 | 4/2010 | Rafiee et al. |
| 7,704,269 | B2 | 4/2010 | St. Goar et al. |
| 7,704,277 | B2 | 4/2010 | Zakay et al. |
| 7,708,775 | B2 | 5/2010 | Rowe et al. |
| 7,717,951 | B2 * | 5/2010 | Flagle ............... A61M 25/0043 623/2.11 |
| 7,717,952 | B2 | 5/2010 | Case et al. |
| 7,717,955 | B2 | 5/2010 | Lane et al. |
| 7,722,666 | B2 | 5/2010 | Lafontaine |
| 7,731,741 | B2 | 6/2010 | Eidenschink |
| 7,731,742 | B2 | 6/2010 | Schlick et al. |
| 7,736,388 | B2 | 6/2010 | Goldfarb et al. |
| 7,748,389 | B2 | 7/2010 | Salahieh et al. |
| 7,753,922 | B2 | 7/2010 | Starksen |
| 7,753,924 | B2 | 7/2010 | Starksen et al. |
| 7,753,949 | B2 | 7/2010 | Lamphere et al. |
| 7,758,595 | B2 | 7/2010 | Allen et al. |
| 7,758,632 | B2 | 7/2010 | Hojeibane et al. |
| 7,758,640 | B2 | 7/2010 | Vesely |
| 7,771,467 | B2 | 8/2010 | Svensson |
| 7,771,469 | B2 | 8/2010 | Liddicoat |
| 7,776,080 | B2 | 8/2010 | Bei et al. |
| 7,776,083 | B2 | 8/2010 | Vesely |
| 7,780,726 | B2 | 8/2010 | Seguin |
| 7,785,341 | B2 | 8/2010 | Forster et al. |
| 7,799,069 | B2 | 9/2010 | Bailey et al. |
| 7,803,181 | B2 | 9/2010 | Furst et al. |
| 7,811,296 | B2 | 10/2010 | Goldfarb et al. |
| 7,811,316 | B2 | 10/2010 | Kalmann et al. |
| 7,824,442 | B2 | 11/2010 | Salahieh et al. |
| 7,837,645 | B2 | 11/2010 | Bessler et al. |
| 7,837,727 | B2 | 11/2010 | Goetz et al. |
| 7,842,081 | B2 | 11/2010 | Yadin |
| 7,850,725 | B2 | 12/2010 | Vardi et al. |
| 7,871,368 | B2 | 1/2011 | Zollinger et al. |
| 7,871,432 | B2 | 1/2011 | Bergin |
| 7,871,433 | B2 | 1/2011 | Lattouf |
| 7,871,436 | B2 | 1/2011 | Ryan et al. |
| 7,887,583 | B2 | 2/2011 | Macoviak |
| 7,892,281 | B2 | 2/2011 | Seguin et al. |
| 7,896,915 | B2 | 3/2011 | Guyenot et al. |
| 7,914,544 | B2 | 3/2011 | Nguyen et al. |
| 7,914,569 | B2 | 3/2011 | Nguyen et al. |
| 7,927,370 | B2 | 4/2011 | Webler et al. |
| 7,927,371 | B2 | 4/2011 | Navia et al. |
| 7,942,927 | B2 | 5/2011 | Kaye et al. |
| 7,947,072 | B2 | 5/2011 | Yang et al. |
| 7,947,075 | B2 | 5/2011 | Goetz et al. |
| 7,951,195 | B2 | 5/2011 | Antonsson et al. |
| 7,955,375 | B2 | 6/2011 | Agnew |
| 7,955,377 | B2 | 6/2011 | Melsheimer |
| 7,955,384 | B2 | 6/2011 | Rafiee et al. |
| 7,959,666 | B2 | 6/2011 | Salahieh et al. |
| 7,959,672 | B2 | 6/2011 | Salahieh et al. |
| 7,967,833 | B2 | 6/2011 | Sterman et al. |
| 7,967,857 | B2 | 6/2011 | Lane |
| 7,981,151 | B2 | 7/2011 | Rowe |
| 7,981,153 | B2 | 7/2011 | Fogarty et al. |
| 7,988,725 | B2 | 8/2011 | Gross et al. |
| 7,992,567 | B2 | 8/2011 | Hirotsuka et al. |
| 7,993,368 | B2 | 8/2011 | Gambale et al. |
| 7,993,393 | B2 | 8/2011 | Carpentier et al. |
| 7,993,397 | B2 | 8/2011 | Lashinski |
| 8,002,825 | B2 | 8/2011 | Letac et al. |
| 8,002,826 | B2 | 8/2011 | Seguin |
| 8,012,201 | B2 | 9/2011 | Lashinski et al. |
| 8,016,877 | B2 | 9/2011 | Seguin et al. |
| 8,016,882 | B2 | 9/2011 | Macoviak |
| 8,021,420 | B2 | 9/2011 | Dolan |
| 8,021,421 | B2 | 9/2011 | Fogarty et al. |
| 8,025,695 | B2 | 9/2011 | Fogarty et al. |
| 8,029,518 | B2 | 10/2011 | Goldfarb et al. |
| 8,029,557 | B2 | 10/2011 | Sobrino-Serrano et al. |
| 8,029,564 | B2 | 10/2011 | Johnson et al. |
| 8,034,103 | B2 | 10/2011 | Burriesci |
| 8,034,104 | B2 | 10/2011 | Carpentier et al. |
| 8,038,720 | B2 | 10/2011 | Wallace et al. |
| 8,043,360 | B2 | 10/2011 | McNamara et al. |
| 8,048,138 | B2 | 11/2011 | Sulivan et al. |
| 8,048,140 | B2 | 11/2011 | Purdy |
| 8,048,153 | B2 | 11/2011 | Salahieh et al. |
| 8,052,592 | B2 | 11/2011 | Goldfarb et al. |
| 8,052,741 | B2 | 11/2011 | Bruszewski et al. |
| 8,052,749 | B2 | 11/2011 | Salahieh et al. |
| 8,057,493 | B2 | 11/2011 | Goldfarb et al. |
| 8,057,532 | B2 | 11/2011 | Hoffman |
| 8,057,540 | B2 | 11/2011 | Letac et al. |
| 8,062,355 | B2 | 11/2011 | Figulla et al. |
| 8,062,359 | B2 | 11/2011 | Marquez et al. |
| 8,070,708 | B2 | 12/2011 | Rottenberg et al. |
| 8,070,800 | B2 | 12/2011 | Lock et al. |
| 8,070,802 | B2 | 12/2011 | Lamphere et al. |
| 8,070,804 | B2 | 12/2011 | Hyde |
| 8,070,805 | B2 | 12/2011 | Vidlund |
| 8,075,611 | B2 | 12/2011 | Milwee et al. |
| 8,075,616 | B2 | 12/2011 | Solem |
| 8,080,054 | B2 | 12/2011 | Rowe |
| 8,083,793 | B2 | 12/2011 | Lane et al. |
| D652,927 | S | 1/2012 | Braido et al. |
| D653,341 | S | 1/2012 | Braido et al. |
| 8,092,518 | B2 | 1/2012 | Schreck |
| 8,092,520 | B2 | 1/2012 | Quadri |
| 8,092,521 | B2 | 1/2012 | Figulla et al. |
| 8,100,964 | B2 | 1/2012 | Spence |
| 8,105,377 | B2 | 1/2012 | Liddicoat |
| 8,109,996 | B2 | 2/2012 | Stacchino et al. |
| 8,118,866 | B2 | 2/2012 | Herrmann et al. |
| 8,123,800 | B2 | 2/2012 | McCarthy |
| 8,123,801 | B2 | 2/2012 | Milo |
| 8,323,334 | B2 | 2/2012 | Deem et al. |
| 8,133,270 | B2 | 3/2012 | Kheradvar et al. |

(56) References Cited

U.S. PATENT DOCUMENTS

| | | |
|---|---|---|
| 8,136,218 B2 | 3/2012 | Millwee et al. |
| 8,137,398 B2 | 3/2012 | Tuval et al. |
| 8,142,492 B2 | 3/2012 | Forster et al. |
| 8,142,493 B2 | 3/2012 | Spence et al. |
| 8,142,494 B2 | 3/2012 | Rahdert et al. |
| 8,142,495 B2 | 3/2012 | Hasenkam et al. |
| 8,142,496 B2 | 3/2012 | Berreklouw |
| 8,142,497 B2 | 3/2012 | Friedman |
| 8,147,504 B2 | 4/2012 | Ino et al. |
| 8,147,542 B2 | 4/2012 | Maisano et al. |
| 8,152,844 B2 | 4/2012 | Rao |
| 8,157,852 B2 | 4/2012 | Bloom et al. |
| 8,157,853 B2 | 4/2012 | Laske et al. |
| 8,157,860 B2 | 4/2012 | McNamara et al. |
| 8,163,008 B2 | 4/2012 | Wilson et al. |
| 8,163,013 B2 | 4/2012 | Machold et al. |
| 8,163,014 B2 | 4/2012 | Lane et al. |
| D660,433 S | 5/2012 | Braido et al. |
| D660,967 S | 5/2012 | Braido et al. |
| 8,167,894 B2 | 5/2012 | Miles et al. |
| 8,167,932 B2 | 5/2012 | Bourang et al. |
| 8,167,935 B2 | 5/2012 | McGuckin, Jr. et al. |
| 8,172,896 B2 | 5/2012 | McNamara et al. |
| 8,172,898 B2 | 5/2012 | Alferness et al. |
| 8,177,836 B2 | 5/2012 | Lee et al. |
| 8,182,528 B2 | 5/2012 | Salahieh et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez-Duran |
| 8,211,169 B2 | 7/2012 | Lane et al. |
| 8,216,256 B2 | 7/2012 | Raschdorf, Jr. et al. |
| 8,216,301 B2 | 7/2012 | Bonhoeffer et al. |
| 8,221,492 B2 | 7/2012 | Case et al. |
| 8,221,493 B2 | 7/2012 | Boyle et al. |
| 8,226,710 B2 | 7/2012 | Nguyen et al. |
| 8,226,711 B2 | 7/2012 | Mortier et al. |
| 8,231,670 B2 | 7/2012 | Salahieh et al. |
| 8,231,671 B2 | 7/2012 | Kim |
| 8,236,045 B2 | 8/2012 | Benichou et al. |
| 8,236,049 B2 | 8/2012 | Rowe et al. |
| 8,241,351 B2 | 8/2012 | Cabiri |
| 8,252,042 B2 | 8/2012 | McNamara et al. |
| 8,252,050 B2 | 8/2012 | Maisano et al. |
| 8,252,051 B2 | 8/2012 | Chau et al. |
| 8,252,052 B2 | 8/2012 | Salahieh et al. |
| 8,257,390 B2 | 9/2012 | Carley et al. |
| 8,262,725 B2 | 9/2012 | Subramanian |
| 8,267,988 B2 | 9/2012 | Hamer et al. |
| 8,277,501 B2 | 10/2012 | Chalekian et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,298,280 B2 | 10/2012 | Yadin et al. |
| 8,303,608 B2 | 11/2012 | Goldfarb et al. |
| 8,303,653 B2 | 11/2012 | Bonhoeffer et al. |
| 8,308,798 B2 | 11/2012 | Pintor et al. |
| 8,317,853 B2 | 11/2012 | Agnew |
| 8,317,855 B2 | 11/2012 | Gregorich et al. |
| 8,323,335 B2 | 12/2012 | Rowe et al. |
| 8,328,868 B2 | 12/2012 | Paul et al. |
| 8,333,777 B2 | 12/2012 | Schaller et al. |
| 8,337,541 B2 | 12/2012 | Quadri et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,348,999 B2 | 1/2013 | Kheradvar et al. |
| 8,349,002 B2 | 1/2013 | Milo |
| 8,353,956 B2 | 1/2013 | Miller et al. |
| 8,357,195 B2 | 1/2013 | Kuehn |
| 8,361,144 B2 | 1/2013 | Fish et al. |
| 8,366,767 B2 | 2/2013 | Zhang |
| 8,372,140 B2 | 2/2013 | Hoffman et al. |
| 8,377,119 B2 | 2/2013 | Drews et al. |
| 8,382,829 B1 | 2/2013 | Call et al. |
| 8,388,680 B2 | 3/2013 | Starksen et al. |
| 8,393,517 B2 | 3/2013 | Milo |
| 8,398,708 B2 | 3/2013 | Meiri et al. |
| 8,403,981 B2 | 3/2013 | Forster et al. |
| 8,403,983 B2 | 3/2013 | Quadri et al. |
| 8,408,214 B2 | 4/2013 | Spenser |
| 8,414,644 B2 | 4/2013 | Quadri et al. |
| 8,425,593 B2 | 4/2013 | Braido et al. |
| 8,430,926 B2 | 4/2013 | Kirson |
| 8,430,934 B2 | 4/2013 | Das |
| 8,444,689 B2 | 5/2013 | Zhang |
| 8,449,599 B2 | 5/2013 | Chau et al. |
| 8,449,625 B2 | 5/2013 | Campbell et al. |
| 8,454,686 B2 | 6/2013 | Alkhatib |
| 8,460,365 B2 | 6/2013 | Haverkost et al. |
| 8,460,370 B2 | 6/2013 | Zakay et al. |
| 8,460,371 B2 | 6/2013 | Hlavka et al. |
| 8,474,460 B2 | 7/2013 | Barrett et al. |
| 8,475,491 B2 | 7/2013 | Milo |
| 8,480,732 B2 | 7/2013 | Subramanian |
| 8,500,800 B2 | 8/2013 | Maisano et al. |
| 8,500,821 B2 | 8/2013 | Sobrino-Serrano et al. |
| 8,512,400 B2 | 8/2013 | Tran et al. |
| 8,518,107 B2 | 8/2013 | Tsukashima et al. |
| 8,523,881 B2 | 9/2013 | Cabiri et al. |
| 8,523,940 B2 | 9/2013 | Richardson et al. |
| 8,529,431 B2 | 9/2013 | Baker et al. |
| 8,539,662 B2 | 9/2013 | Stacchino et al. |
| 8,540,767 B2 | 9/2013 | Zhang |
| 8,545,544 B2 | 10/2013 | Spenser et al. |
| 8,545,553 B2 | 10/2013 | Zipory et al. |
| 8,551,160 B2 | 10/2013 | Figulla et al. |
| 8,551,161 B2 | 10/2013 | Dolan |
| 8,562,672 B2 | 10/2013 | Bonhoeffer et al. |
| 8,568,475 B2 | 10/2013 | Nguyen et al. |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,460 B2 | 11/2013 | Wilson et al. |
| 8,591,570 B2 | 11/2013 | Revuelta et al. |
| 8,591,576 B2 | 11/2013 | Hasenkam et al. |
| 8,608,797 B2 | 12/2013 | Gross et al. |
| 8,623,075 B2 | 1/2014 | Murray et al. |
| 8,623,080 B2 | 1/2014 | Fogarty et al. |
| 8,628,569 B2 | 1/2014 | Benichou et al. |
| 8,628,570 B2 | 1/2014 | Seguin |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,652,204 B2 | 2/2014 | Quill et al. |
| 8,657,872 B2 | 2/2014 | Seguin |
| 8,663,322 B2 | 3/2014 | Keranen |
| 8,673,020 B2 | 3/2014 | Sobrino-Serrano et al. |
| 8,679,174 B2 | 3/2014 | Ottma et al. |
| 8,685,086 B2 | 4/2014 | Navia et al. |
| 8,690,939 B2 | 4/2014 | Miller et al. |
| 8,696,742 B2 | 4/2014 | Pintor et al. |
| 8,715,342 B2 | 5/2014 | Zipory et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,507 B2 | 5/2014 | Keranen |
| 8,740,920 B2 | 6/2014 | Goldfarb et al. |
| 8,747,460 B2 | 6/2014 | Tuval et al. |
| 8,771,345 B2 | 7/2014 | Tuval et al. |
| 8,778,021 B2 | 7/2014 | Cartledge |
| 8,784,472 B2 | 7/2014 | Eidenschink |
| 8,784,479 B2 | 7/2014 | Antonsson et al. |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,801,776 B2 | 8/2014 | House et al. |
| 8,808,366 B2 | 8/2014 | Braido et al. |

(56) References Cited

U.S. PATENT DOCUMENTS

| | | |
|---|---|---|
| 8,808,368 B2 | 8/2014 | Maisano et al. |
| 8,808,371 B2 | 8/2014 | Cartledge |
| 8,840,663 B2 | 9/2014 | Salahieh et al. |
| 8,840,664 B2 | 9/2014 | Karapetian et al. |
| 8,845,717 B2 | 9/2014 | Khairkhahan et al. |
| 8,845,722 B2 | 9/2014 | Gabbay |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,870,950 B2 | 10/2014 | Hacohen |
| 8,876,800 B2 | 11/2014 | Behan |
| 8,888,843 B2 | 11/2014 | Khairkhahan et al. |
| 8,894,702 B2 | 11/2014 | Quadri et al. |
| 8,900,294 B2 | 12/2014 | Paniagua et al. |
| 8,900,295 B2 | 12/2014 | Migliazza et al. |
| 8,906,083 B2 | 12/2014 | Obermiller et al. |
| 8,911,455 B2 | 12/2014 | Quadri et al. |
| 8,911,461 B2 | 12/2014 | Traynor et al. |
| 8,911,489 B2 | 12/2014 | Ben-Muvhar |
| 8,911,493 B2 | 12/2014 | Rowe et al. |
| 8,911,494 B2 | 12/2014 | Hammer et al. |
| 8,926,695 B2 | 1/2015 | Gross et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,042 B2 | 1/2015 | Miller et al. |
| 8,940,044 B2 | 1/2015 | Hammer et al. |
| 8,945,177 B2 | 2/2015 | Dell et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,979,922 B2 | 3/2015 | Jayasinghe et al. |
| 8,986,370 B2 | 3/2015 | Annest |
| 8,986,373 B2 | 3/2015 | Chau et al. |
| 8,986,375 B2 | 3/2015 | Garde et al. |
| 8,992,599 B2 | 3/2015 | Thubrikar et al. |
| 8,992,604 B2 | 3/2015 | Gross et al. |
| 8,992,608 B2 | 3/2015 | Haug et al. |
| 8,998,982 B2 | 4/2015 | Richter et al. |
| 9,005,273 B2 | 4/2015 | Salahieh et al. |
| 9,011,468 B2 | 4/2015 | Ketai et al. |
| 9,011,520 B2 | 4/2015 | Miller et al. |
| 9,011,527 B2 | 4/2015 | Li et al. |
| 9,011,530 B2 | 4/2015 | Reich et al. |
| 9,017,399 B2 | 4/2015 | Gross et al. |
| D730,520 S | 5/2015 | Braido et al. |
| D730,521 S | 5/2015 | Braido et al. |
| 9,023,100 B2 | 5/2015 | Quadri et al. |
| 9,034,032 B2 | 5/2015 | McLean et al. |
| 9,034,033 B2 | 5/2015 | McLean et al. |
| 9,039,757 B2 | 5/2015 | McLean et al. |
| D732,666 S | 6/2015 | Nguyen et al. |
| 9,050,188 B2 | 6/2015 | Schweich et al. |
| 9,060,858 B2 | 6/2015 | Thornton et al. |
| 9,072,603 B2 | 7/2015 | Tuval et al. |
| 9,084,676 B2 | 7/2015 | Chau et al. |
| 9,095,434 B2 | 8/2015 | Rowe |
| 9,119,719 B2 | 9/2015 | Zipory et al. |
| 9,125,632 B2 | 9/2015 | Loulmet et al. |
| 9,125,738 B2 | 9/2015 | Figulla et al. |
| 9,125,740 B2 | 9/2015 | Morriss et al. |
| 9,132,006 B2 | 9/2015 | Spenser et al. |
| 9,132,009 B2 | 9/2015 | Hacohen et al. |
| 9,138,312 B2 | 9/2015 | Tuval et al. |
| 9,155,619 B2 | 10/2015 | Liu et al. |
| 9,173,646 B2 | 11/2015 | Fabro |
| 9,173,659 B2 | 11/2015 | Bodewadt et al. |
| 9,173,738 B2 | 11/2015 | Murray et al. |
| 9,180,005 B1 | 11/2015 | Lashinski et al. |
| 9,192,472 B2 | 11/2015 | Gross et al. |
| 9,220,594 B2 | 12/2015 | Braido et al. |
| 9,226,820 B2 | 1/2016 | Braido et al. |
| 9,226,825 B2 | 1/2016 | Starksen et al. |
| 9,226,839 B1 | 1/2016 | Kariniemi et al. |
| 9,232,995 B2 | 1/2016 | Kovalsky et al. |
| 9,241,790 B2 | 1/2016 | Lane et al. |
| 9,241,791 B2 | 1/2016 | Braido et al. |
| 9,241,792 B2 | 1/2016 | Benichou et al. |
| 9,241,794 B2 | 1/2016 | Braido et al. |
| 9,248,014 B2 | 2/2016 | Lane et al. |
| 9,265,608 B2 | 2/2016 | Miller et al. |
| 9,277,994 B2 | 3/2016 | Miller et al. |
| 9,289,290 B2 | 3/2016 | Alkhatib et al. |
| 9,289,291 B2 | 3/2016 | Gorman et al. |
| 9,295,550 B2 | 3/2016 | Nguyen et al. |
| 9,295,551 B2 | 3/2016 | Straubinger et al. |
| 9,295,552 B2 | 3/2016 | McLean et al. |
| 9,301,836 B2 | 4/2016 | Buchbinder et al. |
| 9,308,087 B2 | 4/2016 | Lane et al. |
| 9,320,591 B2 | 4/2016 | Bolduc |
| D755,384 S | 5/2016 | Pesce et al. |
| 9,326,852 B2 | 5/2016 | Spenser |
| 9,326,876 B2 | 5/2016 | Acosta et al. |
| 9,345,573 B2 | 5/2016 | Nyuli et al. |
| 9,351,830 B2 | 5/2016 | Gross et al. |
| 9,387,078 B2 | 7/2016 | Gross et al. |
| 9,393,110 B2 | 7/2016 | Levi et al. |
| 9,421,098 B2 | 8/2016 | Gifford et al. |
| 9,427,303 B2 | 8/2016 | Liddy et al. |
| 9,427,316 B2 | 8/2016 | Schweich, Jr. et al. |
| 9,439,757 B2 | 9/2016 | Wallace et al. |
| 9,463,102 B2 | 10/2016 | Kelly |
| 9,474,599 B2 | 10/2016 | Keränen |
| 9,474,638 B2 | 10/2016 | Robinson et al. |
| 9,480,559 B2 | 11/2016 | Vidlund et al. |
| 9,492,273 B2 | 11/2016 | Wallace et al. |
| 9,498,314 B2 | 11/2016 | Behan |
| 9,498,332 B2 | 11/2016 | Hacohen et al. |
| 9,510,947 B2 | 12/2016 | Straubinger et al. |
| 9,532,870 B2 | 1/2017 | Cooper et al. |
| 9,554,897 B2 | 1/2017 | Lane et al. |
| 9,554,899 B2 | 1/2017 | Granada et al. |
| 9,561,103 B2 | 2/2017 | Granada et al. |
| 9,566,152 B2 | 2/2017 | Schweich et al. |
| 9,597,182 B2 | 3/2017 | Straubinger et al. |
| 9,629,716 B2 | 4/2017 | Seguin |
| 9,662,203 B2 | 5/2017 | Sheahan et al. |
| 9,681,952 B2 | 6/2017 | Hacohen et al. |
| 9,717,591 B2 | 8/2017 | Chau et al. |
| 9,743,932 B2 | 8/2017 | Amplatz et al. |
| 9,763,657 B2 | 9/2017 | Hacohen et al. |
| 9,763,817 B2 | 9/2017 | Roeder |
| 9,770,256 B2 | 9/2017 | Cohen et al. |
| D800,908 S | 10/2017 | Hariton et al. |
| 9,788,941 B2 | 10/2017 | Hacohen |
| 9,895,226 B1 | 2/2018 | Harari et al. |
| 9,974,651 B2 | 5/2018 | Hariton et al. |
| 9,987,132 B1 | 6/2018 | Hariton et al. |
| 9,993,360 B2 | 6/2018 | Shalev et al. |
| 10,010,414 B2 | 7/2018 | Cooper et al. |
| 10,045,845 B2 | 8/2018 | Hacohen et al. |
| 10,076,415 B1 | 9/2018 | Metchik et al. |
| 10,098,732 B1 | 10/2018 | Hariton et al. |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,143,552 B2 | 12/2018 | Wallace et al. |
| 10,149,761 B2 | 12/2018 | Granada et al. |
| 10,154,903 B2 | 12/2018 | Albitov et al. |
| 10,154,906 B2 | 12/2018 | Granada et al. |
| 10,159,570 B1 | 12/2018 | Metchik et al. |
| 10,182,908 B2 | 1/2019 | Tubishevitz et al. |
| 10,206,668 B2 | 2/2019 | Mcgoldrick et al. |
| 10,226,341 B2 | 3/2019 | Gross et al. |
| 10,231,831 B2 | 3/2019 | Hacohen |
| 10,231,837 B1 | 3/2019 | Metchik et al. |

(56) References Cited

U.S. PATENT DOCUMENTS

| | | |
|---|---|---|
| 10,238,493 B1 | 3/2019 | Metchik et al. |
| 10,245,143 B2 | 4/2019 | Gross et al. |
| 10,245,144 B1 | 4/2019 | Metchik et al. |
| 10,258,471 B2 | 4/2019 | Lutter et al. |
| 10,292,816 B2 | 5/2019 | Raanani et al. |
| 10,299,927 B2 | 5/2019 | McLean et al. |
| 10,321,995 B1 | 6/2019 | Christianson et al. |
| 10,322,020 B2 | 6/2019 | Lam et al. |
| 10,327,895 B2 | 6/2019 | Lozonschi et al. |
| 10,335,278 B2 | 7/2019 | McLean et al. |
| 10,376,361 B2 | 8/2019 | Gross et al. |
| 10,390,952 B2 | 8/2019 | Hariton et al. |
| 10,426,614 B2 | 10/2019 | Hariton et al. |
| 10,449,047 B2 | 10/2019 | Hariton et al. |
| 10,456,256 B2 | 10/2019 | Braido et al. |
| 10,492,908 B2 | 12/2019 | Hammer et al. |
| 10,507,108 B2 | 12/2019 | Delgado et al. |
| 10,507,109 B2 | 12/2019 | Metchik et al. |
| 10,512,456 B2 | 12/2019 | Hacohen et al. |
| 10,517,719 B2 | 12/2019 | Miller et al. |
| 10,524,792 B2 | 1/2020 | Hernandez et al. |
| 10,524,910 B2 | 1/2020 | Hammer et al. |
| 10,531,866 B2 | 1/2020 | Hariton et al. |
| 10,531,872 B2 | 1/2020 | Hacohen et al. |
| 10,537,426 B2 | 1/2020 | Iamberger et al. |
| 10,548,726 B2 | 2/2020 | Hacohen et al. |
| 10,548,731 B2 | 2/2020 | Lashinski et al. |
| 10,575,948 B2 | 3/2020 | Iamberger et al. |
| 10,595,992 B2 | 3/2020 | Chambers |
| 10,595,997 B2 | 3/2020 | Metchik et al. |
| 10,610,358 B2 | 4/2020 | Vidlund et al. |
| 10,610,359 B2 | 4/2020 | Hacohen |
| 10,631,871 B2 | 4/2020 | Goldfarb et al. |
| 10,631,982 B2 | 4/2020 | Hammer et al. |
| 10,646,342 B1 | 5/2020 | Marr et al. |
| 10,660,751 B2 | 5/2020 | Hacohen |
| 10,667,908 B2 | 6/2020 | Hariton et al. |
| 10,667,912 B2 | 6/2020 | Dixon et al. |
| 10,682,227 B2 | 6/2020 | Hariton et al. |
| 10,695,173 B2 | 6/2020 | Gross et al. |
| 10,695,177 B2 | 6/2020 | Hariton et al. |
| 10,702,385 B2 | 7/2020 | Hacohen |
| 10,736,742 B2 | 8/2020 | Hariton et al. |
| 10,758,342 B2 | 9/2020 | Chau et al. |
| 10,779,939 B2 | 9/2020 | Hariton et al. |
| 10,813,760 B2 | 10/2020 | Metchik et al. |
| 10,820,998 B2 | 11/2020 | Marr et al. |
| 10,835,377 B2 | 11/2020 | Hacohen et al. |
| 10,842,627 B2 | 11/2020 | Delgado et al. |
| 10,856,972 B2 | 12/2020 | Hariton et al. |
| 10,856,975 B2 | 12/2020 | Hariton et al. |
| 10,856,978 B2 | 12/2020 | Straubinger et al. |
| 10,874,514 B2 | 12/2020 | Dixon et al. |
| 10,888,422 B2 | 1/2021 | Hariton et al. |
| 10,888,425 B2 | 1/2021 | Delgado et al. |
| 10,888,644 B2 | 1/2021 | Ratz et al. |
| 10,905,548 B2 | 2/2021 | Hariton et al. |
| 10,905,552 B2 | 2/2021 | Dixon et al. |
| 10,905,554 B2 | 2/2021 | Cao |
| 10,918,481 B2 | 2/2021 | Hariton et al. |
| 10,918,483 B2 | 2/2021 | Metchik et al. |
| 10,925,732 B2 | 2/2021 | Delgado et al. |
| 10,945,843 B2 | 3/2021 | Delgado et al. |
| 10,945,844 B2 | 3/2021 | McCann et al. |
| 10,952,850 B2 | 3/2021 | Hariton et al. |
| 10,959,846 B2 | 3/2021 | Marr et al. |
| 10,993,809 B2 | 5/2021 | McCann et al. |
| 11,065,114 B2 | 7/2021 | Raanani et al. |
| 11,083,582 B2 | 8/2021 | McCann et al. |
| 11,135,059 B2 | 10/2021 | Hammer et al. |
| 11,147,672 B2 | 10/2021 | McCann et al. |
| 11,179,240 B2 | 11/2021 | Delgado et al. |
| 11,246,704 B2 | 2/2022 | Hariton et al. |
| 11,291,545 B2 | 4/2022 | Hacohen |
| 11,291,546 B2 | 4/2022 | Gross et al. |
| 11,291,547 B2 | 4/2022 | Gross et al. |
| 11,291,844 B2 | 4/2022 | Gross |
| 11,304,805 B2 | 4/2022 | Hariton et al. |
| 11,304,806 B2 | 4/2022 | Hariton et al. |
| 11,389,297 B2 | 7/2022 | Franklin et al. |
| 11,426,155 B2 | 8/2022 | Hacohen et al. |
| 11,517,429 B2 | 12/2022 | Gross et al. |
| 11,517,436 B2 | 12/2022 | Hacohen |
| 2001/0002445 A1 | 5/2001 | Vesely |
| 2001/0005787 A1 | 6/2001 | Oz et al. |
| 2001/0021872 A1 | 9/2001 | Bailey et al. |
| 2001/0021874 A1 | 9/2001 | Carpentier et al. |
| 2001/0044656 A1 | 11/2001 | Williamson et al. |
| 2001/0056295 A1 | 12/2001 | Solem |
| 2002/0013571 A1 | 1/2002 | Goldfarb et al. |
| 2002/0022862 A1 | 2/2002 | Grafton et al. |
| 2002/0029080 A1 | 3/2002 | Mortier et al. |
| 2002/0032481 A1 | 3/2002 | Gabbay |
| 2002/0042621 A1 | 4/2002 | Liddicoat et al. |
| 2002/0082525 A1 | 6/2002 | Oslund et al. |
| 2002/0087048 A1 | 7/2002 | Brock et al. |
| 2002/0099436 A1 | 7/2002 | Thornton et al. |
| 2002/0103532 A1 | 8/2002 | Langberg et al. |
| 2002/0151916 A1 | 10/2002 | Muramatsu et al. |
| 2002/0151961 A1 | 10/2002 | Lashinski et al. |
| 2002/0151970 A1 | 10/2002 | Garrison et al. |
| 2002/0169358 A1 | 11/2002 | Mortier et al. |
| 2002/0173841 A1 | 11/2002 | Ortiz et al. |
| 2002/0177894 A1 | 11/2002 | Acosta et al. |
| 2002/0177904 A1 | 11/2002 | Huxel et al. |
| 2002/0198586 A1 | 12/2002 | Inoue |
| 2003/0009236 A1 | 1/2003 | Godin |
| 2003/0018358 A1 | 1/2003 | Saadat |
| 2003/0036791 A1 | 2/2003 | Philipp et al. |
| 2003/0050693 A1 | 3/2003 | Quijano et al. |
| 2003/0050694 A1 | 3/2003 | Yang et al. |
| 2003/0060846 A1 | 3/2003 | Egnelov et al. |
| 2003/0060875 A1 | 3/2003 | Wittens |
| 2003/0069635 A1 | 4/2003 | Cartledge |
| 2003/0074052 A1 | 4/2003 | Besselink |
| 2003/0078465 A1 | 4/2003 | Pai et al. |
| 2003/0078653 A1 | 4/2003 | Vesely et al. |
| 2003/0083742 A1 | 5/2003 | Spence et al. |
| 2003/0100943 A1 | 5/2003 | Bolduc |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0130731 A1 | 7/2003 | Vidlund et al. |
| 2003/0158578 A1 | 8/2003 | Pantages et al. |
| 2003/0167062 A1 | 9/2003 | Gambale et al. |
| 2003/0171760 A1 | 9/2003 | Gambale |
| 2003/0191528 A1 | 10/2003 | Quijano et al. |
| 2003/0199974 A1 | 10/2003 | Lee et al. |
| 2003/0204195 A1 | 10/2003 | Keane et al. |
| 2003/0229350 A1 | 12/2003 | Kay |
| 2003/0229395 A1 | 12/2003 | Cox |
| 2003/0233142 A1 | 12/2003 | Morales et al. |
| 2004/0010272 A1 | 1/2004 | Manetakis et al. |
| 2004/0019377 A1 | 1/2004 | Taylor et al. |
| 2004/0024451 A1 | 2/2004 | Johnson et al. |
| 2004/0030382 A1 | 2/2004 | St. Goar et al. |
| 2004/0039414 A1 | 2/2004 | Carley et al. |
| 2004/0039436 A1 | 2/2004 | Spenser et al. |
| 2004/0039442 A1 | 2/2004 | St. Goar et al. |
| 2004/0049207 A1 | 3/2004 | Goldfarb et al. |
| 2004/0059413 A1 | 3/2004 | Argento |
| 2004/0092962 A1 | 5/2004 | Thornton et al. |
| 2004/0093060 A1 | 5/2004 | Seguin et al. |
| 2004/0122448 A1 | 6/2004 | Levine |
| 2004/0122503 A1 | 6/2004 | Campbell et al. |
| 2004/0122514 A1 | 6/2004 | Fogarty et al. |
| 2004/0127982 A1 | 7/2004 | Machold et al. |
| 2004/0127983 A1 | 7/2004 | Mortier et al. |
| 2004/0133220 A1 | 7/2004 | Lashinski et al. |
| 2004/0133267 A1 | 7/2004 | Lane |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |

(56) References Cited

U.S. PATENT DOCUMENTS

| | | |
|---|---|---|
| 2004/0143315 A1 | 7/2004 | Bruun et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153146 A1 | 8/2004 | Lashinski et al. |
| 2004/0172046 A1 | 9/2004 | Hlavka et al. |
| 2004/0176788 A1 | 9/2004 | Opolski |
| 2004/0176839 A1 | 9/2004 | Huynh et al. |
| 2004/0181287 A1 | 9/2004 | Gellman |
| 2004/0186558 A1 | 9/2004 | Pavcnik et al. |
| 2004/0186565 A1 | 9/2004 | Schreck |
| 2004/0186566 A1 | 9/2004 | Hindrichs et al. |
| 2004/0210244 A1 | 10/2004 | Vargas et al. |
| 2004/0210304 A1 | 10/2004 | Seguin et al. |
| 2004/0220593 A1 | 11/2004 | Greenhalgh |
| 2004/0225354 A1 | 11/2004 | Allen et al. |
| 2004/0236354 A1 | 11/2004 | Seguin |
| 2004/0236419 A1 | 11/2004 | Milo |
| 2004/0249433 A1 | 12/2004 | Freitag |
| 2004/0249453 A1 | 12/2004 | Cartledge et al. |
| 2004/0260317 A1 | 12/2004 | Bloom et al. |
| 2004/0260389 A1 | 12/2004 | Case et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0021056 A1 | 1/2005 | St. Goar et al. |
| 2005/0027305 A1 | 2/2005 | Shiu et al. |
| 2005/0027348 A1 | 2/2005 | Case et al. |
| 2005/0038494 A1 | 2/2005 | Eidenschink |
| 2005/0055038 A1 | 3/2005 | Kelleher et al. |
| 2005/0055086 A1 | 3/2005 | Stobie |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075726 A1 | 4/2005 | Svanidze et al. |
| 2005/0075727 A1 | 4/2005 | Wheatley |
| 2005/0075731 A1 | 4/2005 | Artof et al. |
| 2005/0080430 A1 | 4/2005 | Wright et al. |
| 2005/0080474 A1 | 4/2005 | Andreas et al. |
| 2005/0085900 A1 | 4/2005 | Case et al. |
| 2005/0085903 A1 | 4/2005 | Lau |
| 2005/0090827 A1 | 4/2005 | Gedebou |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137695 A1 | 6/2005 | Salahieh et al. |
| 2005/0137697 A1 | 6/2005 | Salahieh et al. |
| 2005/0137699 A1 | 6/2005 | Salahieh et al. |
| 2005/0143809 A1 | 6/2005 | Salahieh et al. |
| 2005/0149160 A1 | 7/2005 | McFerran |
| 2005/0154443 A1 | 7/2005 | Linder et al. |
| 2005/0159728 A1 | 7/2005 | Armour et al. |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0182483 A1 | 8/2005 | Osborne et al. |
| 2005/0182486 A1 | 8/2005 | Gabbay |
| 2005/0187613 A1 | 8/2005 | Bolduc et al. |
| 2005/0192596 A1 | 9/2005 | Jugenheimer et al. |
| 2005/0197695 A1 | 9/2005 | Stacchino et al. |
| 2005/0197696 A1 | 9/2005 | Gomez Duran |
| 2005/0203549 A1 | 9/2005 | Realyvasquez |
| 2005/0203606 A1 | 9/2005 | VanCamp |
| 2005/0203618 A1 | 9/2005 | Sharkawy et al. |
| 2005/0216039 A1 | 9/2005 | Lederman |
| 2005/0216079 A1 | 9/2005 | MaCoviak |
| 2005/0222665 A1 | 10/2005 | Aranyi |
| 2005/0222678 A1 | 10/2005 | Lashinski et al. |
| 2005/0234508 A1 | 10/2005 | Cummins et al. |
| 2005/0240200 A1 | 10/2005 | Bergheim |
| 2005/0251251 A1 | 11/2005 | Cribier |
| 2005/0256532 A1 | 11/2005 | Nayak et al. |
| 2005/0256566 A1 | 11/2005 | Gabbay |
| 2005/0267478 A1 | 12/2005 | Corradi et al. |
| 2005/0267573 A9 | 12/2005 | Macoviak et al. |
| 2005/0273138 A1 | 12/2005 | To et al. |
| 2005/0288776 A1 | 12/2005 | Shaoulian et al. |
| 2005/0288778 A1 | 12/2005 | Shaoulian et al. |
| 2005/0288781 A1 | 12/2005 | Moaddeb et al. |
| 2006/0004439 A1 | 1/2006 | Spenser et al. |
| 2006/0004442 A1 | 1/2006 | Spenser et al. |
| 2006/0004443 A1 | 1/2006 | Liddicoat et al. |
| 2006/0004469 A1 | 1/2006 | Sokel |
| 2006/0015171 A1 | 1/2006 | Armstrong |
| 2006/0020275 A1 | 1/2006 | Goldfarb et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025855 A1 | 2/2006 | Lashinski et al. |
| 2006/0025858 A1 | 2/2006 | Alameddine |
| 2006/0030885 A1 | 2/2006 | Hyde |
| 2006/0041189 A1 | 2/2006 | Vancaillie |
| 2006/0041319 A1 | 2/2006 | Taylor et al. |
| 2006/0052867 A1 | 3/2006 | Revuelta et al. |
| 2006/0052868 A1 | 3/2006 | Mortier |
| 2006/0058871 A1 | 3/2006 | Zakay et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0089627 A1 | 4/2006 | Burnett et al. |
| 2006/0095009 A1 | 5/2006 | Lampropoulos et al. |
| 2006/0106423 A1 | 5/2006 | Weisel et al. |
| 2006/0111773 A1 | 5/2006 | Rittgers et al. |
| 2006/0116750 A1 | 6/2006 | Herbert et al. |
| 2006/0116757 A1 | 6/2006 | Lashinski et al. |
| 2006/0122692 A1 | 6/2006 | Gilad et al. |
| 2006/0129166 A1 | 6/2006 | Lavelle |
| 2006/0135964 A1 | 6/2006 | Vesley |
| 2006/0149280 A1 | 7/2006 | Harvine et al. |
| 2006/0149368 A1 | 7/2006 | Spence |
| 2006/0155357 A1 | 7/2006 | Melsheimer |
| 2006/0161250 A1 | 7/2006 | Shaw |
| 2006/0161265 A1 | 7/2006 | Levine et al. |
| 2006/0047297 A1 | 8/2006 | Case |
| 2006/0178700 A1 | 8/2006 | Quinn |
| 2006/0178740 A1 | 8/2006 | Stacchino et al. |
| 2006/0184203 A1 | 8/2006 | Martin et al. |
| 2006/0184240 A1 | 8/2006 | Jimenez et al. |
| 2006/0184242 A1 | 8/2006 | Lichtenstein |
| 2006/0190036 A1 | 8/2006 | Wendel et al. |
| 2006/0190038 A1 | 8/2006 | Carley et al. |
| 2006/0195134 A1 | 8/2006 | Crittenden |
| 2006/0195183 A1 | 8/2006 | Navia et al. |
| 2006/0195184 A1 | 8/2006 | Lane et al. |
| 2006/0201519 A1 | 9/2006 | Frazier et al. |
| 2006/0212107 A1* | 9/2006 | Case ................. A61B 5/02007 623/1.11 |
| 2006/0212111 A1 | 9/2006 | Case et al. |
| 2006/0216404 A1 | 9/2006 | Seyler et al. |
| 2006/0229708 A1 | 10/2006 | Powell et al. |
| 2006/0241622 A1 | 10/2006 | Zergiebel |
| 2006/0241656 A1 | 10/2006 | Starksen et al. |
| 2006/0241745 A1 | 10/2006 | Solem |
| 2006/0241748 A1 | 10/2006 | Lee et al. |
| 2006/0247680 A1 | 11/2006 | Amplatz et al. |
| 2006/0247763 A1 | 11/2006 | Slater |
| 2006/0253191 A1 | 11/2006 | Salahieh et al. |

(56) References Cited

U.S. PATENT DOCUMENTS

| | | |
|---|---|---|
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0271166 A1 | 11/2006 | Thill et al. |
| 2006/0271171 A1 | 11/2006 | McQuinn et al. |
| 2006/0271175 A1 | 11/2006 | Woolfson |
| 2006/0282150 A1 | 12/2006 | Olson et al. |
| 2006/0282161 A1 | 12/2006 | Huyn et al. |
| 2006/0287661 A1 | 12/2006 | Bolduc et al. |
| 2006/0287716 A1 | 12/2006 | Banbury et al. |
| 2006/0287719 A1 | 12/2006 | Rowe et al. |
| 2007/0001627 A1 | 1/2007 | Lin et al. |
| 2007/0008018 A1 | 1/2007 | Nagashima et al. |
| 2007/0016286 A1 | 1/2007 | Herrmann et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027528 A1 | 2/2007 | Agnew |
| 2007/0027533 A1 | 2/2007 | Douk |
| 2007/0027536 A1 | 2/2007 | Mihaljevic et al. |
| 2007/0027549 A1 | 2/2007 | Godin |
| 2007/0038221 A1 | 2/2007 | Fine et al. |
| 2007/0038293 A1 | 2/2007 | St. Goar et al. |
| 2007/0038295 A1 | 2/2007 | Case et al. |
| 2007/0043435 A1 | 2/2007 | Seguin et al. |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0055340 A1 | 3/2007 | Pryor |
| 2007/0056346 A1 | 3/2007 | Spenser et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0078510 A1 | 4/2007 | Ryan |
| 2007/0080188 A1 | 4/2007 | Spence et al. |
| 2007/0083168 A1 | 4/2007 | Whiting et al. |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0173932 A1 | 7/2007 | Cali et al. |
| 2007/0197858 A1 | 8/2007 | Goldfarb et al. |
| 2007/0198077 A1 | 8/2007 | Cully et al. |
| 2007/0198082 A1 | 8/2007 | Kapadia et al. |
| 2007/0198097 A1 | 8/2007 | Zegdi |
| 2007/0208550 A1 | 9/2007 | Cao et al. |
| 2007/0213582 A1 | 9/2007 | Zollinger et al. |
| 2007/0213810 A1 | 9/2007 | Newhauser et al. |
| 2007/0213813 A1 | 9/2007 | Von Segesser et al. |
| 2007/0219558 A1 | 9/2007 | Deutsch |
| 2007/0219630 A1 | 9/2007 | Chu |
| 2007/0225759 A1 | 9/2007 | Thommen et al. |
| 2007/0225760 A1 | 9/2007 | Moszner et al. |
| 2007/0233186 A1 | 10/2007 | Meng |
| 2007/0233237 A1 | 10/2007 | Krivoruchko |
| 2007/0233239 A1 | 10/2007 | Navia et al. |
| 2007/0239208 A1 | 10/2007 | Crawford |
| 2007/0239272 A1 | 10/2007 | Navia et al. |
| 2007/0239273 A1 | 10/2007 | Allen |
| 2007/0244546 A1 | 10/2007 | Francis |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0270943 A1 | 11/2007 | Solem et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004688 A1 | 1/2008 | Spenser et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Mackoviak et al. |
| 2008/0071361 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0077235 A1 | 3/2008 | Kirson |
| 2008/0082083 A1 | 4/2008 | Forde et al. |
| 2008/0082159 A1 | 4/2008 | Tseng et al. |
| 2008/0082166 A1 | 4/2008 | Styrc et al. |
| 2008/0086138 A1 | 4/2008 | Stone et al. |
| 2008/0086164 A1 | 4/2008 | Rowe et al. |
| 2008/0086203 A1 | 4/2008 | Roberts |
| 2008/0086204 A1 | 4/2008 | Rankin |
| 2008/0091257 A1 | 4/2008 | Andreas et al. |
| 2008/0091261 A1 | 4/2008 | Long et al. |
| 2008/0097523 A1 | 4/2008 | Bolduc et al. |
| 2008/0097595 A1 | 4/2008 | Gabbay |
| 2008/0103581 A1* | 5/2008 | Goto ..................... A61F 2/962 623/1.11 |
| 2008/0132989 A1 | 6/2008 | Snow et al. |
| 2008/0140003 A1 | 6/2008 | Bei et al. |
| 2008/0140116 A1 | 6/2008 | Bonutti |
| 2008/0147182 A1 | 6/2008 | Righini et al. |
| 2008/0161910 A1 | 7/2008 | Revuelta et al. |
| 2008/0167705 A1 | 7/2008 | Agnew |
| 2008/0167714 A1 | 7/2008 | St. Goar et al. |
| 2008/0188929 A1 | 8/2008 | Schreck |
| 2008/0195126 A1 | 8/2008 | Solem |
| 2008/0195200 A1 | 8/2008 | Vidlund et al. |
| 2008/0200980 A1 | 8/2008 | Robin et al. |
| 2008/0208265 A1 | 8/2008 | Frazier et al. |
| 2008/0208328 A1 | 8/2008 | Antocci et al. |
| 2008/0208330 A1 | 8/2008 | Keranen |
| 2008/0208332 A1 | 8/2008 | Lamphere et al. |
| 2008/0221672 A1 | 9/2008 | Lamphere et al. |
| 2008/0234813 A1 | 9/2008 | Heuser |
| 2008/0234814 A1 | 9/2008 | Salahieh et al. |
| 2008/0243245 A1 | 10/2008 | Thambar et al. |
| 2008/0255580 A1 | 10/2008 | Hoffman et al. |
| 2008/0262609 A1 | 10/2008 | Gross et al. |
| 2008/0269879 A1 | 10/2008 | Sathe et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281411 A1 | 11/2008 | Berreklouw |
| 2008/0288044 A1 | 11/2008 | Osborne |
| 2008/0288062 A1 | 11/2008 | Andrieu et al. |
| 2008/0294234 A1 | 11/2008 | Hartley et al. |
| 2008/0294248 A1 | 11/2008 | Yang et al. |
| 2008/0300629 A1 | 12/2008 | Surti |
| 2009/0005863 A1 | 1/2009 | Goetz et al. |
| 2009/0036966 A1 | 2/2009 | O'Connor et al. |
| 2009/0043153 A1 | 2/2009 | Zollinger et al. |
| 2009/0043381 A1 | 2/2009 | Macoviak et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082844 A1 | 3/2009 | Zacharias et al. |
| 2009/0088836 A1 | 4/2009 | Bishop et al. |
| 2009/0088837 A1 | 4/2009 | Gillinov et al. |
| 2009/0099554 A1 | 4/2009 | Forster et al. |
| 2009/0099650 A1 | 4/2009 | Bolduc et al. |

(56) References Cited

U.S. PATENT DOCUMENTS

| | | |
|---|---|---|
| 2009/0105794 A1 | 4/2009 | Ziarno et al. |
| 2009/0105816 A1 | 4/2009 | Olsen et al. |
| 2009/0112159 A1 | 4/2009 | Slattery et al. |
| 2009/0125098 A1 | 5/2009 | Chuter |
| 2009/0125102 A1 | 5/2009 | Cartledge |
| 2009/0149872 A1 | 6/2009 | Gross et al. |
| 2009/0157175 A1 | 6/2009 | Benichou |
| 2009/0163934 A1 | 6/2009 | Raschdorf, Jr. et al. |
| 2009/0177274 A1 | 6/2009 | Scorsin et al. |
| 2009/0171363 A1 | 7/2009 | Chocron |
| 2009/0171439 A1 | 7/2009 | Nissl |
| 2009/0177266 A1 | 7/2009 | Powell et al. |
| 2009/0177277 A1 | 7/2009 | Milo |
| 2009/0177278 A1 | 7/2009 | Spence |
| 2009/0192601 A1 | 7/2009 | Rafiee et al. |
| 2009/0210052 A1 | 8/2009 | Forster et al. |
| 2009/0222081 A1 | 9/2009 | Linder et al. |
| 2009/0240320 A1 | 9/2009 | Tuval et al. |
| 2009/0241656 A1 | 10/2009 | Jacquemin |
| 2009/0248143 A1 | 10/2009 | Laham |
| 2009/0248148 A1 | 10/2009 | Shaolian et al. |
| 2009/0254103 A1 | 10/2009 | Deustch |
| 2009/0259306 A1 | 10/2009 | Rowe |
| 2009/0259307 A1 | 10/2009 | Gross et al. |
| 2009/0264859 A1 | 10/2009 | Mas |
| 2009/0264994 A1 | 10/2009 | Saadat |
| 2009/0264995 A1 | 10/2009 | Subramanian |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0287304 A1 | 11/2009 | Dahlgren et al. |
| 2009/0299409 A1 | 12/2009 | Coe et al. |
| 2009/0299449 A1 | 12/2009 | Styrc |
| 2009/0306768 A1 | 12/2009 | Quardi |
| 2009/0319037 A1 | 12/2009 | Rowe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0022823 A1 | 1/2010 | Goldfarb et al. |
| 2010/0023117 A1 | 1/2010 | Yoganathan et al. |
| 2010/0023118 A1 | 1/2010 | Medlock et al. |
| 2010/0023120 A1 | 1/2010 | Holecek et al. |
| 2010/0030014 A1 | 2/2010 | Ferrazzi |
| 2010/0036479 A1 | 2/2010 | Hill et al. |
| 2010/0036484 A1 | 2/2010 | Hariton et al. |
| 2010/0042147 A1 | 2/2010 | Janovsky et al. |
| 2010/0049306 A1 | 2/2010 | House et al. |
| 2010/0049313 A1 | 2/2010 | Alon et al. |
| 2010/0063542 A1 | 3/2010 | Van Der Burg et al. |
| 2010/0063550 A1 | 3/2010 | Felix et al. |
| 2010/0063586 A1 | 3/2010 | Hasenkam et al. |
| 2010/0069852 A1 | 3/2010 | Kelley |
| 2010/0076499 A1 | 3/2010 | McNamara et al. |
| 2010/0076548 A1 | 3/2010 | Konno |
| 2010/0082094 A1 | 4/2010 | Quadri et al. |
| 2010/0094248 A1 | 4/2010 | Nguyen et al. |
| 2010/0100167 A1 | 4/2010 | Bortlein et al. |
| 2010/0114180 A1 | 5/2010 | Rock |
| 2010/0114299 A1 | 5/2010 | Ben-Muvhar et al. |
| 2010/0121349 A1 | 5/2010 | Meier |
| 2010/0130992 A1 | 5/2010 | Machold et al. |
| 2010/0131054 A1 | 5/2010 | Tuval et al. |
| 2010/0137979 A1 | 6/2010 | Tuval et al. |
| 2010/0152845 A1 | 6/2010 | Bloom et al. |
| 2010/0160958 A1 | 6/2010 | Clark |
| 2010/0161036 A1 | 6/2010 | Pintor et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168845 A1 | 7/2010 | Wright |
| 2010/0174358 A1 | 7/2010 | Rabkin et al. |
| 2010/0174363 A1 | 7/2010 | Castro |
| 2010/0179574 A1 | 7/2010 | Longoria et al. |
| 2010/0179643 A1 | 7/2010 | Shalev |
| 2010/0179648 A1 | 7/2010 | Richter et al. |
| 2010/0179649 A1 | 7/2010 | Richter et al. |
| 2010/0185277 A1 | 7/2010 | Braido et al. |
| 2010/0198347 A1 | 8/2010 | Zakay et al. |
| 2010/0217382 A1 | 8/2010 | Chau et al. |
| 2010/0222810 A1 | 9/2010 | DeBeer et al. |
| 2010/0228285 A1 | 9/2010 | Miles et al. |
| 2010/0234935 A1 | 9/2010 | Bashiri et al. |
| 2010/0234940 A1 | 9/2010 | Dolan |
| 2010/0249908 A1 | 9/2010 | Chau et al. |
| 2010/0249915 A1 | 9/2010 | Zhang |
| 2010/0249917 A1 | 9/2010 | Zhang |
| 2010/0249920 A1 | 9/2010 | Bolling et al. |
| 2010/0256737 A1 | 10/2010 | Pollock et al. |
| 2010/0262232 A1 | 10/2010 | Annest |
| 2010/0262233 A1 | 10/2010 | He |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0280606 A1 | 11/2010 | Naor |
| 2010/0286628 A1 | 11/2010 | Gross |
| 2010/0286767 A1 | 11/2010 | Zipory et al. |
| 2010/0305475 A1 | 12/2010 | Hinchliffe et al. |
| 2010/0312333 A1 | 12/2010 | Navia et al. |
| 2010/0324595 A1 | 12/2010 | Linder et al. |
| 2010/0331971 A1 | 12/2010 | Keränen et al. |
| 2011/0004210 A1 | 1/2011 | Johnson et al. |
| 2011/0004227 A1 | 1/2011 | Goldfarb et al. |
| 2011/0004296 A1 | 1/2011 | Lutter et al. |
| 2011/0004298 A1 | 1/2011 | Lee et al. |
| 2011/0004299 A1 | 1/2011 | Navia et al. |
| 2011/0011917 A1 | 1/2011 | Loulmet |
| 2011/0015729 A1 | 1/2011 | Jimenez et al. |
| 2011/0015731 A1 | 1/2011 | Carpentier et al. |
| 2011/0015739 A1 | 1/2011 | Cheung et al. |
| 2011/0021985 A1 | 1/2011 | Spargias |
| 2011/0022165 A1 | 1/2011 | Oba et al. |
| 2011/0178597 A9 | 1/2011 | Navia et al. |
| 2011/0026208 A1 | 2/2011 | Otsuro et al. |
| 2011/0029066 A1 | 2/2011 | Gilad et al. |
| 2011/0029067 A1 | 2/2011 | Mcguckin, Jr. et al. |
| 2011/0029072 A1 | 2/2011 | Gabbay |
| 2011/0035000 A1 | 2/2011 | Nieminen et al. |
| 2011/0040374 A1 | 2/2011 | Goetz et al. |
| 2011/0040375 A1 | 2/2011 | Letac et al. |
| 2011/0046662 A1 | 2/2011 | Moszner et al. |
| 2011/0054466 A1 | 3/2011 | Rothstein et al. |
| 2011/0054596 A1 | 3/2011 | Taylor |
| 2011/0054598 A1 | 3/2011 | Johnson |
| 2011/0066231 A1 | 3/2011 | Cartledge et al. |
| 2011/0066233 A1 | 3/2011 | Thornton et al. |
| 2011/0067770 A1 | 3/2011 | Pederson et al. |
| 2011/0071626 A1 | 3/2011 | Wright et al. |
| 2011/0077730 A1 | 3/2011 | Fentster |
| 2011/0082538 A1 | 4/2011 | Dahlgren et al. |
| 2011/0087146 A1 | 4/2011 | Ryan et al. |
| 2011/0087322 A1 | 4/2011 | Letac et al. |
| 2011/0093002 A1 | 4/2011 | Rucker et al. |
| 2011/0093063 A1 | 4/2011 | Schreck |
| 2011/0098525 A1 | 4/2011 | Kermode et al. |
| 2011/0098802 A1 | 4/2011 | Braido et al. |
| 2011/0106245 A1 | 5/2011 | Miller et al. |
| 2011/0106247 A1 | 5/2011 | Miller et al. |
| 2011/0112625 A1 | 5/2011 | Ben-Muvhar et al. |
| 2011/0112632 A1 | 5/2011 | Chau et al. |
| 2011/0113768 A1 | 5/2011 | Bauer et al. |
| 2011/0118830 A1 | 5/2011 | Liddicoat et al. |
| 2011/0118832 A1 | 5/2011 | Punjabi |
| 2011/0125257 A1 | 5/2011 | Seguin et al. |
| 2011/0125258 A1 | 5/2011 | Centola |
| 2011/0137326 A1 | 6/2011 | Bachman |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0144703 A1 | 6/2011 | Krause et al. |
| 2011/0144742 A1 | 6/2011 | Madrid et al. |
| 2011/0166636 A1 | 7/2011 | Rowe |
| 2011/0166649 A1 | 7/2011 | Gross et al. |
| 2011/0172784 A1 | 7/2011 | Richter |

(56) References Cited

U.S. PATENT DOCUMENTS

| | | |
|---|---|---|
| 2011/0184510 A1 | 7/2011 | Maisano et al. |
| 2011/0190877 A1 | 8/2011 | Lane et al. |
| 2011/0190879 A1 | 8/2011 | Bobo et al. |
| 2011/0202076 A1 | 8/2011 | Richter |
| 2011/0202130 A1 | 8/2011 | Cartledge et al. |
| 2011/0208283 A1 | 8/2011 | Rust |
| 2011/0208293 A1 | 8/2011 | Tabor |
| 2011/0208298 A1 | 8/2011 | Tuval et al. |
| 2011/0213459 A1 | 9/2011 | Garrison et al. |
| 2011/0213461 A1 | 9/2011 | Seguin et al. |
| 2011/0218619 A1 | 9/2011 | Benichou et al. |
| 2011/0218620 A1 | 9/2011 | Meiri et al. |
| 2011/0224785 A1 | 9/2011 | Hacohen |
| 2011/0230941 A1 | 9/2011 | Markus |
| 2011/0230961 A1 | 9/2011 | Langer et al. |
| 2011/0238088 A1 | 9/2011 | Bodluc et al. |
| 2011/0238094 A1 | 9/2011 | Thomas et al. |
| 2011/0238159 A1 | 9/2011 | Guyenot et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251678 A1 | 10/2011 | Eidenschink et al. |
| 2011/0251679 A1 | 10/2011 | Weimeyer et al. |
| 2011/0251680 A1 | 10/2011 | Tran et al. |
| 2011/0251682 A1 | 10/2011 | Murray, III et al. |
| 2011/0251683 A1* | 10/2011 | Tabor .................. A61F 2/2436 623/2.11 |
| 2011/0257433 A1 | 10/2011 | Walker |
| 2011/0257633 A1 | 10/2011 | Cartledge et al. |
| 2011/0257721 A1 | 10/2011 | Tabor |
| 2011/0257728 A1 | 10/2011 | Kuehn |
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0264208 A1 | 10/2011 | Duffy |
| 2011/0270276 A1 | 11/2011 | Rothstein et al. |
| 2011/0271967 A1 | 11/2011 | Mortier et al. |
| 2011/0276062 A1 | 11/2011 | Bolduc |
| 2011/0276128 A1 | 11/2011 | Cao et al. |
| 2011/0282361 A1 | 11/2011 | Miller et al. |
| 2011/0282438 A1 | 11/2011 | Drews et al. |
| 2011/0282439 A1 | 11/2011 | Thill et al. |
| 2011/0282440 A1 | 11/2011 | Cao |
| 2011/0283514 A1 | 11/2011 | Fogarty et al. |
| 2011/0288435 A1 | 11/2011 | Christy et al. |
| 2011/0288632 A1 | 11/2011 | White |
| 2011/0288634 A1 | 11/2011 | Tuval et al. |
| 2011/0288635 A1 | 11/2011 | Miller et al. |
| 2011/0295354 A1 | 12/2011 | Bueche et al. |
| 2011/0295363 A1 | 12/2011 | Girard et al. |
| 2011/0301498 A1 | 12/2011 | Maenhout et al. |
| 2011/0301688 A1 | 12/2011 | Dolan |
| 2011/0301698 A1 | 12/2011 | Miller et al. |
| 2011/0301701 A1 | 12/2011 | Padala et al. |
| 2011/0301702 A1 | 12/2011 | Rust et al. |
| 2011/0306916 A1 | 12/2011 | Nitzan et al. |
| 2011/0307049 A1 | 12/2011 | Kao |
| 2011/0313452 A1 | 12/2011 | Carley et al. |
| 2011/0313515 A1 | 12/2011 | Quadri et al. |
| 2011/0319988 A1 | 12/2011 | Schankereli et al. |
| 2011/0319989 A1 | 12/2011 | Lane et al. |
| 2011/0319991 A1 | 12/2011 | Hariton et al. |
| 2012/0010694 A1 | 1/2012 | Lutter et al. |
| 2012/0016468 A1 | 1/2012 | Robin et al. |
| 2012/0022557 A1 | 1/2012 | Cabiri et al. |
| 2012/0022629 A1 | 1/2012 | Perera et al. |
| 2012/0022633 A1 | 1/2012 | Olson et al. |
| 2012/0022637 A1 | 1/2012 | Ben-Movhar et al. |
| 2012/0022639 A1 | 1/2012 | Hacohen et al. |
| 2012/0022640 A1 | 1/2012 | Gross et al. |
| 2012/0022644 A1 | 1/2012 | Reich et al. |
| 2012/0035703 A1 | 2/2012 | Lutter et al. |
| 2012/0035712 A1 | 2/2012 | Maisano et al. |
| 2012/0035713 A1 | 2/2012 | Lutter et al. |
| 2012/0035722 A1 | 2/2012 | Tuval et al. |
| 2012/0041547 A1 | 2/2012 | Duffy et al. |
| 2012/0041551 A1 | 2/2012 | Spenser et al. |
| 2012/0046738 A1 | 2/2012 | Lau et al. |
| 2012/0046742 A1 | 2/2012 | Tuval et al. |
| 2012/0053676 A1 | 3/2012 | Ku et al. |
| 2012/0053680 A1 | 3/2012 | Bolling et al. |
| 2012/0053682 A1 | 3/2012 | Kovalsky et al. |
| 2012/0053688 A1 | 3/2012 | Fogarty et al. |
| 2012/0059337 A1 | 3/2012 | Eilat |
| 2012/0059454 A1 | 3/2012 | Millwee et al. |
| 2012/0059458 A1 | 3/2012 | Buchbinder et al. |
| 2012/0065464 A1 | 3/2012 | Ellis et al. |
| 2012/0078237 A1 | 3/2012 | Wang et al. |
| 2012/0078353 A1 | 3/2012 | Quadri et al. |
| 2012/0078355 A1 | 3/2012 | Zipory et al. |
| 2012/0078357 A1 | 3/2012 | Conklin |
| 2012/0078359 A1 | 3/2012 | Li et al. |
| 2012/0083832 A1 | 4/2012 | Delaloye et al. |
| 2012/0083839 A1 | 4/2012 | Letac et al. |
| 2012/0083874 A1* | 4/2012 | Dale .................. A61F 2/2427 623/2.11 |
| 2012/0083879 A1 | 4/2012 | Eberhardt et al. |
| 2012/0089022 A1 | 4/2012 | House et al. |
| 2012/0089223 A1 | 4/2012 | Nguyen et al. |
| 2012/0095552 A1 | 4/2012 | Spence et al. |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0109155 A1 | 5/2012 | Robinson et al. |
| 2012/0123511 A1 | 5/2012 | Brown |
| 2012/0123529 A1 | 5/2012 | Levi et al. |
| 2012/0123530 A1 | 5/2012 | Carpentier et al. |
| 2012/0130473 A1 | 5/2012 | Norris et al. |
| 2012/0130474 A1 | 5/2012 | Buckley |
| 2012/0130475 A1 | 5/2012 | Shaw |
| 2012/0136434 A1 | 5/2012 | Carpentier et al. |
| 2012/0136436 A1 | 5/2012 | Cabiri et al. |
| 2012/0143323 A1 | 6/2012 | Hasenkam et al. |
| 2012/0150218 A1 | 6/2012 | Sandgren et al. |
| 2012/0150290 A1 | 6/2012 | Gabbay |
| 2012/0158021 A1 | 6/2012 | Morrill |
| 2012/0165915 A1 | 6/2012 | Melsheimer et al. |
| 2012/0165930 A1 | 6/2012 | Gifford, III et al. |
| 2012/0179086 A1 | 7/2012 | Shank |
| 2012/0179244 A1 | 7/2012 | Schankereli et al. |
| 2012/0191182 A1 | 7/2012 | Hauser et al. |
| 2012/0197292 A1 | 8/2012 | Chin-Chen et al. |
| 2012/0197388 A1 | 8/2012 | Khairkhahan et al. |
| 2012/0215303 A1 | 8/2012 | Quadri et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0277845 A1 | 11/2012 | Bowe |
| 2012/0283757 A1 | 11/2012 | Miller et al. |
| 2012/0283824 A1 | 11/2012 | Lutter et al. |
| 2012/0290062 A1 | 11/2012 | McNamara et al. |
| 2012/0296349 A1 | 11/2012 | Smith et al. |
| 2012/0296360 A1 | 11/2012 | Norris et al. |
| 2012/0296417 A1 | 11/2012 | Hill et al. |
| 2012/0296418 A1 | 11/2012 | Bonyuet et al. |
| 2012/0296419 A1 | 11/2012 | Richardson |
| 2012/0300063 A1 | 11/2012 | Majkrzak et al. |
| 2012/0123531 A1 | 12/2012 | Tsukashima et al. |
| 2012/0310328 A1 | 12/2012 | Olson et al. |
| 2012/0310330 A1 | 12/2012 | Buchbinder et al. |
| 2012/0323313 A1 | 12/2012 | Seguin |
| 2012/0323316 A1 | 12/2012 | Chau et al. |
| 2012/0330408 A1 | 12/2012 | Hillukka et al. |
| 2012/0330410 A1 | 12/2012 | Hammer et al. |

(56) References Cited

U.S. PATENT DOCUMENTS

| | | |
|---|---|---|
| 2012/0330411 A1 | 12/2012 | Gross et al. |
| 2013/0006347 A1 | 1/2013 | McHugo |
| 2013/0018450 A1 | 1/2013 | Hunt |
| 2013/0018458 A1 | 1/2013 | Yohanan et al. |
| 2013/0023758 A1 | 1/2013 | Fabro |
| 2013/0030519 A1 | 1/2013 | Tran et al. |
| 2013/0030522 A1 | 1/2013 | Rowe et al. |
| 2013/0035759 A1 | 2/2013 | Gross et al. |
| 2013/0041204 A1 | 2/2013 | Heilman et al. |
| 2013/0041451 A1 | 2/2013 | Patterson et al. |
| 2013/0046373 A1 | 2/2013 | Cartledge et al. |
| 2013/0066341 A1 | 3/2013 | Ketai et al. |
| 2013/0066342 A1 | 3/2013 | Dell et al. |
| 2013/0079872 A1 | 3/2013 | Gallagher |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0116779 A1 | 5/2013 | Weber |
| 2013/0116780 A1 | 5/2013 | Miller et al. |
| 2013/0123896 A1 | 5/2013 | Bloss et al. |
| 2013/0123900 A1 | 5/2013 | Eblacas et al. |
| 2013/0123910 A1 | 5/2013 | Cartledge et al. |
| 2013/0131791 A1 | 5/2013 | Hlavka et al. |
| 2013/0131792 A1 | 5/2013 | Miller et al. |
| 2013/0150945 A1 | 6/2013 | Crawford et al. |
| 2013/0150956 A1 | 6/2013 | Yohanan et al. |
| 2013/0158647 A1 | 6/2013 | Norris et al. |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0172992 A1 | 7/2013 | Gross et al. |
| 2013/0178930 A1 | 7/2013 | Straubinger et al. |
| 2013/0190857 A1 | 7/2013 | Svanidze et al. |
| 2013/0190861 A1 | 7/2013 | Chau et al. |
| 2013/0190863 A1 | 7/2013 | Call et al. |
| 2013/0190866 A1 | 7/2013 | Zipory et al. |
| 2013/0197632 A1 | 8/2013 | Kovach et al. |
| 2013/0204361 A1 | 8/2013 | Adams et al. |
| 2013/0211501 A1 | 8/2013 | Buckley et al. |
| 2013/0211508 A1 | 8/2013 | Lane et al. |
| 2013/0226289 A1 | 8/2013 | Shaolian et al. |
| 2013/0226290 A1 | 8/2013 | Yellin et al. |
| 2013/0231735 A1 | 9/2013 | Deem et al. |
| 2013/0245742 A1 | 9/2013 | Norris |
| 2013/0253643 A1 | 9/2013 | Rolando et al. |
| 2013/0261737 A1 | 10/2013 | Costello |
| 2013/0261738 A1 | 10/2013 | Clague et al. |
| 2013/0268069 A1 | 10/2013 | Zakai et al. |
| 2013/0274870 A1 | 10/2013 | Lombardi et al. |
| 2013/0282059 A1 | 10/2013 | Ketai et al. |
| 2013/0289711 A1 | 10/2013 | Liddy et al. |
| 2013/0289718 A1 | 10/2013 | Tsukashima et al. |
| 2013/0289740 A1 | 10/2013 | Liddy et al. |
| 2013/0297013 A1 | 11/2013 | Klima et al. |
| 2013/0304093 A1 | 11/2013 | Serina et al. |
| 2013/0304197 A1 | 11/2013 | Buchbinder et al. |
| 2013/0304200 A1 | 11/2013 | McLean et al. |
| 2013/0310928 A1 | 11/2013 | Morriss et al. |
| 2013/0325114 A1 | 12/2013 | McLean et al. |
| 2013/0325118 A1 | 12/2013 | Cartledge |
| 2013/0331929 A1 | 12/2013 | Mitra et al. |
| 2014/0000112 A1 | 1/2014 | Braido et al. |
| 2014/0005767 A1 | 1/2014 | Glazier et al. |
| 2014/0005778 A1 | 1/2014 | Buchbinder et al. |
| 2014/0018911 A1 | 1/2014 | Zhou et al. |
| 2014/0018914 A1 | 1/2014 | Zipory et al. |
| 2014/0018915 A1 | 1/2014 | Biadillah et al. |
| 2014/0031928 A1 | 1/2014 | Murphy et al. |
| 2014/0046430 A1 | 2/2014 | Shaw |
| 2014/0052237 A1 | 2/2014 | Lane et al. |
| 2014/0067050 A1 | 3/2014 | Costello et al. |
| 2014/0067054 A1 | 3/2014 | Chau et al. |
| 2014/0081376 A1 | 3/2014 | Burkart et al. |
| 2014/0088368 A1 | 3/2014 | Park |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0099726 A1 | 4/2014 | Heller |
| 2014/0100653 A1 | 4/2014 | Savage et al. |
| 2014/0106951 A1 | 4/2014 | Brandon |
| 2014/0120287 A1 | 5/2014 | Jacoby et al. |
| 2014/0121749 A1 | 5/2014 | Roeder |
| 2014/0121763 A1 | 5/2014 | Duffy et al. |
| 2014/0135799 A1 | 5/2014 | Henderson |
| 2014/0135894 A1 | 5/2014 | Norris et al. |
| 2014/0135895 A1 | 5/2014 | Andress et al. |
| 2014/0142619 A1 | 5/2014 | Serina et al. |
| 2014/0142681 A1 | 5/2014 | Norris |
| 2014/0142688 A1 | 5/2014 | Duffy et al. |
| 2014/0142695 A1 | 5/2014 | Gross et al. |
| 2014/0148849 A1 | 5/2014 | Serina et al. |
| 2014/0148891 A1 | 5/2014 | Johnson |
| 2014/0148898 A1 | 5/2014 | Gross et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0172069 A1 | 6/2014 | Roeder et al. |
| 2014/0172077 A1 | 6/2014 | Bruchman et al. |
| 2014/0172082 A1 | 6/2014 | Bruchman et al. |
| 2014/0188108 A1 | 7/2014 | Goodine et al. |
| 2014/0188140 A1 | 7/2014 | Meier et al. |
| 2014/0188210 A1 | 7/2014 | Beard et al. |
| 2014/0188215 A1 | 7/2014 | Hlavka et al. |
| 2014/0188221 A1 | 7/2014 | Chung et al. |
| 2014/0194970 A1 | 7/2014 | Chobotov |
| 2014/0194976 A1 | 7/2014 | Starksen et al. |
| 2014/0194981 A1 | 7/2014 | Menk et al. |
| 2014/0194983 A1 | 7/2014 | Kovalsky et al. |
| 2014/0200649 A1 | 7/2014 | Essinger et al. |
| 2014/0207175 A1* | 7/2014 | Aggerholm ........ A61B 17/1214 606/200 |
| 2014/0207231 A1 | 7/2014 | Hacohen et al. |
| 2014/0214157 A1 | 7/2014 | Börtlein et al. |
| 2014/0214159 A1 | 7/2014 | Vidlund et al. |
| 2014/0222136 A1 | 8/2014 | Geist et al. |
| 2014/0222137 A1 | 8/2014 | Miller et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0249622 A1 | 9/2014 | Carmi et al. |
| 2014/0257461 A1 | 9/2014 | Robinson et al. |
| 2014/0257467 A1 | 9/2014 | Lane et al. |
| 2014/0257475 A1 | 9/2014 | Gross et al. |
| 2014/0257476 A1 | 9/2014 | Montorfano et al. |
| 2014/0275757 A1 | 9/2014 | Goodwin et al. |
| 2014/0276648 A1 | 9/2014 | Hammer et al. |
| 2014/0277358 A1 | 9/2014 | Slazas |
| 2014/0277409 A1 | 9/2014 | Börtlein et al. |
| 2014/0277411 A1 | 9/2014 | Börtlein et al. |
| 2014/0277412 A1 | 9/2014 | Bortlein et al. |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296962 A1 | 10/2014 | Cartledge et al. |
| 2014/0296969 A1 | 10/2014 | Tegels et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0324164 A1 | 10/2014 | Gross et al. |
| 2014/0329225 A1 | 11/2014 | Morin |
| 2014/0330371 A1 | 11/2014 | Gloss et al. |
| 2014/0331475 A1 | 11/2014 | Duffy et al. |
| 2014/0336744 A1 | 11/2014 | Tani et al. |
| 2014/0343668 A1 | 11/2014 | Zipory et al. |
| 2014/0343670 A1 | 11/2014 | Bakis et al. |
| 2014/0350662 A1 | 11/2014 | Vaturi |
| 2014/0350670 A1 | 11/2014 | Keränen |
| 2014/0358222 A1 | 12/2014 | Gorman, III et al. |

(56) References Cited

U.S. PATENT DOCUMENTS

| | | |
|---|---|---|
| 2014/0358224 A1 | 12/2014 | Tegels et al. |
| 2014/0378331 A1 | 12/2014 | Morin |
| 2014/0379006 A1 | 12/2014 | Sutherland et al. |
| 2014/0379065 A1 | 12/2014 | Johnson et al. |
| 2014/0379074 A1 | 12/2014 | Spence et al. |
| 2014/0379076 A1 | 12/2014 | Vidlund et al. |
| 2015/0012087 A1 | 1/2015 | Miller et al. |
| 2015/0018940 A1 | 1/2015 | Quill et al. |
| 2015/0018944 A1 | 1/2015 | O'Connor et al. |
| 2015/0032205 A1 | 1/2015 | Matheny |
| 2015/0045880 A1 | 2/2015 | Hacohen |
| 2015/0045881 A1 | 2/2015 | Lim |
| 2015/0051697 A1 | 2/2015 | Spence et al. |
| 2015/0081011 A1* | 3/2015 | Young .................. A61F 2/2436 623/2.11 |
| 2015/0081014 A1 | 3/2015 | Gross et al. |
| 2015/0094802 A1 | 4/2015 | Buchbinder et al. |
| 2015/0105855 A1 | 4/2015 | Cabiri et al. |
| 2015/0119970 A1 | 4/2015 | Nakayama et al. |
| 2015/0127097 A1 | 5/2015 | Neumann et al. |
| 2015/0142100 A1 | 5/2015 | Morriss et al. |
| 2015/0142103 A1 | 5/2015 | Vidlund |
| 2015/0148894 A1 | 5/2015 | Damm et al. |
| 2015/0157457 A1 | 6/2015 | Hacohen |
| 2015/0157458 A1 | 6/2015 | Thambar et al. |
| 2015/0164640 A1 | 6/2015 | McLean et al. |
| 2015/0173896 A1 | 6/2015 | Richter et al. |
| 2015/0173897 A1 | 6/2015 | Raanani et al. |
| 2015/0182336 A1 | 7/2015 | Zipory et al. |
| 2015/0196390 A1 | 7/2015 | Ma et al. |
| 2015/0196393 A1 | 7/2015 | Vidlund et al. |
| 2015/0216661 A1 | 8/2015 | Hacohen et al. |
| 2015/0230923 A1 | 8/2015 | Levi |
| 2015/0230924 A1 | 8/2015 | Miller et al. |
| 2015/0238313 A1 | 8/2015 | Spence et al. |
| 2015/0245934 A1 | 9/2015 | Lombardi et al. |
| 2015/0250588 A1 | 9/2015 | Yang et al. |
| 2015/0272730 A1 | 10/2015 | Melnick et al. |
| 2015/0272731 A1* | 10/2015 | Racchini ............ A61F 2/2418 623/2.11 |
| 2015/0272734 A1 | 10/2015 | Sheps et al. |
| 2015/0282964 A1 | 10/2015 | Beard et al. |
| 2015/0305903 A1 | 10/2015 | Kitaoka |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0335429 A1 | 11/2015 | Morriss et al. |
| 2015/0342736 A1 | 12/2015 | Rabito et al. |
| 2015/0351903 A1 | 12/2015 | Morriss et al. |
| 2015/0351904 A1 | 12/2015 | Cooper et al. |
| 2015/0351906 A1 | 12/2015 | Hammer et al. |
| 2015/0359629 A1 | 12/2015 | Ganesan et al. |
| 2016/0030169 A1 | 2/2016 | Shahriari |
| 2016/0030171 A1 | 2/2016 | Quijano et al. |
| 2016/0089482 A1 | 3/2016 | Siegenthaler |
| 2016/0095700 A1 | 4/2016 | Righini |
| 2016/0100939 A1 | 4/2016 | Armstrong et al. |
| 2016/0106539 A1 | 4/2016 | Buchbinder et al. |
| 2016/0113766 A1 | 4/2016 | Ganesan et al. |
| 2016/0113768 A1 | 4/2016 | Ganesan et al. |
| 2016/0125160 A1 | 5/2016 | Heneghan et al. |
| 2016/0157862 A1 | 6/2016 | Hernandez et al. |
| 2016/0175095 A1 | 6/2016 | Dienno et al. |
| 2016/0200773 A1 | 7/2016 | Morin |
| 2016/0213473 A1 | 7/2016 | Hacohen et al. |
| 2016/0220367 A1 | 8/2016 | Barrett |
| 2016/0228247 A1 | 8/2016 | Maimon et al. |
| 2016/0228249 A1* | 8/2016 | Mantanus ............ A61F 2/2436 |
| 2016/0242902 A1 | 8/2016 | Morriss et al. |
| 2016/0245802 A1 | 8/2016 | Morin et al. |
| 2016/0258939 A1 | 9/2016 | Morin et al. |
| 2016/0266089 A1 | 9/2016 | Morin et al. |
| 2016/0270911 A1 | 9/2016 | Ganesan et al. |
| 2016/0296328 A1 | 10/2016 | Tabor et al. |
| 2016/0296330 A1 | 10/2016 | Hacohen |
| 2016/0296332 A1* | 10/2016 | Zhou .................. A61M 25/0662 |
| 2016/0310268 A1 | 10/2016 | Oba et al. |
| 2016/0310274 A1 | 10/2016 | Gross et al. |
| 2016/0317301 A1 | 11/2016 | Quadri et al. |
| 2016/0317305 A1 | 11/2016 | Pelled et al. |
| 2016/0324633 A1 | 11/2016 | Gross et al. |
| 2016/0324635 A1 | 11/2016 | Vidlund et al. |
| 2016/0324640 A1 | 11/2016 | Gifford et al. |
| 2016/0331526 A1 | 11/2016 | Schweich et al. |
| 2016/0331527 A1 | 11/2016 | Vidlund et al. |
| 2016/0338706 A1 | 11/2016 | Rowe |
| 2016/0367360 A1 | 12/2016 | Cartledge et al. |
| 2016/0367368 A1 | 12/2016 | Vidlund et al. |
| 2016/0374801 A1 | 12/2016 | Jimenez et al. |
| 2016/0374802 A1 | 12/2016 | Levi et al. |
| 2017/0042678 A1 | 2/2017 | Ganesan et al. |
| 2017/0049435 A1 | 2/2017 | Sauer et al. |
| 2017/0056166 A1 | 3/2017 | Ratz et al. |
| 2017/0056171 A1 | 3/2017 | Cooper et al. |
| 2017/0065407 A1 | 3/2017 | Hacohen et al. |
| 2017/0065411 A1 | 3/2017 | Grundeman et al. |
| 2017/0074855 A1 | 3/2017 | Morin et al. |
| 2017/0100236 A1 | 4/2017 | Robertson et al. |
| 2017/0128205 A1 | 5/2017 | Tamir et al. |
| 2017/0135816 A1 | 5/2017 | Lashinski et al. |
| 2017/0165054 A1 | 6/2017 | Benson et al. |
| 2017/0165063 A1* | 6/2017 | Anderson ............ A61F 2/2427 |
| 2017/0189174 A1 | 7/2017 | Braido et al. |
| 2017/0196688 A1 | 7/2017 | Christianson et al. |
| 2017/0196692 A1 | 7/2017 | Kirk et al. |
| 2017/0209264 A1 | 7/2017 | Chau et al. |
| 2017/0216026 A1 | 8/2017 | Quill et al. |
| 2017/0224323 A1 | 8/2017 | Rowe et al. |
| 2017/0231757 A1 | 8/2017 | Gassler |
| 2017/0231759 A1 | 8/2017 | Geist et al. |
| 2017/0231760 A1 | 8/2017 | Lane et al. |
| 2017/0231766 A1 | 8/2017 | Hariton et al. |
| 2017/0234850 A1 | 8/2017 | Morin |
| 2017/0239048 A1 | 8/2017 | Goldfarb et al. |
| 2017/0252159 A1 | 9/2017 | Hacohen et al. |
| 2017/0266003 A1 | 9/2017 | Hammer et al. |
| 2017/0281337 A1 | 10/2017 | Campbell |
| 2017/0333183 A1 | 11/2017 | Backus |
| 2017/0333187 A1 | 11/2017 | Hariton et al. |
| 2017/0349940 A1 | 12/2017 | Morin et al. |
| 2017/0360426 A1 | 12/2017 | Hacohen et al. |
| 2017/0367823 A1 | 12/2017 | Hariton et al. |
| 2018/0000580 A1 | 1/2018 | Wallace et al. |
| 2018/0014930 A1 | 1/2018 | Hariton et al. |
| 2018/0014932 A1 | 1/2018 | Hammer et al. |
| 2018/0021129 A1 | 1/2018 | Peterson et al. |
| 2018/0023114 A1 | 1/2018 | Morin et al. |
| 2018/0023115 A1 | 1/2018 | Morin et al. |
| 2018/0028215 A1 | 2/2018 | Cohen |
| 2018/0028311 A1 | 2/2018 | Hacohen |
| 2018/0049873 A1 | 2/2018 | Manash et al. |
| 2018/0055628 A1 | 3/2018 | Patel et al. |
| 2018/0055629 A1 | 3/2018 | Oba et al. |
| 2018/0055630 A1 | 3/2018 | Patel et al. |
| 2018/0098850 A1 | 4/2018 | Rafiee et al. |
| 2018/0116790 A1 | 5/2018 | Ratz et al. |
| 2018/0116843 A1 | 5/2018 | Schreck et al. |
| 2018/0125644 A1 | 5/2018 | Conklin |
| 2018/0132999 A1 | 5/2018 | Perouse |
| 2018/0133003 A1 | 5/2018 | Levi |
| 2018/0147059 A1 | 5/2018 | Hammer et al. |
| 2018/0153687 A1 | 6/2018 | Hariton et al. |
| 2018/0153689 A1 | 6/2018 | Maimon et al. |
| 2018/0153695 A1 | 6/2018 | Cunningham et al. |
| 2018/0153696 A1 | 6/2018 | Albitov et al. |
| 2018/0161159 A1 | 6/2018 | Lee et al. |
| 2018/0177593 A1 | 6/2018 | Hariton et al. |
| 2018/0177594 A1 | 6/2018 | Patel et al. |
| 2018/0185148 A1 | 7/2018 | Hariton et al. |
| 2018/0206982 A1 | 7/2018 | Haivatov et al. |
| 2018/0206983 A1 | 7/2018 | Noe et al. |
| 2018/0214263 A1 | 8/2018 | Rolando et al. |
| 2018/0243086 A1 | 8/2018 | Barbarino et al. |
| 2018/0250126 A1 | 9/2018 | O'Connor et al. |

(56) References Cited

U.S. PATENT DOCUMENTS

| | | |
|---|---|---|
| 2018/0250147 A1 | 9/2018 | Syed |
| 2018/0271654 A1 | 9/2018 | Hariton et al. |
| 2018/0280136 A1 | 10/2018 | Hariton et al. |
| 2018/0296333 A1 | 10/2018 | Dixon et al. |
| 2018/0296336 A1 | 10/2018 | Cooper et al. |
| 2018/0296341 A1 | 10/2018 | Noe et al. |
| 2018/0325671 A1 | 11/2018 | Abunassar et al. |
| 2018/0344457 A1 | 12/2018 | Gross et al. |
| 2018/0344490 A1 | 12/2018 | Fox et al. |
| 2018/0353294 A1 | 12/2018 | Calomeni et al. |
| 2018/0360457 A1 | 12/2018 | Ellis et al. |
| 2019/0000613 A1 | 1/2019 | Delgado et al. |
| 2019/0015200 A1 | 1/2019 | Delgado et al. |
| 2019/0021852 A1 | 1/2019 | Delgado et al. |
| 2019/0021857 A1 | 1/2019 | Hacohen et al. |
| 2019/0038404 A1 | 2/2019 | Iamberger et al. |
| 2019/0038405 A1 | 2/2019 | Iamberger et al. |
| 2019/0053896 A1 | 2/2019 | Adamek-Bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0069998 A1 | 3/2019 | Hacohen |
| 2019/0076245 A1 | 3/2019 | Arcaro et al. |
| 2019/0083248 A1 | 3/2019 | Hariton et al. |
| 2019/0083249 A1 | 3/2019 | Hariton et al. |
| 2019/0083261 A1 | 3/2019 | Perszyk et al. |
| 2019/0083262 A1 | 3/2019 | Hariton et al. |
| 2019/0105153 A1 | 4/2019 | Barash et al. |
| 2019/0117391 A1 | 4/2019 | Humair |
| 2019/0167423 A1* | 6/2019 | Hariton .................... A61F 2/24 |
| 2019/0175339 A1 | 6/2019 | Vidlund |
| 2019/0175342 A1 | 6/2019 | Hariton et al. |
| 2019/0183639 A1 | 6/2019 | Moore |
| 2019/0183644 A1 | 6/2019 | Hacohen |
| 2019/0192295 A1 | 6/2019 | Spence et al. |
| 2019/0216602 A1 | 7/2019 | Lozonschi |
| 2019/0224008 A1 | 7/2019 | Bressloff et al. |
| 2019/0231525 A1 | 8/2019 | Hariton et al. |
| 2019/0240010 A1 | 8/2019 | Hacohen |
| 2019/0262507 A1 | 8/2019 | Adamek-Bowers et al. |
| 2019/0321172 A1 | 10/2019 | Gross et al. |
| 2019/0336280 A1 | 11/2019 | Naor |
| 2019/0350701 A1 | 11/2019 | Adamek-Bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2020/0000449 A1 | 1/2020 | Goldfarb et al. |
| 2020/0000579 A1 | 1/2020 | Manash et al. |
| 2020/0000580 A1 | 1/2020 | Hacohen |
| 2020/0015964 A1 | 1/2020 | Noe et al. |
| 2020/0030098 A1 | 1/2020 | Delgado et al. |
| 2020/0038181 A1 | 2/2020 | Hariton et al. |
| 2020/0046496 A1 | 2/2020 | Hammer et al. |
| 2020/0054335 A1 | 2/2020 | Hernandez et al. |
| 2020/0060818 A1 | 2/2020 | Geist et al. |
| 2020/0069417 A1 | 3/2020 | Morin et al. |
| 2020/0078002 A1 | 3/2020 | Hacohen et al. |
| 2020/0113677 A1 | 4/2020 | McCann et al. |
| 2020/0113689 A1 | 4/2020 | McCann et al. |
| 2020/0113692 A1 | 4/2020 | McCann et al. |
| 2020/0138567 A1 | 5/2020 | Marr et al. |
| 2020/0146824 A1 | 5/2020 | Hammer et al. |
| 2020/0163760 A1 | 5/2020 | Hariton et al. |
| 2020/0163761 A1 | 5/2020 | Hariton et al. |
| 2020/0205969 A1 | 7/2020 | Hacohen |
| 2020/0214832 A1 | 7/2020 | Metchik et al. |
| 2020/0237512 A1 | 7/2020 | McCann et al. |
| 2020/0246136 A1 | 8/2020 | Marr et al. |
| 2020/0246140 A1 | 8/2020 | Hariton et al. |
| 2020/0253600 A1 | 8/2020 | Darabian |
| 2020/0261094 A1 | 8/2020 | Goldfarb et al. |
| 2020/0306037 A1 | 10/2020 | Siegel et al. |
| 2020/0315786 A1 | 10/2020 | Metchik et al. |
| 2020/0330221 A1 | 10/2020 | Hacohen |
| 2020/0330227 A1 | 10/2020 | Hacohen |
| 2020/0337842 A1 | 10/2020 | Metchik et al. |
| 2020/0360139 A1 | 11/2020 | Hammer et al. |
| 2020/0390548 A1 | 12/2020 | Hariton et al. |
| 2021/0093449 A1 | 4/2021 | Hariton et al. |
| 2021/0106419 A1 | 4/2021 | Abunassar |
| 2021/0113331 A1 | 4/2021 | Quadri et al. |
| 2021/0137680 A1 | 5/2021 | Kizuka et al. |
| 2021/0145578 A1 | 5/2021 | Hariton et al. |
| 2021/0196461 A1 | 7/2021 | Hariton et al. |
| 2021/0259835 A1 | 8/2021 | Tyler, II et al. |
| 2021/0330456 A1 | 10/2021 | Hacohen et al. |
| 2021/0361422 A1 | 11/2021 | Gross et al. |
| 2021/0361426 A1 | 11/2021 | Hacohen |
| 2021/0401573 A1 | 12/2021 | Gross et al. |
| 2022/0000612 A1 | 1/2022 | Hacohen |
| 2022/0023036 A1 | 1/2022 | Levi et al. |
| 2022/0061984 A1 | 3/2022 | Humair et al. |
| 2022/0105238 A1 | 4/2022 | Reimer et al. |
| 2022/0151779 A1 | 5/2022 | Pintor |
| 2023/0201015 A1* | 6/2023 | Gurovich .............. A61F 2/2409 623/2.11 |

FOREIGN PATENT DOCUMENTS

| | | |
|---|---|---|
| CN | 101653365 | 2/2010 |
| CN | 103974674 | 8/2014 |
| CN | 103997990 | 8/2014 |
| CN | 105324091 | 2/2016 |
| CN | 112603598 | 4/2021 |
| EP | 0170262 | 2/1986 |
| EP | 06/14342 | 9/1994 |
| EP | 10/06905 | 6/2000 |
| EP | 0954257 | 8/2000 |
| EP | 1258437 | 11/2002 |
| EP | 1264582 | 12/2002 |
| EP | 0871417 | 10/2003 |
| EP | 1266641 | 10/2004 |
| EP | 1034753 | 2/2005 |
| EP | 1258232 | 1/2006 |
| EP | 1637092 | 3/2006 |
| EP | 1990014 | 11/2008 |
| EP | 1562522 | 12/2008 |
| EP | 1420723 | 1/2009 |
| EP | 1903991 | 9/2009 |
| EP | 1418865 | 10/2009 |
| EP | 2119399 | 11/2009 |
| EP | 1531762 | 4/2010 |
| EP | 1450733 | 2/2011 |
| EP | 2446915 A1 | 5/2012 |
| EP | 2088965 | 11/2012 |
| EP | 2641569 | 9/2013 |
| EP | 1768630 | 1/2015 |
| EP | 1861045 | 3/2015 |
| EP | 1465555 | 5/2015 |
| EP | 2349124 | 10/2018 |
| EP | 2739214 | 10/2018 |
| EP | 3417813 | 12/2018 |
| EP | 3583922 | 12/2019 |
| EP | 3270825 | 4/2020 |
| EP | 2485795 | 9/2020 |
| IL | 223448 | 12/2012 |
| JP | S53152790 | 12/1978 |
| KR | 20010046894 | 6/2001 |
| WO | 92/05093 | 4/1992 |
| WO | 93/10714 | 6/1993 |
| WO | 96/39963 | 12/1996 |
| WO | 96/40344 | 12/1996 |
| WO | 97/01369 | 1/1997 |
| WO | 98/46149 | 10/1998 |
| WO | 1998/043557 | 10/1998 |
| WO | 1999/030647 | 6/1999 |
| WO | 00/22981 | 4/2000 |
| WO | 2000-047139 | 8/2000 |
| WO | 01/26586 | 4/2001 |
| WO | 01/56457 | 8/2001 |
| WO | 2001-062189 | 8/2001 |
| WO | 01/82832 | 11/2001 |
| WO | 02/085250 | 10/2002 |

(56) References Cited

FOREIGN PATENT DOCUMENTS

| | | |
|---|---|---|
| WO | 02/085251 | 10/2002 |
| WO | 02/085252 | 10/2002 |
| WO | 2003/020179 | 3/2003 |
| WO | 2003/028558 | 4/2003 |
| WO | 03/047467 | 6/2003 |
| WO | 2003/049647 | 6/2003 |
| WO | 2003/105667 | 12/2003 |
| WO | 2004/028399 | 4/2004 |
| WO | 04/103434 | 12/2004 |
| WO | 2004/108191 | 12/2004 |
| WO | 05/021063 | 3/2005 |
| WO | 05/046488 | 5/2005 |
| WO | 2005/062931 | 7/2005 |
| WO | 2005/107650 | 11/2005 |
| WO | 2006/007389 | 1/2006 |
| WO | 2006/007401 | 1/2006 |
| WO | 06/012013 | 2/2006 |
| WO | 06/012038 | 2/2006 |
| WO | 06/054930 | 5/2006 |
| WO | 2006/065212 | 6/2006 |
| WO | 2006/070372 | 7/2006 |
| WO | 06/086434 | 8/2006 |
| WO | 2006/089236 | 8/2006 |
| WO | 2006/091163 | 8/2006 |
| WO | 06/097931 | 9/2006 |
| WO | 06/105084 | 10/2006 |
| WO | 2006/113906 | 10/2006 |
| WO | 06/116558 | 11/2006 |
| WO | 2006/128193 | 11/2006 |
| WO | 07/011799 | 1/2007 |
| WO | 2007/030063 | 3/2007 |
| WO | 2007/047488 | 4/2007 |
| WO | 2007/059252 | 5/2007 |
| WO | 07/121314 | 10/2007 |
| WO | 07/136783 | 11/2007 |
| WO | 07/136981 | 11/2007 |
| WO | 08/013915 | 1/2008 |
| WO | 2008/014144 | 1/2008 |
| WO | 2008/029296 | 3/2008 |
| WO | 2008/031103 | 3/2008 |
| WO | 2008/058940 | 5/2008 |
| WO | 08/068756 | 6/2008 |
| WO | 2008/070797 | 6/2008 |
| WO | 2008/103722 | 8/2008 |
| WO | 2009/026563 | 2/2009 |
| WO | 09/033469 | 3/2009 |
| WO | 09/053497 | 4/2009 |
| WO | 2009/080801 | 7/2009 |
| WO | 2009/091509 | 7/2009 |
| WO | 2009/160631 | 10/2009 |
| WO | 10/004546 | 1/2010 |
| WO | 2010/000454 | 1/2010 |
| WO | 2010/005827 | 1/2010 |
| WO | 2010/006627 | 1/2010 |
| WO | 2010/006905 | 1/2010 |
| WO | 2010/027485 | 3/2010 |
| WO | 2010/037141 | 4/2010 |
| WO | 2010/044851 | 4/2010 |
| WO | 2010/045297 | 4/2010 |
| WO | 2010/057262 | 5/2010 |
| WO | 2010/073246 | 7/2010 |
| WO | 2010/081033 | 7/2010 |
| WO | 2010/085649 | 7/2010 |
| WO | 2010/121076 | 10/2010 |
| WO | 2010/128502 | 11/2010 |
| WO | 2010/128503 | 11/2010 |
| WO | 2010/150178 | 12/2010 |
| WO | 2011/025972 | 3/2011 |
| WO | 2011/051942 | 5/2011 |
| WO | 2011/057087 | 5/2011 |
| WO | 2011/067770 | 6/2011 |
| WO | 2011/069048 | 6/2011 |
| WO | 2011/072084 | 6/2011 |
| WO | 2011/089401 | 7/2011 |
| WO | 2011/089601 | 7/2011 |
| WO | 2011/106137 | 9/2011 |
| WO | 2011/111047 | 9/2011 |
| WO | 01/87190 | 11/2011 |
| WO | 2011/137531 | 11/2011 |
| WO | 2011-143263 | 11/2011 |
| WO | 2011/144351 | 11/2011 |
| WO | 2011/148374 | 12/2011 |
| WO | 2011/154942 | 12/2011 |
| WO | 2012/011108 | 1/2012 |
| WO | 2012/014201 | 2/2012 |
| WO | 2012/024428 | 2/2012 |
| WO | 2012/036740 | 3/2012 |
| WO | 2012/048035 | 4/2012 |
| WO | 2012/068541 | 5/2012 |
| WO | 2012/127309 | 9/2012 |
| WO | 2012/176195 | 12/2012 |
| WO | 2012/177942 | 12/2012 |
| WO | 2012/178115 | 12/2012 |
| WO | 2013/021374 | 2/2013 |
| WO | 2013/021375 | 2/2013 |
| WO | 2013/021384 | 2/2013 |
| WO | 2013/028387 | 2/2013 |
| WO | 2013/059743 | 4/2013 |
| WO | 2013/059747 | 4/2013 |
| WO | 2013/069019 | 5/2013 |
| WO | 2013/072496 | 5/2013 |
| WO | 2013/078497 | 6/2013 |
| WO | 2013/088327 | 6/2013 |
| WO | 2013/114214 | 8/2013 |
| WO | 2013/128436 | 9/2013 |
| WO | 2013/175468 | 11/2013 |
| WO | 2014/022124 | 2/2014 |
| WO | 2014/064694 | 5/2014 |
| WO | 2014/064695 | 5/2014 |
| WO | 2014/076696 | 5/2014 |
| WO | 2014/087402 | 6/2014 |
| WO | 2014/115149 | 7/2014 |
| WO | 2014/121275 | 8/2014 |
| WO | 2014/121280 A2 | 8/2014 |
| WO | 2014/144937 | 9/2014 |
| WO | 2014/145338 | 9/2014 |
| WO | 2014/164364 | 10/2014 |
| WO | 2014/194178 | 12/2014 |
| WO | 2014/195786 | 12/2014 |
| WO | 2015/059699 | 4/2015 |
| WO | 2015/173794 | 11/2015 |
| WO | 2015/191923 | 12/2015 |
| WO | 2016/016899 | 2/2016 |
| WO | 2016/093877 | 6/2016 |
| WO | 2016/125160 | 8/2016 |
| WO | 2016/183526 | 11/2016 |
| WO | 2017/223486 | 12/2017 |
| WO | 2018/025260 | 2/2018 |
| WO | 2018/025263 | 2/2018 |
| WO | 2018/029680 | 2/2018 |
| WO | 2018/039631 | 3/2018 |
| WO | 2018/106837 | 6/2018 |
| WO | 2018/112429 | 6/2018 |
| WO | 2018/118717 | 6/2018 |
| WO | 2018/131042 | 7/2018 |
| WO | 2018/131043 | 7/2018 |
| WO | 2019/026059 | 2/2019 |
| WO | 2019/027507 | 2/2019 |
| WO | 2019/030753 | 2/2019 |
| WO | 2019/077595 | 4/2019 |
| WO | 2019/086958 | 5/2019 |
| WO | 2019/116369 | 6/2019 |
| WO | 2019/138400 | 7/2019 |
| WO | 2019/195860 | 10/2019 |
| WO | 2019/202579 | 10/2019 |
| WO | 2020/058972 | 3/2020 |
| WO | 2020/167677 | 8/2020 |
| WO | 2021/156866 A1 | 8/2021 |
| WO | 2021/178400 | 9/2021 |
| WO | 2021/186424 A1 | 9/2021 |
| WO | 2022/015910 | 1/2022 |
| WO | 2022/046568 | 3/2022 |

(56) References Cited

FOREIGN PATENT DOCUMENTS

WO 2022/061017 3/2022
WO 2023/009379 2/2023

OTHER PUBLICATIONS

An Office Action dated Jul. 8, 2022, which issued during the prosecution of U.S. Appl. No. 16/144,054.
An Office Action dated Jun. 28, 2022, which issued during the prosecution of U.S. Appl. No. 16/135,969.
An Office Action together with an English Summary dated May 7, 2022 which issued during the prosecution of Chinese Patent Application No. 201880058940.2.
Ex Parte Quayle dated May 2, 2022, which issued during the prosecution of U.S. Appl. No. 16/879,952.
IPR2021-00383 Decision Final Written Decision dated Jul. 18, 2022.
IPR2021-01051 Preliminary Guidance Patent Owner's Motion to Amend dated Jun. 24, 2022.
Notice of Allowance dated May 4, 2022, which issued during the prosecution of U.S. Appl. No. 16/680,739.
Notice of Allowance dated Sep. 20, 2023, which issued during the prosecution of U.S. Appl. No. 17/839,538.
An Office Action dated Oct. 13, 2023, which issued during the prosecution of U.S. Appl. No. 17/181,722.
Grounds of Opposition to European Patent No. EP 2 948 103, filed Sep. 6, 2023.
An Office Action dated Aug. 31, 2023, which issued during the prosecution of U.S. Appl. No. 17/397,235.
An Office Action dated Sep. 8, 2023, which issued during the prosecution of U.S. Appl. No. 18/216,391.
An Office Action dated Sep. 8, 2023, which issued during the prosecution of U.S. Appl. No. 18/218,419.
Opposition to European Patent No. EP 2 948 103, filed Sep. 6, 2023.
An International Search Report and a Written Opinion both dated Aug. 23, 2023, 2023, which issued during the prosecution of Applicant's PCT/IL2023/050586.
An Office Action dated Aug. 3, 2023, which issued during the prosecution of U.S. Appl. No. 17/683,875.
An International Search Report and a Written Opinion both dated Sep. 13, 2023, which issued during the prosecution of Applicant's PCT/IL2023/050587.
An Office Action dated Mar. 3, 2023, which issued during the prosecution of European Patent Application No. 17751143.3.
An Office Action dated Mar. 20, 2023, which issued during the prosecution of U.S. Appl. No. 17/181,722.
An Office Action dated Sep. 29, 2022, which issued during the prosecution of U.S. Appl. No. 17/010,886.
An Office Action dated Sep. 29, 2022, which issued during the prosecution of U.S. Appl. No. 16/656,790.
An Office Action dated Nov. 2, 2022, which issued during the prosecution of U.S. Appl. No. 17/004,693.
An Office Action dated Nov. 28, 2022, which issued during the prosecution of U.S. Appl. No. 17/141,853.
An Office Action dated Oct. 19, 2022, which issued during the prosecution of U.S. Appl. No. 17/875,589.
An Office Action dated Oct. 26, 2022, which issued during the prosecution of U.S. Appl. No. 16/746,489.
European Search Report dated Mar. 20, 2023 which issued during the prosecution of Applicant's European App No. 22204764.9.
Notice of Allowance dated Apr. 6, 2023, which issued during the prosecution of U.S. Appl. No. 16/746,489.
An Office Action dated Apr. 14, 2023, which issued during the prosecution of U.S. Appl. No. 16/144,054.
An Office Action dated May 15, 2023, which issued during the prosecution of U.S. Appl. No. 16/656,790.
An Office Action dated May 16, 2023, which issued during the prosecution of U.S. Appl. No. 17/114,771.

An Office Action dated May 17, 2023, which issued during the prosecution of U.S. Appl. No. 17/466,785.
An Office Action dated May 25, 2023, which issued during the prosecution of U.S. Appl. No. 17/397,235.
An Office Action dated Nov. 3, 2023, which issued during the prosecution of Canadian Patent Application No. 3.162.308.
An International Search Report and a Written Opinion both dated Oct. 18. 2022, which issued during the prosecution of PCT/US2022/037864.
An Office Action dated Jan. 25, 2024, which issued during the prosecution of U.S. Appl. No. 18/090,058.
An International Search Report and a Written Opinion both dated Jan. 18, 2024, which issued during the prosecution of Applicant's PCT/IL2023/050958.
An Office Action dated Feb. 20, 2024, which issued during the prosecution of Canadian Patent Application No. 3.071,598.
European Search Report dated Nov. 14, 2023 which issued during the prosecution of Applicant's European App No. 23191562.0.
Notice of Allowance dated Mar. 13. 2024, which issued during the prosecution of U.S. Appl. No. 18/216,391.
Notice of Allowance dated Nov. 8, 2023, which issued during the prosecution of U.S. Appl. No. 16/656,790.
An Office Action dated Oct. 20, 2023, which issued during the prosecution of Canadian Patent Application No. 3,170,042.
An Office Action dated Sep. 29, 2023, which issued during the prosecution of Chinese Patent Application No. 201880076340.9.
An Office Action dated Dec. 19. 2023, which issued during the prosecution of U.S. Appl. No. 17/010,886.
An Office Action dated Nov. 23. 2012, which issued during the prosecution of U.S. Appl. No. 13/033,852.
An Office Action dated Dec. 31. 2012, which issued during the prosecution of U.S. Appl. No. 13/044,694.
An Office Action dated Feb. 6, 2013, which issued during the prosecution of U.S. Appl. No. 13/412,814.
Langer F et al., "RING plus STRING: Papillary muscle repositioning as an adjunctive repair technique for ischemic mitral regurgitation," J Thorac Cardiovasc Surg 133:247-9, Jan. 2007.
Langer F et al., "RING+STRING: Successful repair technique for ischemic mitral regurgitation with severe leaflet tethering," Circulation 120[suppl 1]: S85-S91, Sep. 2009.
"Transcatheter Valve-in-Valve Implantation for Failed Bioprosthetic Heart Valves", J Webb et al., Circulation. Apr. 2010; 121: 1848-1857.
Jansen, J., Willeke, S., Reul, H. and Rum, G. (1992), Detachable Shape-Memory Sewing Ring for Heart Valves. Artificial Organs, 16:294-297. 1992 (an abstract).
Alexander S. Geha, et al., Replacement of degenerated mitral and aortic bioprostheses without explanation Ann Thorac Surg. Jun. 2001; 72:1509-1514.
An International Search Report and a Written Opinion both dated Oct. 13, 2011 which issued during the prosecution of Applicant's PCT/IL11/00231.
An Office Action dated Jul. 1, 2016, which issued during the prosecution of U.S. Appl. No. 14/161,921.
An International Search Report and a Written Opinion both dated December 5. 2011, which issued during the prosecution of Applicant's PCT/IL11/00582.
An Office Action dated May 29, 2012, which issued during the prosecution of U.S. Appl. No. 12/840,463.
U.S. Appl. No. 61/555,160, filed Nov. 3, 2011.
U.S. Appl. No. 61/525.281, filed Aug. 19, 2011.
U.S. Appl. No. 61/537,276, filed Sep. 21, 2011.
U.S. Appl. No. 61/515,372, filed Aug. 5, 2011.
U.S. Appl. No. 61/492,449, filed Jun. 2, 2011.
U.S. Appl. No. 61/588,892, filed Jan. 20, 2012.
An International Search Report and a Written Opinion both dated Feb. 06. 2013, which issued during the prosecution of Applicant's PCT/IL12/00292.
An International Search Report and a Written Opinion both dated Feb. 6, 2013, which issued during the prosecution of Applicant's PCT/IL12/00293.
An Office Action dated Nov. 28, 2012, which issued during the prosecution of U.S. Appl. No. 12/961,721.

(56) References Cited

OTHER PUBLICATIONS

An Office Action dated Feb. 15, 2013, which issued during the prosecution of U.S. Appl. No. 12/840,463.
An Office Action dated Feb. 10, 2014, which issued during the prosecution of U.S. Appl. No. 13/031,852.
An Office Action dated Sep. 19, 2014, which issued during the prosecution of U.S. Appl. No. 13/044,694.
An International Search Report and a Written Opinion both dated Sep. 4, 2014 which issued during the prosecution of Applicant's PCT/IL2014/050087.
Invitation to Pay Additional Fees dated Jun. 12, 2014 PCT/IL2014/050087.
An Office Action dated Jun. 17, 2014, which issued during the prosecution of U.S. Appl. No. 12/961,721.
An Office Action dated Jul. 3, 2014, which issued during the prosecution of U.S. Appl. No. 13/033,852.
An Office Action dated May 23, 2014, which issued during the prosecution of U.S. Appl. No. 13/411,814.
Dominique Himbert; Mitral Regurgitation and Stenosis from Bioprosthesis and Annuloplasty Failure: Transcatheter approaches and outcomes, 24 pages Oct. 28, 2013.
An International Search Report and a Written Opinion both dated Mar. 17, 2014 which issued during the prosecution of Applicant's PCT/IL2013/050937.
An International Preliminary Report on patentabilty dated Dec. 2, 2013, which issued during the prosecution of Applicant's PCT/IL11/00582.
AN An Office Action dated Sep. 12, 2013, which issued during the prosecution of U.S. Appl. No. 13/412,814.
An Office Action dated Aug. 2, 2013, which issued during the prosecution of U.S. Appl. No. 13/033,852.
An International Preliminary Report on patentability dated Sep. 11, 2012, which issued during the prosecution of Applicant's PCT/IL2011/000231.
An Office Action dated Jul. 2, 2014, which issued during the prosecution of U.S. Appl. No. 13/811,308.
An Office Action dated Jan. 20, 2016, which issued during the prosecution of U.S. Appl. No. 14/161,921.
An Office Action dated Jul. 23, 2013, which issued during the prosecution of U.S. Appl. No. 12/961,721.
An Office Action dated Jul. 18, 2013, which issued during the prosecution of U.S. Appl. No. 13/044,694.
An Office Action dated Nov. 8, 2013, which issued during the prosecution of U.S. Appl. No. 12/840,463.
An Office Action dated Jun. 4, 2014, which issued during the prosecution of U.S. Appl. No. 12/840,463.
An Office Action dated Aug. 13, 2012, which issued during the prosecution of U.S. Appl. No. 13/044,694.
An Office Action dated Jul. 2, 2012, which issued during the prosecution of U.S. Appl. No. 13/033,852.
An Office Action dated Feb. 3, 2014, which issued during the prosecution of U.S. Appl. No. 13/811,308.
An International Preliminary Report on patentability dated Feb. 11, 2014, which issued during the prosecution of Applicant's PCT/IL12/00292.
An International Preliminary Report on patentability dated Feb. 11, 2014, which issued during the prosecution of Applicant's PCT/IL12/00293.
A Notice of Allowance dated Aug. 15, 2014, which issued during the prosecution of U.S. Appl. No. 13/411,814.
An Office Action dated Aug. 14. 2012, which issued during the prosecution of U.S. Appl. No. 12/961,721.
U.S. Appl. No. 61/283,819, filed Dec. 8, 2009.
Notice of Allowance dated April 8. 2016, which issued during the prosecution of U.S. Appl. No. 14/237,258.
U.S. Appl. No. 61/756,034, filed Jan. 24, 2013.
U.S. Appl. No. 61/756,049, filed Jan. 24, 2013.
An International Preliminary Report on Patentability dated Jan. 31, 2017, which issued during the prosecution of Applicant's PCT/IL2015/050792.

U.S. Appl. No. 62/372,861, filed Aug. 10, 2016.
Notice of Allowance dated Aug. 13, 2018, which issued during the prosecution of U.S. Appl. No. 15/995,597.
Notice of Allowance dated Apr. 20, 2018, which issued during the prosecution of U.S. Appl. No. 15/878,206.
An Office Action dated Dec. 10, 2015, which issued during the prosecution of U.S. Appl. No. 14/237,258.
An International Preliminary Report on Patentability dated Jul. 28, 2015, which issued during the prosecution of Applicant's PCT/IL2014/050087.
An Office Action dated Nov. 27, 2015, which issued during the prosecution of U.S. Appl. No. 14/626,267.
An Office Action dated Jan. 21, 2016, which issued during the prosecution of U.S. Appl. No. 14/237,264.
An Office Action dated Jan. 30, 2015, which issued during the prosecution of UK Patent Application No. 1413474.6.
An International Search Report and a Written Opinion both dated May 30, 2016, which issued during the prosecution of Applicant's PCT/IL2016/050125.
An Office Action dated Sep. 26, 2016, which issued during the prosecution of U.S. Appl. No. 14/761,004.
An Office Action dated Jan. 18, 2017, which issued during the prosecution of U.S. Appl. No. 14/626,267.
An Office Action dated Feb. 7, 2017, which issued during the prosecution of U.S. Appl. No. 14/689,608.
An Office Action dated Feb. 8, 2017, which issued during the prosecution of UK Patent Application No. 1613219.3.
An Office Action together dated Feb. 10, 2017, which issued during the prosecution of European Patent Application No. 12821522.5.
International Search Report and a Written Opinion both dated Oct. 27, 2015, which issued during the prosecution of Applicant's PCT/IL2015/050792.
European Search Report dated Feb. 18. 2015, which issued during the prosecution of Applicant's European App No. 12821522.5.
Saturn Project—a novel solution for transcatheter heart valve replacement specifically designed to address clinical therapeutic needs on mitral valve: Dec. 2016.
Righini presentation EuroPCR May 2015 (Saturn)—(downloaded from: https://www.pcronline.com/Cases-resourcesimages/Resources/Course-videos-slides/2015/Cardiovascularinnovation-pipeline-Mitral-and-tricuspid-valve-interventions).
An Advisory Action dated Apr. 2, 2018, which issued during the prosecution of U.S. Appl. No. 14/763,004.
An Office Action dated Jul. 26, 2018, which issued during the prosecution of U.S. Appl. No. 15/872,501.
An Office Action dated May 4, 2018, which issued during the prosecution of U.S. Appl. No. 15/872,501.
An Office Action dated Apr. 20, 2018, which issued during the prosecution of U.S. Appl. No. 15/886,517.
An Office Action dated Aug. 9, 2018, which issued during the prosecution of U.S. Appl. No. 15/899,858.
An Office Action dated Aug. 9, 2018, which issued during the prosecution of U.S. Appl. No. 15/902,403.
An Office Action dated Jun. 28. 2018, which issued during the prosecution of U.S. Appl. No. 29/635,658.
An Office Action dated Jun. 28, 2018, which issued during the prosecution of U.S. Appl. No. 29/635,661.
Georg Lutter, MD, et al, "Percutaneous Valve Replacement: Current State and Future Prospects", The Annals of Thoracic Surgery ; vol. 78, pp. 2199-2206, Dec. 2004.
An Office Action dated Jun. 6, 2018, which issued during the prosecution of UK Patent Application No. 1720803.4.
An International Search Report and a Written Opinion both dated Jun. 20, 2018, which issued during the prosecution of Applicant's PCT/IL2018/050024.
An Office Action dated Jun. 18, 2018, which issued during the prosecution of UK Patent Application No. 1800399.6.
An Office Action dated Oct. 23, 2017, which issued during the prosecution of U.S. Appl. No. 14/761,004.
An Office Action dated Dec. 7, 2017, which issued during the prosecution of U.S. Appl. No. 15/213,791.
Interview Summary dated Feb. 8, 2018, which issued during the prosecution of U.S. Appl. No. 15/211,791.

(56) References Cited

OTHER PUBLICATIONS

An Office Action dated Feb. 7, 2018, which issued during the prosecution of U.S. Appl. No. 15/197,069.
An International Search Report and a Written Opinion both dated Nov. 24, 2017, which issued during the prosecution of Applicant's PCT/IL2017/050873.
An Office Action dated Jan. 5, 2018, which issued during the prosecution of U.S. Appl. No. 15/541,783.
An Office Action dated Feb. 2, 2018, which issued during the prosecution of U.S. Appl. No. 15/329,920.
An Invitation to pay additional fees dated January 2. 2018, which issued during the prosecution of Applicant's PCT/IL2017/050849.
An Invitation to pay additional fees dated Sep. 29, 2017, which issued during the prosecution of Applicant's PCT/IL2017/050873.
European Search Report dated Jun. 29, 2017, which issued during the prosecution of Applicant's European App No. 11809374.9.
An Invitation to pay additional fees dated Oct. 11. 2018, which issued during the prosecution of Applicant's PCT/IL2018/050725.
An Office Action dated Dec. 4, 2018, which issued during the prosecution of U.S. Appl. No. 16/045,059.
An Office Action together with the English translation dated Nov. 5, 2018 which issued during the prosecution of Chinese Patent Application No. 201680008328.5.
Notice of Allowance dated Sep. 25, 2018, which issued during the prosecution of U.S. Appl. No. 15/188,507.
European Search Report dated Sep. 26, 2018 which issued during the prosecution of Applicant's European App No. 18186784.7.
An Office Action dated Jun. 30, 2015, which issued during the prosecution of U.S. Appl. No. 14/522,987.
Notice of Allowance dated Dec. 13. 2013, which issued during the prosecution of U.S. Appl. No. 13/675,119.
An International Preliminary Report on Patentability dated Aug. 8, 2017, which issued during the prosecution of Applicant's PCT/IL2016/050125.
An Office Action dated Jan. 17, 2018, which issued during the prosecution of U.S. Appl. No. 14/763,004.
An Office Action dated Mar. 25, 2015, which issued during the prosecution of U.S. Appl. No. 12/840,463.
An Office Action dated Feb. 25, 2016, which issued during the prosecution of U.S. Appl. No. 14/522,987.
An Office Action dated Apr. 13, 2016, which issued during the prosecution of U.S. Appl. No. 14/626,267.
An Office Action dated Aug. 28, 2015, which issued during the prosecution of U.S. Appl. No. 14/237,264.
Maisano (2015) TCR presentation re Cardiovalve.
Notice of Allowance dated Sep. 29, 2016, which issued during the prosecution of U.S. Appl. No. 14/442,541.
Notice of Allowance dated May 10, 2016, which issued during the prosecution of U.S. Appl. No. 14/237,258.
Notice of Allowance dated May 20, 2016, which issued during the prosecution of U.S. Appl. No. 14/237,258.
An International Preliminary Report on Patentability dated May 19, 2015, which issued during the prosecution of Applicant's PCT/IL2013/050937.
Dusan Pavcnik, MD, PhD2, et al.; "Development and Initial Experimental Evaluation of a Prosthetic Aortic Valve for Transcatheter Placement", Cardiovascular Radiology. Radiology Apr. 1992, vol. 183, pp. 151-154.
Notice of Allowance dated Oct. 16, 2013, which issued during the prosecution of U.S. Appl. No. 13/675,119.
Notice of Allowance dated Feb. 11. 2015, which issued during the prosecution of U.S. Appl. No. 13/033,852.
Notice of Allowance dated May 5, 2015, which issued during the prosecution of U.S. Appl. No. 12/840,463.
Notice of Allowance dated Mar. 10, 2015, which issued during the prosecution of U.S. Appl. No. 13/811,308.
Notice of Allowance dated Jul. 1, 2016, which issued during the prosecution of U.S. Appl. No. 14/442,541.
An Office Action dated Mar. 25, 2019, which issued during the prosecution of European Patent Application No. 14710060.6.
An International Search Report and a Written Opinion both dated Nov. 9, 2018, which issued during the prosecution of Applicant's PCT/IL2018/050869.
An International Search Report and a Written Opinion both dated Dec. 5, 2018, which issued during the prosecution of Applicant's PCT/IL2018/050725.
An International Search Report and a Written Opinion both dated Apr. 25. 2019, which issued during the prosecution of Applicant's PCT/IL2019/050142.
An International Preliminary Report on Patentability dated Feb. 12. 2019, which issued during the prosecution of Applicant's PCT/IL2017/050873.
An Office Action dated Sep. 13, 2019, which issued during the prosecution of U.S. Appl. No. 16/460,313.
An Office Action dated Nov. 26, 2019, which issued during the prosecution of U.S. Appl. No. 16/532,945.
An Office Action dated Aug. 16, 2019, which issued during the prosecution of U.S. Appl. No. 15/668,659.
An Office Action dated Nov. 1, 2019, which issued during the prosecution of U.S. Appl. No. 15/872,501.
An Office Action dated Jun. 14, 2019, which issued during the prosecution of U.S. Appl. No. 15/703,385.
An Office Action dated Oct. 4, 2019, which issued during the prosecution of U.S. Appl. No. 16/183,140.
An Office Action dated Jun. 13, 2019, which issued during the prosecution of U.S. Appl. No. 16/388,038.
An International Preliminary Report on Patentability dated Feb. 4, 2020, which issued during the prosecution of Applicant's PCT/IL2018/050725.
An International Search Report and a Written Opinion both dated Jan. 25. 2019, which issued during the prosecution of Applicant's PCT/IL2018/051122.
An International Search Report and a Written Opinion both dated May 13, 2019, which issued during the prosecution of Applicant's PCT/IL2018/051350.
An International Preliminary Report on Patentability dated Feb. 5, 2019, which issued during the prosecution of Applicant's PCT/IL2017/050849.
An Office Action dated Oct. 25, 2018, which issued during the prosecution of U.S. Appl. No. 14/763,004.
An Office Action dated Mar. 4, 2019, which issued during the prosecution of U.S. Appl. No. 14/763,004.
An Office Action dated Jan. 9, 2019, which issued during the prosecution of U.S. Appl. No. 15/329,920.
An Office Action dated Jan. 30, 2019, which issued during the prosecution of U.S. Appl. No. 15/872,501.
An Office Action dated Feb. 5, 2019, which issued during the prosecution of U.S. Appl. No. 15/899,858.
An Office Action dated May 23, 2019, which issued during the prosecution of U.S. Appl. No. 15/668,659.
An Office Action dated May 1, 2019, which issued during the prosecution of U.S. Appl. No. 15/691,032.
An Office Action dated Aug. 1, 2019, which issued during the prosecution of U.S. Appl. No. 15/668,559.
An Office Action dated Jun. 19, 2019, which issued during the prosecution of U.S. Appl. No. 15/682,789.
Notice of Allowance dated Jan. 13, 2020, which issued during the prosecution of U.S. Appl. No. 15/956,956.
An Office Action dated Jun. 25, 2019, which issued during the prosecution of U.S. Appl. No. 15/329,920.
An Office Action dated May 16, 2019, which issued during the prosecution of U.S. Appl. No. 15/433,547.
U.S. Appl. No. 62/560,384, filed Sep. 19, 2017.
U.S. Appl. No. 62/112,343, filed Feb. 5, 2015.
An International Preliminary Report on Patentability dated Feb. 11. 2020, which issued during the prosecution of Applicant's PCT/IL2018/050869.
An International Preliminary Report on Patentability dated Oct. 20, 2020, which issued during the prosecution of Applicant's PCT/IL2019/050142.
An Office Action dated Jan. 6, 2020, which issued during the prosecution of U.S. Appl. No. 16/660,231.

(56) References Cited

OTHER PUBLICATIONS

An Office Action dated Dec. 31, 2019, which issued during the prosecution of U.S. Appl. No. 16/183,140.
Notice of Allowance dated Apr. 24, 2019, which issued during the prosecution of U.S. Appl. No. 16/045,059.
An Office Action dated Jan. 14, 2020, which issued during the prosecution of U.S. Appl. No. 16/284,331.
European Search Report dated Mar. 5, 2020, which issued during the prosecution of Applicant's European App No. 17752184.6.
European Search Report dated Mar. 4, 2020, which issued during the prosecution of Applicant's European App No. 16706913.7.
Notice of Allowance dated Mar. 12, 2020, which issued during the prosecution of U.S. Appl. No. 16/460,313.
An Office Action dated Jan. 9, 2020, which issued during the prosecution of U.S. Appl. No. 16/600,190.
An Office Action dated Jan. 3, 2020, which issued during the prosecution of U.S. Appl. No. 16/678,355.
An Office Action dated Feb. 6, 2020, which issued during the prosecution of U.S. Appl. No. 15/668,659.
Notice of Allowance dated Jan. 16, 2020, which issued during the prosecution of U.S. Appl. No. 16/532,945.
Notice of Allowance dated Aug. 19, 2020, which issued during the prosecution of U.S. Appl. No. 16/637,166.
Notice of Allowance dated Jun. 23, 2020, which issued during the prosecution of U.S. Appl. No. 16/637,166.
Notice of Allowance dated May 7, 2020, which issued during the prosecution of U.S. Appl. No. 16/637,166.
Sündermann, Simon H., et al. "Feasibility of the Engager™ aortic transcatheter valve system using a flexible over-the-wire design." European Journal of Cardio-Thoracic Surgery 42.4 (2012): e48-e52.
An Office Action summarized English translation and Search Report dated Jul. 3, 2020, which issued during the prosecution of Chinese Patent Application No. 201780061210.3.
Serruys, P. W., Piazza, N., Cribier, A., Webb, J., Laborde, J. C., & de Jaegere, P. (Eds.). (2009). Transcatheter aortic valve implantation: tips and tricks to avoid failure. CRC Press.—Screenshots from Google Books downloaded from: https://books.google.co.il/books?id=FLzLBqAAQBAJ&1pg=PA198&ots=soqWrDH-y_&dq=%20%22Edwards%20SAPIEN%22&1r&pg=PA20#v=onepage&q=%22Edwards%20SAPIEN%22&f=false ; Downloaded on Jun. 18, 2020.
An International Search Report and a Written Opinion both dated Jun. 24, 2020, which issued during the prosecution of Applicant's PCT/IL2019/051398.
An Office Action dated Jul. 14, 2020, which issued during the prosecution of U.S. Appl. No. 16/324,339.
Notice of Allowance dated Aug. 28, 2020, which issued during the prosecution of U.S. Appl. No. 16/324,339.
Notice of Allowance dated Jul. 29, 2020, which issued during the prosecution of U.S. Appl. No. 16/132,937.
An Office Action dated Jul. 29, 2020, which issued during the prosecution of U.S. Appl. No. 16/269,328.
Notice of Allowance dated Aug. 26, 2020, which issued during the prosecution of U.S. Appl. No. 16/269,328.
An Office Action dated Aug. 7, 2020, which issued during the prosecution of U.S. Appl. No. 15/668,659.
Tchetche, D. and Nicolas M. Van Mieghem: "New-generation TAVI devices: description and specifications" EuroIntervention, 2014, No. 10:U90-U100;.
An Office Action dated Aug. 23, 2019, which issued during the prosecution of U.S. Appl. No. 15/600,190.
Symetis S.A.: "ACURATE neo ™ Aortic Bioprosthesis for Implantation using the ACURATE neo ™ TA Transapical Delivery System in Patients with Severe Aortic Stenosis," Clinical Investigation Plan, Protocol No. 2015-01, Vs. No. 2, 2015:1-76.
Notice of Allowance dated Sep. 10, 2020, which issued during the prosecution of U.S. Appl. No. 15/600,190.
Notice of Allowance dated Sep. 10, 2020, which issued during the prosecution of U.S. Appl. No. 16/324,339.
Notice of Allowance dated Oct. 19, 2020, which issued during the prosecution of U.S. Appl. No. 16/324,339.
Notice of Allowance dated Sep. 21. 2020, which issued during the prosecution of U.S. Appl. No. 16/269,328.
Notice of Allowance dated Oct. 28, 2020, which issued during the prosecution of U.S. Appl. No. 16/269,328.
Notice of Allowance dated Jan. 16. 2020, which issued during the prosecution of U.S. Appl. No. 15/872,501.
An Office Action dated May 11, 2020, which issued during the prosecution of U.S. Appl. No. 16/811,732.
An Office Action dated Sep. 24, 2020, which issued during the prosecution of U.S. Appl. No. 16/811,732.
Notice of Allowance dated Mar. 29, 2017, which issued during the prosecution of U.S. Appl. No. 14/161,921.
Agarwal et al. International Cardiology Perspective Functional Tricuspid Regurgitation, Circ Cardiovasc Interv 2009;2;2;565-573 (2009).
Alfieri et al., "An effective technique to correct anterior mitral leaflet prolapse," J Card 14(6):468-470 (1999).
Alfieri et al., "The double orifice technique in mitral valve repair: a simple solution for complex problems," Journal of Thoracic Cardiovascular Surgery 122:674-681 (2001).
Alfieri, "The edge-to-edge repair of the mitral valve," [Abstract] 6th Annual NewEra Cardiac Care: Innovation & Technology, Heart Surgery Forum pp. 103. (2000).
Alfieri et al."Novel Suture Device for Beating-Heart Mitral Leaflet Approximation", Ann Thorac Surg. 2002, 74:1488-1493.
Alfieri et al., "The edge to edge technique," The European Association for Cardio-Thoracic Surgery $14^{th}$ Annual Meeting October 7-11, Book of Procees. (2000).
Amplatzer Cardiac Plug brochure (English pages), AGA Medical Corporation (Plymouth, MN) (copyright 2008-2010, downloaded Jan. 11, 2011).
Amplatzer® Cribriform Occluder. A patient guide to Percutaneous, Transcatheter, Atrial Septal Defect Closuer, AGA Medical Corporation, Apr. 2008.
An Amplatzer® Septal Occluder. A patient guide to the Non-Surgical Closuer of the Atrial Septal Defect Using the AMPLATZER Septal Occluder System, AGA Medical Corporation, Apr. 2008.
Brennan, Jennifer, 510(k) Summary of safety and effectiveness, Jan. 2008.
Dictionary.com definition of "lock", Jul. 29, 2013.
Dang NC et al. "Simplified Placement of Multiple Artificial Mitral Valve Chords," The Heart Surgery Forum #2005-1005, 8 (3) (2005).
Maisano, The double-orifice technique as a standardized approach to treat mitral . . . , European Journal of Cardio-thoracic Surgery 17 (2000) 201-205.
"Two dimensional real-time ultrasonic imaging of the heart and great vessels", Mayo Clin Proc. vol. 53:271-303, 1978.
Odell JA et al., "Early Results o4yf a Simplified Method of Mitral Valve Annuloplasty," Circulation 92:150-154 (1995).
O'Reilly S et al., "Heart valve surgery pushes the envelope," Medtech Insight 8(3):73, 99-108 (2006).
Swain CP et al., "An endoscopically deliverable tissue-transfixing device for securing biosensors in the gastrointestinal tract," Gastrointestinal Endoscopy 40(6): 730-734 (1994).
An Invitation to pay additional fees dated Jan. 31, 2014, which issued during the prosecution of Applicant's PCT/IL2013/050860.
U.S. Appl. No. 62/030,715, filed Jul. 30, 2014.
U.S. Appl. No. 62/139,854, filed Mar. 30, 2015.
U.S. Appl. No. 61/312,412, filed Mar. 10, 2010.
An Invitation to pay additional fees dated Jan. 31, 2014, which issued during the prosecution of Applicant's PCT/IL2013/050861.
An International Preliminary Report on Patentability dated Dec. 23, 2013, which issued during the prosecution of Applicant's PCT/IL2012/000250.
An International Preliminary Report on Patentability dated Sep. 18, 2007, which issued during the prosecution of Applicant's PCT/IL2006/000342.
An International Preliminary Report on Patentability dated Jun. 5, 2012, which prosecution of Applicant's PCT/IL2010/001024.

(56) References Cited

OTHER PUBLICATIONS

An International Preliminary Report on Patentability dated Apr. 28, 2015, which issued during the prosecution of Applicant's PCT/IL2013/050861.
An International Preliminary Report on Patentability dated Apr. 26, 2016, which issued during the prosecution of Applicant's PCT/IL2014/050914.
An International Preliminary Report on Patentability dated Jun. 10, 2009, which issued during the prosecution of Applicant's PCT/IL07/01503.
An International Preliminary Report on Patentability dated Dec. 18, 2010, which issued during the prosecution of Applicant's PCT/IL09/00593.
An International Preliminary Report on Patentability dated Jun. 29, 2011, which issued during the prosecution of Applicant's PCT/IL2009/001209.
Notice of Allowance dated Aug. 18, 2017, which issued during the prosecution of U.S. Appl. No. 14/689,608.
Notice of Allowance dated Jul. 6, 2017, which issued during the prosecution of U.S. Appl. No. 14/689,608.
Notice of Allowance dated May 22, 2017, which issued during the prosecution of U.S. Appl. No. 14/682,608.
An Office Action dated Apr. 21, 2017, which issued during the prosecution of U.S. Appl. No. 15/213,791.
An Office Action dated Sep. 29, 2017, which issued during the prosecution of U.S. Appl. No. 15/191,069.
An International Preliminary Report on Patentability dated Nov. 9, 2011, which issued during the prosecution of Applicant's PCT/IL2010/000357.
An International Preliminary Report on Patentability dated Nov. 9, 2011 which issued during the prosecution of Applicant's PCT/IL2010/000358.
An International Preliminary Report on Patentability dated Nov. 27, 2012, which issued during the prosecution of Applicant's PCT/IL2011/000404.
An International Preliminary Report on Patentability dated Feb. 4, 2014, which issued during the prosecution of Applicant's PCT/IL2011/000446.
An International Preliminary Report on Patentability dated Jan. 29, 2013, which issued during the prosecution of Applicant's PCT/IL2011/000600.
An International Preliminary Report on Patentability dated Dec. 23, 2014, which issued during the prosecution of Applicant's PCT/IL2012/050451.
A Notice of Allowance dated Jul. 30, 2015, which issued during the prosecution of U.S. Appl. No. 13/319,007.
An Office Action dated Sep. 29, 2014, which issued during the prosecution of U.S. Appl. No. 13/504,870.
An Office Action dated Jan. 13, 2015, which issued during the prosecution of U.S. Appl. No. 13/707,013.
An Office Action dated Mar. 23, 2015, which issued during the prosecution of U.S. Appl. No. 13/707,013.
AN Notice of Allowance dated Mar. 25, 2015, which issued during the prosecution of U.S. Appl. No. 13/749,153.
An Office Action dated Oct. 3, 2014, which issued during the prosecution of U.S. Appl. No. 13/749,153.
Notice of Allowance dated May 22, 2015, which issued during the prosecution of U.S. Appl. No. 13/749,153.
Notice of Allowance dated Aug. 3, 2015, which issued during the prosecution of U.S. Appl. No. 13/749,153.
An Office Action dated Dec. 19, 2013, which issued during the prosecution of U.S. Appl. No. 14/027,934.
An Office Action dated Jun. 11, 2014, which issued during the prosecution of U.S. Appl. No. 14/027,934.
An Office Action dated Aug. 22. 2014, which issued during the prosecution of U.S. Appl. No. 14/027,934.
An Office Action dated Apr. 2, 2015, which issued during the prosecution of U.S. Appl. No. 14/027,934.
An Office Action dated Jan. 5, 2016, which issued during the prosecution of U.S. Appl. No. 14/027,934.

An Office Action dated Jan. 5, 2016, which issued during the prosecution of U.S. Appl. No. 14/084,426.
An Office Action dated Mar. 16, 2015, which issued during the prosecution of U.S. Appl. No. 14/084,426.
An Office Action dated Jan. 6, 2016, which issued during the prosecution of U.S. Appl. No. 14/128,756.
An Office Action dated May 11, 2016, which issued during the prosecution of U.S. Appl. No. 14/128,756.
Notice of Allowance dated Oct. 20, 2015, which issued during the prosecution of U.S. Appl. No. 12/795,192.
Notice of Allowance dated Feb. 19, 2014, which issued during the prosecution of U.S. Appl. No. 12/795,192.
An Office Action dated Jul. 20, 2012, which issued during the prosecution of U.S. Appl. No. 12/843,412.
An Office Action dated Mar. 27. 2013, which issued during the prosecution of U.S. Appl. No. 12/843,412.
A Restriction Requirement dated May 1, 2012, which issued during the prosecution of U.S. Appl. No. 12/843,412.
A Notice of Allowance dated May 02. 2013, which issued during the prosecution of U.S. Appl. No. 12/843,412.
A Restriction Requirement dated Nov. 19, 2012, which issued during the prosecution of U.S. Appl. No. 12/926,673.
An Office Action dated Feb. 12. 2013, which issued during the prosecution of U.S. Appl. No. 12/926,673.
An Office Action dated Oct. 22, 2013, which issued during the prosecution of U.S. Appl. No. 12/926,673.
A Notice of Allowance dated Jan. 07. 2014, which issued during the prosecution of U.S. Appl. No. 12/926,673.
An Office Action dated Oct. 9, 2013, which issued during the prosecution of U.S. Appl. No. 12/996,954.
An Office Action dated Mar. 24, 2015, which issued during the prosecution of U.S. Appl. No. 12/996,954.
An Office Action dated Oct. 5, 2013, which issued during the prosecution of U.S. Appl. No. 12/996,954.
Notice of Allowance dated Jul. 7, 2015, which issued during the prosecution of U.S. Appl. No. 12/996,954.
An Office Action dated Nov. 16, 2018, which issued during the prosecution of U.S. Appl. No. 16/042,028.
An International Search Report with Written Opinion both dated Feb. 2, 2012, which issued during the prosecution of Applicant's PCT/IL2011/000600.
An International Search Report together with Written Opinion both dated Mar. 30, 2011, which issued during the prosecution of Applicant's PCT/IL2010/001024.
An International Search Report together with Written Opinion both dated Feb. 10, 2011, which issued during the prosecution of Applicant's PCT/IL10/00890.
An Office Action dated May 28, 2015, which issued during the prosecution of U.S. Appl. No. 14/128,756.
An Office Action dated September 6. 2018, which issued during the prosecution of U.S. Appl. No. 15/994,022.
An Office Action dated Sep. 7, 2018, which issued during the prosecution of U.S. Appl. No. 15/995,725.
An Office Action dated Nov. 26. 2018, which issued during the prosecution of U.S. Appl. No. 16/040,831.
An Office Action dated Jul. 11. 2018, which issued during the prosecution of U.S. Appl. No. 15/978,494.
An Office Action dated Nov. 23, 2018, which issued during the prosecution of U.S. Appl. No. 16/041,208.
An Office Action dated Jun. 15, 2018, which issued during the prosecution of U.S. Appl. No. 15/970,314.
An Office Action dated Oct. 12. 2018, which issued during the prosecution of U.S. Appl. No. 15/970,314.
An Office Action dated Jul. 26, 2018, which issued during the prosecution of U.S. Appl. No. 15/979,686.
An Office Action dated Sep. 10, 2018, which issued during the prosecution of U.S. Appl. No. 16/008,618.
An International Preliminary Report on Patentability dated Apr. 28, 2015, which issued during the prosecution of Applicant's PCT/IL2013/050860.
An Office Action dated Apr. 22, 2019, which issued during the prosecution of U.S. Appl. No. 15/668,559.

(56) References Cited

OTHER PUBLICATIONS

Notice of Allowance dated Aug. 30, 2019, which issued during the prosecution of U.S. Appl. No. 15/682,789.
Notice of Allowance dated Mar. 29, 2019, which issued during the prosecution of U.S. Appl. No. 15/541,783.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
An Advisory Action dated Dec. 13, 2013, which issued during the prosecution of U.S. Appl. No. 12/961,721.
An Office Action dated Aug. 7, 2015, which issued during the prosecution of U.S. Appl. No. 14/128,756.
An Office Action dated May 19, 2011, which issued during the prosecution of U.S. Appl. No. 12/706,868.
An Office Action dated Sep. 1, 2011, which issued during the prosecution of U.S. Appl. No. 12/706,868.
An Office Action dated May 30, 2012, which issued during the prosecution of U.S. Appl. No. 12/706,868.
A Notice of Allowance dated Sep. 18, 2012, which issued during the prosecution of U.S. Appl. No. 12/706,868.
Restriction Requirement dated May 5, 2011, which issued during the prosecution of U.S. Appl. No. 12/706,868.
A Restriction Requirement dated Mar. 30, 2012, which issued during the prosecution of U.S. Appl. No. 12/785,717.
An Office Action dated October 5. 2020, which issued during the prosecution of Canadian Patent Application No. 2,973,940.
An Office Action dated Nov. 30, 2020, which issued during the prosecution of U.S. Appl. No. 16/138,129.
An Office Action summarized English translation and Search Report dated Nov. 25, 2020, which issued during the prosecution of Chinese Patent Application No. 201910449820.1.
Notice of Allowance dated Nov. 19, 2020, which issued during the prosecution of U.S. Appl. No. 16/318,025.
An Office Action dated Aug. 2, 2011, which issued during the prosecution of U.S. Appl. No. 12/435,291.
Notice of Allowance dated Dec. 7, 2011, which issued during the prosecution of U.S. Appl. No. 12/435,291.
An Office Action dated Apr. 6, 2010, which issued during the prosecution of Applicant's U.S. Appl. No. 12/484,512.
An Office Action dated Oct. 6, 2010, which issued during the prosecution of Applicant's U.S. Appl. No. 12/484,512.
Notice of Allowance dated Apr. 20, 2011, which issued during the prosecution of U.S. Appl. No. 12/484,512.
Notice of Allowance dated Mar. 23, 2011, which issued during the prosecution of U.S. Appl. No. 12/484,512.
An Office Action dated Jan. 27, 2012, which issued during the prosecution of U.S. Appl. No. 12/548,991.
An Office Action dated Aug. 6, 2012, which issued during the prosecution of U.S. Appl. No. 12/548,991.
An Advisory Action dated Sep. 6, 2012 which issued during the prosecution of U.S. Appl. No. 12/548,991.
Notice of Allowance dated Jun. 23, 2014, which issued during the prosecution of U.S. Appl. No. 12/548,991.
A Restriction Requirement dated Nov. 14, 2011 which issued during the prosecution of U.S. Appl. No. 12/548,991.
Amendment, Terminal Disclaimer and Extension dated Jun. 27, 2012, which issued during the prosecution of U.S. Appl. No. 12/548,991.
A Restriction Requirement dated Jul. 5, 2012, which issued during the prosecution of U.S. Appl. No. 12/563,930.
An Office Action dated Apr. 2, 2013, which issued during the prosecution of U.S. Appl. No. 12/785,717.
An Office Action dated Dec. 27, 2013, which issued during the prosecution of U.S. Appl. No. 12/785,717.
An Office Action dated Nov. 5, 2012, which issued during the prosecution of U.S. Appl. No. 12/795,026.
An Office Action dated May 10, 2012, which issued during the prosecution of U.S. Appl. No. 12/795,026.
Notice of Allowance dated Nov. 13, 2014, which issued during the prosecution of U.S. Appl. No. 12/795,026.
Notice of Allowance dated Dec. 24, 2014, which issued during the prosecution of U.S. Appl. No. 12/791,026.
A Restriction Requirement dated Jan. 6, 2012, which issued during the prosecution of U.S. Appl. No. 12/791,026.
A Restriction Requirement dated Sep. 14, 2012, which issued during the prosecution of U.S. Appl. No. 12/795,192.
An Office Action dated Aug. 15, 2013, which issued during the prosecution of U.S. Appl. No. 12/795,192.
An Office Action dated Jan. 17, 2013, which issued during the prosecution of U.S. Appl. No. 12/795,192.
Notice of Allowance dated Nov. 19, 2013, which issued during the prosecution of U.S. Appl. No. 12/795,192.
A Notice of Allowance dated Jun. 26, 2012, which issued during the prosecution of U.S. Appl. No. 12/608,316.
An Office Action dated Nov. 14, 2011, which issued during the prosecution of U.S. Appl. No. 12/608,316.
A Restriction Requirement dated Apr. 1, 2011, which issued during the prosecution of U.S. Appl. No. 12/608,316.
An Office Action dated Jul. 6, 2012, which issued during the prosecution of U.S. Appl. No. 12/692,061.
An Office Action dated Jan. 23, 2012, which issued during the prosecution of U.S. Appl. No. 12/692,061.
An Office Action dated Mar. 9, 2012, which issued during the prosecution of U.S. Appl. No. 12/689,635.
An Office Action dated Nov. 30, 2012, which issued during the prosecution of U.S. Appl. No. 12/689,635.
A Notice of Allowance dated May 22, 2013, which issued during the prosecution of U.S. Appl. No. 12/689,635.
Restriction Requirement dated Nov. 14, 2011, which issued during the prosecution of U.S. Appl. No. 12/689,635.
An Office Action dated May 6, 2013, which issued during the prosecution of U.S. Appl. No. 12/689,693.
An Office Action dated Feb. 3, 2014, which issued during the prosecution of US Patent Application No. 12/689.693.
Notice of Allowance dated Jun. 11, 2014, which issued during the prosecution of U.S. Appl. No. 12/689,693.
A Restriction Requirement dated Sep. 17, 2012, which issued during the prosecution of U.S. Appl. No. 12/689,693.
A Notice of Allowance dated Sep. 3, 2014, which issued during the prosecution of U.S. Appl. No. 12/689,693.
European Search Report dated Jul. 8, 2016, which issued during the prosecution of Applicant's European App No. 13849843.1.
A Supplementary European Search Report dated Dec. 4, 2012, which issued during the prosecution of European Patent Application No. EP 09834225.6.
A Supplementary European Search Report dated Mar. 28, 2013, which issued during the prosecution of European Patent Application No. EP 1077 2091.4.
Search Report in European Patent Application 10772090.6 dated Jan. 17, 2014.
Supplementary European Search Report dated Oct. 23, 2014 which issued during the prosecution of Applicant's European App No. 10826224.7.
Notice of Allowance dated May 6, 2016, which issued during the prosecution of U.S. Appl. No. 14/667,090.
Notice of Allowance dated Apr. 12, 2016, which issued during the prosecution of U.S. Appl. No. 14/667,090.
An Office Action dated Jun. 7, 2013 which issued during the prosecution of U.S. Appl. No. 13/141,606.
An Office Action dated Jun. 13, 2014, which issued during the prosecution of U.S. Appl. No. 13/141,606.
Notice of Allowance dated Sep. 29, 2014, which issued during the prosecution of U.S. Appl. No. 13/141,606.
An Office Action dated Feb. 4, 2013 which issued during the prosecution of U.S. Appl. No. 13/141,606.
An English translation of an Office Action dated Apr. 23, 2014 which issued during the prosecution of Chinese Patent Application No. 201080059948.4.
Communication dated Jul. 25, 2014, issued by the State Intellectual Property Office of the P.R. of China in counterpart Application No. 200980157331.3.

(56) References Cited

OTHER PUBLICATIONS

An International Search Report and a Written Opinion both dated Jan. 25, 2016, which issued during the prosecution of Applicant's PCT/IL2015/051027.
An International Search Report dated May 19, 2011, which issued during the prosecution of Applicant's PCT/IL2011/00064.
An International Search Report and a Written Opinion both dated Feb. 22, 2013, which issued during the prosecution of Applicant's PCT/IL201/050451.
An International Search Report & Written Opinion both dated Mar. 21. 2014, which issued during the prosecution of Applicant's PCT/IL13/50992.
An International Search Report and Written Opinion both dated Apr. 9, 2014, which issued during the prosecution of Applicant's PCT/IL13/50860.
An International Search Report and a Written Opinion both dated Apr. 15, 2014, which issued during the prosecution of Applicant's PCT/IL2013/050861.
An International Search Report & Written Opinion both dated May 12, 2015, which issued during the prosecution of Applicant's PCT/IL2014/050914.
An International Search Report and a Written Opinion both dated May 30, 2007, which issued during the prosecution of Applicant's PCT/IL2006/000342.
An International Search Report and a Written Opinion both dated Jun. 10, 2010, which issued during the prosecution of Applicant's PCT/IL09/01209.
An International Search Report and a Written Opinion both dated Aug. 17, 2010. which issued during the prosecution of Applicant's PCT/IL10/00357.
An International Search Report & Written Opinion both dated Sep. 8, 2009, which issued during the prosecution of Applicant's PCT/IL09/00593.
An International Search Report and a Written Opinion both dated Sep. 12, 2008, which issued during the prosecution of Applicant's PCT/IL07/01503.
An International Search Report and Written Opinion dated Nov. 8, 2010, which issued during the prosecution of Applicant's PCT/IL2010/000358.
An International Search Report and a Written Opinion both dated Nov. 23, 2011, which issued during the prosecution of Applicant's PCT/IL2011/000446.
Supplementary European Search Report dated Sep. 25, 2015, which issued during the prosecution of Applicant's European App No. 09794095.1.
A Supplementary European Search Report dated Feb. 1, 2011, which issued during the prosecution of European Patent Application No. EP 07849540.
An English translation of an Office Action dated Dec. 12, 2013 which issued during the prosecution of Chinese Patent Application No. 200980157331.3.
Communication regarding amended claims filed dated Dec. 27, 2012, regarding European App No. 11792047.0.
An Office Action dated Mar. 23, 2015, which issued during the prosecution of European Patent Application No. EP 09834225.6.
An English translation of an Office Action dated Jul. 17, 2015 which issued during the prosecution of Chinese Patent Application No. 201080059948.4.
An English translation of an Office Action dated Dec. 16, 2015 which issued during the prosecution of Chinese Patent Application No. 201080059948.4.
Communication from the European Patent Office dated Jun. 11, 2015, which issued during the prosecution of European Patent Application No. 11811934.
A communication from the European Patent Office dated Sep. 28, 2011 which issued during the prosecution of European Application No. 09834225.6.
A communication from the European Patent Office dated Oct. 19, 2012 which issued during the prosecution of European Application No. 11792047.0.
An Office Action dated Oct. 23, 2012, which issued during the prosecution of Japanese Patent Application No. 2009-539871.
An English Translation of an Office Action dated Nov. 24, 2015, which issued during the prosecution of Israel Patent Application No. 223448. (the relevant part only).
Notice of Allowance dated Nov. 17, 2015, which issued during the prosecution of U.S. Appl. No. 14/486,226.
Notice of Allowance dated Jan. 29, 2016, which issued during the prosecution of U.S. Appl. No. 14/551,951.
An Office Action dated Jun. 18, 2015, which issued during the prosecution of U.S. Appl. No. 14/551,951.
An Office Action dated Jan, 4, 2016, which issued during the prosecution of U.S. Appl. No. 14/589,100.
An Office Action dated May 4, 2016, which issued during the prosecution of U.S. Appl. No. 14/589,100.
An International Search Report and a Written Opinion both dated Nov. 14, 2011, which issued during the prosecution of Applicant's PCT/IL2011/000404.
An International Search Report and a Written Opinion both dated Dec. 6, 2012 which issued during the prosecution of Applicant's PCT/IL2012/000250.
A Notice of Allowance dated Apr. 3, 2013, which issued during the prosecution of U.S. Appl. No. 12/563,930.
An Office Action dated Aug. 24, 2012, which issued during the prosecution of U.S. Appl. No. 12/563,930.
An Office Action dated Dec. 29, 2011, which issued during the prosecution of U.S. Appl. No. 12/563,952.
A Restriction Requirement dated Oct. 27, 2011, which issued during the prosecution of U.S. Appl. No. 12/563,952.
A Notice of Allowance dated May 24, 2012, which issued during the prosecution of U.S. Appl. No. 12/563,952.
An Office Action dated Apr. 1, 2013 which issued during the prosecution of U.S. Appl. No. 13/161,476.
An Office Action dated Nov. 21, 2013, which issued during the prosecution of U.S. Appl. No. 13/161,476.
An Advisory Action dated Feb. 4, 2014, which issued during the prosecution of U.S. Appl. No. 13/161,476.
A Restriction Requirement dated Oct. 25, 2012 which issued during the prosecution of U.S. Appl. No. 13/167,444.
An Office Action dated Jan. 17, 2013, which issued during the prosecution of U.S. Appl. No. 13/167,444.
An Office Action dated Aug. 26, 2014 which issued during the prosecution of U.S. Appl. No. 13/167,444.
An Office Action dated Aug. 23, 2013 which issued during the prosecution of U.S. Appl. No. 13/167,444.
Notice of Allowance dated Nov. 12, 2015, which issued during the prosecution of U.S. Appl. No. 13/319,007.
Notice of Allowance dated Jan. 7, 2016, which issued during the prosecution of U.S. Appl. No. 13/319,007.
An Office Action dated Oct. 2, 2013, which issued during the prosecution of U.S. Appl. No. 13/167,492.
A Restriction Requirement dated Nov. 2, 2012, which issued during the prosecution of U.S. Appl. No. 13/167,492.
An Office Action dated Feb. 14, 2013 which issued during the prosecution of US Patent Application No. 13/167.492.
Notice of Allowance dated Nov. 7, 2014, which issued during the prosecution of U.S. Appl. No. 13/167,492.
An Office Action dated Jun. 10, 2014, which issued during the prosecution of U.S. Appl. No. 13/167,492.
Notice of Allowance dated Dec. 9, 2014, which issued during the prosecution of U.S. Appl. No. 13/167,476.
Notice of Allowance dated Jan. 22. 2015, which issued during the prosecution of U.S. Appl. No. 13/167,444.
An International Preliminary Report on Patentability dated May 1, 2012, which issued during the prosecution of Applicant's PCT/IL2010/000890.
An International Preliminary Report on Patentability dated Jun. 9, 2015, which issued during the prosecution of Applicant's PCT/IL2013/050992.
U.S. Appl. No. 60/873,075, filed Dec. 5, 2006.
U.S. Appl. No. 60/902,146, filed Feb. 16, 2007.
An Office Action dated Mar. 29, 2018, which issued during the prosecution of U.S. Appl. No. 15/188,507.

(56) References Cited

OTHER PUBLICATIONS

Notice of Allowance dated Sep. 17, 2014, which issued during the prosecution of U.S. Appl. No. 12/961,721.
An Office Action dated Oct. 1, 2015, which issued during the prosecution of U.S. Appl. No. 14/141,228.
A Restriction Requirement dated Jun. 2, 2014, which issued during the prosecution of U.S. Appl. No. 13/319,030.
An Office Action dated Oct. 14, 2014, which issued during the prosecution of U.S. Appl. No. 13/319,030.
An Office Action dated Jun. 18, 2015, which issued during the prosecution of U.S. Appl. No. 13/319,030.
An Office Action dated May 3, 2016, which issued during the prosecution of U.S. Appl. No. 13/319,030.
Notice of Allowance dated Dec. 30, 2016, which issued during the prosecution of U.S. Appl. No. 13/319,030.
An Office Action dated Apr. 7, 2015, which issued during the prosecution of U.S. Appl. No. 13/319,007.
An Office Action dated Apr. 8, 2016, which issued during the prosecution of U.S. Appl. No. 14/141,228.
An Office Action dated Oct. 5, 2015, which issued during the prosecution of U.S. Appl. No. 14/246,417.
An Office Action dated Apr. 7, 2016, which issued during the prosecution of U.S. Appl. No. 14/242,151.
An Office Action dated May 23, 2016, which issued during the prosecution of U.S. Appl. No. 14/209,171.
An Office Action dated Jul. 20, 2016, which issued during the prosecution of U.S. Appl. No. 14/246,417.
An Office Action dated Jun. 14, 2016, which issued during the prosecution of U.S. Appl. No. 14/273,155.
An Office Action dated Jun. 17, 2016, which issued during the prosecution of U.S. Appl. No. 14/357,040.
An Office Action dated Mar. 24, 2015, which issued during the prosecution of U.S. Appl. No. 14/486,226.
U.S. Appl. No. 61/001,013, filed Oct. 29, 2007.
U.S. Appl. No. 61/132,295, filed Jun. 16, 2008.
U.S. Appl. No. 61/265,936, filed Dec. 2, 2009.
U.S. Appl. No. 61/283,445, filed Dec. 2, 2009.
U.S. Appl. No. 61/207,908, filed Feb. 17, 2009.
U.S. Appl. No. 61/733,979, filed Dec. 6, 2012.
U.S. Appl. No. 61/717,303, filed Oct. 23, 2012.
U.S. Appl. No. 61/820,979, filed May 8, 2013.
U.S. Appl. No. 61/745,848, filed Dec. 6, 2012.
U.S. Appl. No. 61/555,570, filed Nov. 4, 2011.
U.S. Appl. No. 61/557,082, filed Nov. 8, 2011.
U.S. Appl. No. 60/662,616, filed Mar. 17, 2005.
U.S. Appl. No. 60/700,542, filed Jul. 18, 2005.
U.S. Appl. No. 61/782,121, filed Mar. 14, 2013.
European Search Report dated Jul. 15, 2016, which issued during the prosecution of Applicant's European App No. 13849947.0.
European Search Report dated Nov. 4, 2015, which issued during the prosecution of European Patent Application No. EP 1077 2091.4.
Search Report in European Patent Application 10826224.7 dated Nov. 16, 2015.
Supplementary European Search Report dated Dec. 23, 2014 which issued during the prosecution of Applicant's European App No. 10834311.
Supplementary European Search Report dated Jan. 21, 2014 which issued during the prosecution of Applicant's European App No. 11 78 6226.
A Supplementary European Search Report dated Jan. 20, 2015, which issued during the prosecution of European Patent Application No. 12803037.6.
Supplementary European Search Report dated Aug. 4, 2014 which issued during the prosecution of Applicant's European App No. 11 81 1934.6.
European Search Report dated Jun. 24, 2016, which issued during the prosecution of European Patent Application No. EP 12847363.
Supplementary European Search Report dated Apr. 29, 2015, which issued during the prosecution of Applicant's European App No. 14200202.
An Office Action dated Dec. 16, 2013, which issued during the prosecution of U.S. Appl. No. 13/666,262.
An Office Action dated Dec. 18, 2013, which issued during the prosecution of U.S. Appl. No. 13/666,141.
Notice of Allowance dated Jun. 25, 2014, which issued during the prosecution of U.S. Appl. No. 13/666,262.
A Notice of Allowance dated Feb. 2, 2015, which issued during the prosecution of U.S. Appl. No. 13/504,870.
Notice of Allowance dated Aug. 19, 2013, which issued during the prosecution of U.S. Appl. No. 11/908,906.
An Office Action dated Jun. 8, 2012, which issued during the prosecution of U.S. Appl. No. 11/908,906.
An Office Action dated Dec. 21, 2013, which issued during the prosecution of U.S. Appl. No. 11/908,906.
A Restriction Requirement dated Aug. 5, 2011, which issued during the prosecution of U.S. Appl. No. 11/908,906.
An Office Action dated Sep. 16, 2009 which issued during the prosecution of U.S. Appl. No. 11/950,930.
Notice of Allowance dated Sep. 12, 2014, which issued during the prosecution of U.S. Appl. No. 11/950,930.
An Office Action dated Aug. 5, 2010 which issued during the prosecution of U.S. Appl. No. 11/950,930.
An Office Action dated Feb. 17, 2010 which issued during the prosecution of U.S. Appl. No. 11/950,930.
A Restriction Requirement dated Apr. 19, 2010 which issued during the prosecution of U.S. Appl. No. 12/341,960.
An Office Action dated Sep. 28, 2011, which issued during the prosecution of U.S. Appl. No. 12/437,103.
An Office Action dated Jun. 13, 2012, which issued during the prosecution of U.S. Appl. No. 12/437,103.
A Restriction Requirement dated Jul. 12, 2011, which issued during the prosecution of U.S. Appl. No. 12/437,103.
Notice of Allowance dated Mar. 6, 2014, which issued during the prosecution of U.S. Appl. No. 12/437,103.
Notice of Allowance dated Dec. 20, 2013, which issued during the prosecution of U.S. Appl. No. 12/437,103.
Notice of Allowance dated Apr. 27, 2012, which issued during the prosecution of U.S. Appl. No. 12/341,960.
An Office Action dated Mar. 29, 2011, which issued during the prosecution of U.S. Appl. No. 12/341,960.
An Office Action dated Aug. 4, 2010, which issued during the prosecution of U.S. Appl. No. 12/341,960.
An Interview Summary dated Jul. 27, 2011, which issued during the prosecution of U.S. Appl. No. 12/341,960.
Notice of Allowance dated Aug. 21, 2019, which issued during the prosecution of U.S. Appl. No. 15/703,385.
Notice of Allowance dated Oct. 16, 2019, which issued during the prosecution of U.S. Appl. No. 15/703,385.
Notice of Allowance dated Dec. 24, 2020, which issued during the prosecution of U.S. Appl. No. 15/668,659.
Notice of Allowance dated Oct. 21, 2020, which issued during the prosecution of U.S. Appl. No. 15/668,659.
Declaration of Ivan Vesely, Ph.D., in Support of Petition for Inter Partesreview of U.S. Pat. No. 7,563,267—dated May 29, 2019.
U.S. Appl. No. 60/128,690, filed Apr. 9, 1999.
U.S. Appl. No. 60/613,867, filed Sep. 27, 2004.
An Office Action dated Dec. 24, 2020, which issued during the prosecution of U.S. Appl. No. 16/144,054.
An Office Action dated February 2. 2021, which issued during the prosecution of U.S. Appl. No. 16/811,732.
An Office Action dated Jan. 13, 2021, which issued during the prosecution of European Patent Application No. 15751089.2.
An Office Action together with an English summary dated Mar. 3, 2021, which issued during the prosecution of Chinese Patent Application No. 201780047391.4.
Declaration of Dr. Ivan Vesely, Ph.D. in Support of Petition for Inter Partes Review of U.S. Pat. No. 10,226,341—dated Dec. 17, 2020.
Petition for Inter Partes Review of U.S. Pat. No. 10,226,341 and Exhibits 1001-1013—dated Dec. 29, 2020.

(56) References Cited

OTHER PUBLICATIONS

Batista, Randas JV, et al. "Partial left ventriculectomy to treat end-stage heart disease." The Annals of thoracic surgery 64.3 (1997): 634-638.
Beall Jr, Arthur C., et al. "Clinical experience with a dacron velour-covered teflon-disc mitral-valve prosthesis." The Annals of thoracic surgery 5.5 (1968): 402-410.
Kalbacher, D., et al. "1000 MitraClip™ procedures: Lessons learnt from the largest single-centre experience worldwide." (2019): 3137-3139.
Maisano, F., et al. "The edge-to-edge technique: a simplified method to correct mitral insufficiency." European journal of cardio-thoracic surgery 13.3 (1998): 240-246.
Fucci, C., et al. "Improved results with mitral valve repair using new surgical techniques." European journal of cardio-thoracic surgery 9.11 (1995): 621-627.
Notice of Allowance dated Nov. 19, 2019, which issued during the prosecution of U.S. Appl. No. 15/668,559.
Mitral Valve Academic Research Consortium. "Clinical Trial Design Principles and Endpoint Definitions for Transcatheter Mitral Valve Repair and Replacement: Part 1: Clinical Trial Design Principles a Consensus Document from the Mitral Valve Academic Research Consortium." Journal of the American College of Cardiology 66.3 (2015): 278-307.
An Office Action dated Aug. 29, 2018, which issued during the prosecution of U.S. Appl. No. 15/329,920.
An Office Action dated May 8, 2018, which issued during the prosecution of U.S. Appl. No. 15/902,403.
An Office Action dated May 11, 2018, which issued during the prosecution of U.S. Appl. No. 15/899,858.
Notice of Allowance dated Oct. 5, 2018, which issued during the prosecution of U.S. Appl. No. 15/886,517.
Notice of Allowance dated Jul. 19, 2019, which issued during the prosecution of U.S. Appl. No. 15/899,858.
Notice of Allowance dated Nov. 16, 2020, which issued during the prosecution of U.S. Appl. No. 16/324,339.
Notice of Allowance dated Apr. 27, 2020, which issued during the prosecution of U.S. Appl. No. 16/591,330.
An Advisory Action dated Jan. 2, 2020, which issued during the prosecution of U.S. Appl. No. 15/668,659.
Notice of Allowance dated Oct. 17, 2019, which issued during the prosecution of U.S. Appl. No. 15/329,920.
An Office Action dated Dec. 31, 2019, which issued during the prosecution of U.S. Appl. No. 16/591,330.
Notice of Allowance dated Feb. 9, 2021, which issued during the prosecution of U.S. Appl. No. 16/937,216.
An Advisory Action dated Nov. 18, 2020, which issued during the prosecution of U.S. Appl. No. 16/811,732.
An International Search Report and a Written Opinion both dated Mar. 27, 2018, which issued during the prosecution of Applicant's PCT/IL2017/050849.
Notice of Allowance dated Jun. 11, 2021, which issued during the prosecution of U.S. Appl. No. 16/811,732.
Notice of Allowance dated Jul. 16, 2021, which issued during the prosecution of U.S. Appl. No. 16/811,732.
Patent Trial and Appeal Board Decision Granting Institution in U.S. Pat. No. 10,226,341—Dated Jul. 20, 2021.
European Search Report dated Jun. 10, 2021 which issued during the prosecution of Applicant's European App No. 21157988.3.
Notice of Allowance dated Nov. 19, 2018, which issued during the prosecution of U.S. Appl. No. 15/197,069.
Poirier, Nancy C., et al. "A novel repair for patients with atrioventricular septal defect requiring reoperation for left atrioventricular valve regurgitation." European journal of cardio-thoracic surgery 18.1 (2000): 54-61.
An Office Action dated Mar. 29, 2021, which issued during the prosecution of U.S. Appl. No. 16/738,516.
Ando, Tomo, et al. "Iatrogenic ventricular septal defect following transcatheter aortic valve replacement: a systematic review." Heart, Lung and Circulation 25.10 (2016): 968-974.

Urena, Marina, et al. "Transseptal transcatheter mitral valve replacement using balloon-expandable transcatheter heart valves: a step-by-step approach." JACC: Cardiovascular Interventions 10.19 (2017): 1905-1919.
An English summary of an Official Action dated Mar. 29, 2021, which issued during the prosecution of Chinese Patent Application No. 201780061210.3.
An International Search Report and a Written Opinion both dated Jan. 28, 2020, which issued during the prosecution of Applicant's PCT/IL2019/051031.
An International Preliminary Report on Patentability dated Mar. 9, 2021, which issued during the prosecution of Applicant's PCT/IL2019/051031.
An Office Action dated May 4, 2021, which issued during the prosecution of U.S. Appl. No. 16/636,204.
Notice of Allowance dated May 17. 2021, which issued during the prosecution of U.S. Appl. No. 16/138,129.
Notice of Allowance dated June 4. 2021, which issued during the prosecution of U.S. Appl. No. 16/802,353.
An Office Action dated May 12. 2021, which issued during the prosecution of Canadian Patent Application No. 2,973,940.
Petition for Inter Partes Review of U.S. Pat. No. 10,702,385—dated Jun. 4, 2021.
Declaration of Ivan Vesely, Ph.D. In Support of Petition for Inter Partes Review of U.S. Pat. No. 10,702,385—dated Jun. 4, 2021.
Notice of Allowance dated Oct. 30, 2018, which issued during the prosecution of U.S. Appl. No. 15/197,069.
An International Search Report and a Written Opinion both dated Jul. 12, 2021, which issued during the prosecution of Applicant's PCT/IL2021/050132.
Notice of Allowance dated Oct. 3, 2019, which issued during the prosecution of U.S. Appl. No. 15/691,032.
An Office Action dated Sep. 6, 2018, which issued during the prosecution of U.S. Appl. No. 15/213,791.
Condado, José Antonio, et al. "Percutaneous edge-to-edge mitral valve repair: 2-year follow-up in the first human case." Catheterization and cardiovascular interventions 67.2 (2006): 323-325.
Notice of Allowance dated Mar. 18. 2020, which issued during the prosecution of U.S. Appl. No. 16/284,331.
Feldman, Ted, et al. "Percutaneous mitral repair with the MitraClip system: safety and midterm durability in the initial EVEREST (Endovascular Valve Edge-to-Edge REpair Study) cohort." Journal of the American College of Cardiology 54.8 (2009): 686-694.
Notice of Allowance dated Nov. 21, 2018, which issued during the prosecution of U.S. Appl. No. 15/213,791.
Notice of Allowance dated Jul. 3, 2019, which issued during the prosecution of U.S. Appl. No. 15/691,032.
IPR2021-00383 Petitioners' Authorized Reply to Patent Owner's Preliminary Response dated May 27, 2021.
Exhibit 1014—Transcript of proceedings held May 20, 2021 (*Edwards Lifesciences* vs. *Cardiovalve*).
Exhibit 1015—Facilitate, Meriam-Webster.com, https://www.merriamwebster.com/dictionary/facilitate (visited May 26, 2021).
Patent Owner's Authorized Surreply to Petitioner's Reply to Patent Owner's Preliminary Response dated Jun. 4, 2021(*Edwards Lifesciences* vs. *Cardiovalve*).
An Invitation to pay additional fees dated May 19, 2021, which issued during the prosecution of Applicant's PCT/IL2021/050132.
An Office Action dated Aug. 18, 2021, which issued during the prosecution of U.S. Appl. No. 17/210,183.
An Office Action dated Sep. 9, 2021, which issued during the prosecution of U.S. Appl. No. 16/768,909.
An Office Action dated Sep. 15, 2021, which issued during the prosecution of U.S. Appl. No. 16/135,599.
Notice of Allowance dated Oct. 14, 2021, which issued during the prosecution of U.S. Appl. No. 16/680,739.
An Office Action dated Oct. 21, 2021, which issued during the prosecution of U.S. Appl. No. 17/331,845.
European Search Report dated Oct. 11, 2021 which issued during the prosecution of Applicant's European App No. 21176010.3.
Fann, James I., et al. "Beating heart catheter-based edge-to-edge mitral valve procedure in a porcine model: efficacy and healing response." Circulation 110.8 (2004): 988-993.

(56) References Cited

OTHER PUBLICATIONS

IPR2021-00383 Patent Owner's Contingent Motion to Amend Under 37 CPR. §42.121 dated Oct. 13, 2021.
IPR2021-00383 Patent Owner's Response Pursuant to 37 C.F.R. §42.120 dated Oct. 13, 2021.
IPR2021-00383 Second Declaration of Dr. Michael Sacks dated Oct. 13, 2021.
An Office Action dated Oct. 21, 2021, which issued during the prosecution of U.S. Appl. No. 17/306,231.
Maisano, Francesco, et al. "The evolution from surgery to percutaneous mitral valve interventions: the role of the edge-to-edge technique." Journal of the American College of Cardiology 58.21 (2011): 2174-2182.
An Office Action dated Nov. 6, 2015, which issued during the prosecution of U.S. Appl. No. 14/626,267.
An Office Action dated Jan. 26, 2022, which issued during the prosecution of U.S. Appl. No. 16/888,210.
IPR2021-00383 Deposition of Dr. Ivan Vesely, dated Sep. 22, 2021.
Cardiovalve Exhibit 2009—Percutaneous Mitral Leaflet Repair: MitraClip® Therapy for Mitral Regurgitation (2012).
Feldman, Ted, et al. "Percutaneous mitral valve repair using the edge-to-edge technique: six-month results of the EVEREST Phase I Clinical Trial." Journal of the American College of Cardiology 46.11 (2005): 2134-2140.
An Office Action summarized English translation and Search Report dated Oct. 8, 2021, which issued during the prosecution of Chinese Patent Application No. 201780061210.3.
An Office Action dated Nov. 4, 2021, which issued during the prosecution of U.S. Appl. No. 17/366,711.
An Office Action summarized English translation and Search Report dated Aug. 12, 2021, which issued during the prosecution of Chinese Patent Application No. 201880058940.2.
U.S. Appl. No. 63/120,808, filed Dec. 3, 2020.
An Office Action dated Nov. 25, 2021, which issued during the prosecution of European Patent Application No. 18826823.9.
IPR2021-01051 Institution decision dated Dec. 10, 2021.
Notice of Allowance dated Dec. 7, 2021, which issued during the prosecution of U.S. Appl. No. 17/394,307.
Notice of Allowance dated Dec. 6, 2021, which issued during the prosecution of U.S. Appl. No. 16/738,516.
Notice of Allowance dated Dec. 29, 2021, which issued during the prosecution of U.S. Appl. No. 17/210,183.
IPR2021-00383 Petitioners' Reply to Patent Owner's Response dated Jan. 5, 2022.
IPR2021-00383 Petitioners' Opposition to Patent Owner's Contingent Motion to Amend dated Jan. 5, 2022.
An Office Action dated Sep. 22, 2021, which issued during the prosecution of European Patent Application No. 20714289.4.
Summary of Examination Notice dated Jan. 6, 2022, which issued during the prosecution of Chinese Patent Application No. 201880064313.X.
An Office Action dated Jan. 12, 2022, which issued during the prosecution of U.S. Appl. No. 17/101,787.
Notice of Allowance dated Jun. 20, 2017, which issued during the prosecution of U.S. Appl. No. 14/626,267.
Notice of Allowance dated Oct. 20, 2021, which issued during the prosecution of U.S. Appl. No. 16/636,204.
Notice of Allowance dated Jan. 31, 2022, which issued during the prosecution of U.S. Appl. No. 17/479,418.
An Office Action dated Jan. 13, 2022, which issued during the prosecution of U.S. Appl. No. 17/473,472.
An Office Action dated Apr. 11, 2022, which issued during the prosecution of U.S. Appl. No. 17/473,472.
IPR2021-00383 Preliminary Guidance dated Jan. 31, 2022.
An Office Action dated Mar. 18, 2022, which issued during the prosecution of U.S. Appl. No. 16/746,489.
Notice of Allowance dated Mar. 22, 2022, which issued during the prosecution of U.S. Appl. No. 17/366,711.
Notice of Allowance dated Mar. 4, 2022, which issued during the prosecution of U.S. Appl. No. 16/768,909.
An Office Action dated Dec. 9, 2021, which issued during the prosecution of U.S. Appl. No. 16/135,969.
An Office Action dated Jan. 24, 2022, which issued during the prosecution of U.S. Appl. No. 16/135,466.
An Office Action dated Aug. 1, 2022, which issued during the prosecution of European Patent Application No. 18826823.9.
An Office Action dated Aug. 5, 2022, which issued during the prosecution of U.S. Appl. No. 16/760,147.
An Office Action dated Jul. 20, 2022, which issued during the prosecution of U.S. Appl. No. 17/101,787.
An Office Action dated Jul. 27, 2022, which issued during the prosecution of U.S. Appl. No. 16/881,350.
An Office Action dated Sep. 16, 2022, which issued during the prosecution of U.S. Appl. No. 16/135,466.
An Office Action dated Sep. 21, 2022, which issued during the prosecution of U.S. Appl. No. 16/776,581.
An Office Action dated Sep. 8, 2022, which issued during the prosecution of U.S. Appl. No. 16/896,858.
European Search Report dated Sep. 6, 2022 which issued during the prosecution of Applicant's European App No. 22161862.2.
IPR2021-01051 Patent Owner's Sur-Reply to Petitioners' Reply to Preliminary Guidance dated Aug. 23, 2022.
IPR2021-01051 Petitioners' Reply to Preliminary Guidance dated Aug. 2, 2022.
An Office Action summarized English translation and Search Report dated Sep. 25, 2024, which issued during the prosecution of Chinese Patent Application No. 202180010997.7.
An Office Action dated Jan. 20, 2025, which issued during the prosecution of Canadian Patent Application No. 3,166,824.

* cited by examiner

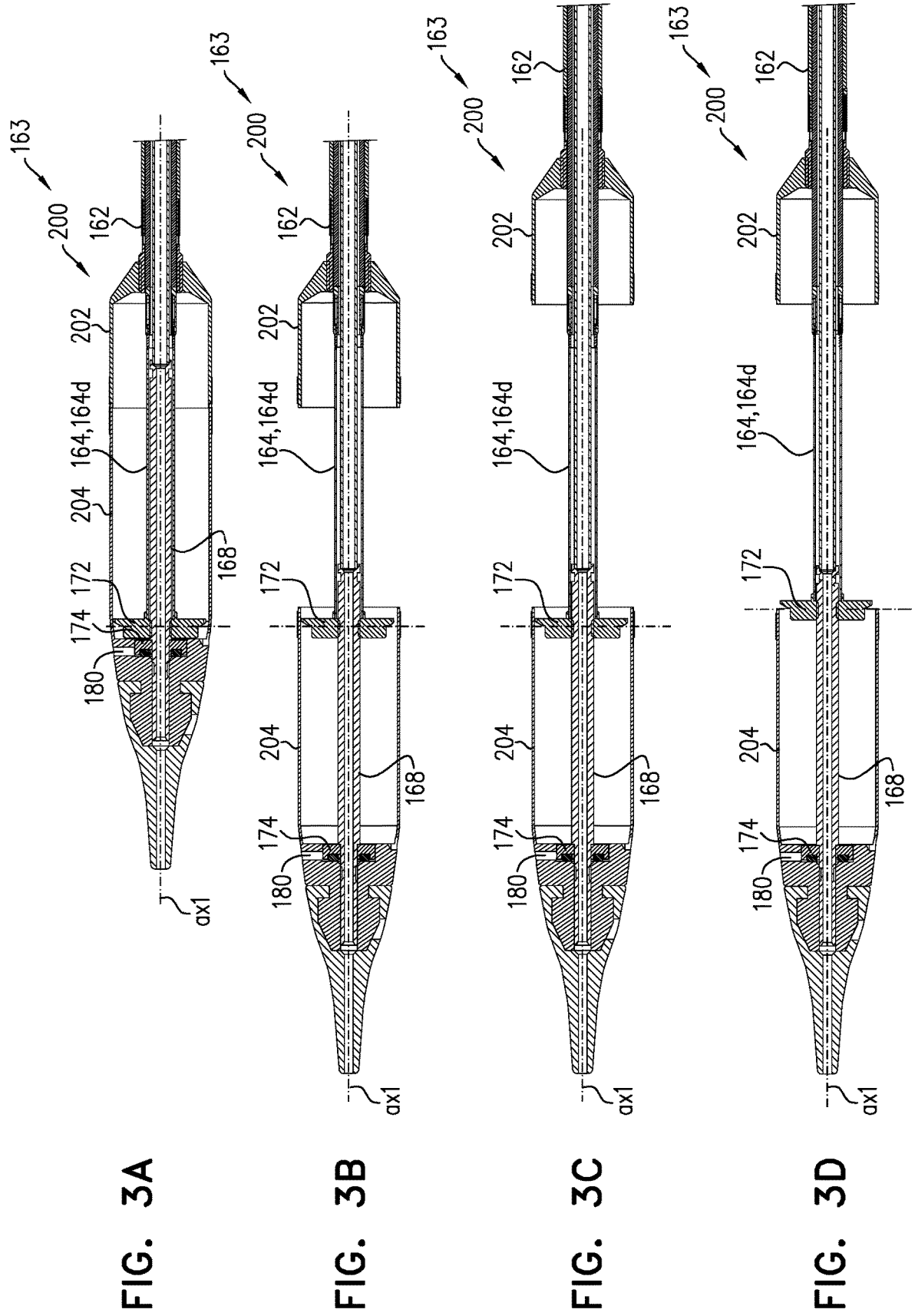

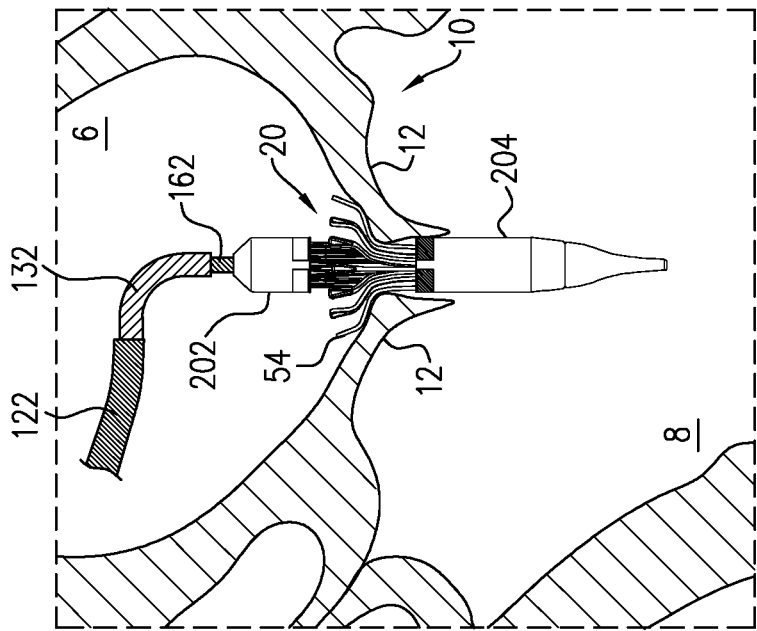
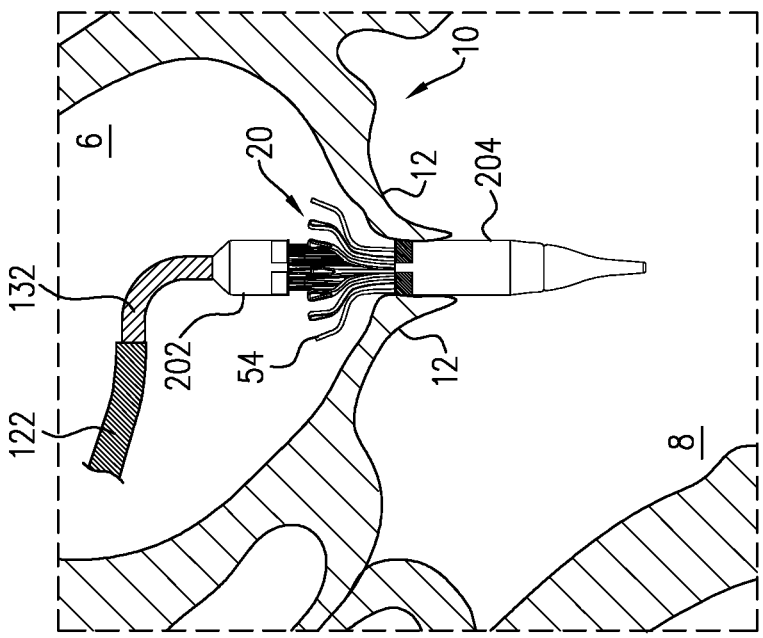

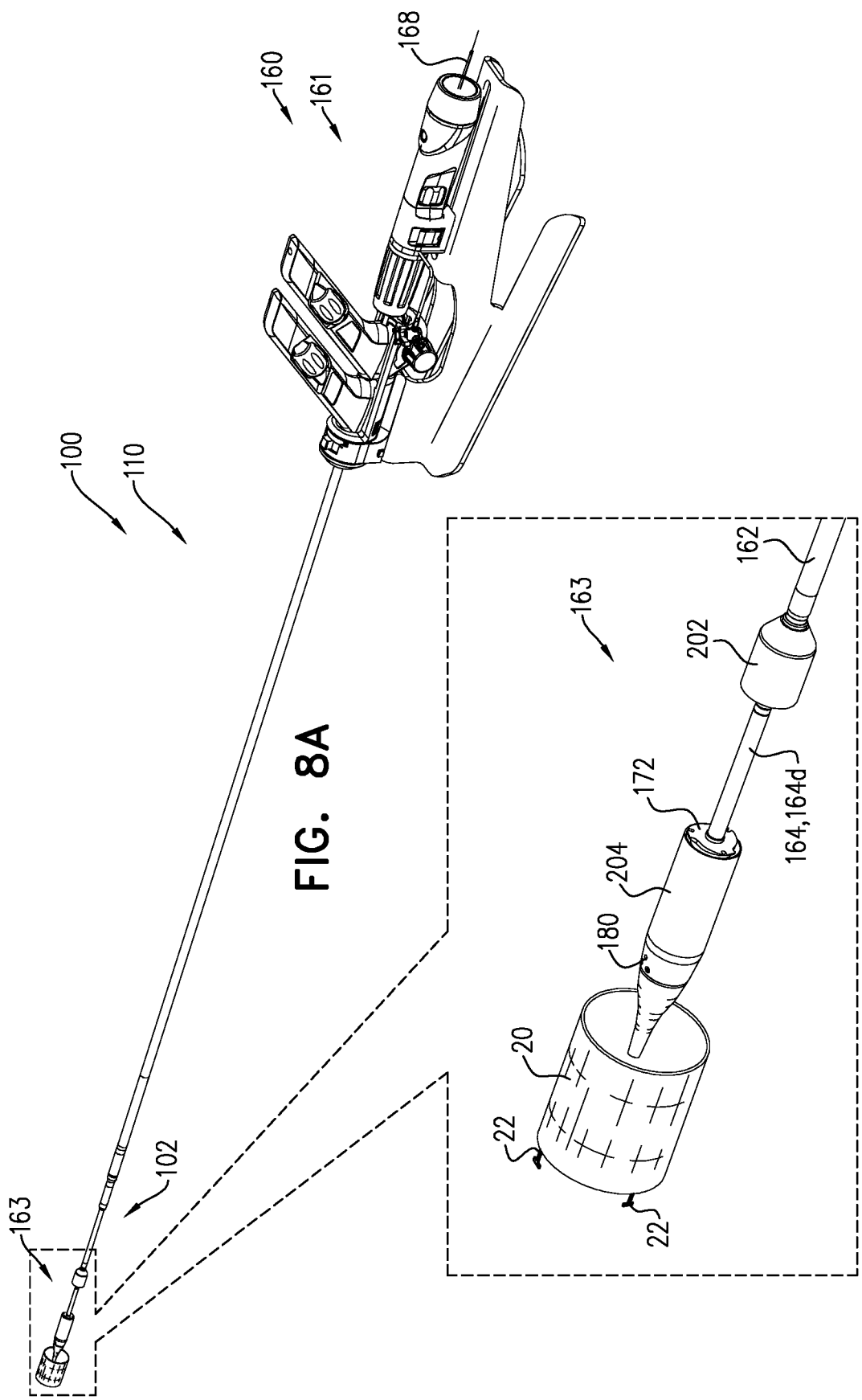

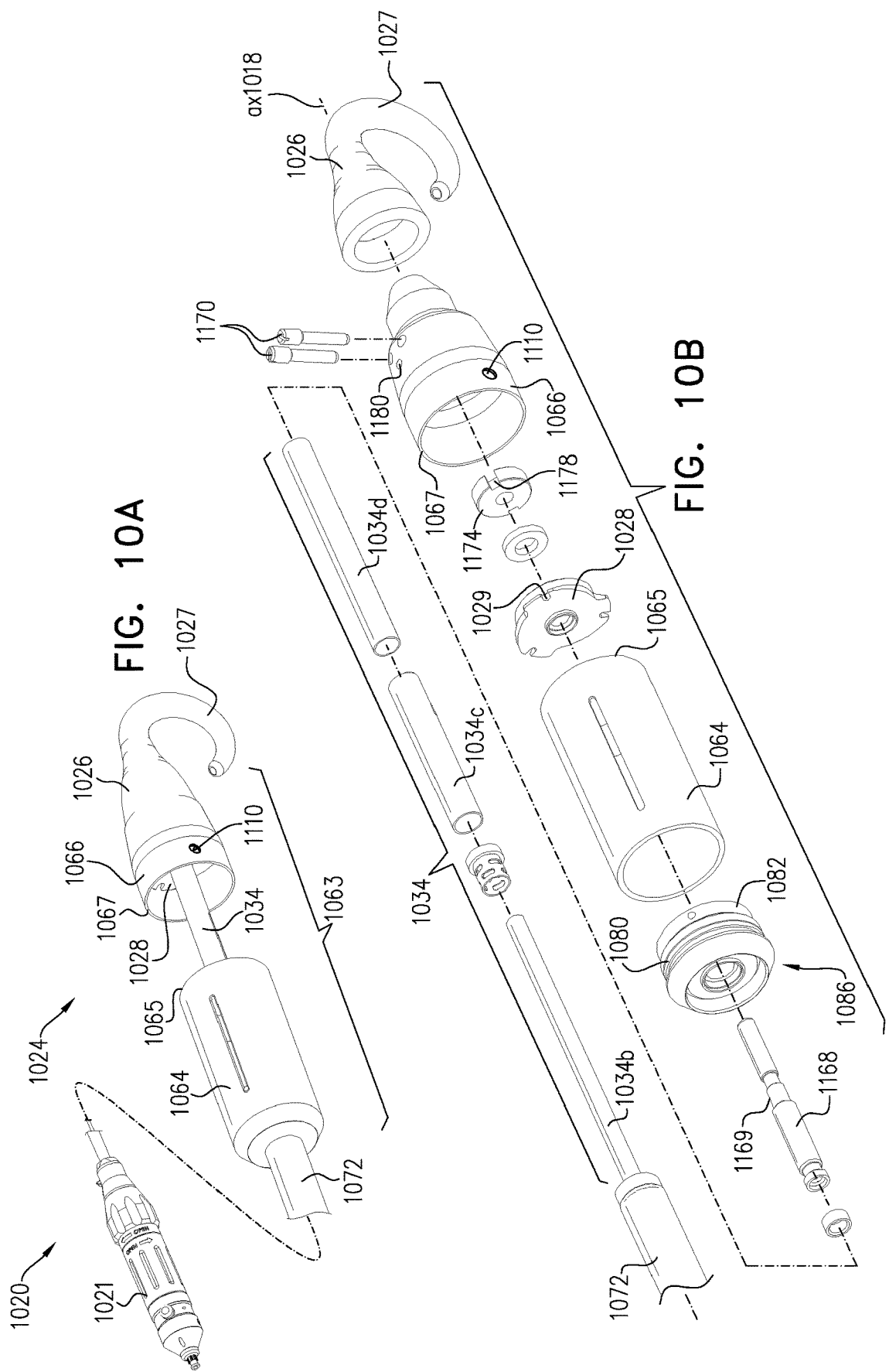

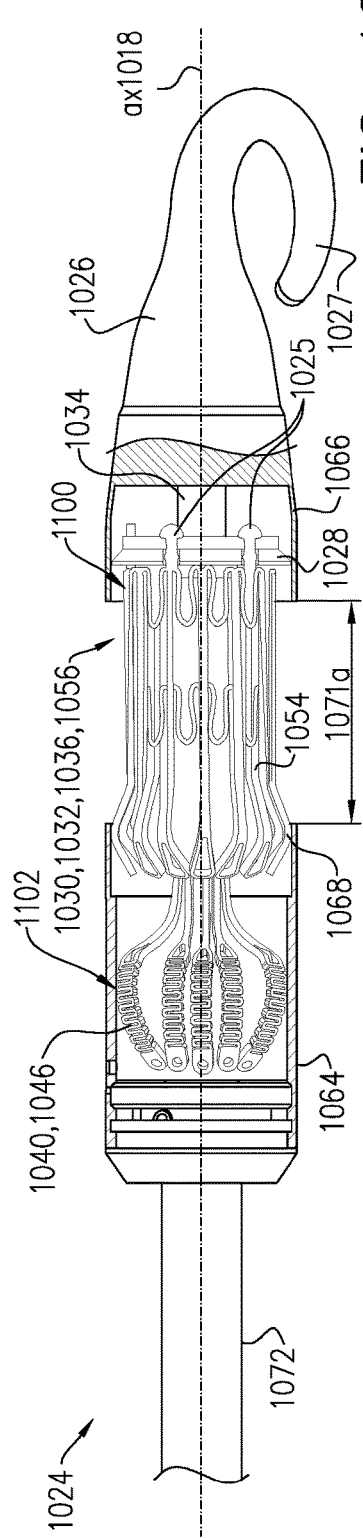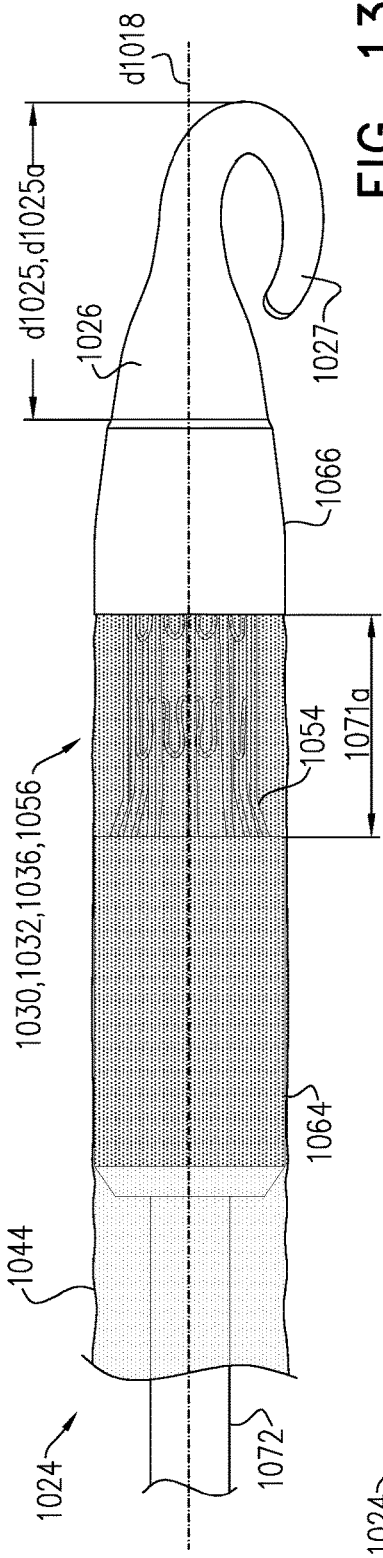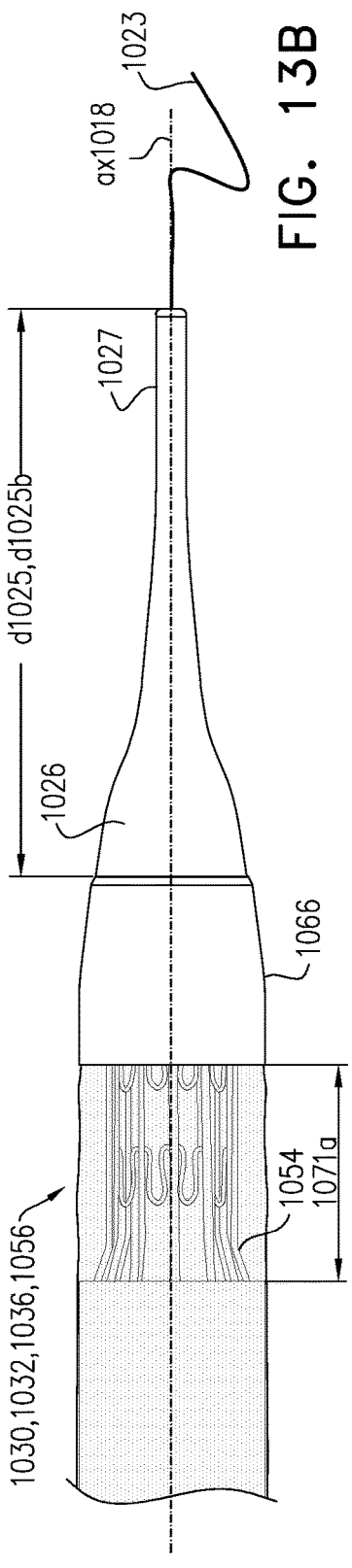

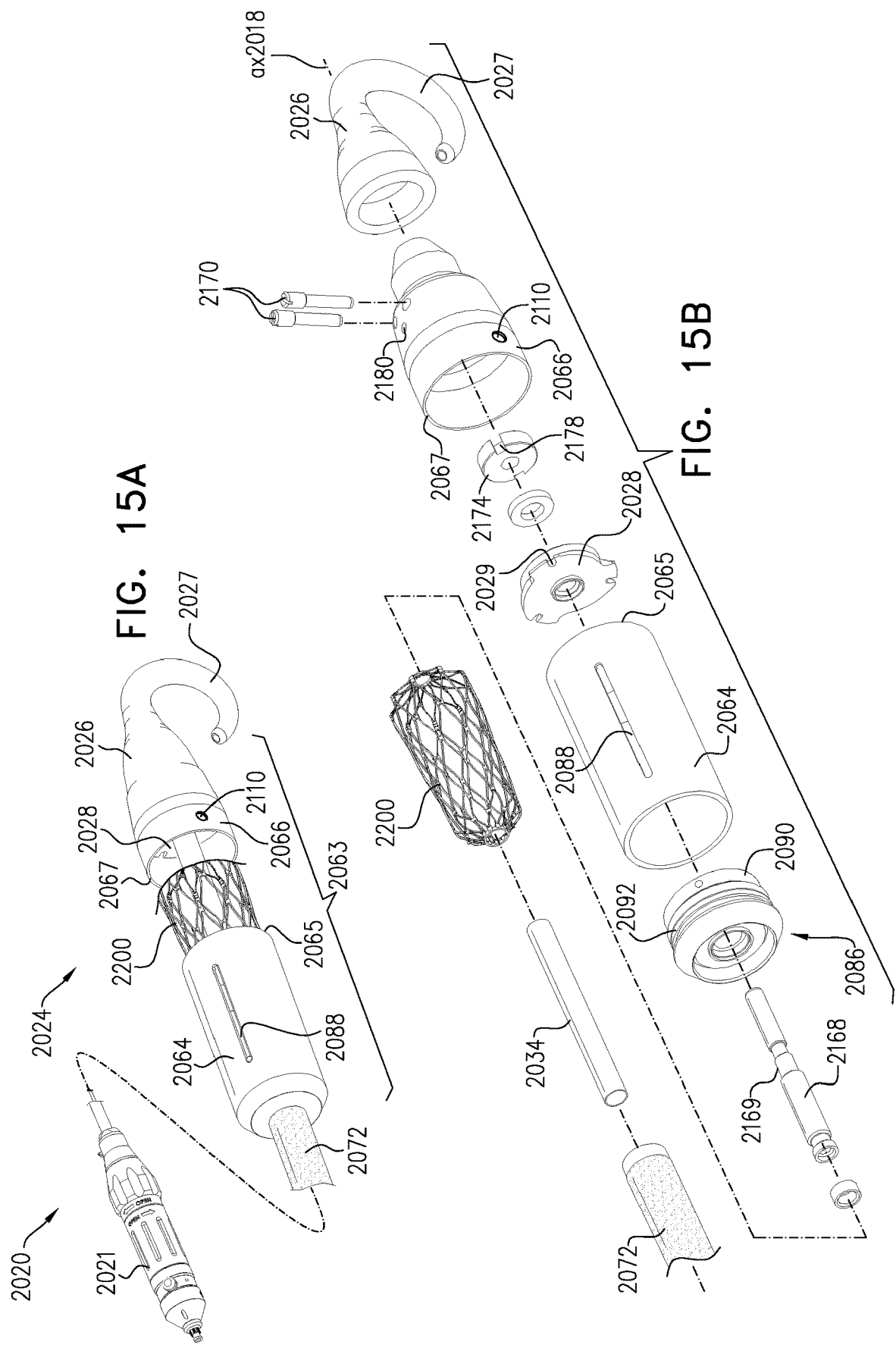

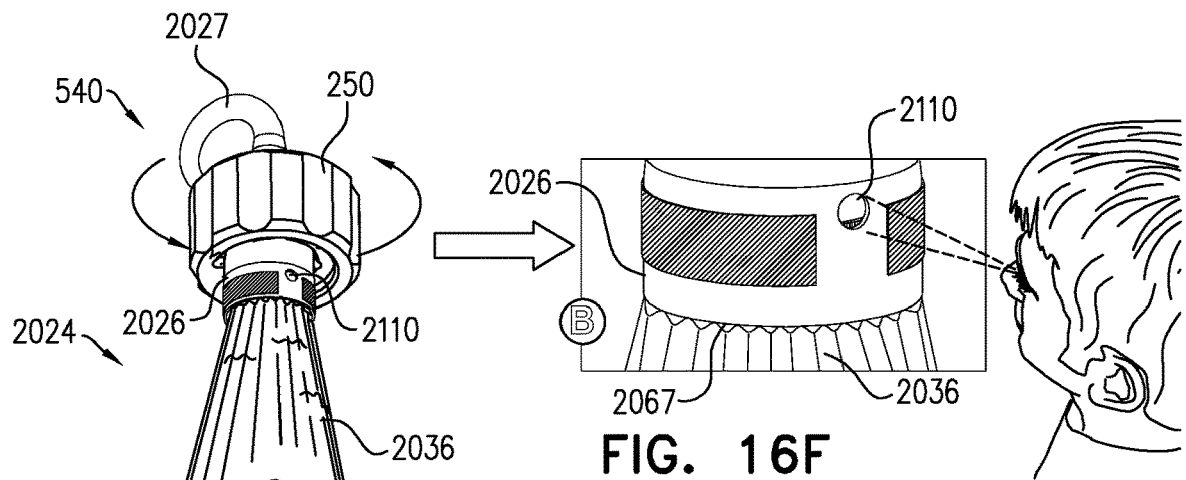
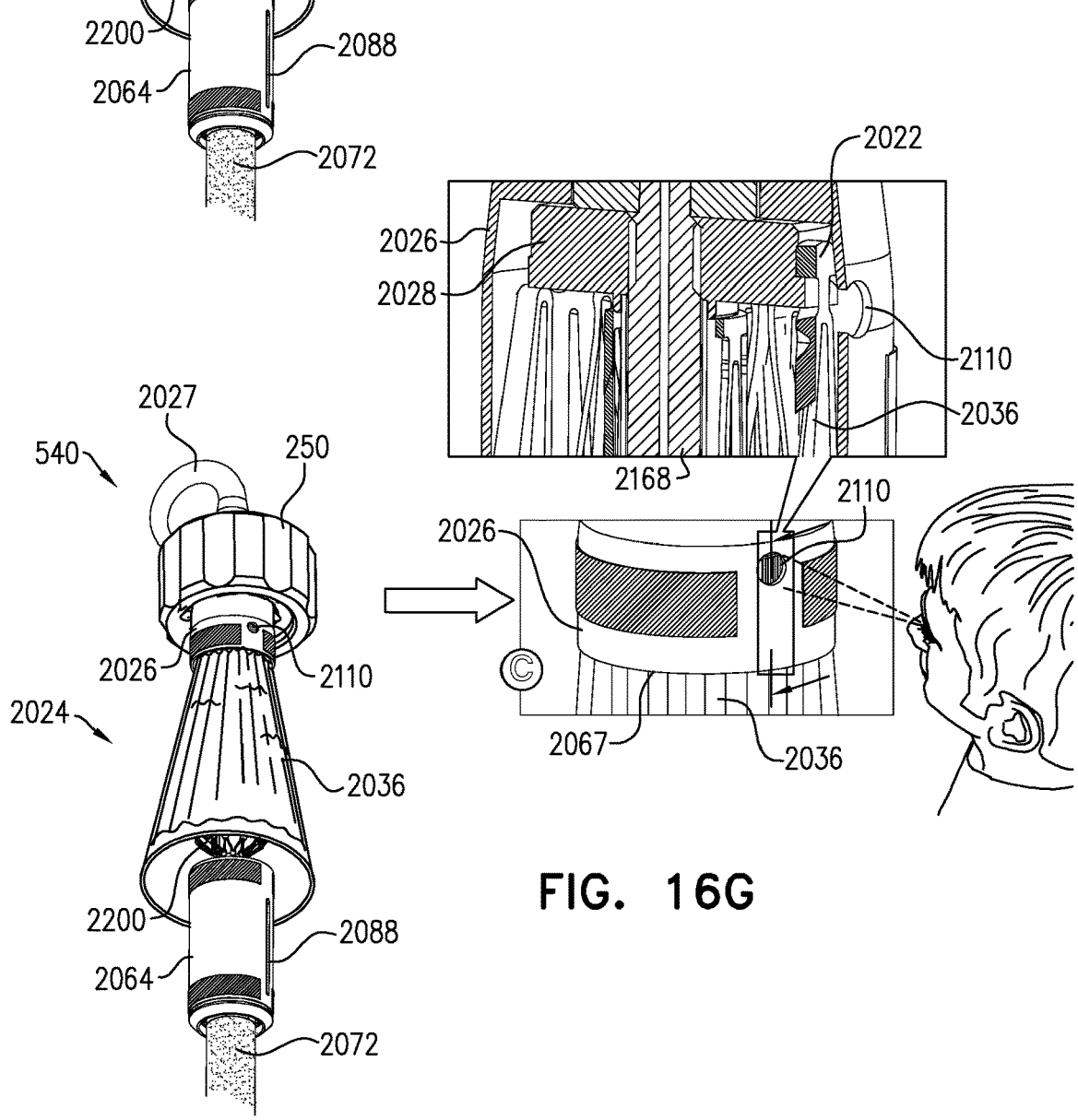
FIG. 16F
FIG. 16G

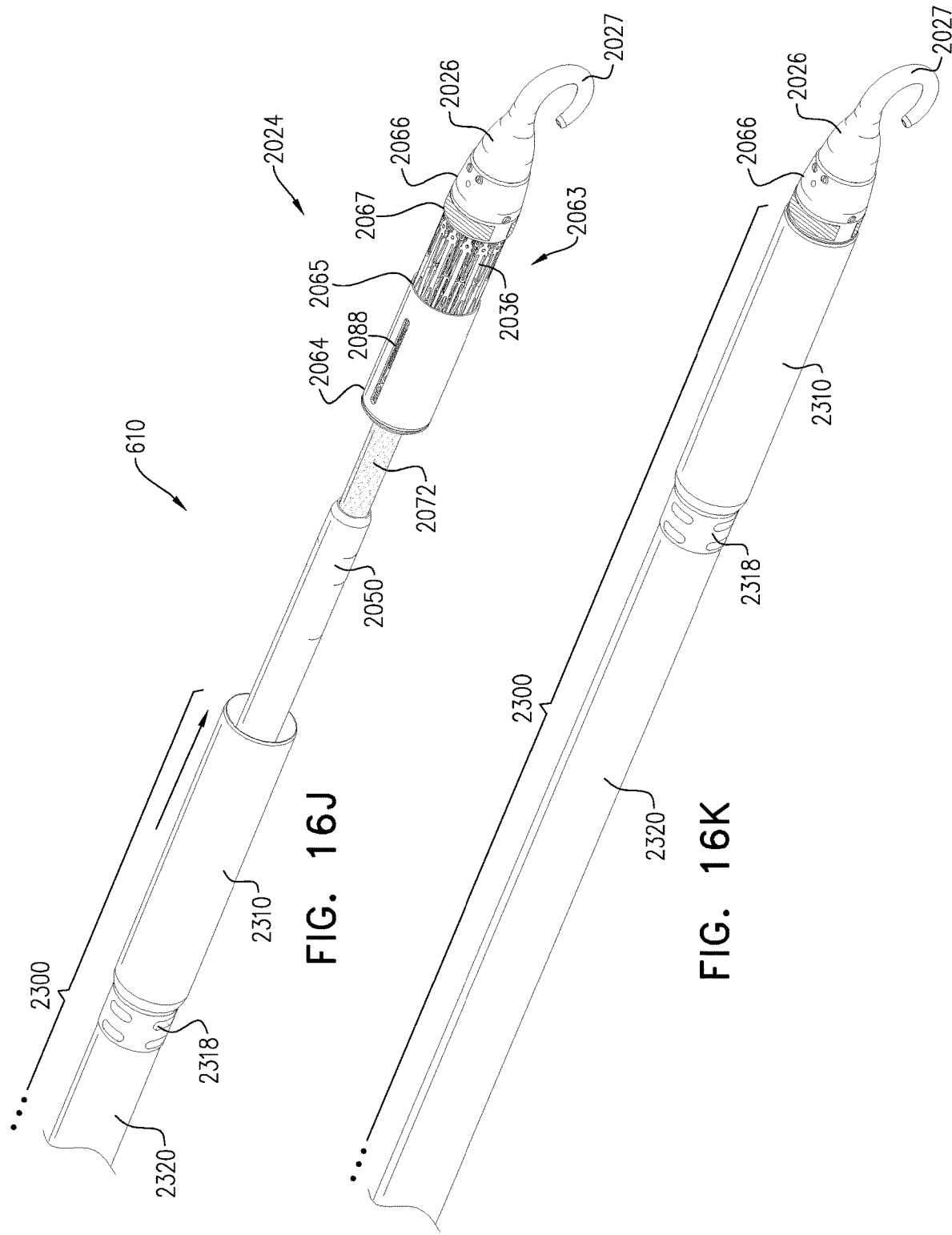

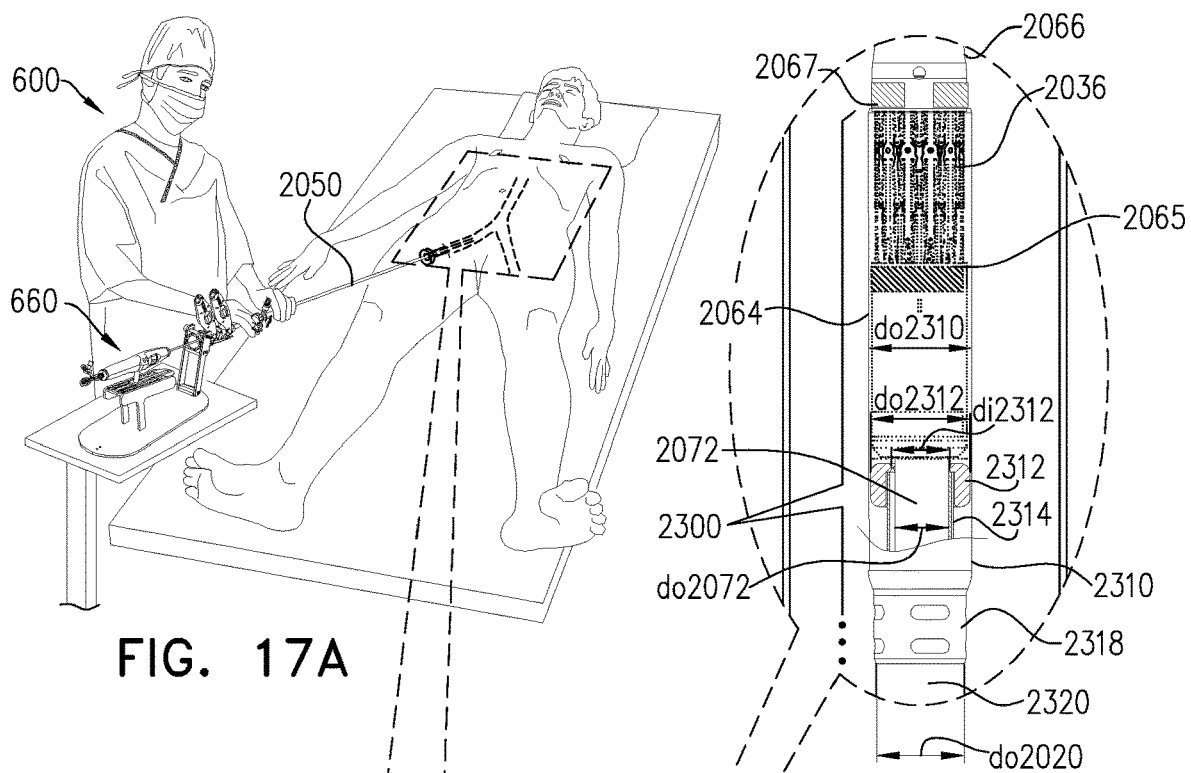
FIG. 17A
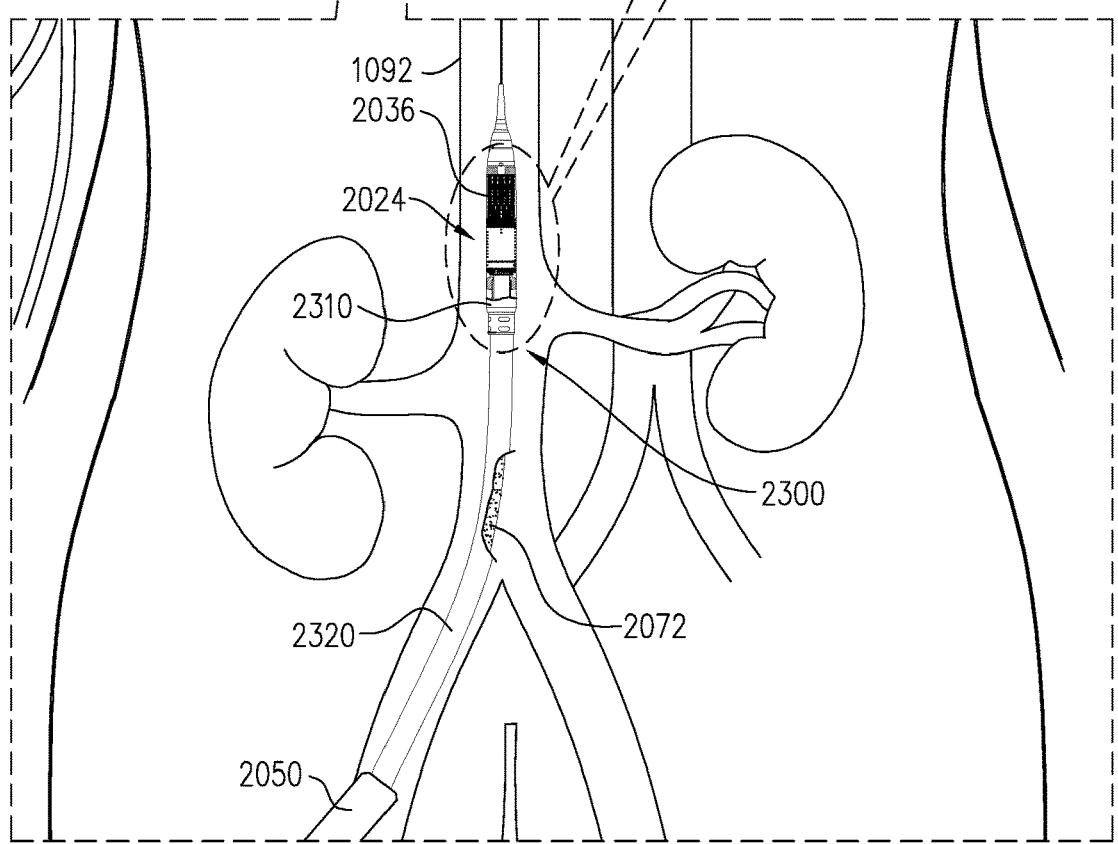

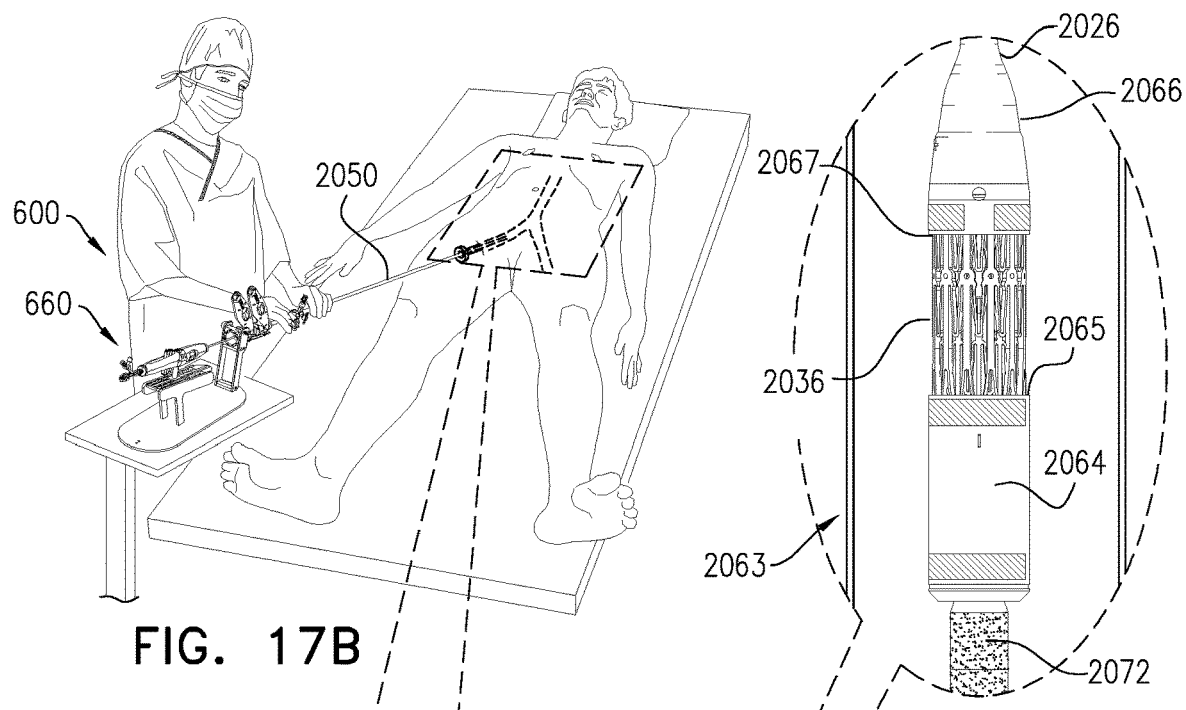
FIG. 17B
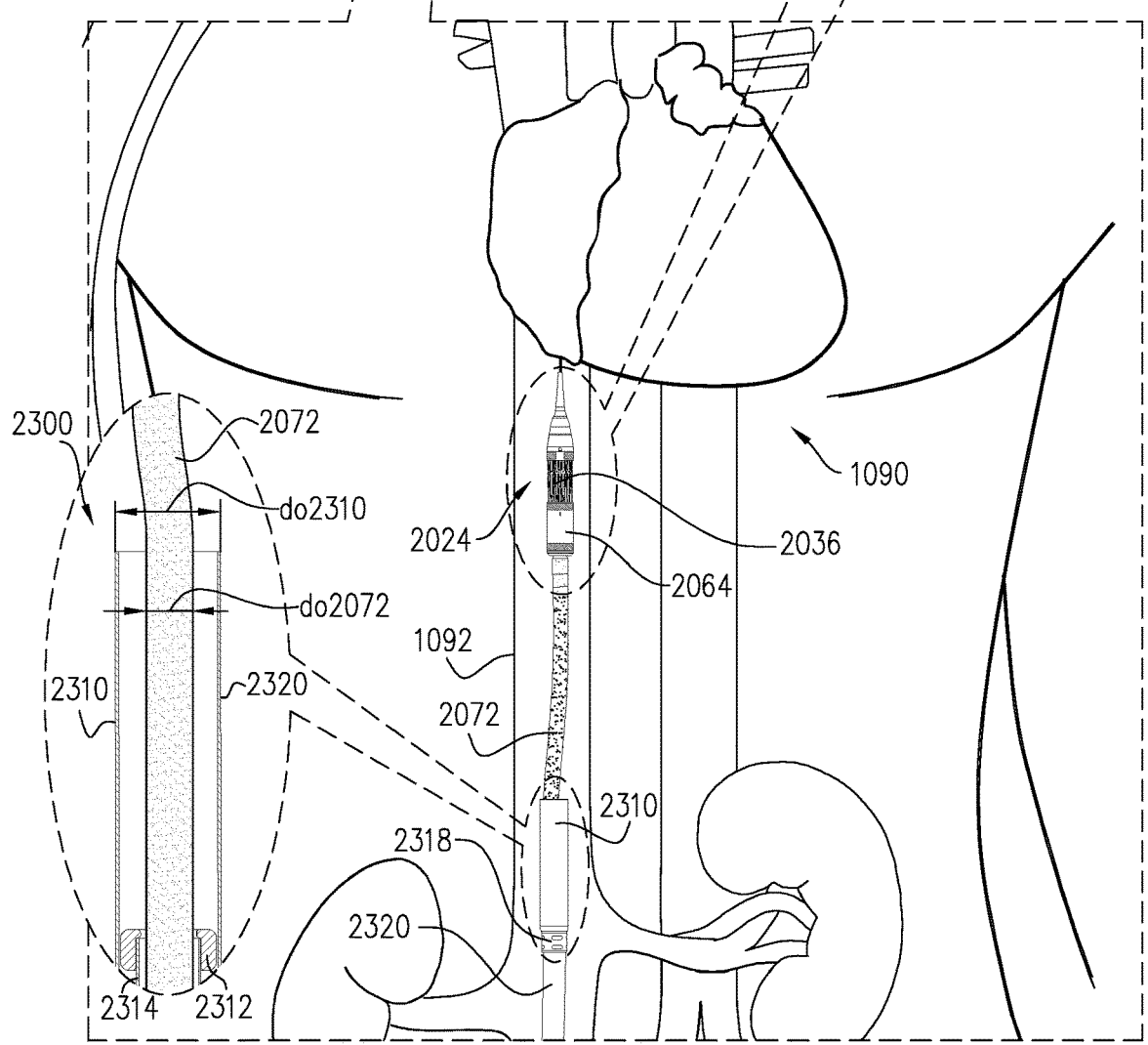

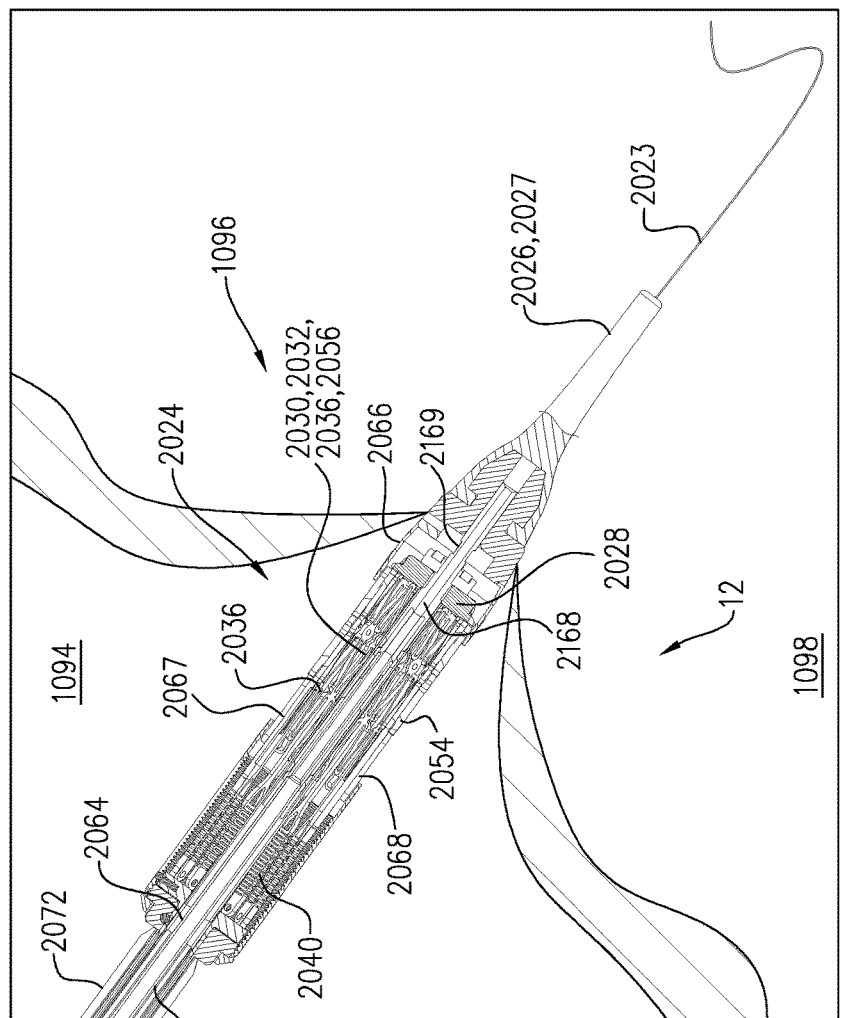
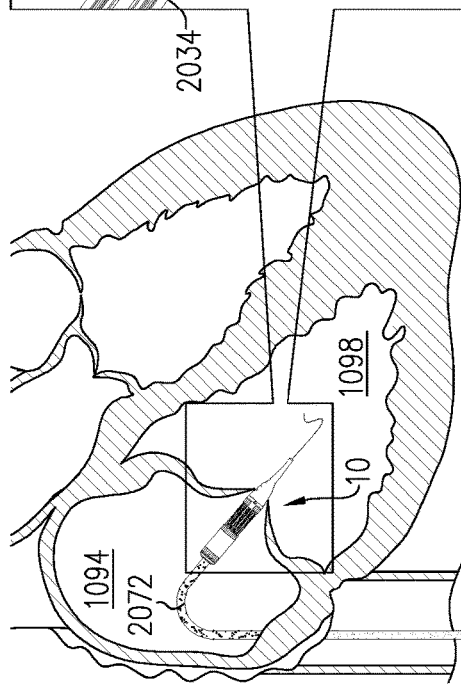
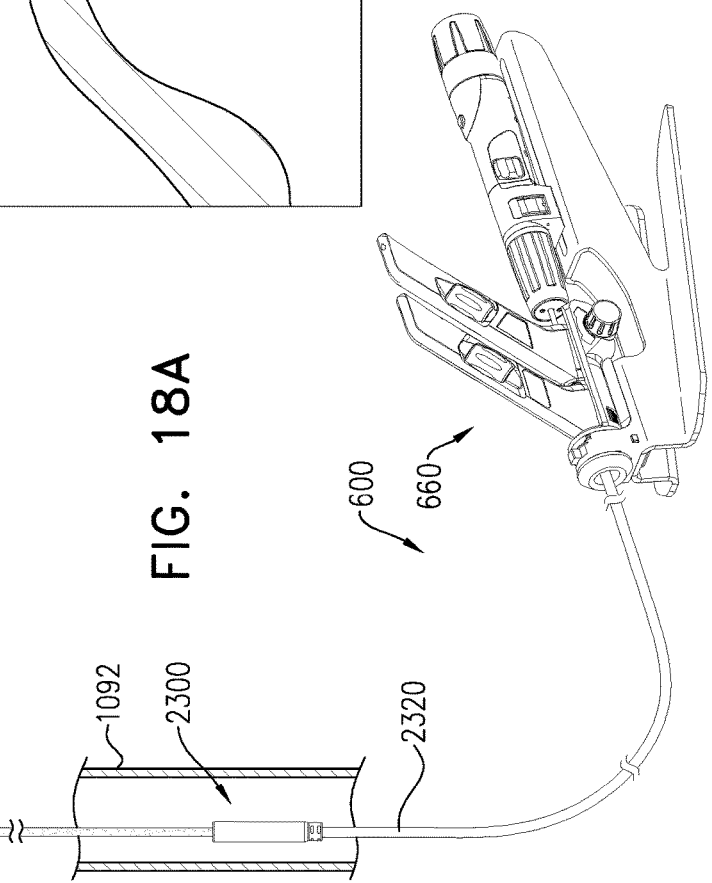
FIG. 18A

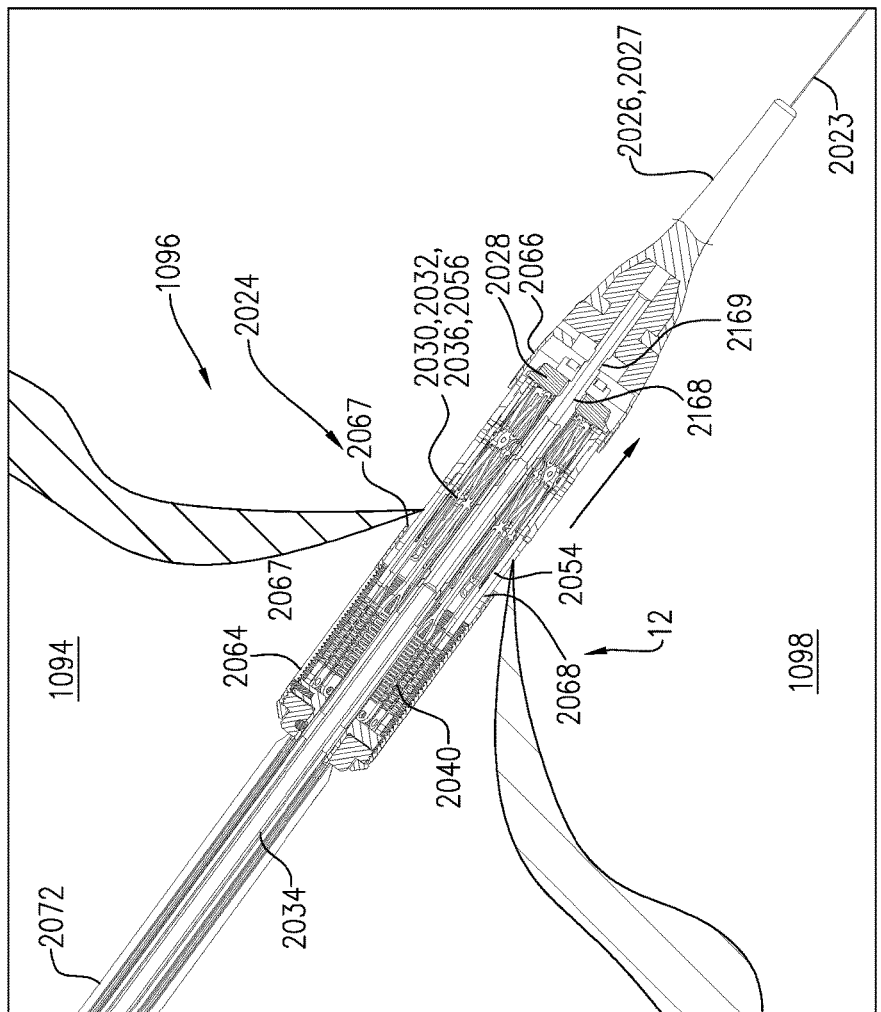
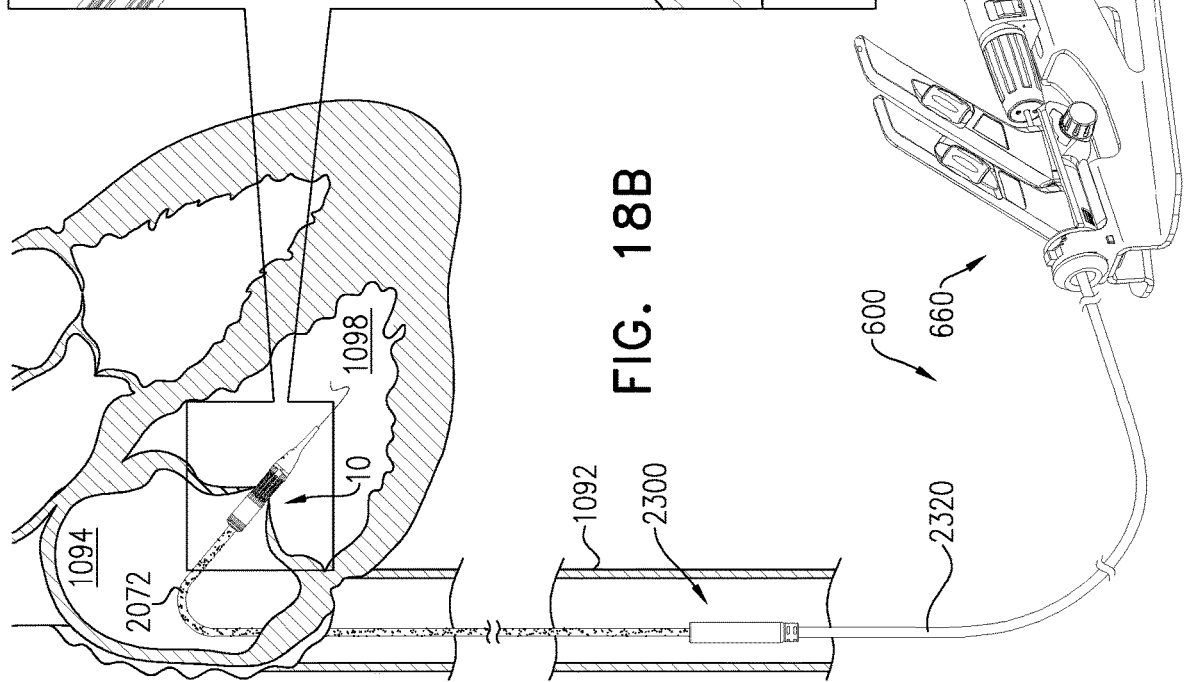
FIG. 18B

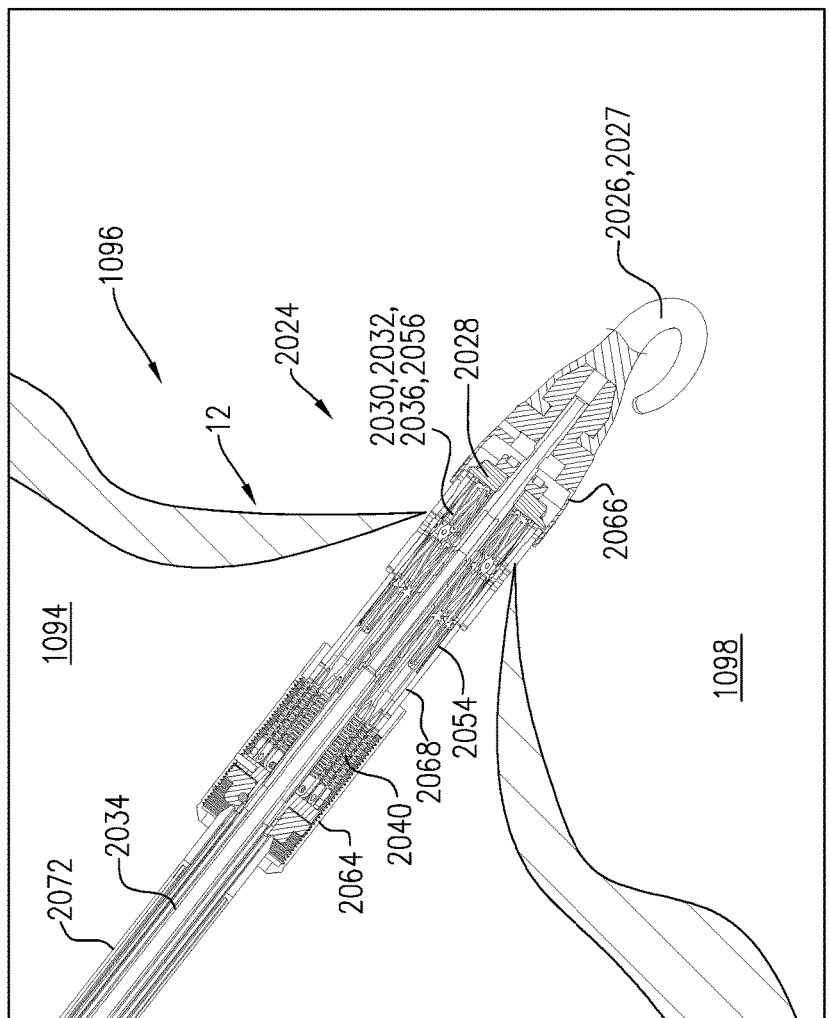
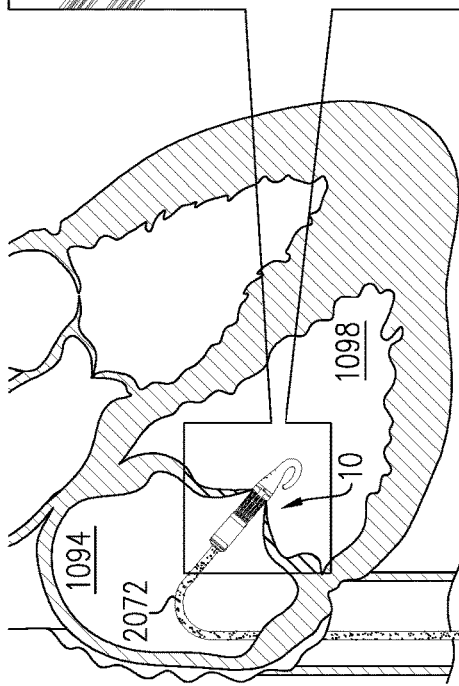
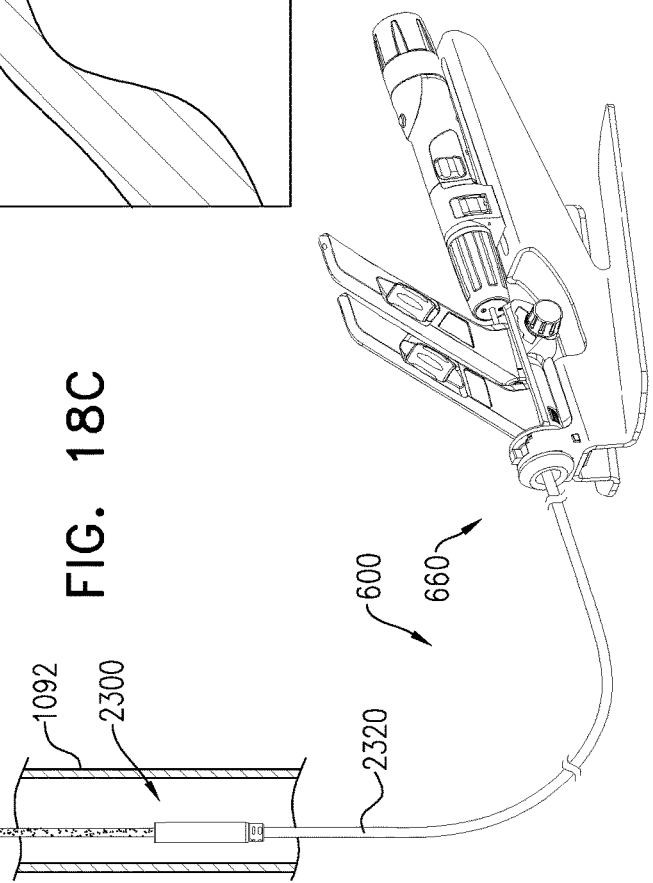
FIG. 18C

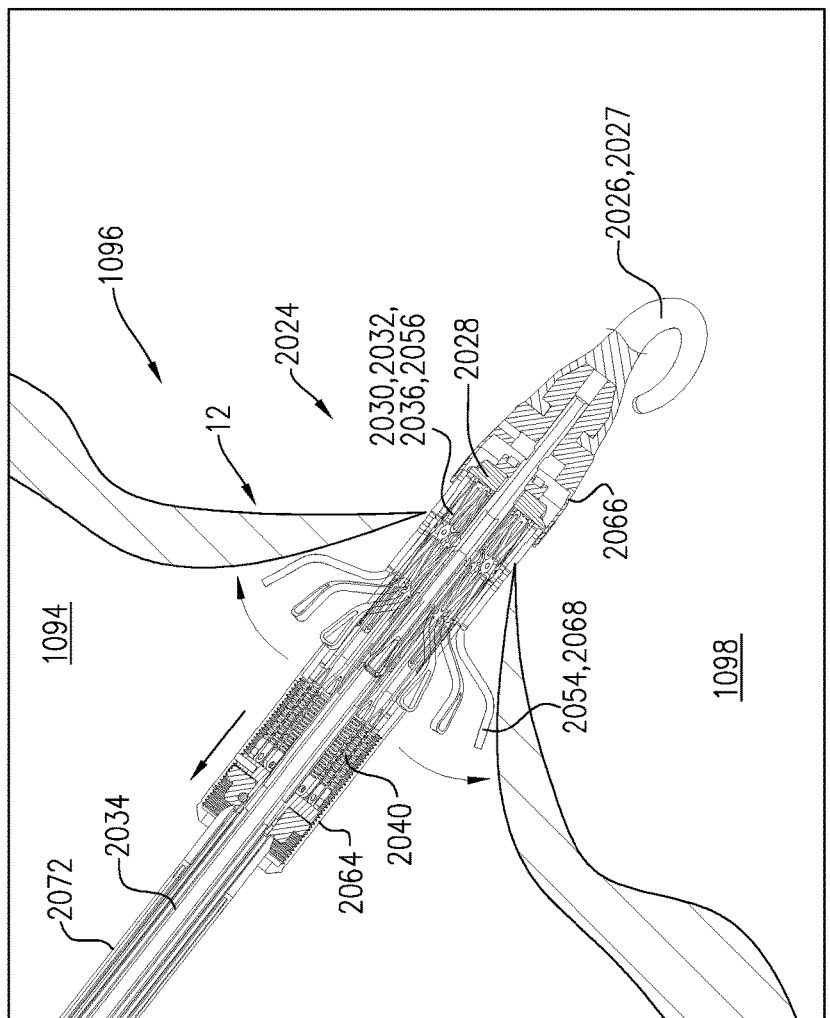
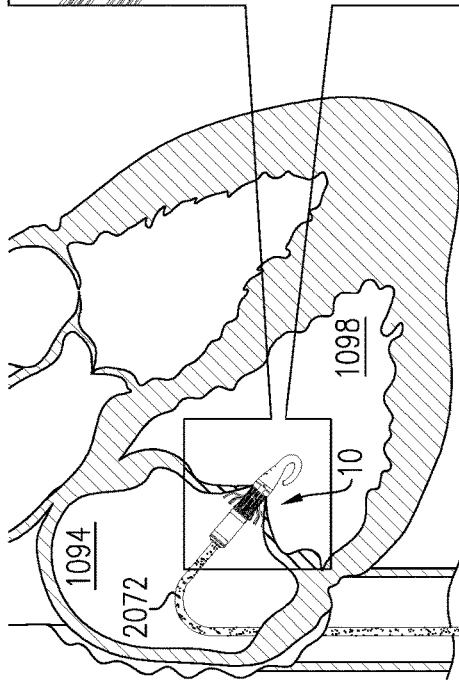
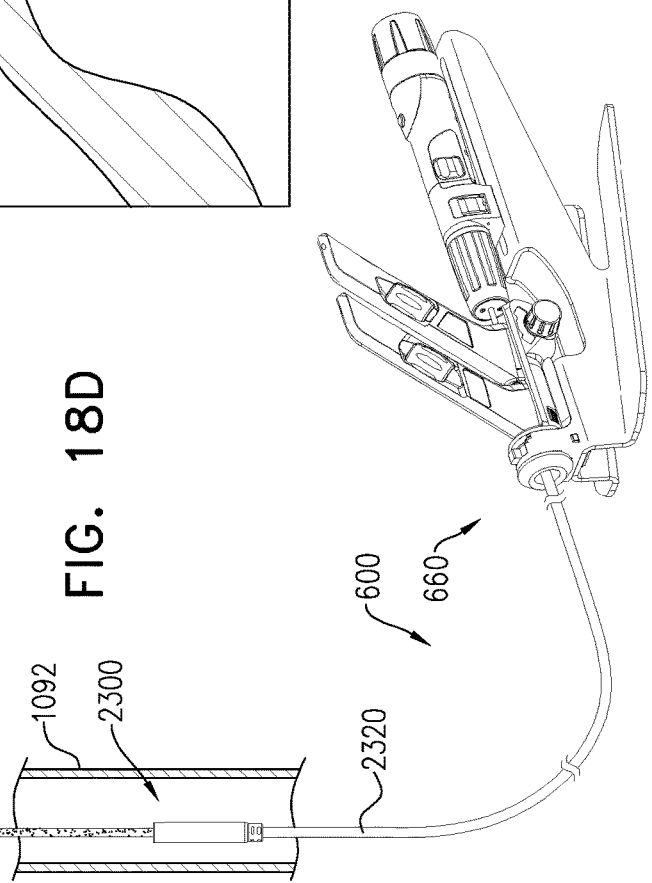
FIG. 18D

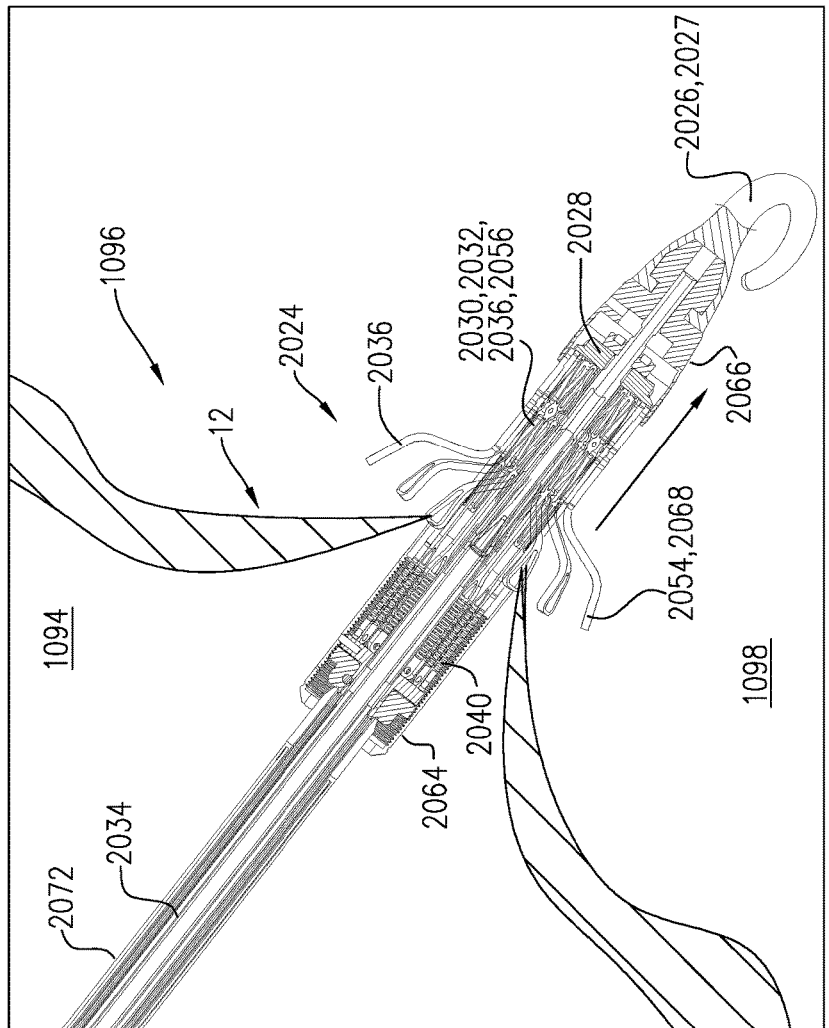
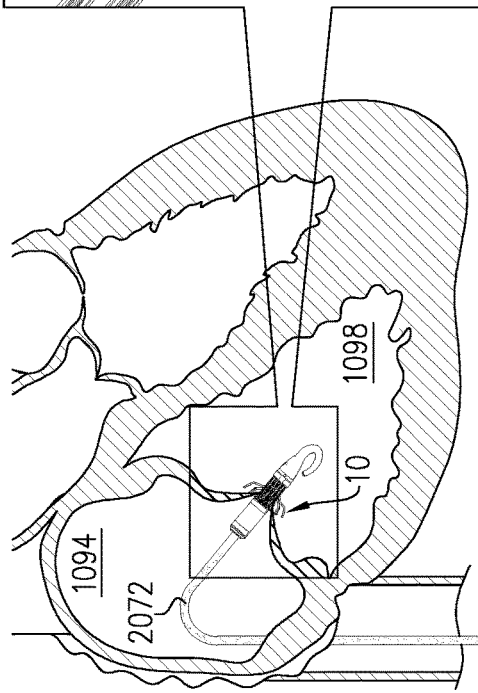
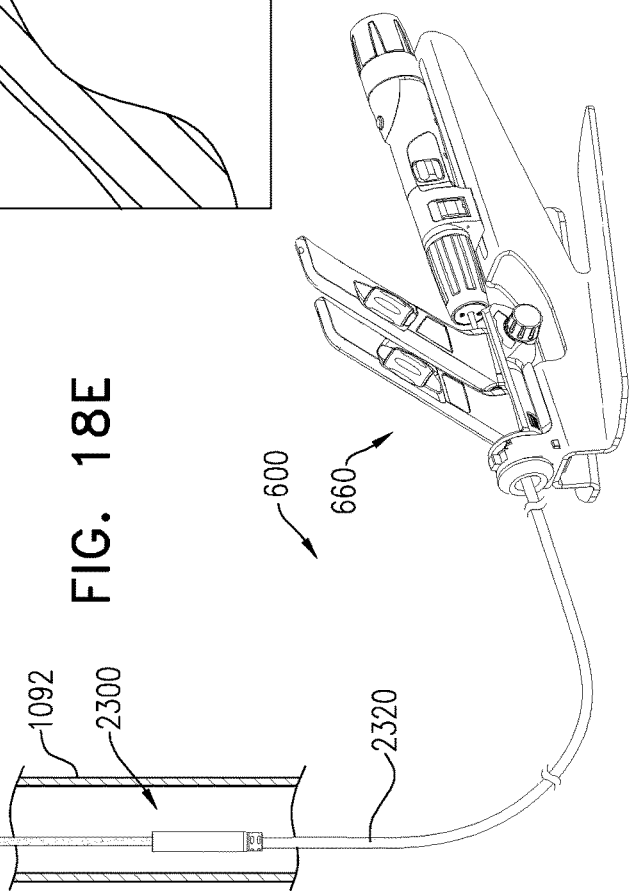
FIG. 18E

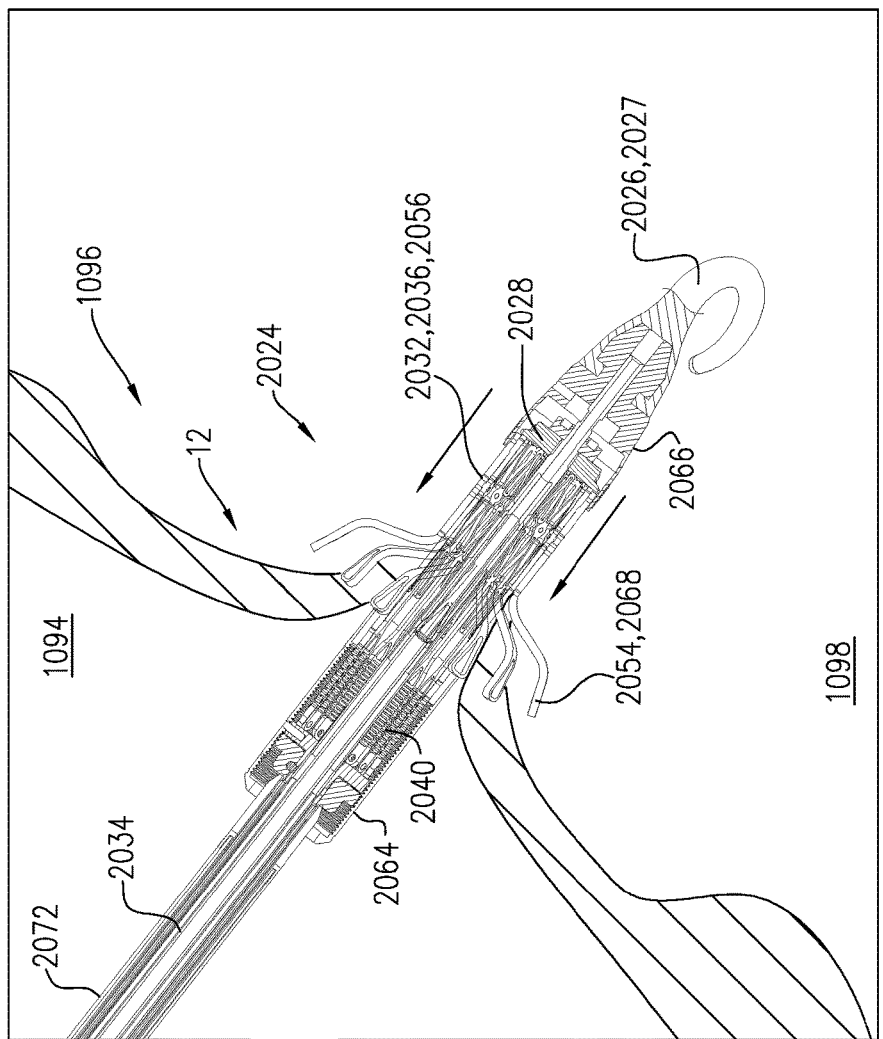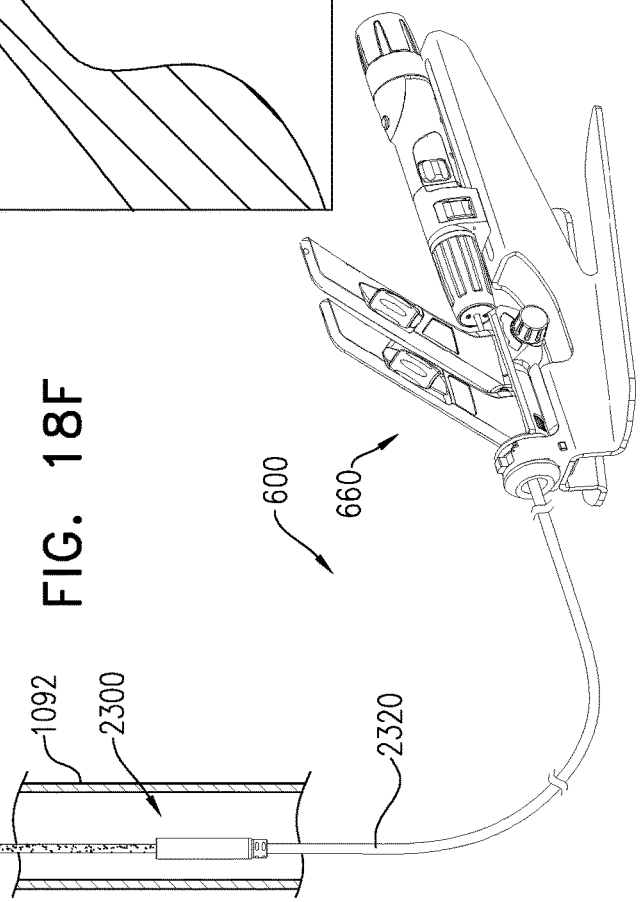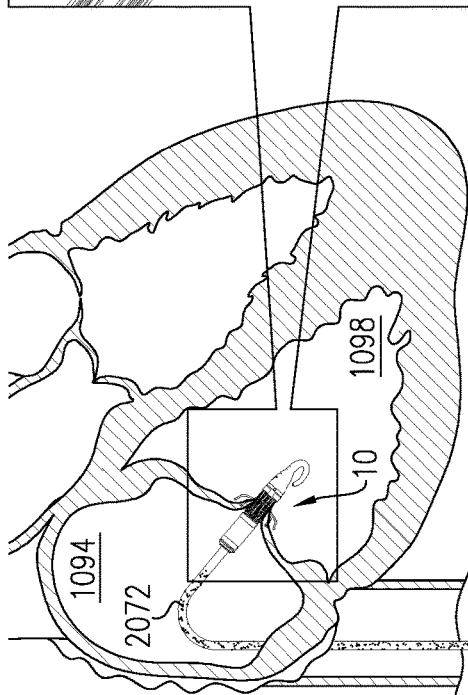
FIG. 18F

TRANSLUMINAL DELIVERY SYSTEM

CROSS-REFERENCE TO RELATED APPLICATIONS

The present application claims priority from U.S. Provisional Application 63/120,808, filed Dec. 3, 2020, entitled, "TRANSLUMINAL DELIVERY SYSTEM," which is assigned to the assignee of the present application and is incorporated herein by reference.

FIELD OF THE INVENTION

Some applications of the present invention relate in general to transluminal implant-delivery systems. More specifically, some applications of the present invention relate to prosthetic heart valves, and transluminal delivery systems therefor.

BACKGROUND

Dilation of the annulus of a heart valve, such as that caused by ischemic heart disease, prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF THE INVENTION

Applications of the present invention are directed to apparatus and methods for delivering an implant to a subject.

For some applications, aspects of the present invention include a transluminal delivery tool that includes a multi-catheter system and an implantation instrument. The implantation instrument has a distal part that is configured to be advanced into the subject, as well as a proximal part that includes an extracorporeal control system.

The catheter system typically includes a first catheter unit and a second catheter unit, each catheter unit including a respective catheter that is mounted at a proximal end thereof to a respective handle. Selective adjustment of the axial and/or rotational position of each handle facilitates adjustment of the axial and/or rotational position of the corresponding catheter. Typically, the respective handles, and the proximal portion of the implantation instrument, are mounted on a mount for stabilization during use.

For some applications, a first catheter extends distally from within a second catheter. For some such applications, sliding a first-catheter distal portion distally over a second-catheter distal portion, ensheathes the second-catheter distal portion within the first-catheter distal portion, and sliding the first-catheter distal portion proximally over the second-catheter distal portion exposes the second-catheter distal portion from the first catheter.

Typically for such applications, actuation of a first-catheter controller actively bends the first-catheter distal portion via a first-catheter control element, and actuation of a second-controller actively bends a second-catheter distal portion via a second-catheter control element.

For some applications, each control element includes a pull wire that extends from a respective controller, through a secondary lumen of the respective catheter, to a distal portion of the catheter, to which the pull wire is fixed.

For some applications, each catheter (e.g., a distal end thereof) is bendable, by actuation of the respective controller, along a respective steering plane. For some such applications, the second catheter is rotationally oriented with respect to the first catheter such that, while the first-catheter distal end is bent in a first-catheter steering plane, bending of the second-catheter distal end causes the second-catheter distal end to rotate with respect to the first-catheter distal end such that the second-catheter steering plane moves toward being perpendicular to the fist-catheter steering plane.

For some applications, a distal part of the second catheter is coupled to a capsule assembly. For some such applications, the capsule assembly includes a proximal capsule and a distal capsule. For example, each capsule may have a respective open end that faces the open end of the other capsule.

For some applications, the distal part of the delivery tool includes a plurality of coaxial tubular members that extend distally from the proximal portion of the instrument (e.g., through the second catheter of the catheter system). Typically for such applications, a capsule catheter extends distally through the second catheter and out an open distal end of the second catheter. Further typically for such applications, a shaft extends distally from the proximal portion of the delivery tool, through the capsule catheter and out of the open end of the proximal capsule. For example, a mount (e.g., to which the implant may be engaged) may be fixedly coupled to a distal end of the shaft.

For some such applications, a rod extends out of a distal end of the shaft, such that a distal portion of the rod is disposed outside of the distal end of the shaft. Typically for such applications, the rod is operatively coupled to the shaft such that the rod may be screwed through the shaft.

Typically, the implant may be ensheathed (e.g., restrained from expanding) within the capsule assembly. For some applications, the implant comprises a proximal-implant portion, a distal-implant portion and a flange. Typically for such applications, the implant is ensheathed during delivery of the delivery tool such that the proximal-implant portion and at least a flange end-portion of the flange are restrained within the proximal capsule. Further typically for such applications, the distal-implant portion of the implant is restrained within the distal capsule.

For some applications, the implant may be unsheathed from the distal capsule by moving the distal capsule linearly off of the implant (e.g., without screwing the distal capsule with respect to the rod). For some such applications, the distal capsule is rotationally coupled to the distal portion of the rod, such that rotation of the rod does not rotate the distal capsule. For example, the distal capsule may be advanced distally off of the implant by screwing the rod through the shaft while the distal capsule is axially locked with respect to the rod, yet rotationally coupled to the rod.

For some such applications, the capsule assembly includes a plurality of pins that are axially aligned with a circumferential recess defined by the rod. Typically for such applications, the pins inhibit rotation of the distal capsule by traversing the distal capsule sufficiently closely to the rod to inhibit axial movement of the rod with respect to the pins, while providing sufficient clearance between the pins and the rod (e.g., the recess defined thereby) to allow the rod to rotate with respect to the pins.

For some applications, the distal capsule is reversibly rotationally lockable or unlockable with respect to the rod, such that the implant may be ensheathed in the distal capsule by moving the distal capsule helically over the implant, and unsheathed by moving the distal capsule linearly off of the implant. For example, an accessory may be introduced (e.g., defining a detent shaped to fit into the recess defined by the rod and the distal capsule) configured to rotationally lock the rod with respect to the distal capsule. In this way, the accessory may be attached for ensheathing of the implant within the distal capsule, and the accessory subsequently removed before unsheathing (e.g., before transluminal delivery) of the implant.

For some applications, aspects of the present invention include a delivery system that comprises a delivery tool and the prosthetic valve. For some such applications, the delivery tool is used to deliver the prosthetic valve to a native valve of a heart of the subject. For example, the native valve may be a tricuspid valve.

For some applications, the delivery tool has a proximal portion and a distal portion. For some such applications, the distal portion comprises a proximal capsule and a distal capsule, each of the capsules defining a respective open end.

Typically for such applications, the open end of the proximal capsule faces the proximal end of the distal capsule. For some such applications, the open end of the proximal capsule may face the open end of the distal capsule. For example, while the delivery tool is in a delivery state for transluminally delivering the delivery tool to the heart, an inter-capsule gap may separate between the open end of the proximal capsule and the open end of the distal capsule.

For some such applications, the prosthetic valve comprises a tubular portion that defines a lumen, within which a plurality of prosthetic leaflets are disposed. Typically for such applications, the prosthetic valve further comprises an upstream support portion that extends from the tubular portion, and defines a plurality of flanges. Each flange is coupled to the tubular portion at a coupling point, from which the flange extends to flange end-portion.

For some applications, while the delivery tool is in the delivery state, the prosthetic valve is restrained in a compressed state by the delivery tool. For some such applications, while the delivery tool is in the delivery state, the tubular portion of the prosthetic valve is engaged with a mount of the delivery tool. Alternatively or in addition, the prosthetic valve may be engaged with a portion of the shaft, mutans mutandis.

For some applications, w % bile the delivery tool is in the delivery state, the mount and a downstream end of the tubular portion are disposed within the distal capsule, and the upstream support portion and the flange end-portions are disposed within the proximal capsule. Further typically, while the delivery tool is in the delivery state, a segment of the tubular portion is disposed at the inter-capsule gap.

For some applications, the delivery tool is transluminally advanced to a ventricle of the heart, such that the distal capsule is disposed within the ventricle. For some such applications, the delivery tool comprises a flexible sheath, and the sheath is retracted, exposing the proximal capsule from the sheath.

For some applications, the delivery system comprises a guidewire along which the delivery tool is transluminally advanced to the heart. For some such applications, the delivery tool comprises a nosecone having a flexible distal end-portion. For example, the distal end-portion may have a relaxed curled shape, and the distal end-portion may be straightened when the guidewire occupies the distal end-portion.

For some applications, the delivery tool comprises a shaft that comprises a rigid proximal shaft segment that extends from the proximal portion of the delivery tool to the distal portion of the delivery tool. For some such applications, the shaft comprises a flexible shaft segment that extends from the rigid proximal shaft segment to a rigid distal shaft segment. Typically for such applications, the rigid distal shaft segment extends through at least part of the proximal capsule and/or of the distal capsule.

Typically, the proximal capsule is then proximally retracted, such that the flange end-portions are released from the proximal capsule and expand radially outward. For some applications, the delivery tool comprises a disc-assembly comprising a proximal disc that is rotatably coupled to a distal disc. The proximal disc defines outer threading that is complementary to inner threading defined by the proximal capsule. Typically for such applications, rotation of a capsule catheter that is fixedly coupled to the proximal disc, screws the proximal capsule over the disc-assembly, with respect to the mount.

Further typically, the distal portion is then retracted, such that the flange end-portions contact tissue of the native valve. The proximal capsule is then retracted, such that the upstream support portion is released from the proximal capsule, and expands radially outward. In this way, tissue of the native valve is squeezed between the upstream support portion and the flange end-portions.

Subsequently, the distal capsule is advanced with respect to the mount, thereby releasing the mount and the downstream end of the tubular portion from the distal capsule. Thus, the tubular portion expands radially outward at the native valve, such that the prosthetic valve assumes an expanded state.

Subsequently, the proximal capsule is advanced toward the mount, such that the open end of the proximal capsule abuts the distal capsule. For some applications, the open end of the proximal capsule abuts the open end of the distal capsule. For some applications, the distal capsule is retracted toward the mount, prior to advancing the proximal capsule. While the proximal capsule abuts the distal capsule, the distal portion of the delivery tool is retracted through the lumen of the tubular portion.

There is therefore provided, in accordance with an application of the present invention, an apparatus for use at a heart of a subject, the apparatus including:

a delivery tool dimensioned for percutaneous delivery to the heart, the delivery tool having a distal portion that defines a central longitudinal axis at the distal portion and includes:
 a shaft; and
 a proximal capsule and a distal capsule, each of the capsules:
  having a respective open end, the open end of the proximal capsule facing the open end of the distal capsule, and
  coupled to the shaft in a manner that allows axial movement of the capsule with respect to the shaft, along the central longitudinal axis at the distal portion; and
 a prosthetic heart valve including:
 a tubular portion that defines a lumen; and
 a plurality of prosthetic leaflets disposed within the lumen,
 the prosthetic heart valve is restrainable in a compressed state by the delivery tool, such that a downstream end of the tubular portion is disposed within the distal capsule, and
 the distal capsule is shaped so as to define an opening for visualizing ensheathing of at least a portion of the downstream end of the tubular portion within the distal capsule.

In an application, the opening defines a window.

In an application, the delivery tool further includes a mount surrounding the shaft and configured to engage the downstream end of the tubular portion, and the opening is configured to allow visualizing of the mount and the downstream end of the tubular portion.

In an application, the mount is shaped so as to define one or more slots, and the downstream end of the tubular portion is shaped so as to define one or more adaptors, each one of the adaptors being configured to be received within a respective one of the one or more slots so as to facilitate engaging between the mount and the downstream end of the tubular portion.

In an application, in the compressed state of the prosthetic heart valve, the distal capsule maintains coupling between the downstream end of the tubular portion and the mount by surrounding the one or more adaptors and maintaining each one of the one or more adaptors within the respective slot of the mount.

In an application, the prosthetic heart valve includes:
an upstream support portion that extends from the tubular portion; and
a plurality of flanges, each of the flanges coupled to the tubular portion at a respective coupling point that is downstream of the upstream support portion, and extends from the coupling point to a respective flange end-portion of the flange.

In an application, the prosthetic heart valve is restrainable in the compressed state by the delivery tool such that the upstream support portion and the flange end-portions are disposed within the proximal capsule.

There is additionally provided, in accordance with an application of the present invention, a method for preparing a prosthetic heart valve for implantation, the method including:
using a crimping tool, crimping the prosthetic heart valve around a distal portion of a shaft of a delivery tool; and
subsequently to the crimping, ensheathing the prosthetic heart valve in a capsule by extracorporeally (i) coupling an ensheathing tool directly to the distal portion and (ii) applying a rotational force to the ensheathing tool to effect linear movement of the capsule with respect to the prosthetic heart valve.

In an application, the method further includes:
subsequently to the ensheathing, advancing the ensheathed prosthetic heart valve and the distal portion of the delivery tool into a subject, while retaining a proximal portion of the delivery tool outside of the subject; and
subsequently, deploying the prosthetic heart valve within a heart of the subject from the capsule by extracorporeally applying an unsheathing force to a controller at the proximal portion of the delivery tool.

In an application:
the capsule is a distal capsule,
the delivery tool further includes a proximal capsule, each of the proximal and distal capsules:
having a respective open end, the open end of the proximal capsule facing the open end of the distal capsule, and
being coupled to the shaft in a manner that allows axial movement of the capsule with respect to the shaft, along a central longitudinal axis at the distal portion; and ensheathing the prosthetic heart valve in the capsule includes:
ensheathing a downstream end of the prosthetic heart valve in the distal capsule; and
subsequently, ensheathing an upstream end of the prosthetic heart valve in the proximal capsule.

In an application, the ensheathing tool is a distal-capsule ensheathing tool and ensheathing the downstream end of the prosthetic heart valve includes applying a first ensheathing force to the distal portion of the delivery tool using the distal-capsule ensheathing tool directly coupled to the distal capsule.

In an application, the application further includes coupling the distal-capsule ensheathing tool directly to the distal capsule.

In an application, ensheathing the upstream end of the prosthetic heart valve in the proximal capsule includes applying a second ensheathing force to the distal portion of the delivery tool using a proximal-capsule ensheathing tool directly coupled to the distal portion.

In an application, the method further includes:
subsequently to the ensheathing the of the upstream end of the prosthetic heart valve, advancing the ensheathed prosthetic heart valve and the distal portion of the delivery tool into a heart of a subject, while retaining a proximal portion of the delivery tool outside of the subject; and
subsequently, deploying the prosthetic heart valve within the heart of the subject from the proximal and distal capsules by extracorporeally applying an unsheathing force to a controller at the proximal portion of the delivery tool.

In an application, the method further includes, during the ensheathing of the downstream end of the prosthetic heart valve in the distal capsule, visualizing the ensheathing of at least a portion of the downstream end of the prosthetic heart valve within the distal capsule through an opening defined in the distal capsule for visualizing the ensheathing.

In an application, the delivery tool further includes a mount surrounding the shaft and configured to engage the downstream end of the prosthetic heart valve, and visualizing the ensheathing of the at least the portion of the downstream end of the prosthetic heart valve within the distal capsule includes visualizing the mount and the downstream end of the prosthetic heart valve.

In an application:
the mount is shaped so as to define one or more slots,
the downstream end of the prosthetic heart valve is shaped so as to define one or more adaptors, each one of the adaptors being configured to be received within a respective one of the one or more slots so as to facilitate engaging between the mount and the downstream end of the prosthetic heart valve, and
ensheathing the downstream end of the prosthetic heart valve in the distal capsule includes ensheathing the downstream end of the prosthetic heart valve such that the one or more adapters fit within the one or more slots.

In an application, ensheathing the downstream end of the prosthetic heart valve in the distal capsule includes maintaining coupling between the downstream end of the prosthetic heart valve and the mount by the ensheathing of the downstream end of the prosthetic heart valve in the distal capsule.

There is further provided, in accordance with an application of the present invention, a method for preparing a prosthetic heart valve for implantation, the method including:
using a crimping tool, crimping the prosthetic heart valve around a distal portion of a shaft of a delivery tool; and
subsequently to the crimping, ensheathing a downstream end of the prosthetic heart valve in a capsule, and during the ensheathing, visualizing the ensheathing of at least a portion of the downstream end of the prosthetic heart valve within the capsule through an opening defined in the capsule for visualizing the ensheathing.

In an application:

the capsule is a distal capsule, and the opening is defined in the distal capsule, the delivery tool further includes a proximal capsule, each of the capsules:

having a respective open end, the open end of the proximal capsule facing the open end of the distal capsule, and being coupled to the shaft in a manner that allows axial movement of the capsule with respect to the shaft, along a central longitudinal axis at the distal portion; and ensheathing the prosthetic heart valve in the capsule includes:

ensheathing a downstream end of the prosthetic heart valve in the distal capsule; and subsequently, ensheathing an upstream end of the prosthetic heart valve in the proximal capsule subsequently to the ensheathing of the downstream end of the prosthetic heart valve in the distal capsule.

In an application, ensheathing the downstream end of the prosthetic heart valve includes applying a first ensheathing force to the distal portion of the delivery tool using a distal-capsule ensheathing tool directly coupled to the distal capsule.

In an application, the method further includes coupling the distal-capsule ensheathing tool directly to the distal capsule.

In an application, the method further includes ensheathing an upstream end of the prosthetic heart valve in the proximal capsule subsequently to the ensheathing of the downstream end of the prosthetic heart valve in the distal capsule by applying a second ensheathing force to the distal portion of the delivery tool using a proximal-capsule ensheathing tool directly coupled to the distal portion.

In an application, the method further includes:

subsequently to the ensheathing the of the upstream end of the prosthetic heart valve, advancing the ensheathed prosthetic heart valve and the distal portion of the delivery tool into a heart of a subject, while retaining a proximal portion of the delivery tool outside of the subject; and subsequently, deploying the prosthetic heart valve within the heart of the subject from the capsule by extracorporeally applying an unsheathing force to a controller at the proximal portion of the delivery tool.

In an application, the method further includes the delivery tool further includes a mount surrounding the shaft and configured to engage the downstream end of the prosthetic heart valve, and visualizing the ensheathing of the at least the portion of the downstream end of the prosthetic heart valve within the distal capsule includes visualizing the mount and the downstream end of the prosthetic heart valve.

In an application:

the mount is shaped so as to define one or more slots, the downstream end of the prosthetic heart valve is shaped so as to define one or more adaptors, each one of the adaptors being configured to be received within a respective one of the one or more slots so as to facilitate engaging between the mount and the downstream end of the prosthetic heart valve, and ensheathing the downstream end of the prosthetic heart valve in the distal capsule includes crimping the downstream end of the prosthetic heart valve such that the one or more adapters fit within the one or more slots.

In an application, ensheathing the downstream end of the prosthetic heart valve in the distal capsule includes maintaining coupling between the downstream end of the prosthetic heart valve and the mount by the ensheathing of the downstream end of the prosthetic heart valve in the distal capsule.

There is also provided, in accordance with ab application of the present invention, apparatus, including:

a delivery tool for use with a prosthetic heart valve, the delivery tool including:

a tubular shaft:

a rod:

extending from within the shaft out of a distal end of the shaft such that a distal portion of the rod is disposed outside of the distal end of the shaft, and operatively coupled to the shaft such that rotational movement of the rod with respect to the shaft is converted into axial movement of the rod with respect to the shaft; and a proximal capsule and a distal capsule, each of the capsules:

having a respective open end, the open end of the proximal capsule facing the open end of the distal capsule, and coupled to the shaft in a manner that allows axial movement of the capsule with respect to the shaft, along a central longitudinal axis at the distal portion, and a first accessory, including a detent, the first accessory being couplable to the distal capsule such that the detent rotationally locks the distal capsule to the rod; and a second accessory being operatively couplable to the proximal capsule such that rotational movement of the second accessory with respect to the shaft is converted into axial movement of the distal capsule with respect to the shaft.

In an application, the prosthetic heart valve includes:

a tubular portion that defines a lumen; and a plurality of prosthetic leaflets disposed within the lumen, the prosthetic heart valve is restrainable in a compressed state by the delivery tool, such that a downstream end of the tubular portion is disposed within the distal capsule, and an upstream end of the tubular portion is disposed within the proximal capsule.

In an application, the second accessory includes a cuff shaped to surround the shaft, and the cuff includes:

a user grip for facilitating rotating of the second accessory with respect to the shaft, and a distal coupling portion configured to reversibly couple the second accessory to the distal portion.

In an application, the distal coupling portion is sized to fit within an opening in the distal portion so as to couple the second accessory to the distal portion.

In an application, the distal coupling portion includes one or more pins shaped so as to fit within respective holes defined by the distal portion, to couple the second accessory to the distal portion.

There is yet further provided, in accordance with an application of the present invention, apparatus for use with a prosthetic heart valve, the apparatus including:

a delivery tool for delivering the prosthetic heart valve to a heart of a subject, the delivery tool including:

a catheter system including one or more catheters, the catheter system having a catheter-system outer diameter;

a housing for housing the prosthetic heart valve, the housing being disposed at a distal portion of the catheter system and having a housing inner diameter that is greater than a diameter of at least one of the catheters of the catheter system;

a catheter alignment mechanism including:
   an elongate oversheath shaped so as to define an elongate-oversheath lumen for slidable passage therethrough of the catheter system;
   a distal supplemental tube coupled to a distal end of the elongate oversheath, the supplemental tube shaped so as to define a supplemental-tube lumen sized for encasing at least a portion of the housing during (1) at least a portion of transluminally delivering the distal portion of the delivery tool to the heart, and (2) retracting of the housing out of a body of the subject;
   an intermediate alignment tube disposed between the oversheath and the one or more catheters of the catheter system during the delivery state; and
   an aligner disposed between the intermediate alignment tube and the distal supplemental tube, and configured to align the one or more catheters of the catheter system with respect to the distal supplemental tube.

In an application, the aligner includes a ring.

In an application, the aligner and a distal portion of the intermediate alignment tube are axially slidable within the distal supplemental-tube lumen from a proximal-to-distal direction by distally advancing the intermediate alignment tube along the one or more catheters to distally advance the aligner in order to align the one or more catheters of the catheter system with respect to the distal supplemental tube prior to the encasing of the at least the portion of the housing within the supplemental tube.

In an application, the housing has a housing outer diameter that is larger than an outer diameter of at least one of the catheters of the catheter system.

In an application, the distal supplemental tube has a supplemental-tube outer diameter that is larger than an outer diameter of the elongate oversheath.

In an application, the elongate oversheath has an elongate-oversheath outer diameter, and the distal supplemental tube has a supplemental-tube outer diameter that is larger than the elongate-oversheath outer diameter.

In an application, the intermediate alignment tube is slidable within the elongate-oversheath lumen and within the supplemental-tube lumen such that the aligner is slidable between the supplemental tube and the one or more catheters.

In an application, the aligner includes a ring and has an inner diameter that is 0.05-3.0 mm larger than an outer diameter of a largest catheter of the one or more catheters.

In an application, the distal supplemental tube has a supplemental-tube inner diameter, and the intermediate alignment tube has an intermediate-alignment-tube outer diameter that is 1.9-5.5 mm smaller than the supplemental-tube inner diameter.

In an application:
the housing includes a proximal capsule and a distal capsule, each of the capsules having a respective open end, the open end of the proximal capsule facing the open end of the distal capsule,
the prosthetic heart valve is restrainable in a compressed state by the delivery tool within the housing in a manner in which an upstream portion of the prosthetic heart valve is ensheathed by the proximal capsule and a downstream portion of the prosthetic heart valve is ensheathed by the distal capsule, and
the supplemental-tube lumen is sized for encasing the proximal capsule and at least a proximal portion of the distal capsule.

In an application, the delivery tool is configured such that during the delivery state, an inter-capsule gap separates the open end of the proximal capsule from the open end of the distal capsule, and a segment of the prosthetic heart valve is disposed at the inter-capsule gap.

In an application:
during entry of the delivery tool within the body of the subject, the supplemental tube surrounds the proximal capsule and the at least the proximal portion of the distal capsule, and the segment of the prosthetic heart valve disposed at the inter-capsule gap, and
subsequently to the entry, the proximal capsule and the at least the proximal portion of the distal capsule and the prosthetic heart valve are exposed form within the supplemental tube and are advanceable toward the heart by advancement of at least one catheter of the catheter system.

In an application, the prosthetic heart valve includes:
a tubular portion that defines a lumen;
a plurality of prosthetic leaflets disposed within the lumen:
an upstream support portion that extends from the tubular portion; and
a plurality of flanges, each of the flanges coupled to the tubular portion at a respective coupling point that is downstream of the upstream support portion, and extending from the coupling point to a respective flange end-portion of the flange.

In an application, the distal portion is configured such that while the delivery tool is in the delivery state, the prosthetic heart valve is engaged with the delivery tool such that:
a downstream end of the tubular portion is disposed within the distal capsule, and
the upstream support portion and the flange end-portions are disposed within the proximal capsule.

In an application, during entry of the delivery tool within the body of the subject, the supplemental tube surrounds the proximal capsule and at least a proximal portion of the distal capsule.

In an application, during extracting of the delivery tool from within the body of the subject, the supplemental tube surrounds the proximal capsule a distal end of the supplemental tube abuts the distal capsule.

There is also provided, in accordance with an application of the present invention, a method, including:
using a delivery tool, introducing into vasculature of a subject a prosthetic heart valve configured for implantation in a heart of the subject, the delivery tool including:
   a catheter system including one or more catheters, the catheter system having a catheter-system outer diameter;
   a housing for housing the prosthetic heart valve, the housing being disposed at a distal portion of the catheter system and having a housing inner diameter that is greater than a diameter of at least one of the catheters of the catheter system;
   a catheter alignment mechanism including:
      an elongate oversheath shaped so as to define an elongate-oversheath lumen for slidable passage therethrough of the catheter system;
      a distal supplemental tube coupled to a distal end of the elongate oversheath, the supplemental tube shaped so as to define a supplemental-tube lumen sized for encasing at least a portion of the housing during (1) at least a portion of a delivery state for transluminally delivering the distal portion of the delivery tool to the heart, and (2) retracting of the housing out of a body of the subject;

an intermediate alignment tube disposed between the oversheath and the one or more catheters of the catheter system; and an aligner disposed between the intermediate alignment tube and the distal supplemental tube, and positioned to align the one or more catheters of the catheter system with respect to the distal supplemental tube;

exposing the housing from within the supplemental tube;

advancing the housing to the heart by pushing the one or more catheter distally:

deploying the prosthetic heart valve from within the housing and during the exposing, implanting the prosthetic heart valve at the heart;

subsequently to the implanting, retracting proximally the housing toward the supplemental tube by proximally retracting one or more catheters;

aligning (i) one or more catheters of the catheter system with respect to the supplemental tube and thereby (ii) the housing with respect to the supplemental tube by moving the aligner, and by the moving, orienting the aligner to align the one or more catheters of the catheter system with respect to the distal supplemental tube;

subsequently to the aligning, retracting proximally the one or more catheters and by the retracting encasing the housing within the supplemental tube; and subsequently to the encasing, extracting the delivery tool from within the body of the subject.

In an application, aligning includes straightening a portion of the one or more catheters such that the one or more catheters and the supplemental tube are concentrically disposed.

In an application, exposing the housing from within the supplemental tube includes pushing the one or more catheters distally while retaining the oversheath in place.

In an application, the aligning includes (i) aligning one or more catheters of the catheter system with respect to the supplemental tube and thereby (ii) aligning the housing with respect to the supplemental tube at a location within the vasculature that is outside the heart of the subject.

In an application, a distal portion of at least one catheter of the catheter system is configured to assume a curved orientation.

In an application, the distal portion is biased to assume the curved orientation in an absence of a force applied to the distal portion.

In an application, moving the aligner includes moving the aligner distally.

In an application, moving the aligner distally includes distally pushing the intermediate alignment tube.

In an application, the method further includes retracting proximally the one or more catheters during the moving distally of aligner.

In an application, exposing the housing from within the supplemental tube includes retracting the oversheath proximally with respect to the one or more catheters.

In an application, exposing the housing from within the supplemental tube includes advancing the one or more catheters distally during the retracting of the oversheath proximally.

There is further provided, in accordance with an application of the present invention, an apparatus for use at a heart of a subject, the apparatus including:

a delivery tool dimensioned for percutaneous delivery to the heart, the delivery tool having a distal portion that defines a distal portion axis and includes:

a shaft, and a proximal capsule and a distal capsule, each of the capsules:

having a respective open end, the open end of the proximal capsule facing the open end of the distal capsule, and being coupled to the shaft in a manner that facilitates axial movement of the capsule with respect to the shaft, along the distal portion axis; and a prosthetic valve including:

a tubular portion that defines a lumen:

a plurality of prosthetic leaflets disposed within the lumen;

an upstream support portion that extends from the tubular portion; and a plurality of flanges, each of the flanges coupled to the tubular portion at a respective coupling point that is downstream of the upstream support portion, and extending from the coupling point to a respective flange end-portion of the flange;

and the prosthetic valve is restrainable in a compressed state by the delivery tool, such that:

the shaft and a downstream end of the tubular portion are disposed within the distal capsule, and the upstream support portion and the flange end-portions are disposed within the proximal capsule.

In an application, the distal capsule is coupled to the shaft in a manner that facilitates proximal and distal movement of the distal capsule, with respect to the shaft.

In an application, the proximal and distal capsules are coupled to the shaft in a manner that facilitates proximal and distal movement of the proximal and distal capsules, with respect to the shaft.

In an application, the proximal capsule is coupled to the shaft in a manner that facilitates proximal and distal movement of the proximal capsule, with respect to the shaft.

In an application:

a capsule catheter extending proximally from the distal portion of the delivery tool; and a disc-assembly coupled to the capsule catheter, the disc-assembly including:

a proximal disc fixedly coupled to the capsule catheter, the proximal disc shaped to define external threading, and a distal disc, the distal disc rotatably coupled to the proximal disc.

In an application, the proximal capsule is shaped to define:

a longitudinal track configured to engage the distal disc, and internal threading, the internal threading:

complementary to the external threading, and traversing the longitudinal track; and the disc-assembly is disposed within the proximal capsule such that:

the external threading fits the internal threading, and rotation of the capsule catheter in a first direction facilitates:

rotation of the proximal disc in the first direction, and longitudinal movement of the proximal capsule, with respect to the disc-assembly.

In an application, the distal disc includes a locking pin that is disposed within the longitudinal track.

In an application, the delivery tool is configured such that while the distal portion of the delivery tool is in a delivery state for transluminally delivering the delivery tool to the heart:
the prosthetic valve is restrained in the compressed state by the delivery tool, and
the proximal capsule and the distal capsule are oriented with respect to each other such that:
an inter-capsule gap separates the open end of the proximal capsule from the open end of the distal capsule, and
a segment of the tubular portion is disposed at the inter-capsule gap.

In an application, the distal capsule and the proximal capsule are each coupled to the shaft such that the distal capsule is translatable toward the proximal capsule, such that the open end of the proximal capsule and the open end of the distal capsule meet, thereby closing the inter-capsule gap.

In an application, the distal capsule and the proximal capsule are each coupled to the shaft such that prior to disengagement of the prosthetic valve from the shaft, the distal capsule is not translatable toward the proximal capsule, such that the open end of the proximal capsule and the open end of the distal capsule meet, thereby closing the inter-capsule gap.

In an application, the delivery tool is configured such that while the distal portion of the delivery tool is in the delivery state, the inter-capsule gap is greater than 5 mm and less than 25 mm in length.

In an application, the delivery tool is configured such that while the distal portion of the delivery tool is in the delivery state, the inter-capsule gap is greater than 10 mm in length.

In an application, the delivery tool is configured such that while the distal portion of the delivery tool is in the delivery state, the inter-capsule gap is less than 15 mm in length.

In an application, the proximal capsule and the distal capsule are each coupled to the shaft such that the distal portion of the delivery tool is transitionable from the delivery state to a deployment state such that (a) the inter-capsule gap while the distal portion is in the deployment state is longer than (b) the inter-capsule gap while the distal portion is in the delivery state.

In an application, the delivery tool is configured such that while the distal portion of the delivery tool is in the deployment state, the inter-capsule gap is 50-200 percent greater than the gap while the distal portion is in the delivery state.

In an application, the delivery tool is configured such that while the distal portion of the delivery tool is in the deployment state, the inter-capsule gap is 100-200 percent greater than the gap while the distal portion is in the delivery state.

In an application, the delivery tool is configured such that while the distal portion of the delivery tool is in the deployment state, the inter-capsule gap is greater than 15 mm and less than 40 mm in length.

In an application, the delivery tool is configured such that while the distal portion of the delivery tool is in the deployment state, the inter-capsule gap is greater than 20 mm and less than 35 mm in length.

There is further provided, in accordance with an application of the present invention, a method for use at a heart of a subject, the method including:
transluminally advancing a delivery system to the heart, the delivery system including:
a delivery tool, the delivery tool having a distal portion that defines a distal portion axis, the distal portion including a proximal capsule and a distal capsule, each of the capsules having a respective open end, the open end of the proximal capsule facing the open end of the distal capsule; and
an implant including:
a proximal-implant portion,
a distal-implant portion, and
a flange having a flange end-portion,
the implant being restrained by the delivery tool such that:
the proximal-implant portion and the flange end-portion are disposed within the proximal capsule, and
the distal-implant portion of the implant is disposed within the distal capsule; and
deploying the implant at the heart by:
proximally retracting the proximal capsule, with respect to the implant, such that the flange end-portion is released from the proximal capsule,
subsequently, proximally retracting the distal portion of the delivery tool, such that the flange end-portion contacts tissue of the heart,
subsequently, further proximally retracting the proximal capsule, with respect to the implant, such that the proximal-implant portion is released from the proximal capsule, and
subsequently. distally advancing the distal capsule, with respect to the implant, such that the distal-implant portion is released from the distal capsule.

In an application:
the step of transluminally advancing includes transluminally advancing the distal portion of the delivery tool to the heart while the proximal capsule and the distal capsule are aligned along the distal portion axis such that an inter-capsule gap separates the open end of the proximal capsule from the open end of the distal capsule.

In an application, the step of transluminally advancing includes transluminally advancing the distal portion of the delivery tool to the heart while the proximal capsule and the distal capsule are aligned along the distal portion axis such that:
an inter-capsule gap separates the open end of the proximal capsule from the open end of the distal capsule, and
a segment of the implant is disposed at the inter-capsule gap.

In an application:
the delivery tool includes a flexible sheath, the sheath circumscribing the inter-capsule gap such that the sheath covers the segment of the implant, and
the method includes, prior to proximally retracting the proximal capsule with respect to the implant, exposing the segment from the sheath by proximally retracting the sheath.

In an application:
the implant includes a frame, the frame being restrained by the delivery tool such that:
the proximal-implant portion includes a proximal portion of the frame, and
the distal-implant portion includes at a distal portion of the frame; and
the step of further proximally retracting the proximal capsule includes further proximally retracting the proximal capsule, with respect to the proximal portion of the frame, such that the proximal portion of the frame is released from the proximal capsule; and
the step of distally advancing the distal capsule includes distally advancing the distal capsule, with respect to the distal portion of the frame, such that the distal portion of the frame is released from the distal capsule.

In an application:
the frame is an inner frame,
the flange is a first flange of a plurality of flanges,
the implant includes an outer frame, the outer frame defining the plurality of flanges,
each of the flanges:
is coupled to the inner frame at a respective coupling point that is longitudinally between the proximal portion of the inner frame and the distal portion of the inner frame, and
extends from the coupling point to a respective flange end-portion; and
the step of proximally retracting the proximal capsule includes proximally retracting the proximal capsule, with respect to the implant, such that the respective flange end-portions are released from the proximal capsule; and
the step of proximally retracting the distal portion of the delivery tool includes proximally retracting the distal portion of the delivery tool, such that the respective flange end-portions contact tissue of the heart.

In an application:
the implant includes a prosthetic valve, and:
the inner frame has a tubular portion that defines a lumen,
a plurality of prosthetic leaflets are disposed within the lumen,
the proximal portion of the inner frame includes an upstream support portion that extends from the tubular portion, and
the distal portion of the inner frame includes a downstream end of the tubular portion:
the distal portion of the delivery tool includes a shaft, the proximal capsule and the distal capsule each being coupled to the shaft, and
the step of transluminally advancing includes:
transluminally delivering the delivery tool to the heart while the delivery tool is in a delivery state in which the prosthetic valve is restrained in a compressed state by the delivery tool, such that:
the tubular portion is engaged with a portion of the shaft,
the portion of the shaft and the downstream end of the tubular portion are restrained within the distal capsule,
the upstream support portion and the flange end-portions are restrained within the proximal capsule,
the proximal capsule and the distal capsule are aligned along the distal portion axis such that an inter-capsule gap separates the open end of the proximal capsule from the open end of the distal capsule, and
a segment of the tubular portion is disposed at the inter-capsule gap; and
transluminally advancing the delivery tool to a ventricle of the heart such that the distal capsule is disposed within the ventricle; and
deploying the implant at the heart includes deploying the prosthetic valve at a native valve of the heart, such that the prosthetic valve automatically expands from the compressed state to an expanded state, by:
proximally retracting the proximal capsule, with respect to the shaft, such that the respective flange end-portions expand radially outward,
proximally retracting the distal portion of the delivery tool, such that the respective flange end-portions contact tissue of the native valve.
further proximally retracting the proximal capsule, with respect to the shaft, such that:
the upstream support portion is released from the proximal capsule, and expands radially outward, and
tissue of the native valve is squeezed between the upstream support portion and the flange end-portions, and distally advancing the distal capsule, with respect to the shaft, such that:
the downstream end of the tubular portion is released from the distal capsule, and
the tubular portion expands radially outward.

In an application, the method includes, subsequently to distally advancing the distal capsule with respect to the shaft, withdrawing the delivery tool from the heart, by:
distally advancing the proximal capsule, with respect to the shaft, such that the open end of the proximal capsule abuts the open end of the distal capsule, and
subsequently, proximally retracting the distal portion of the delivery tool, through the lumen of the tubular portion.

In an application, the method includes, prior to distally advancing the proximal capsule with respect to the shaft:
proximally retracting the distal capsule, with respect to the shaft.

In an application:
the delivery system includes a guidewire,
the delivery tool includes a nosecone having a flexible distal end-portion,
the method includes transluminally advancing the guidewire to the heart,
transluminally advancing the delivery system to the heart includes transluminally advancing the delivery tool along the guidewire, such that the guidewire enters the distal end-portion of the nosecone, and
deploying the implant at the heart includes, prior to retracting the proximal capsule with respect to the implant, proximally withdrawing the guidewire from within the distal end-portion of the nosecone.

In an application, the method includes, subsequently to distally advancing the distal capsule, with respect to the implant, advancing the guidewire into the distal end-portion.

In an application:
the distal portion of the delivery tool includes a shaft, the proximal capsule and the distal capsule each being coupled to the shaft,
the proximal capsule is shaped to define:
a longitudinal track, and
internal threading, the internal threading traversing the longitudinal track;
the delivery tool includes:
a capsule catheter extending proximally from the distal portion of the delivery tool, and
a disc-assembly, the disc-assembly including:
a proximal disc fixedly coupled to the capsule catheter, the proximal disc shaped to define external threading that is complementary to the internal threading, and
a distal disc, the distal disc:
dimensioned to engage the longitudinal track.
fixedly coupled to the shaft, and
rotatably coupled to the proximal disc;
the disc-assembly is disposed within the proximal capsule such that the external threading fits the internal threading; and
proximally retracting the proximal capsule with respect to the implant includes rotating the capsule catheter in a first direction such that:
the proximal disc rotates, in the first direction, along the internal threading, and the proximal capsule moves along the distal portion axis, with respect to:
the disc-assembly, and
the implant.

In an application:
the distal disc includes a locking pin that is disposed within the longitudinal track, and
rotating the capsule catheter in the first direction includes advancing the locking pin along the longitudinal track.

There is further provided, in accordance with an application of the present invention, an apparatus for use at a heart of a subject, the apparatus including:
a delivery tool, the delivery tool having a distal portion that defines a distal portion axis and includes:
a proximal capsule and a distal capsule, each of the capsules:
having a respective open end, the open end of the proximal capsule facing the open end of the distal capsule, such that, while the distal portion of the delivery tool is in a delivery state for transluminally delivering the delivery tool to the heart, an inter-capsule gap separates the open end of the proximal capsule from the open end of the distal capsule; and
an implant, the implant being restrainable in a compressed state by the delivery tool, and
a segment of the implant is disposed at the inter-capsule gap.

In an application, the implant includes a prosthetic valve.
In an application, the prosthetic valve includes:
a tubular portion that defines a lumen;
a plurality of prosthetic leaflets disposed within the lumen:
an upstream support portion that extends from the tubular portion; and
a plurality of flanges, each of the flanges coupled to the tubular portion at a respective coupling point that is downstream of the upstream support portion, and extending from the coupling point to a respective flange end-portion of the flange.

In an application, the distal portion is configured such that while the delivery tool is in the delivery state, the prosthetic valve is engaged with the delivery tool such that:
a downstream end of the tubular portion is disposed within the distal capsule,
the upstream support portion and the flange end-portions are disposed within the proximal capsule, and
the tubular portion is the segment of the implant disposed at the inter-capsule gap.

In an application, the apparatus includes a flexible sheath, the sheath circumscribing the inter-capsule gap such that the sheath covers the segment of the implant.

In an application, the proximal capsule is covered by the sheath.

In an application, a distal end of the sheath abuts the distal capsule.

In an application, a distal end of the sheath is partially disposed within the distal capsule.

In an application, the sheath includes a polymer.
In an application, the sheath includes a fabric.

There is further provided, in accordance with an application of the present invention, an apparatus for percutaneous delivery of an implant to a subject, the apparatus including:
a guidewire; and
a delivery tool having a proximal portion and a distal portion, the delivery tool including:
at the proximal portion of the delivery tool, an extracorporeal controller;
a delivery catheter, the delivery catheter connecting the extracorporeal controller to the distal portion of the delivery tool, the delivery catheter configured such that the guidewire is extendable through the delivery catheter; and
at the distal portion of the delivery tool, a capsule configured to house the implant, the capsule including a nosecone having a flexible distal end-portion, and:
in an absence of the guidewire from the distal end-portion, the distal end-portion has a curled resting shape, and
while the guidewire is positioned within the distal end-portion, the distal end-portion is straightened.

There is further provided, in accordance with an application of the present invention, an apparatus for percutaneous delivery of an implant to a subject, the apparatus including a delivery tool, the delivery tool including:
at a proximal portion of the delivery tool, an extracorporeal controller;
at a distal portion of the delivery tool, a capsule that defines a chamber therein; and
a shaft, extending from the extracorporeal controller to the capsule, and including:
a rigid proximal shaft segment that extends distally from the extracorporeal controller,
a flexible shaft segment that extends distally from the rigid proximal shaft segment, and
a rigid distal shaft segment that extends distally from the flexible shaft segment, and extends through at least part of the chamber of the capsule, each rigid shaft segment being more rigid than the flexible shaft segment.

In an application, the delivery tool includes at least one pull-wire, the pull-wire operatively connecting the distal portion of the delivery tool to the controller, such that operating the controller facilitates using the pull-wire to steer the distal portion.

In an application, the rigid distal shaft segment extends distally out of the chamber of the capsule.

In an application, the rigid distal shaft segment is a first rigid distal shaft segment, and the delivery tool includes a second rigid distal shaft segment, and the first rigid distal shaft segment and the second rigid distal shaft segment are configured to slide telescopically with respect to each other.

In an application, the delivery tool includes a mount, the mount attached to the rigid distal shaft segment, and the implant is:
engaged with the mount, and
compressed onto a portion of the rigid distal shaft segment.

In an application, the implant is housed at least partially within the chamber of the capsule.

In an application, a length of the rigid proximal shaft segment is greater than 50 cm, and less than 100 cm.

In an application, the length of the rigid proximal shaft segment is greater than 70 cm, and less than 75 cm.

In an application, the length of the flexible shaft segment is greater than 5 cm, and less than 10 cm.

In an application, the length of the flexible shaft segment is greater than 6 cm, and less than 8 cm.

In an application, the length of the rigid distal shaft segment is greater than 2 cm, and less than 10 cm.

In an application, the length of the rigid distal shaft segment is greater than 4 cm, and less than 7 cm.

There is further provided, in accordance with an application of the present invention, a method, including:
advancing, into a subject, an implant disposed within a capsule, the capsule coupled to a flexible capsule catheter that extends through a flexible second catheter and out of a second-catheter distal portion of the second catheter, the second-catheter distal portion abutting the capsule;

subsequently, exposing a capsule-catheter distal portion of the capsule catheter, from the second catheter, by axially separating the second catheter from the capsule; and subsequently, releasing the implant from the capsule by moving the capsule proximally away from the implant, by retracting the capsule-catheter distal portion into the second catheter.

In an application, the step of advancing includes advancing the implant into the subject while:

the second-catheter distal portion is disposed within a flexible first catheter, the capsule is disposed distally from the second catheter, and a first-catheter distal portion abuts the capsule.

In an application, the method includes, subsequently to the step of advancing and prior to the step of releasing the implant, exposing the second-catheter distal portion from the first catheter by axially separating the second catheter from the capsule.

In an application, the method includes, subsequently to exposing the second-catheter distal portion, and prior to releasing the implant from the capsule:

bending the second-catheter distal portion with respect to the first catheter by actuating a bend actuator of an extracorporeal control system.

In an application:

the bend actuator is a second-catheter bend-actuator, operably coupled to one or more second-catheter bend-control elements that extend from the second-catheter bend-actuator, along the second catheter to the second-catheter distal portion, and bending the second-catheter distal portion with respect to the first catheter includes bending the second-catheter distal portion with respect to the first catheter by tensioning at least one of the second-catheter bend-control elements, by actuating the second-catheter bend actuator.

In an application, the method includes, prior to releasing the implant from the capsule, bending the first-catheter distal portion by actuating a first-catheter bend actuator of the extracorporeal control system, the first-catheter bend actuator being operably coupled to one or more first-catheter bend-control elements that extend from the first-catheter bend actuator, along the first catheter to the first-catheter distal portion, and bending the first-catheter distal portion includes bending the first-catheter distal portion by tensioning at least one of the first-catheter bend-control elements, by actuating the first-catheter bend actuator.

In an application, during the advancing, the implant is coupled to a mount, the mount being coupled to a shaft that extends through the capsule catheter and into the capsule, and retracting the capsule-catheter distal portion into the second catheter includes sliding the capsule-catheter distal portion proximally over the shaft.

In an application:

the capsule is a first capsule that has an open distal end, a rod extends distally out of the shaft, a second capsule is coupled to a distal portion of the rod, and includes a circumferential wall that extends proximally from the distal portion of the rod to define (i) a chamber, and (ii) an open proximal end that faces the open distal end of the first capsule, during the advancing, a first part of the implant is disposed within the first capsule, and a second part of the implant is disposed within the second capsule, and the method includes releasing the second part of the implant from the second capsule by moving the second capsule distally with respect to the mount, by moving the rod distally through the shaft.

In an application, the rod defines a screw thread, and moving the rod distally through the shaft includes rotating the rod such that the screw thread transforms the rotation of the rod into axial movement of the rod.

In an application, releasing the second part of the implant from the second capsule includes releasing the second part of the implant from the second capsule prior to releasing the first part of the implant from the first capsule.

In an application, releasing the second part of the implant from the second capsule includes releasing the second part of the implant from the second capsule prior to releasing the capsule-catheter distal portion from the second catheter.

In an application, the method includes, subsequently to exposing the capsule-catheter distal portion, and prior to releasing the implant from the capsule, bending the capsule-catheter distal portion with respect to the second catheter by actuating a bend actuator of an extracorporeal control system.

In an application:

during the advancing, the implant is coupled to a mount that is coupled to a shaft that extends through the capsule catheter and into the capsule, the bend actuator is a shaft bend-actuator, operably coupled to one or more shaft bend-control elements that extend along the shaft to a shaft distal portion, and bending the capsule-catheter distal portion with respect to the second catheter includes bending the capsule-catheter distal portion with respect to the second catheter by bending the shaft distal portion while the shaft distal portion is disposed within the capsule-catheter distal portion.

There is further provided, in accordance with an application of the present invention, an apparatus, the apparatus including a delivery tool for use with an implant, the delivery tool including:

an extracorporeal control system at a proximal portion of the delivery tool, the control system including a second-catheter bend-actuator and a shaft bend-actuator;

a flexible second catheter, extending distally from the control system, and including one or more first-tube bend-control elements that are operably coupled to the first-tube bend-actuator, and that extend from the control system and along the second catheter to a first-tube distal portion of the second catheter:

a flexible capsule catheter, extending distally from the control system through the second catheter to a capsule-catheter distal portion of the capsule catheter; and a flexible shaft, extending distally from the control system through the capsule catheter, and including one or more shaft bend-control elements that are operably coupled to the shaft bend-actuator, and that extend from the control system along the shaft to a shaft distal portion of the shaft;

and, via the control system:

the first-tube distal portion is axially slidable (i) distally over the capsule-catheter distal portion to ensheathe the capsule-catheter distal portion within the first-tube distal portion, and (ii) proximally off of the capsule-catheter distal portion to expose the capsule-catheter distal portion from the second catheter;

the capsule-catheter distal portion is axially slidable (i) distally over the shaft distal portion to ensheathe the shaft distal portion within the capsule-catheter distal portion, and (ii) proximally off of the shaft distal portion to expose the shaft distal portion from the capsule catheter:

actuation of the first-tube bend-actuator actively bends the first-tube distal portion via the first-tube bend-control elements;

actuation of the shaft bend-actuator actively bends the shaft distal portion via the shaft bend-control elements; and the control system does not include a capsule-catheter bend actuator, and the capsule catheter does not include bend-control elements via which the capsule-catheter distal portion is actively bendable.

In an application:

each of the first-tube bend-control elements includes a respective pull-wire that extends from the first-tube bend-actuator and through a respective secondary lumen of the second catheter, and is fixed to the second catheter at the first-tube distal portion, and each of the shaft bend-control elements includes a respective pull-wire that extends from the shaft bend-actuator and through a respective secondary lumen of the shaft, and is fixed to the shaft at the shaft distal portion.

In an application, each of the shaft bend-control elements includes a respective pull-wire that extends from the shaft bend-actuator and through a respective secondary lumen of the shaft, and is fixed to the shaft distally from the capsule catheter.

In an application, the capsule-catheter distal portion is sufficiently flexible such that, while the shaft distal portion is ensheathed in the capsule-catheter distal portion, bending of the shaft distal portion by actuation of the shaft bend-actuator causes the capsule-catheter distal portion to passively bend.

In an application, the capsule-catheter distal portion is sufficiently flexible such that, while the capsule-catheter distal portion is ensheathed in the first-tube distal portion, bending of the first-tube distal portion by actuation of the first-tube bend-actuator causes the capsule-catheter distal portion to passively bend.

In an application:

the delivery tool includes a rod and a capsule, the rod extends distally out of the shaft, the capsule is coupled to a distal portion of the rod, and includes a circumferential wall that extends proximally from the distal portion of the rod to define a chamber, and the rod is axially movable with respect to the shaft, axial movement of the rod with respect to the shaft moving the capsule axially with respect to the capsule catheter.

In an application, the delivery tool includes a capsule coupled to the capsule catheter distally from the second catheter, and dimensioned to house at least part of the implant, the shaft extends distally through the capsule, and axial sliding of the capsule-catheter distal portion proximally off of the shaft distal portion causes axial sliding of the capsule proximally along the shaft distal portion.

In an application, each of the shaft bend-control elements includes a respective pull-wire that extends from the shaft bend-actuator and through a respective secondary lumen of the shaft, and is fixed to the shaft within the capsule.

In an application, the second-catheter distal portion is axially slidable distally such that it abuts the capsule.

In an application:

the control system includes a first-catheter bend-actuator, the delivery tool includes a flexible first catheter, extending distally from the control system, and including one or more first-catheter bend-control elements that are operably coupled to the first-catheter bend-actuator, and that extend from the control system and along the first catheter to a first-catheter distal portion of the first catheter, the shaft extends distally from the control system through the first catheter to the shaft distal portion, and is axially slidable (i) proximally through the first catheter such that the shaft distal portion becomes ensheathed in the first-catheter distal portion, and (ii) distally through the first catheter such that the shaft distal portion becomes exposed from the first catheter, and actuation of the first-catheter bend-actuator actively bends the first-catheter distal portion via the first-catheter bend-control elements.

In an application, the control system includes an outer-first juxtaposition actuator, operatively coupled to the first catheter and to the second catheter, such that actuation of the outer-first juxtaposition actuator slides the second catheter axially with respect to the first catheter.

In an application, the second catheter is rotationally locked to the first catheter by (i) a proximal lock defined by the control system, and (ii) a distal lock at which the first catheter includes a first-catheter coupling and the second catheter includes a second-catheter coupling that is rotationally-locked to the first-catheter coupling.

In an application, the second catheter is rotationally locked to the first catheter.

There is further provided, in accordance with an application of the present invention, an apparatus, including:

a delivery tool for use with an implant, the delivery tool including:

a tubular shaft;

a rod:

extending from within the shaft out of a distal end of the shaft, having a distal portion disposed outside of the distal end of the shaft, and operatively coupled to the shaft such that rotational movement of the rod with respect to the shaft is converted into axial movement of the rod with respect to the shaft;

a capsule, coupled to the distal portion of the rod, and including a circumferential wall that extends proximally from the distal portion of the rod to define a chamber; and an accessory, including a detent, the accessory being couplable to the capsule such that the detent rotationally locks the capsule to the rod.

In an application:

the delivery tool has an extended state and a retracted state, axial movement of the rod distally with respect to the shaft extending the delivery tool from the retracted state toward the extended state, in the retracted state, a part of the shaft is disposed within the chamber, and in the extended state, the part of the shaft is disposed outside of the chamber.

In an application:

the apparatus includes a catch, coupled to the rod, the capsule defines a lateral detent-hole that extends from outside the capsule toward the catch, and the accessory is couplable to the capsule such that the detent extends through the detent-hole and engages the catch, rotationally locking the capsule to the rod.

In an application, the accessory includes a clip, and is couplable to the capsule by the clip being clipped to the capsule such that the detent rotationally locks the capsule to the rod.

In an application, the accessory includes a c-shaped clip, and is couplable to the capsule by the c-shaped clip being placed over the capsule such that the detent rotationally locks the capsule to the rod.

In an application, the delivery tool includes a mount, coupled to the shaft, extending radially outward from the shaft, and shaped to define a plurality of implant-receiving slots arranged circumferentially, each implant-receiving slot of the plurality of implant-receiving slots being shaped to receive a respective portion of an implant.

In an application:

the delivery tool has an extended state and a retracted state, axial movement of the rod distally with respect to the shaft extending the delivery tool toward the extended state, and axial movement of the rod proximally with respect to the shaft retracting the delivery tool toward the retracted state, in the retracted state, the plurality of implant-receiving slots is disposed within the chamber, and in the extended state, the plurality of implant-receiving slots is disposed outside of the chamber.

In an application, the rod is shaped to define an external thread, and the operative coupling of the rod to the shaft is provided by the external thread.

In an application, the shaft is shaped to define an internal thread, and the operative coupling of the rod to the shaft is provided by mating between the internal thread and the external thread.

In an application, the accessory includes:

a first component that includes the detent and is couplable to the capsule such that the detent rotationally locks the capsule to the rod, and a knob, couplable to the first component after the first component is coupled to the capsule, and facilitating rotation, by hand, of the accessory, the capsule, and the rod, by gripping and rotating the knob by hand.

In an application, the knob is shaped to define an opening dimensioned (i) to allow passage of a distal tip of the capsule through the opening, and (ii) to receive and engage the first component.

There is further provided, in accordance with an application of the present invention, a method, including:

placing an implant on a distal portion of a delivery tool, the delivery tool: (a) having a proximal portion, and (b) including a capsule at the distal portion and a controller at the proximal portion;

extracorporeally ensheathing the implant in the capsule by moving the capsule helically over the implant;

subsequently advancing the ensheathed implant and the distal portion of the delivery tool into a subject, while retaining the proximal portion of the delivery tool outside of the subject; and subsequently, intracorporeally deploying the implant from the capsule by moving the capsule linearly off of the implant.

In an application, ensheathing the implant in the capsule includes ensheathing the implant in the capsule by moving the capsule helically over the implant by applying, at the distal portion of the delivery tool, a rotational force to the capsule.

In an application, moving the capsule linearly off of the implant includes moving the capsule linearly off of the implant by applying, at the proximal portion of the delivery tool, an unsheathing force to the controller.

In an application, the delivery tool includes a rod that extends between the distal portion and the proximal portion of the delivery tool, and moving the capsule helically over the implant includes rotating the rod in a first rotational direction.

In an application, the delivery tool includes a shaft from which a distal portion of the rod extends distally, and rotating the rod in the first rotational direction includes screwing the distal portion of the rod into the shaft.

In an application, moving the capsule linearly off of the implant includes rotating the rod in a second rotational direction, the second rotational direction being opposite to the first rotational direction.

In an application, rotating the rod in the first rotational direction includes driving rotation of the rod from the distal portion of the delivery tool, and rotating the rod in the second rotational direction includes driving rotation of the rod from the proximal portion of the delivery tool.

In an application:

rotating the rod in the first rotational direction includes rotating the rod in the first rotational direction while the capsule is rotationally locked with respect to the rod, and the method includes, subsequently to extracorporeally ensheathing the implant, and prior to intracorporeally deploying the implant, rotationally unlocking the capsule with respect to the rod.

In an application, rotationally unlocking the capsule with respect to the rod includes rotationally unlocking the capsule with respect to the rod prior to the step of advancing.

In an application:

rotating the rod in the first rotational direction while the capsule is rotationally locked with respect to the rod includes rotating the rod in the first rotational direction while an accessory that includes a detent is coupled to the capsule such that the detent rotationally locks the capsule to the rod, and rotationally unlocking the capsule with respect to the rod includes decoupling the accessory from the capsule.

In an application, rotating the rod in the first rotational direction includes driving rotation of the rod using the accessory.

There is further provided, in accordance with an application of the present invention, a method, including:

placing an implant on a distal portion of a delivery tool, the delivery tool having a proximal portion, and including a capsule at the distal portion, and a controller at the proximal portion;

extracorporeally ensheathing the implant in the capsule by extracorporeally applying an ensheathing force to the distal portion of the delivery tool;

subsequently, advancing the ensheathed implant and the distal portion of the delivery tool into a subject, while retaining the proximal portion of the delivery tool outside of the subject; and subsequently, intracorporeally deploying the implant from the capsule by extracorporeally applying an unsheathing force to the controller.

In an application, extracorporeally applying the ensheathing force to the distal portion of the delivery tool includes extracorporeally applying the ensheathing force to the capsule.

In an application, extracorporeally applying the ensheathing force to the distal portion of the delivery tool includes rotating the capsule.

In an application, the delivery tool includes a rod that extends between the distal portion and the proximal portion of the delivery tool, and extracorporeally applying the ensheathing force to the distal portion of the delivery tool includes rotating the rod in a first rotational direction by extracorporeally applying the ensheathing force to the distal portion of the delivery tool.

In an application, extracorporeally applying the unsheathing force to the controller includes rotating the rod in a second rotational direction by extracorporeally applying the unsheathing force to the controller, the second rotational direction being opposite to the first rotational direction.

In an application:
rotating the rod in the first rotational direction includes rotating the rod in the first rotational direction while the capsule is rotationally locked with respect to the rod, and
the method includes, subsequently to extracorporeally ensheathing the implant, and prior to intracorporeally deploying the implant, rotationally unlocking the capsule with respect to the rod.

In an application, rotationally unlocking the capsule with respect to the rod includes rotationally unlocking the capsule with respect to the rod prior to the step of advancing.

In an application:
rotating the rod in the first rotational direction while the capsule is rotationally locked with respect to the rod includes rotating the rod in the first rotational direction while an accessory that includes a detent is coupled to the capsule such that the detent rotationally locks the capsule to the rod, and
rotationally unlocking the capsule with respect to the rod includes decoupling the accessory from the capsule.

In an application, the ensheathing force is a rotational force, and rotating the rod in the first rotational direction while the capsule is rotationally locked with respect to the rod includes applying the rotational force to the accessory such that the accessory imparts the rotational force to the rod.

There is further provided, in accordance with an application of the present invention, a method, including:
using a delivery tool having a proximal portion and a distal portion, and including:
  a capsule at the distal portion,
  a shaft, and
  a rod that extends from the proximal portion, through the shaft, and out of a distal end of the shaft, and is coupled to the capsule:
placing an implant on the delivery tool such that the implant circumscribes the shaft;
extracorporeally ensheathing the implant in the capsule by rotating the capsule with respect to the shaft but not with respect to the rod; and
subsequently, intracorporeally deploying the implant from the capsule by rotating the rod with respect to the shaft and with respect to the capsule.

There is further provided, in accordance with an application of the present invention, a method, including:
using a delivery tool having a proximal portion and a distal portion, and including:
  a capsule at the distal portion,
  a shaft, and
  a rod that extends between the proximal portion and the distal portion, and is coupled to the capsule:
placing an implant on the delivery tool, proximally from the capsule;
subsequently, extracorporeally ensheathing the implant in the capsule by rotating the rod such that the rod and the capsule move proximally with respect to the implant;
subsequently, at the proximal portion, engaging a rod-controller with a proximal region of the rod, and
subsequently, intracorporeally deploying the implant from the capsule by using the rod-controller to rotate the rod with respect to the shaft such that the rod and the capsule move distally with respect to the implant.

In an application:
the delivery tool includes a shaft, and the rod extends from the proximal region, through the shaft, and out of a distal end of the shaft, and is coupled to the capsule distally from the shaft, and
placing the implant on the delivery tool includes placing the implant on the delivery tool such that the implant circumscribes the shaft, proximally from the capsule.

In an application, the method includes, prior to placing the implant on the delivery tool, moving the capsule distally with respect to the shaft while the rod-controller is not engaged with the rod.

In an application, the method includes disengaging the rod-controller from the rod prior to moving the capsule distally with respect to the shaft.

In an application, moving the capsule distally with respect to the shaft includes twirling the proximal region of the rod between a finger and a thumb.

There is further provided, in accordance with an application of the present invention, an apparatus, including:
a first-catheter controller:
a first catheter:
  extending distally from the first-catheter controller, and
  having a first-catheter distal portion that includes a first-catheter distal end that is operably coupled to the first-catheter controller so as to be bendable, in a first-catheter steering plane, by actuation of the first-catheter controller;
a second-catheter controller; and
a second catheter:
  extending distally from the second-catheter controller, through the first catheter, and
  having a second-catheter distal portion that includes a second-catheter distal end that extends distally out of the first-catheter distal end, and that is operably coupled to the second-catheter controller so as to be bendable, in a second-catheter steering plane, by actuation of the second-catheter controller,
and:
the second catheter is rotationally oriented with respect to the first catheter such that, while the first-catheter distal end is bent in the first-catheter steering plane, bending of the second-catheter distal end by actuation of the second-catheter controller causes the second-catheter distal end to rotate with respect to the first-catheter distal end such that the second-catheter steering plane moves toward being perpendicular to the first-catheter steering plane.

In an application, the second catheter is rotationally locked to the first catheter by (i) a proximal lock defined by the control system, and (ii) a distal lock at which the first catheter includes a first-catheter coupling and the second catheter includes a second-catheter coupling that is rotationally-locked to the first-catheter coupling.

In an application, the second catheter is rotationally locked to the first catheter.

There is further provided, in accordance with an application of the present invention, a method, including:
using a catheter system, the catheter system including:
a first-catheter controller;
a first catheter:
  extending distally from the first-catheter controller, and
  having a first-catheter distal portion that includes a first-catheter distal end that is operably coupled to the first-catheter controller;
a second-catheter controller; and
a second catheter:
  extending distally from the second-catheter controller, through the first catheter, and having a second-catheter distal portion that includes a second-catheter distal end that extends distally out of the first-catheter distal end, and that is operably coupled to the second-catheter controller:
  bending the first-catheter distal end, in a first-catheter steering plane, by actuation of the first-catheter controller; and
  bending the second-catheter distal end, in a second-catheter steering plane, by actuation of the second-catheter controller,
and bending the second-catheter distal end in the second-catheter steering plane includes rotating the second-catheter distal end with respect to the first-catheter distal end such that the second-catheter steering plane moves toward being perpendicular to the first-catheter steering plane.

In an application:
  the catheter system includes a lock configured to rotationally lock the first catheter with respect to the second catheter, and
  the method includes:
    prior to bending the first-catheter distal end, rotationally locking the first catheter with respect to the second catheter; and
    prior to bending the second-catheter distal end, rotationally unlocking the first catheter with respect to the second catheter.

The present invention will be more fully understood from the following detailed description of applications thereof, taken together with the drawings, in which:

BRIEF DESCRIPTION OF THE DRAWINGS

FIGS. 3A-D, 4A-H, 5A-B, 6, and 7 are schematic illustrations showing the delivery tool in various states thereof for use with an implant, in accordance with some applications of the invention;

FIGS. 8A-G and 9 are schematic illustrations showing at least some steps of loading the implant into a capsule assembly of the delivery tool, in accordance with some applications of the invention;

FIGS. 10A-E are schematic illustrations showing a delivery tool, in accordance with some applications of the invention;

FIGS. 12 and 13A-B are schematic illustrations showing the prosthetic valve being restrained in a compressed state by the delivery tool, in accordance with some applications of the invention;

FIGS. 15A-B are schematic illustrations showing a delivery tool, in accordance with some applications of the invention;

FIGS. 16A-I are schematic illustrations showing some steps of loading a prosthetic valve onto a distal portion of a delivery tool, in accordance with some applications of the invention;

FIGS. 16J-K are schematic illustrations showing advancement of an alignment mechanism over a catheter system of the delivery tool, in accordance with some applications of the invention;

FIGS. 17A-B are schematic illustrations showing use of the delivery tool to advance the prosthetic valve toward the heart, in accordance with some applications of the invention.

DETAILED DESCRIPTION OF EMBODIMENTS

Figure 1A:
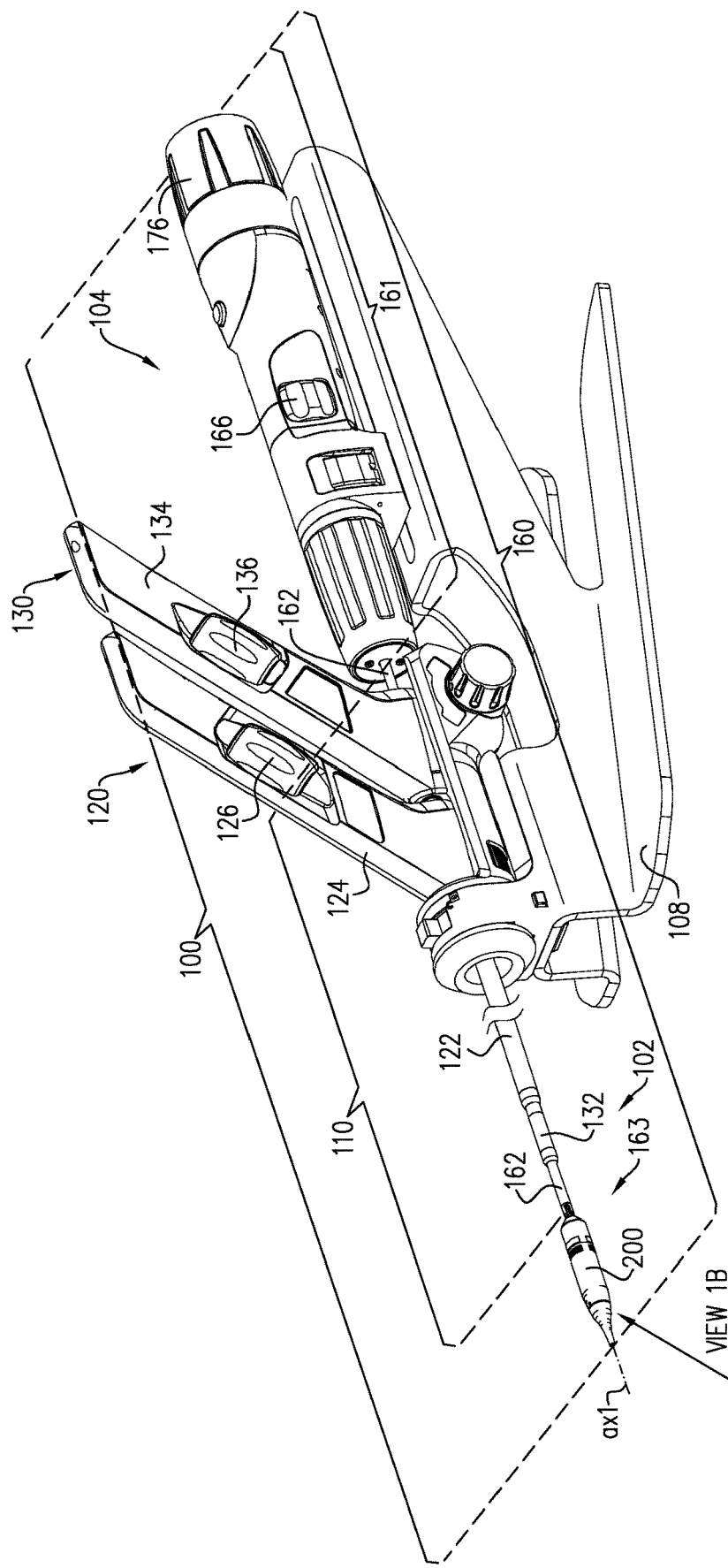
FIGS. 1A-C are schematic illustrations showing a delivery tool, in accordance with some applications of the invention.
Figure 1B:
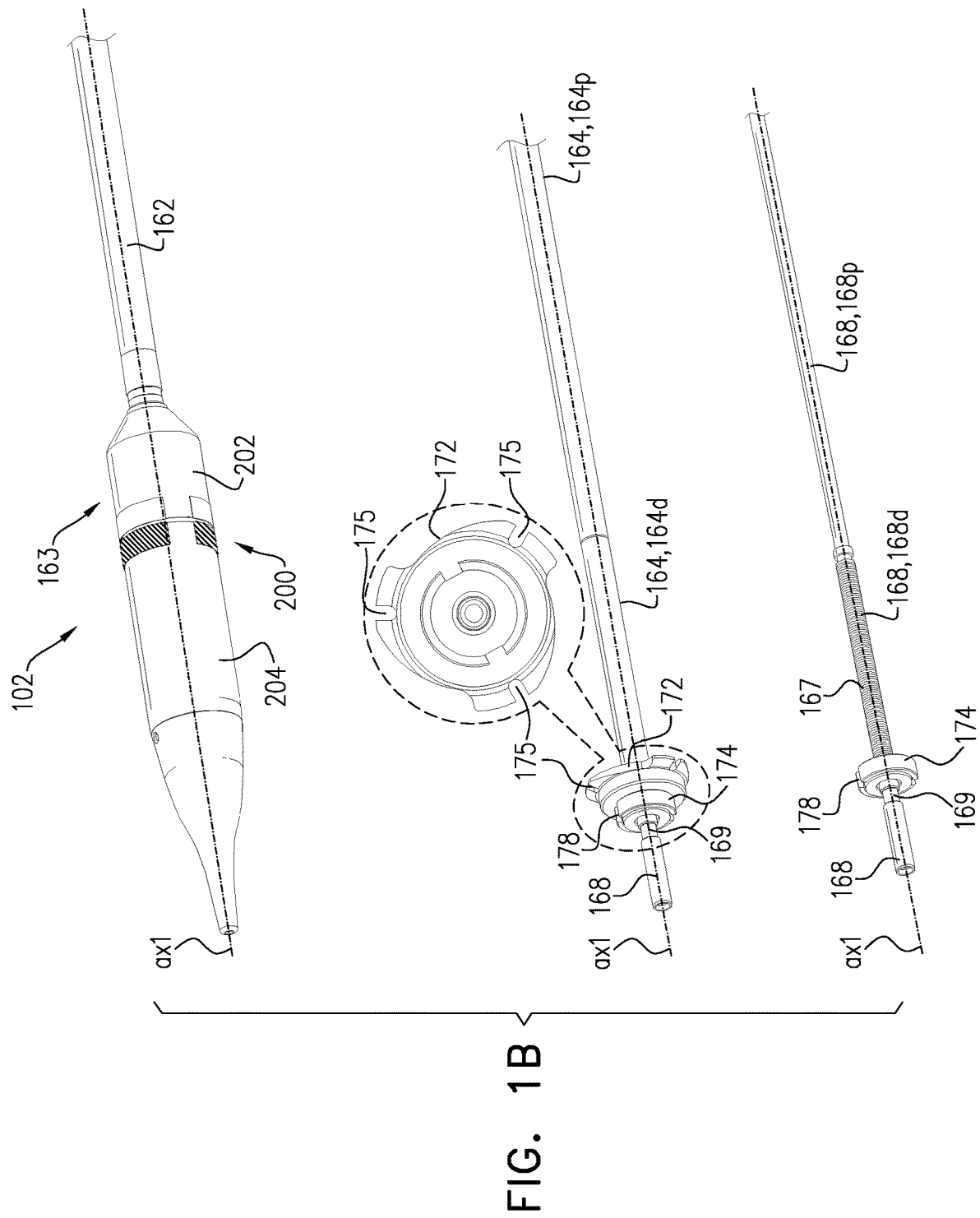
Figure 1C:
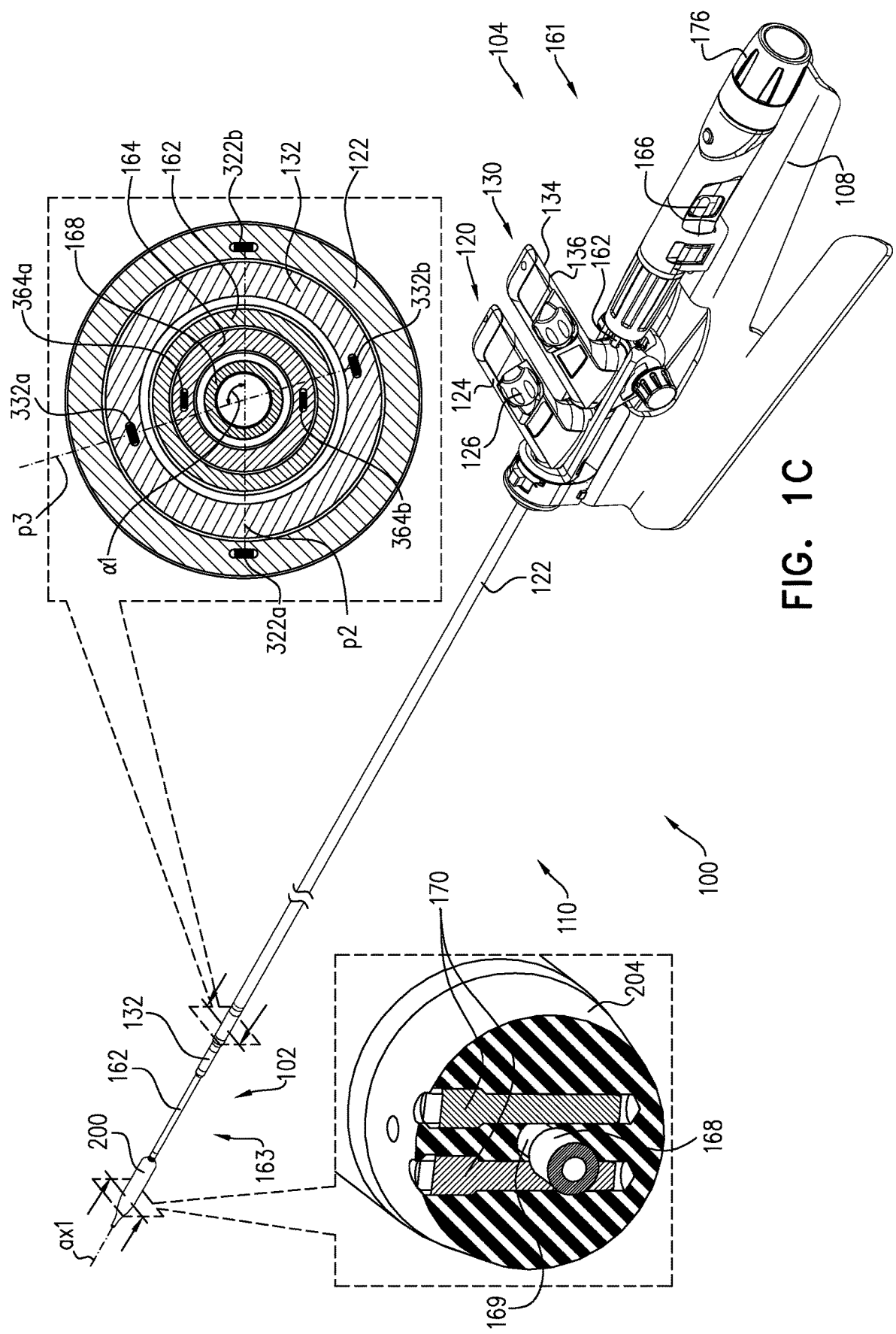

Reference is made to FIGS. 1A-C, which are schematic illustrations of a delivery tool 100, in accordance with some applications of the invention.

As shown in FIG. 1A, delivery tool 100 is a multi-catheter transluminal (e.g., transfemoral) delivery tool, comprising two primary components: a catheter system 110, and an implantation instrument 160.

Catheter system 110 comprises a first catheter unit 120 that comprises a first catheter (e.g., an outer catheter) 122 coupled at a proximal end thereof to a first-catheter handle 124; and a second catheter unit 130 that comprises a second catheter 132 coupled at a proximal end thereof to a second-catheter handle 134. A proximal opening of second catheter 132 is accessible proximally from first catheter 122, and the second catheter extends distally through the lumen of first catheter 122, and out of a distal end of the first catheter. Typically, second-catheter handle 134 is disposed proximally from first-catheter handle 124. Typically, handles 124 and 134 are mounted on a mount 108 to stabilize the handles during use. Further typically, the handles are mounted in a manner that facilitates selective adjustment of the axial and/or rotational position of the handles, and therefore their corresponding catheters.

Typically, each of catheters 122 and 132 is steerable, and this steerability is controlled by respective controllers 126, 136 (which may be alternatively referred to as bend-actuators) of the respective catheter unit, each of the controllers being operably coupled to a steerable distal end-portion of its respective catheter via one or more bend-control elements, such as pull-wires, that extend along and within the respective catheter. This is described in more detail hereinbelow. It is to be noted that the term steerable (including the specification and the claims) means actively steerable (e.g., by an extracorporeal control system), not merely sufficiently flexible to be bent responsively when pressed against a surface. Controllers 126 and 136 are typically mounted on the respective handle of their respective catheter unit. As shown, controllers 126 and 136 may be rotatable controllers such as wheels.

Implantation instrument 160 (FIGS. 1A and 1C) has a proximal portion 161 that is typically disposed proximally from handles 124 and 134, and that is typically also mounted on mount 108. Handle 124, handle 134, and proximal portion 161 are disposed at a proximal part 104 of delivery tool 100 that is configured to remain outside the subject during use. Proximal part 104 may be considered to be an extracorporeal control system. A distal part 102 of delivery tool 100 (e.g., a distal portion 163 of implantation instrument 160) is configured to be advanced into the subject, and comprises a capsule assembly 200 that houses implant 20 during this advancement.

Instrument 160 comprises a plurality of tubular members that extend distally from proximal portion 161, which are coaxial about a central longitudinal axis ax1 of delivery tool 100, and which are discussed in more detail hereinbelow. The outermost of these tubular members is typically a capsule catheter 162 that extends distally from proximal portion 161, through catheter 132, out of an open distal end of catheter 132, to distal part 102, where it abuts, and/or is coupled to a proximal capsule 202 of capsule assembly 200 (FIG. 1B). Proximal capsule 202 comprises a circumferential wall that extends distally from capsule catheter 162 to define a chamber of the proximal capsule. Capsule assembly 200 further comprises a distal capsule 204. Each of capsules 202 and 204 has a respective open end that faces the open end of the other capsule (see description hereinbelow of open ends 1065 and 1067 with reference to FIG. 14G).

As shown in the cross-sectional view shown in the upper inset of FIG. 1C, the tubular members of instrument 160 include a shaft 164 that extends distally from proximal portion 161, coaxially through capsule catheter 162. As shown in FIG. 3A, shaft 164 typically extends through proximal capsule 202, and out of the open end of the proximal capsule.

As described hereinbelow (e.g., with reference to FIGS. 4A-H), for delivery of implant 20, the implant is housed, compressed around shaft 164, within capsule assembly 200. For some applications, a mount 172 (FIGS. 1B, 3A-D) to which the implant may be engaged, is fixedly coupled to a distal end of shaft 164. Alternatively or in addition to the mount engaging the implant, the implant may be engaged with a portion of the shaft, mutatis mutandis.

Typically, a downstream portion (e.g., downstream end 1016 of prosthetic valve 1036 described hereinbelow with reference to frame A of FIG. 11) of an implant is disposed within distal capsule 204 and engaged with mount 172 (e.g., implant-engaging slots 175 thereof), and an upstream portion (e.g., upstream end 1014 of the prosthetic valve described with reference to frame A of FIG. 11) of the implant is disposed within proximal capsule 202.

A rod 168 (upper inset of FIG. 1C) is disposed coaxially through shaft 164. Rod 168 may define a guidewire lumen therethrough, and may therefore be another of the tubular members of instrument 160. Rod 168 extends out of the distal end of shaft 164 (FIG. 1B), such that a distal portion of the rod is disposed outside of the distal end of the shaft. Rod 168 is operatively coupled to shaft 164 such that rotational movement of the rod with respect to the shaft is converted into axial movement (e.g., along longitudinal axis ax1) of the rod with respect to the shaft. This is typically achieved by shaft 164 defining an internal screw thread, and rod 168 defining a complementary external screw thread 167 (FIG. 1B).

For some applications, and as shown, shaft 164 has a rigid distal portion 164*d* within which the internal screw thread is defined. For such applications, more proximal portions of shaft 164 (indicated by reference numeral 164*p* in FIG. 1B) are flexible. Despite the difference in flexibility of portions 164*p* and 164*d*, these portions are typically axially and rotationally locked, and define a continuous lumen throughout the entirety of shaft 164.

Distal capsule 204 is coupled to the distal portion of rod 168, and comprises a circumferential wall that extends proximally from the distal portion of the rod to define a chamber of the distal capsule. Distal capsule 204 is typically axially locked with respect to rod 168, meaning that axial movement of the rod distally or proximally moves the distal capsule axially distally or proximally. However, distal capsule 204 is rotationally coupled to and rotationally movable with respect to rod 168, meaning that rotation of the rod does not necessarily rotate the distal capsule (e.g., if the distal capsule encounters rotational resistance). It is hypothesized by the inventors that this advantageously facilitates generally axial distal sliding of distal capsule 204 off of an implant that is disposed within distal capsule 204 (e.g., rather than the sliding off requiring helical rotation of the distal capsule with respect to the implant, which might increase an amount of abrasion between the distal capsule and the implant).

For some applications, and as shown in the lower inset of FIG. 1C, this axial locking and rotational coupling is provided by pins 170 that extend transversely through distal capsule 204, laterally from rod 168. Pins 170 are typically disposed distally from the chamber of the distal capsule. Pins 170 are typically axially aligned with a circumferential recess 169 defined in rod 168, such that the pins are sufficiently close to the rod to inhibit axial movement of the rod with respect to the pins, while providing sufficient clearance between the pins and the rod (e.g., recess 169) to allow the rod to rotate with respect to the pins.

Reference is made to FIGS. 3A-D, 4A-H, 5A-B, 6, and 7, which are schematic illustrations showing delivery tool 100 in various states thereof for use with an implant 20, in accordance with some applications of the invention.

FIGS. 3A-D show capsule assembly 200 of delivery tool 100 in various states thereof. FIGS. 4A-H show delivery tool 100 being used to deliver implant 20, and being transitioned between the various states in order to implant the implant. Implant 20 is described herein as being a prosthetic valve, but for some applications may be a different implant. For some applications, implant 20 is a prosthetic valve 1036 described hereinbelow, and/or may be identical to implant (prosthetic valve) 420 of WO 2019/026059 to Hariton et al., which is incorporated herein by reference. Implant 20 is typically self-expanding.

Figures 4A, 4B:
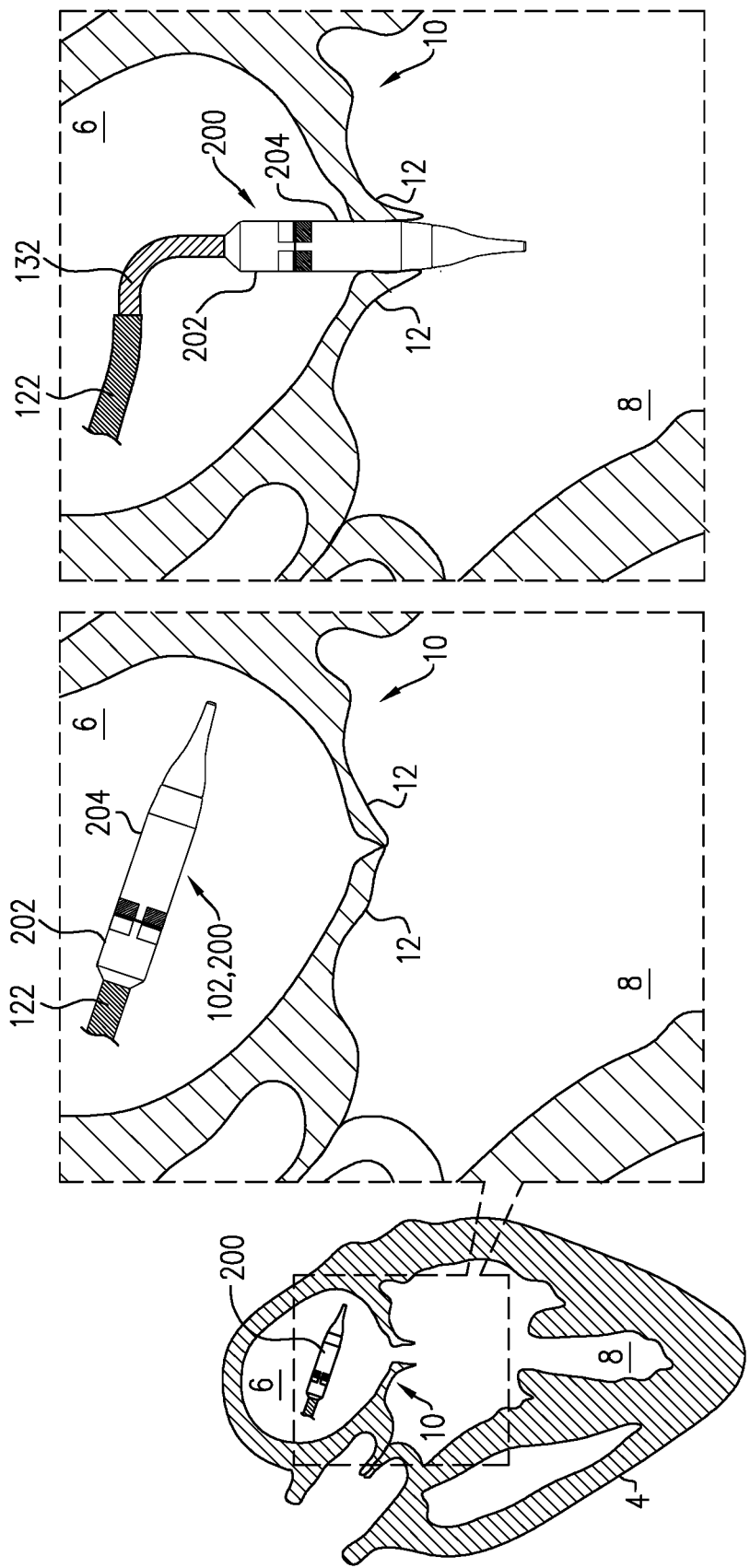

FIG. 3A shows distal portion 163 of instrument 160 (e.g., capsule assembly 200 thereof) in a closed state thereof. In this state, and with implant 20 disposed within capsule assembly 200, the capsule assembly is advanced transluminally (e.g., transfemorally) to a native valve 10 of the heart 4 of a subject (FIGS. 4A-B). Although FIGS. 4A-H show native valve 10 as the mitral valve, delivery tool 100 may alternatively be used to deliver an implant (e.g., a prosthetic valve) to another native valve of the heart, such as the tricuspid valve, the aortic valve, or the pulmonary valve, mutatis mutandis.

For some applications, and as shown in FIGS. 4A-B, during transluminal advancement of delivery tool 100, capsule assembly 200 may be retracted proximally so as to abut the distal open end of second catheter 132, and/or the distal open end of first catheter 122. FIG. 4A shows delivery tool 100 being advanced in this manner, with catheter 132 and capsule catheter 162 hidden inside catheter 122. Once within atrium 6, upstream of native valve 10 (in this case the left atrium, upstream of the mitral valve), catheter 132 is extended from catheter 122 (FIG. 4B), and is steered to point capsule assembly 200 toward and through the native valve.

For some applications, extension of catheter 132 from catheter 122 (e.g., by sliding catheter 132 with respect to catheter 122) is actuated using a juxtaposition actuator 176 (FIGS. 1A and 1C). For some such applications, catheter 132 is extended from catheter 122 while the catheters are rotationally locked with respect to each other. For example, catheters 122, 132 may be rotationally locked via a proximal lock defined by actuator 176. Alternatively or in addition, a distal lock defined by respective couplings of catheters 122, 132 may rotationally lock catheters 122, 132 with respect to each other. For example, the couplings defining the distal lock may be in certain ways similar to those described in U.S. Pat. No. 9,949,828 to Sheps et al. (e.g., with reference to FIG. 1 thereof), which is incorporated herein by reference.

For some applications, and as shown in FIGS. 4B-H, after the initial positioning of capsule assembly 200 (FIG. 4B), catheters 122 and 132 remain stationary throughout subsequent manipulation of the capsule assembly. For such applications, advancement and retraction of capsule catheter 162 from and into catheter 132 facilitates advancement and retraction of capsule assembly 200 as a whole, and of proximal capsule 202, independently of distal capsule 204.

Subsequently, and as shown in FIGS. 4C and 3B, distal capsule 204 is advanced distally, in order to release flanges 54 of implant 20, allowing the flanges to automatically expand radially outward. It is to be noted that the upstream end of implant 20 remains within proximal capsule 202, and mount 172 and the downstream end of the implant remain within distal capsule 204 at this stage. Because mount 172 is fixedly coupled to shaft 164, and distal capsule 204 is axially locked with respect to rod 168, this distal advancement of distal capsule 204 off of implant 20 can be achieved by distally advancing the rod with respect to the shaft (e.g., by screwing the rod through the shaft).

For some applications, and as shown, this step of deploying flanges 54 is performed while the flanges (and the seam between capsules 202 and 204) are disposed within atrium 6. For such applications, while the deployment state of capsule assembly 200 typically remains as shown in FIG. 3B, the capsule assembly is subsequently advanced distally, downstream through native valve 10 (FIGS. 4D-E), until it is determined via imaging (e.g., fluoroscopy) that the leaflets 12 of the native valve are coapting upstream of flanges 54 during ventricular systole (FIG. 4E). This is hypothesized by the inventors to facilitate reliable placement of the flanges downstream of the leaflets, while minimizing the distance downstream of the leaflets that the deployed flanges are advanced, thereby advantageously reducing a likelihood of inadvertently ensnaring ventricular tissue such as chordae tendineae.

Figure 4F:
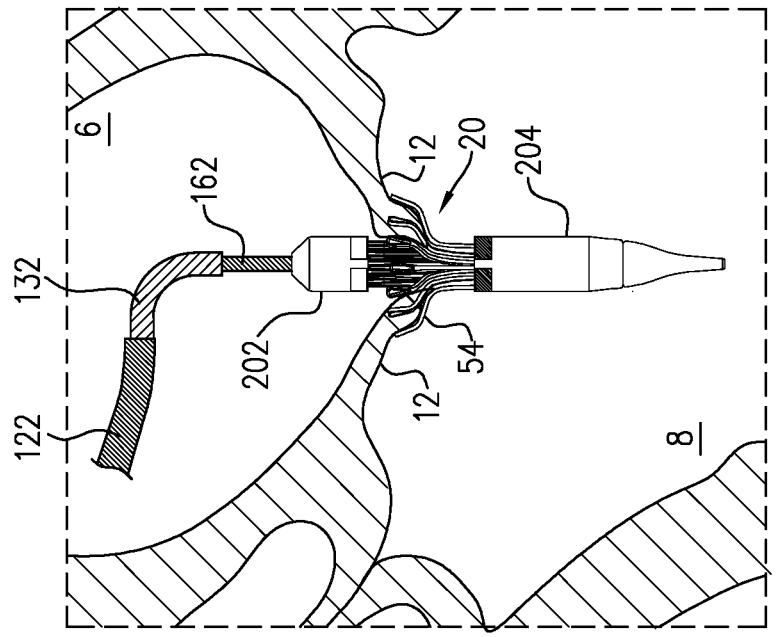
Figure 4E:
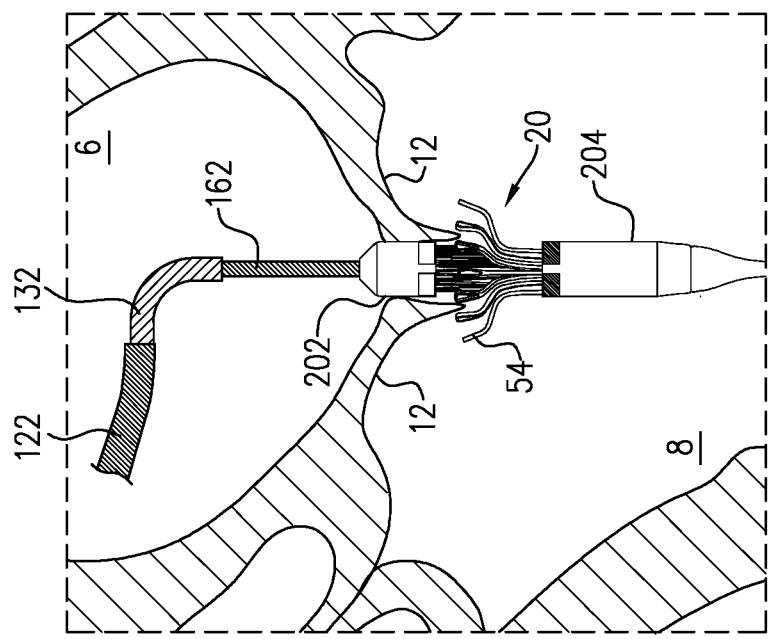

Subsequently, and while the deployment state of capsule assembly 200 typically remains as shown in FIG. 3B, the capsule assembly is retracted proximally, upstream, until it is determined (e.g., via imaging, such as fluoroscopy) that flanges 54 have engaged leaflets 12 (FIG. 4F).

Figure 4H:
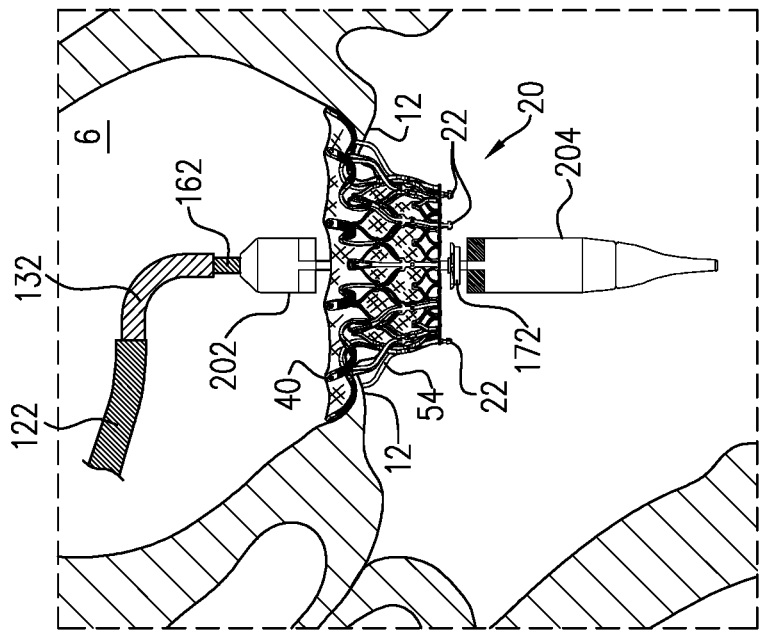
Figure 4G:
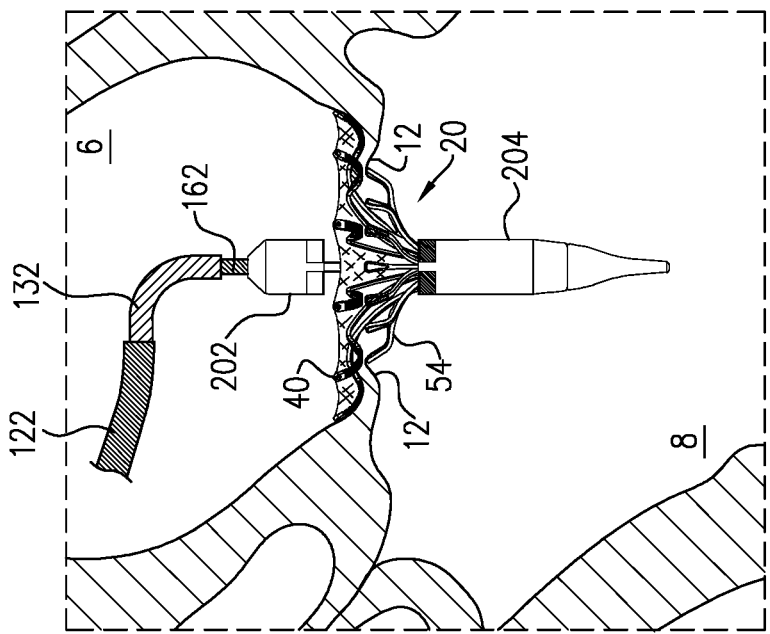

Subsequently, as shown in FIG. 4G, an upstream support portion 40 of implant 20 is deployed by releasing it from proximal capsule 202, by retracting the proximal capsule proximally with respect to mount 172 (and therefore with respect to the implant) (FIG. 3C). This may be achieved by moving capsule catheter 162 proximally (as shown), or may be achieved by rotating the capsule catheter (e.g., as described hereinbelow for delivery tool 1020, mutatis mutandis). Upstream support portion 40 typically comprises a plurality of radial arms, and optionally a flexible sheet covering the arms, and becomes disposed over the upstream surface of the annulus of native valve 10 (FIG. 4G). Leaflets 12 therefore become at least lightly sandwiched between upstream support portion 40 and flanges 54.

Subsequently, as shown in FIG. 4H, implant 20 is fully deployed by releasing the distal end of the implant from distal capsule 204, by advancing the distal capsule distally with respect to mount 172 (FIG. 3D). That is, mount 172 is typically shaped to engage the distal end of the implant (e.g., by slots 175 defined by the mount receiving adaptors 22 defined by the distal end of the implant, as described hereinbelow with reference to FIGS. 8E-G), such that exposing the mount from the distal capsule fully releases the implant from the distal capsule.

For some such applications, distal advancement of distal capsule 204 is accomplished via axial movement of rod 168. Typically for such applications, the axial movement of the rod transitions delivery tool 100 from a retracted state (FIGS. 3A-C), in which a part of shaft 164 and/or implant-receiving slots 175 are within distal capsule 204, to an extended state (FIG. 3D), in which the part of the shaft and/or the slots are outside the distal capsule.

As shown in FIG. 4H, expansion of implant 20 opens a central channel of the implant to blood flow, and allows leaflets of the implant (not shown) to provide one-way valve functionality. The expansion also typically further squeezes leaflets 12 between upstream support portion 40 and flanges 54, thereby securing implant 20 in place, and inhibiting paravalvular leakage.

Figure 5B:
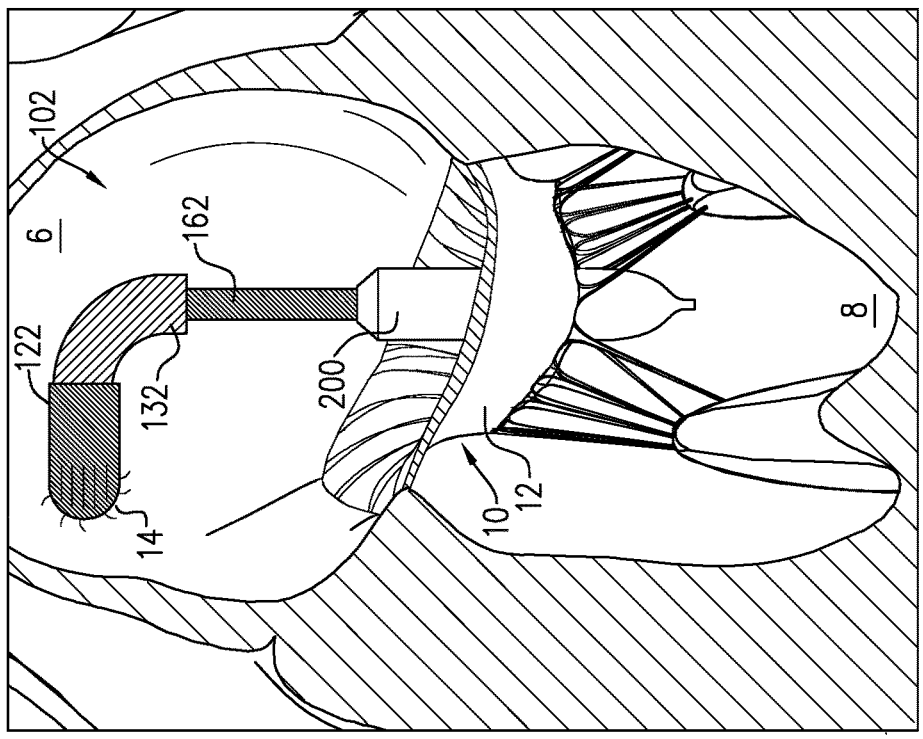
Figure 5A:
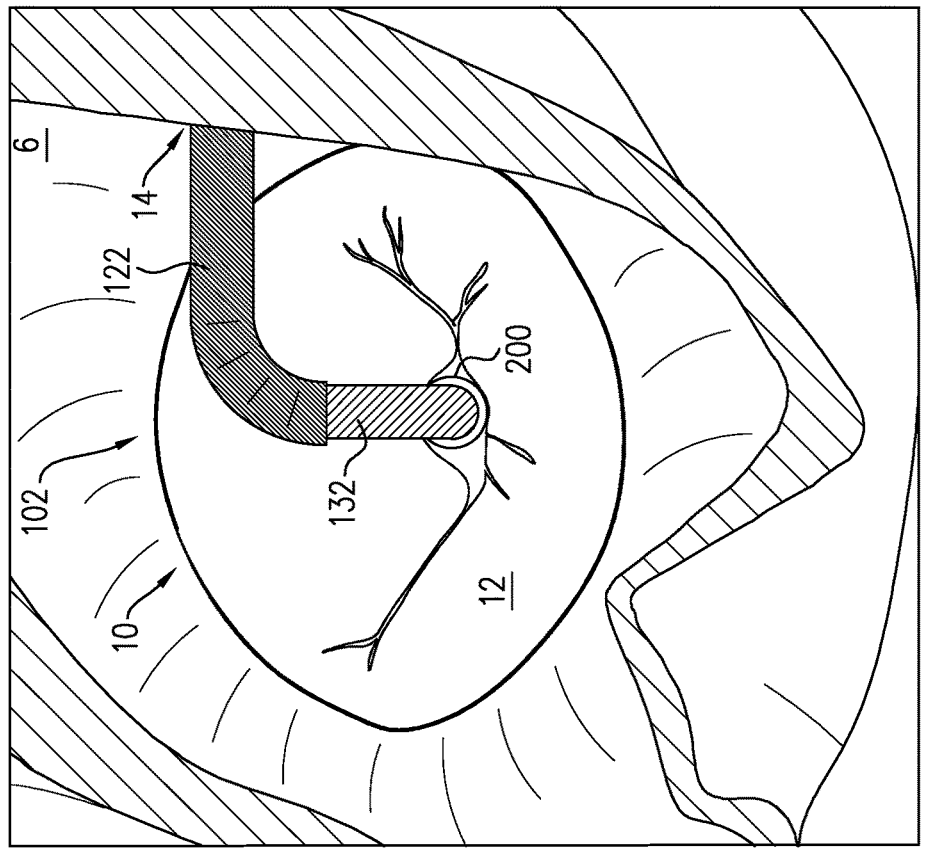
Figure 6:
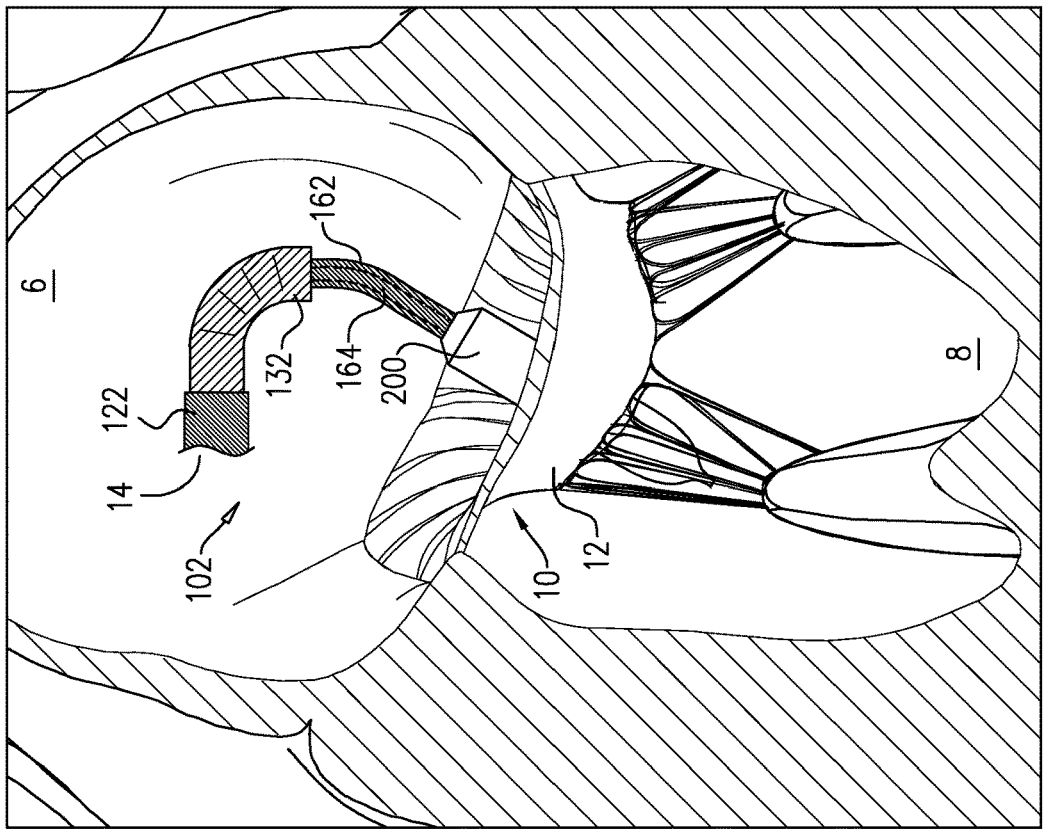

FIGS. 5A-B, 6, and 7 show respective views of distal part 102 of delivery tool 100, at the stage of deployment shown in FIG. 4B, but with certain differences as noted, in order to illustrate some flexibility that delivery tool 100 provides, and which the inventors hypothesize to be advantageous. In both FIG. 4B and FIGS. 5A-B, catheter 122 extends through fossa ovalis 14 into atrium 6, and is steered toward a position that is overhead of valve 10 (e.g., overhead of the center of valve 10). Also, in both FIG. 4B and FIGS. 5A-B, catheter 132 extends out of catheter 122, and is steered downward toward valve 10, such that capsule assembly 200 is disposed between leaflets 12 of the valve. However, in contrast to FIG. 4B, the cardiac anatomy in the example shown in FIGS. 5A-B is such that, in order to position capsule assembly 200 between the leaflets, the capsule assembly has been advanced away from catheter 132 and no longer abuts the catheter. This may be advantageous, for example, if fossa ovalis 14 is particularly high above native valve 10. In contrast to FIG. 4B, the cardiac anatomy in the example shown in FIG. 6 is such that, in order to position capsule assembly 200 between the leaflets, additional steering is desirable. In the example shown in FIG. 7, the cardiac anatomy is such that the distance between fossa ovalis 14 and native valve 10 is shorter than that in FIG. 4B, and the cumulative length of the steerable distal portion of catheter 122 and the steerable distal portion of catheter 132 would be too great to obtain the desired angle of attack.

Figure 7:
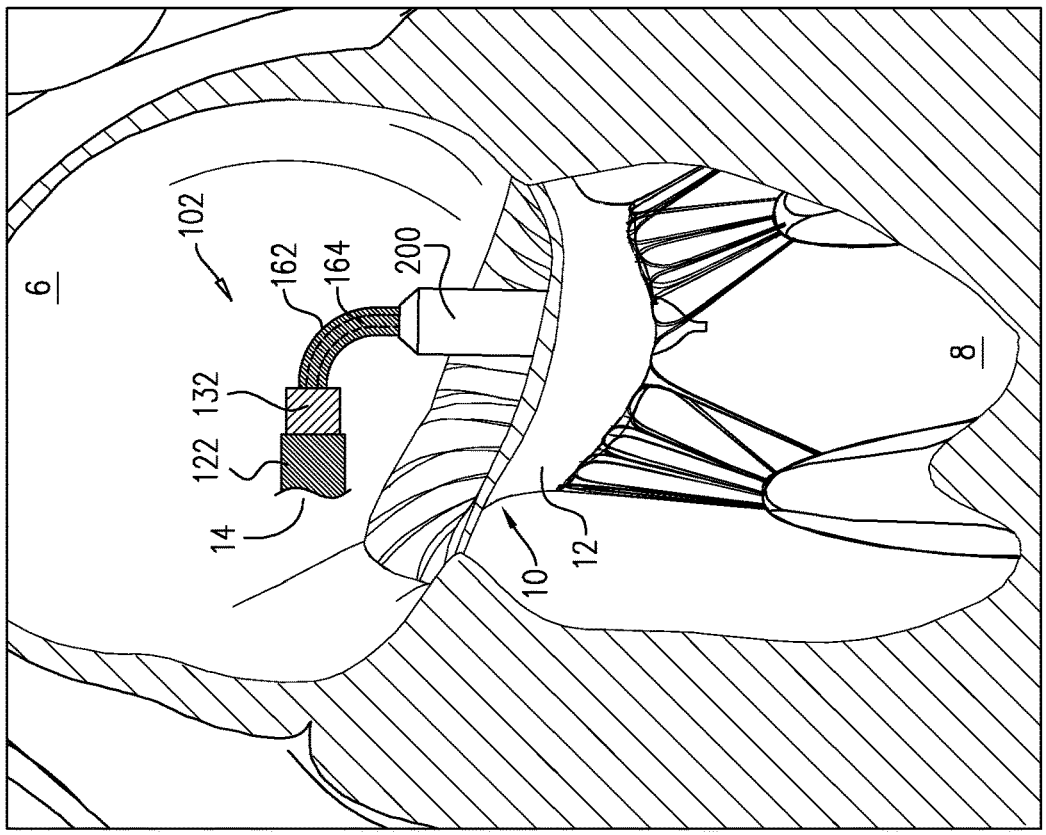

FIGS. 6 and 7 illustrate an additional steering feature that, for some applications, is included in delivery tool 100. This steering feature is the steerability of shaft 164 (or at least a steerable distal region of proximal portion 164p (FIG. 1B)). It is hypothesized that this steering feature advantageously increases the flexibility of delivery tool 100, and its suitability to a greater range of anatomies.

As shown in the upper inset of FIG. 1C, steerability of shaft 164 is provided by pull-wires 364a and 364b that extend from the steerable distal region of the shaft, proximally within the shaft to a controller 166 of proximal portion 161 of implantation instrument 160, similarly to the steerability of catheters 122 and 132, mutatis mutandis. This is described in more detail hereinbelow.

In the example shown in FIG. 6, steering of shaft 164 is used in addition to steering of catheter 132. In the example shown in FIG. 7, steering of shaft 164 is used instead of steering of catheter 132, with catheter 132 barely exposed from catheter 122. It is to be noted that, as shown, while shaft 164 is steerable (meaning actively steerable), it is disposed within catheter 162, which is flexible (but not itself steerable) and therefore passively bends in response to the steering of shaft 164.

Reference is again made to FIG. 1C, which includes a cross-section of delivery tool 100 that illustrates the arrangement of the various tubular members and pull-wires thereof. Two pull-wires 322a and 322b extend proximally from a steerable distal portion of catheter 122 to controller 126, actuation of which steers the steerable portion of catheter 122. Two pull-wires 332a and 332b extend proximally from a steerable distal portion of catheter 132 to controller 136, actuation of which steers the steerable portion of catheter 132. For applications in which shaft 164 is steerable, two pull-wires 364a and 364b extend proximally from a steerable portion of shaft 164 to controller 166 (e.g., a shaft bend-actuator thereof), actuation of which steers the steerable portion of shaft 164.

Figure 2A:
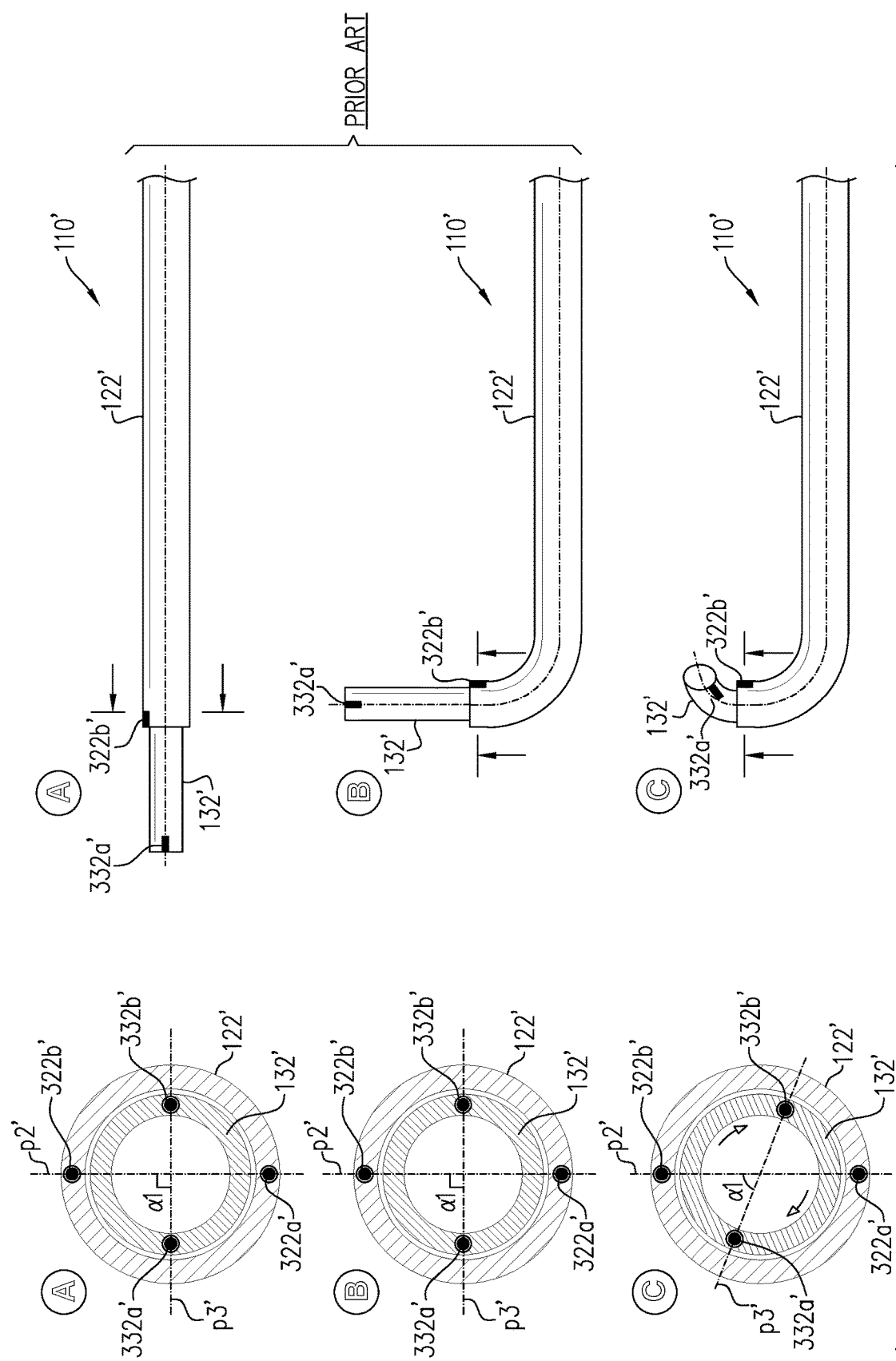
FIG. 2A is a schematic illustration showing, in frames A and B thereof, a two-catheter system, as is known in the prior art, and in frame C thereof, a hypothetical state of the two-catheter system.

Reference is made to FIG. 2A, which is a schematic illustration showing, in frames A and B thereof, a two-catheter system 110', as is known in the prior art. Elements of two-catheter system 110' are labeled with the same reference numerals as corresponding elements of catheter system 110, with the addition of an apostrophe: '. As shown, pull-wire plane p3' passes through both pull-wires 332a' and 332b' of inner catheter 132', and is rotationally offset with respect to pull-wire plane p2' that passes through both pull-wires 322a' and 322b' of outer catheter 122'.

Typically, pull-wire planes p2' and p3' define respective steering planes along which catheters 122', 132' can be bent, and therefore, along which catheter system 110' can be steered. Outer catheter 122' and inner catheter 132' are typically rotationally oriented with respect to each other such that pull-wire planes p2' and p3' are offset by a 90-degree angle_1' (frame A of FIG. 2A).

As shown in frame B of FIG. 2A, tensioning of pull-wire 322b' of outer catheter 122' may not significantly alter the rotational orientation of inner catheter 132' with respect to the outer catheter. That is, while catheter system 110' is steered along pull-wire plane p2' of outer catheter 122', both the outer catheter and inner catheter 132' may bend along pull-wire plane p2', such that angle alpha_1' is maintained at 90 degrees.

Reference is made to frame C of FIG. 2A, which shows a hypothetical state of two-catheter system 110'. As shown, when inner catheter 132' is steered along a steering plane that is different from plane p2', bending of the inner catheter may yield rotational slippage of the inner catheter with respect to the outer catheter (rotational arrows). Thus, steering of inner catheter 132' within bent outer catheter 122' may cause pull-wire planes p2' and p3' to become closer to being co-planar, such that alpha_1' deviates from 90 degrees (e.g., becomes acute in frame C). This rotational slippage may therefore reduce the range of steering of catheter system 110' and/or not yield the desired final steering angle of inner catheter 132'.

It is therefore hypothesized by the inventors that an improved placement of the pull-wires (when the catheter system is at rest) to address this issue is not at a 90-degree offset.

Figure 2B:
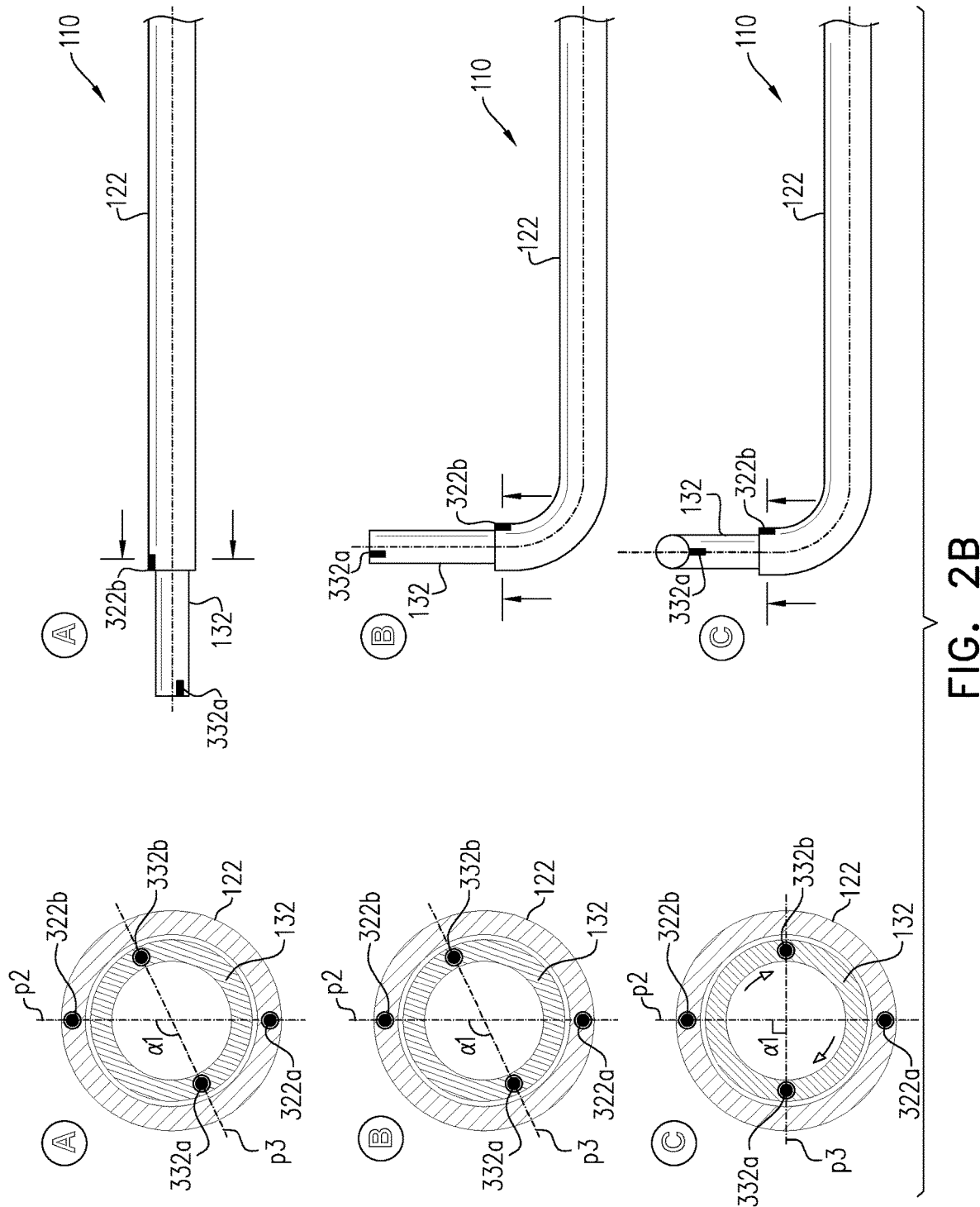
FIG. 2B is a schematic illustration showing a catheter system, in accordance with some applications of the invention.

Reference is made to FIG. 2B, which is a schematic illustration showing catheter system 110, in accordance with some applications of the invention. In catheter system 110, the pull-wires are positioned such that, at rest (e.g., with no steering or bending of the catheters), pull-wire planes p2 and p3 are not offset by 90 degrees. For example, and as shown in frame A, an obtuse angle alpha_1 formed by the intersection of plane p3 and plane p2 may be greater than 95 degrees and/or less than 120 degrees (such as about 110 degrees). For some applications in which catheters 122, 132 are rotationally lockable via a proximal lock and/or a distal lock, as described hereinabove with reference to FIGS. 4A-B, the proximal and/or distal locks may keep pull-wire planes p2 and p3 offset such that angle alpha_1 remains obtuse along a length of the catheters.

Tensioning of pull-wire 322b of first catheter 122 may not significantly alter the rotational orientation of second catheter 132 with respect to the first catheter. That is, while catheter system 110 is steered along pull-wire plane p2 of first catheter 122, both the first catheter and second catheter 132 may bend along pull-wire plane p2, such that angle alpha_1 is maintained as an obtuse angle.

However, because angle alpha_1 is obtuse when catheter system 110 is at rest, rotational slippage of second catheter 132 with respect to first catheter 122 (rotational arrows in frame C of FIG. 2B) resulting from steering the second catheter 132 along plane p3 brings angle alpha_1 closer to 90 degrees, thereby improving the ease of steering of catheter system 110, relative to catheter system 110'. For some applications in which catheters 122, 132 are rotationally lockable via a proximal lock and/or a distal lock, the proximal and/or distal locks may be unlocked prior to steering the second catheter 132 along plane p3, thereby allowing at least a portion of the second catheter to rotate with respect to the first catheter, such that plane p3 moves toward being perpendicular to plane p2.

It is therefore hypothesized by the inventors that positioning pull-wires 322a, 322b, 332a, 332b such that, while at rest, pull-wire planes p2 and p3 are not offset by 90 degrees, facilitates bi-planar steering of catheter system 110. Even if rotational slippage in catheter system 110 continues past the 90-degree position, such that angle alpha_1 becomes less than 90 degrees, this resulting angle is advantageously greater than that of steering system 110', in which the initial angle is 90 degrees.

Reference is now made to FIGS. 8A-G and 9, which are schematic illustrations showing at least some steps of loading implant 20 into capsule assembly 200 of delivery tool 100, in accordance with some applications of the invention. It is hypothesized by the inventors that it is advantageous to load implant 20 into distal capsule 204 in at least two steps. In a first step (FIGS. 8A-B), the implant is slid proximally over distal capsule 204. In a second step (FIGS. 8E-G), distal capsule 204 is slid over the implant by manipulating the distal capsule from distal part 102 of delivery tool 100 (as described hereinbelow), rather than from proximal part 104 of the delivery tool. That is, whereas an unsheathing force applied by the operator during deployment of implant 20 is applied to actuator 176 of proximal portion 161 as described hereinabove (e.g., FIGS. 4C-H), it is hypothesized by the inventors that it is advantageous to apply the ensheathing force directly to distal part 102, e.g., such that greater force can be applied to the implant, and/or such that the application of the ensheathing force is performed near to the site of manipulation of implant 20, thereby improving visibility of the implant to the person performing the ensheathing and/or improving control of the loading process.

For some applications, and as shown in FIG. 8A, actuator 176 (visible in FIGS. 1A and 1C) is entirely removed from instrument 160, prior to ensheathing implant 20 in distal capsule 204. (Alternatively, instrument 160 may be provided with actuator 176 initially separate from the rest of the instrument.)

As described hereinabove, distal capsule 204 is rotationally coupled to rod 168 (FIGS. 1B and 3). Therefore, rotating distal capsule 204 directly (e.g., by grasping the distal capsule by hand) would not necessarily rotate rod 168, and therefore would not result in movement of the distal capsule proximally over mount 172 and implant 20. Therefore, for some applications, an accessory 240 is provided (FIG. 8B), attachment of which to distal portion 163 of implantation instrument 160 (e.g., to distal capsule 204) rotationally locks distal capsule 204 to rod 168, thereby allowing ensheathing of implant 20 within the distal capsule by rotating the distal capsule directly.

Figure 8B:
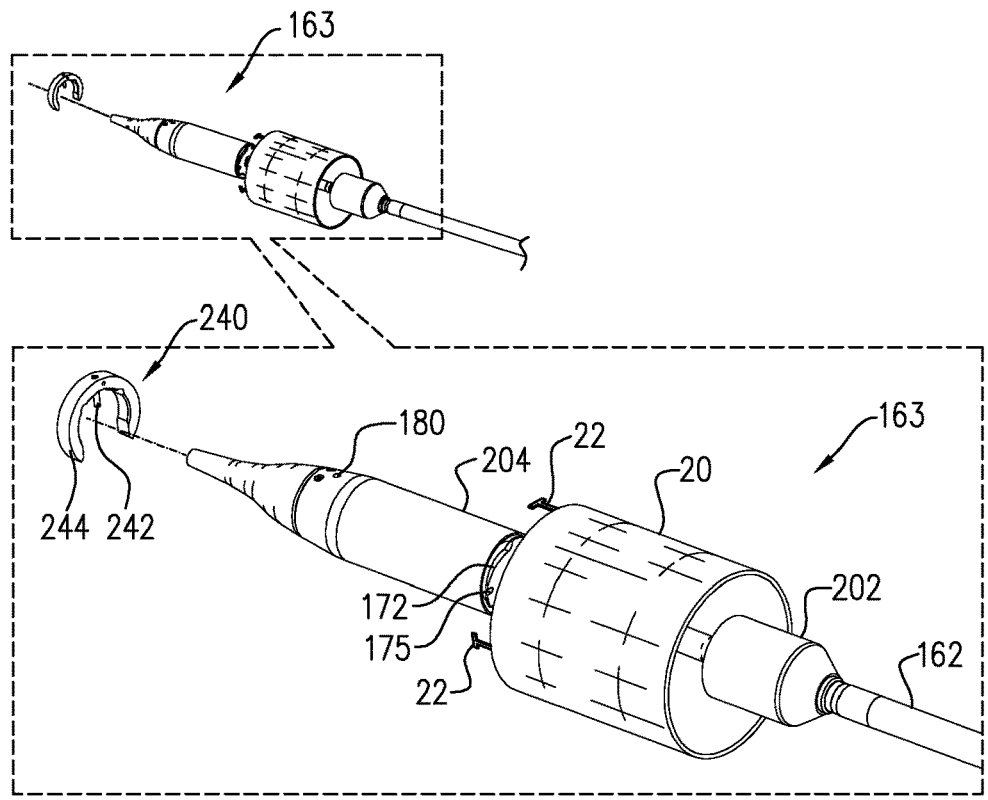
Figure 8C:
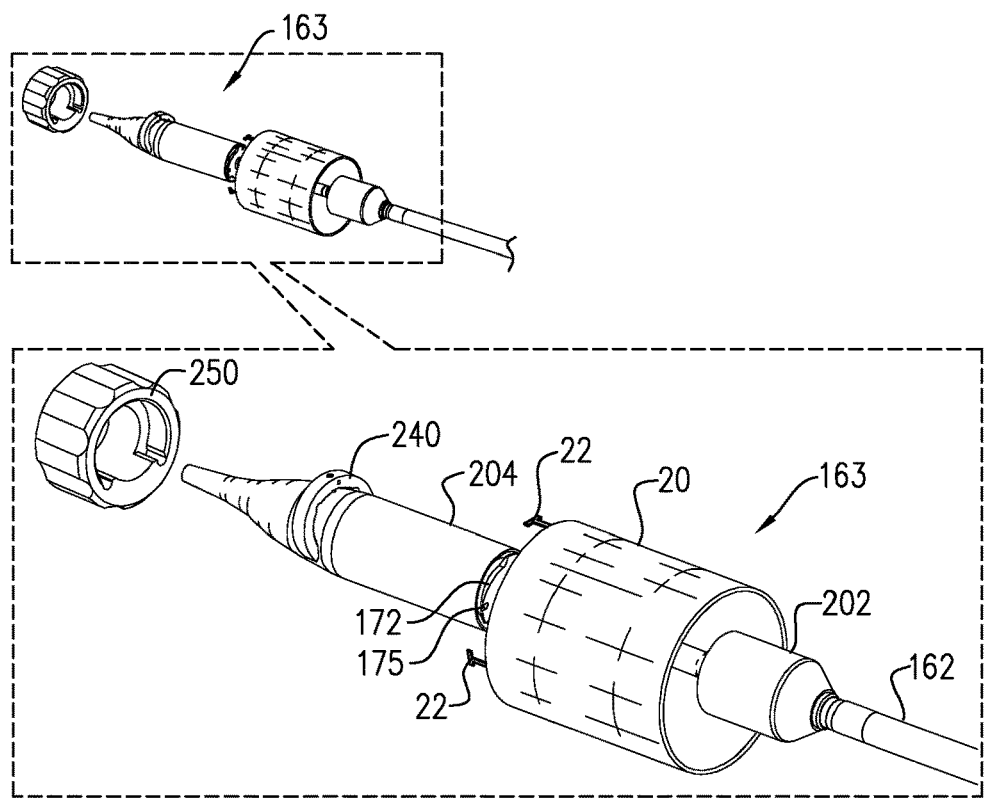
Figure 8D:
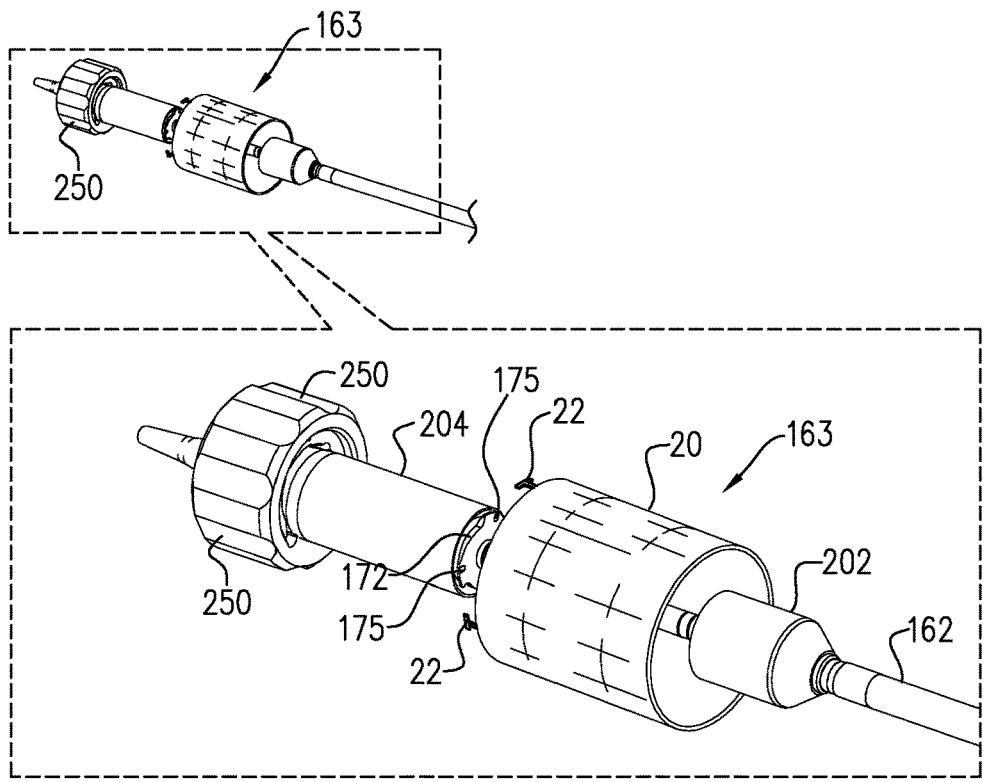

FIG. 8A shows distal portion 163 of implantation instrument 160, with capsule assembly 200 open in the configuration shown in FIG. 3D, such that mount 172 is released proximally from the open end of distal capsule 204. Implant 20 is introduced over the distal end of catheter system 110, over and past distal capsule 204 (FIG. 8B). For applications in which implant 20 is a prosthetic valve, distal capsule 204 typically moves with respect to the leaflets of the valve in an upstream-to-downstream direction (e.g., from an upstream end of the prosthetic valve to a downstream end of the prosthetic valve, as described hereinbelow with reference to prosthetic valve 1036 shown in frame A of FIG. 11). Subsequently, accessory 240 is attached to distal portion 163 of implantation instrument 160 (e.g., to distal capsule 204) (FIGS. 8B-C).

Typically, accessory 240 comprises (or defines) a detent 242, and is configured to be attached to distal capsule 204 such that the detent rotationally locks the distal capsule to rod 168. For some applications, distal capsule 204 defines a detent-hole 180, and the attachment of accessory 240 to the distal capsule is such that detent 242 extends through the detent-hole to rotationally lock the distal capsule to rod 168. For some such applications, delivery tool 100 (e.g., catheter system 110 thereof) comprises a catch to which detent 242 may be engaged. For example, catheter system 110 may define a recess 178 (FIG. 1B) into which detent 242 becomes disposed. For some applications, catheter system 110 comprises a ring 174 that is rotationally and axially fixed with respect to rod 168, and that defines recess 178 (see FIGS. 1B, and 3A-D). For some applications, rod 168 defines ring 174 and/or recess 178.

For some applications, accessory 240 comprises a c-shaped clip 244, and is attached to distal capsule 204 by being placed over the distal capsule (e.g., snapped into place). For such applications, detent 242 is attached to clip 244, and typically extends radially inward from its point of attachment to the clip.

For some applications, a knob 250 is subsequently introduced over the distal end of catheter system 110 (FIGS. 8C-D), and is engaged with clip 244 (and optionally with distal capsule 204), to facilitate rotation by hand of distal capsule 204 with respect to rod 168.

Figure 8E:
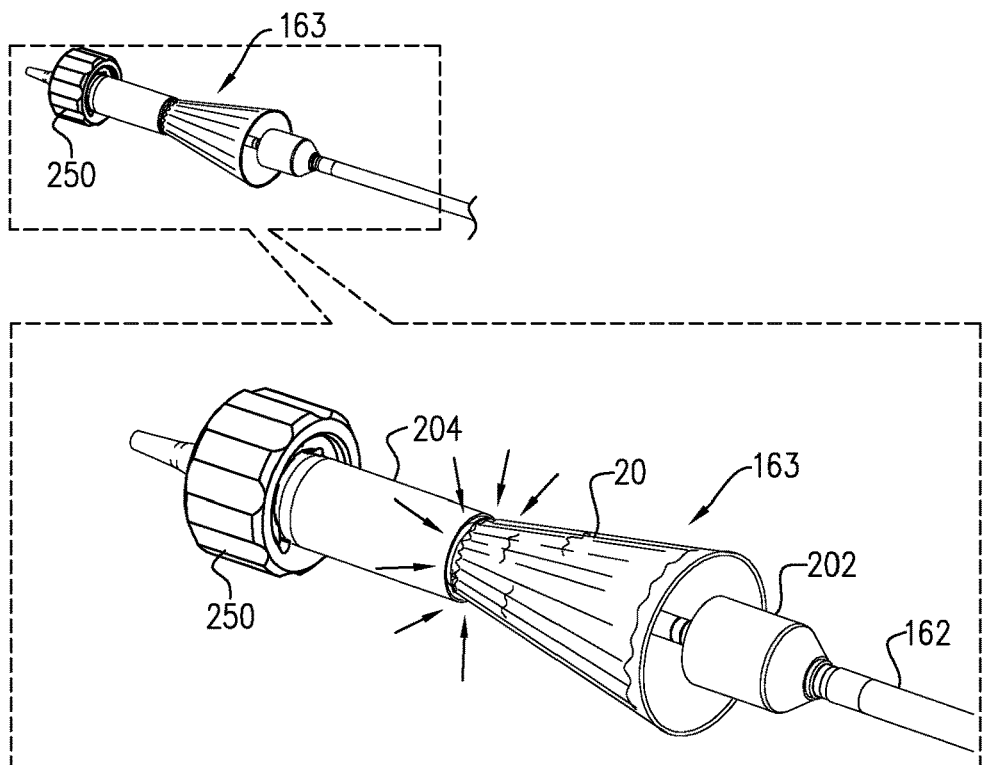

As shown in FIG. 8E, implant 20 is then compressed ("crimped") such that the implant engages mount 172, e.g., with adaptors 22 being received by respective slots 175.

Figure 8F:
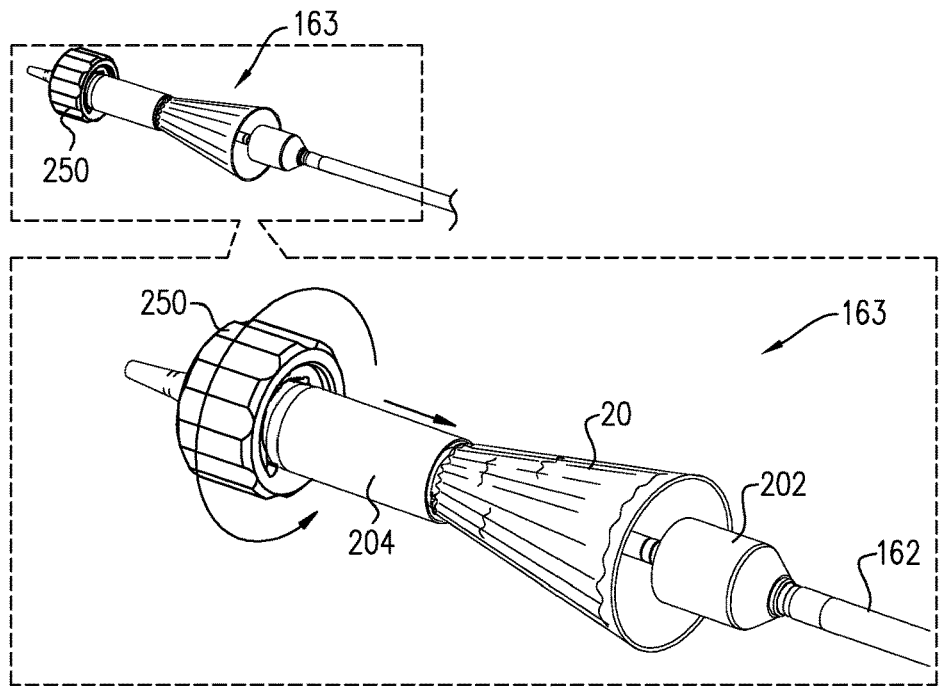
Figure 8G:
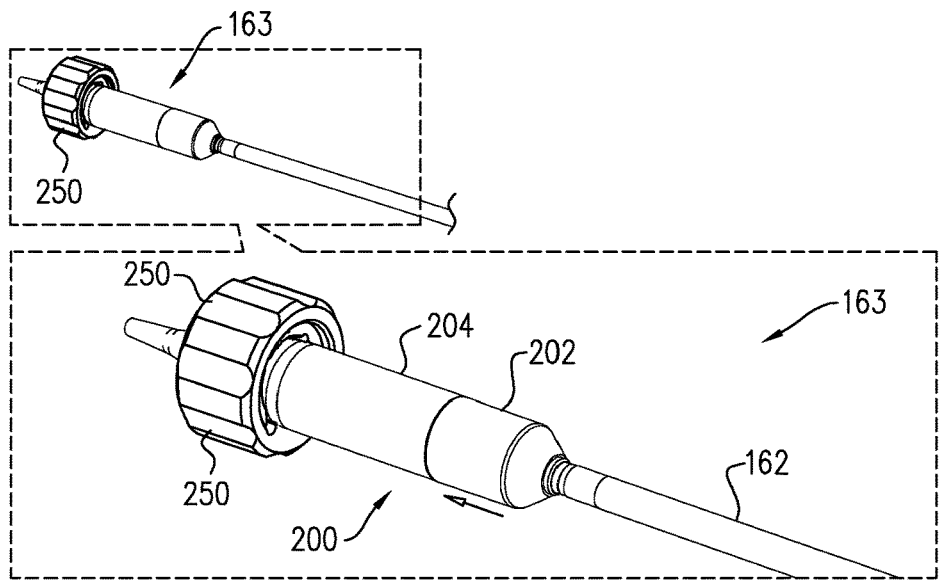

Subsequently, and as shown in FIG. 8F, distal capsule 204 and rod 168 are hand-rotated in a first rotational direction (e.g., by grasping the distal capsule, accessory 240, and/or knob 250), such that rod 168 screws into shaft 164, thereby screwing the distal capsule proximally over implant 20 and mount 172. In this way, at least the downstream end of the implant is ensheathed by the distal capsule, while maintaining the engagement between the implant and the mount. Therefore, implant 20 is ensheathed in distal capsule 204 by moving the distal capsule helically over the implant, but is unsheathed by moving the distal capsule linearly off of the implant, as described hereinabove with reference to FIGS. 3A-D and 4C-H. For some applications, and as shown in FIG. 8G, proximal capsule 202 is advanced distally over the upstream end of implant 20, further ensheathing the implant within capsule assembly 200.

Figure 9:
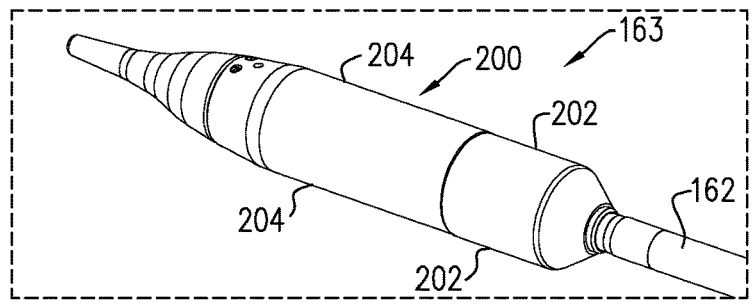

Subsequently to ensheathing the implant, and yet prior to capsule assembly 200 being used to deliver implant 20, accessory 240 (and knob 250, if present) is removed (FIG. 9). Removing accessory 240 from distal capsule 204 rotationally unlocks the distal capsule with respect to rod 168, such that the unsheathing force (e.g., rotation of the rod in a second rotational direction) moves the distal capsule linearly off of the implant.

In any case, if actuator 176 was initially not engaged with rod 168 or was disengaged by the operator from rod 168 prior to ensheathing implant 20 in distal capsule 204, then actuator 176 is engaged (or reengaged) with rod 168 prior to implantation of the implant. Typically for such applications, the unsheathing force is then applied to distal portion 163 of implantation instrument 160 via actuator 176.

Reference is made to FIGS. 10A-E, which are schematic illustrations showing a delivery tool 1020, in accordance with some applications of the invention.

FIG. 10A shows delivery tool 1020 assembled, and FIG. 10B shows an exploded view of a distal portion 1024 of the delivery tool. As shown, delivery tool 1020 comprises an extracorporeal controller 1021 and distal portion 1024 that is dimensioned for transluminal (e.g., transfemoral) delivery to a subject.

Delivery tool 1020 bears certain similarities to delivery tool 100 described hereinabove. Particularly, distal portion 1024 of delivery tool 1020 is in certain ways similar to distal portion 163 of implantation instrument 160 of delivery tool 100. Components that are identically named between delivery tools 100, 1020 typically share similar features and serve similar functions as each other.

As shown, distal portion 1024 comprises a shaft 1034 (e.g., extending distally from within a capsule catheter 1072) to which a proximal capsule 1064 and a distal capsule 1066 (collectively defining a capsule assembly 1063) are coupled. As shown in FIG. 10B, each capsule 1064, 1066 has a respective open end 1065, 1067, such that open end 1065 of proximal capsule 1064 faces the proximal end of distal capsule 1066. For some applications, and as shown, open end 1067 is the proximal end of distal capsule 1066, such that open end 1065 of proximal capsule 1064 faces the open end of the distal capsule.

Similarly to distal portion 163 of instrument 160 described hereinabove, distal portion 1024 further comprises a mount 1028 dimensioned (e.g., defining slots 1029) to engage an implant. Typically, capsules 1064, 1066 can be moved with respect to the mount (e.g., along a distal portion axis ax1018), via extracorporeal controller 1021. For some applications, extracorporeal controller 1021 controllably moves proximal capsule 1064 and/or distal capsule 1066 both distally ("advanced") and proximally ("retracted"), with respect to mount 1028.

For some applications, and as shown in FIG. 10B, distal portion 1024 comprises a rod 1168 that extends out of a distal end of shaft 1034. Similarly to as described hereinabove with reference to rod 168 of instrument 160, delivery tool 1020 is configured to distally advance distal capsule 1066 with respect to mount 1028 by screwing the rod through shaft 1034.

For some such applications, and further similarly to distal capsule 204 of instrument 160, distal capsule 1066 is rotationally coupled to and rotationally movable with respect to rod 1168, such that rotation of rod 1168 does not necessarily rotate distal capsule 1066. Typically for such applications, pins 1170 are fitted within distal capsule 1066, in relation to a recess 1169 defined by rod 1168, so as to axially fix the distal capsule with relation to the rod, while allowing rotation of the rod with respect to the pins, as described hereinabove with reference to instrument 160 regarding FIG. 1C and FIGS. 3A-D.

For some such applications, and as shown, distal capsule 1066 defines a window 1110, and a hole 1180 Typically for such applications, hole 1180 is shaped to facilitate attachment of accessory 240 and/or knob 250 (not shown in FIG. 10B, yet described hereinabove with reference to FIGS. 8B-G) in order to rotationally lock the distal capsule with respect to rod 1168.

For example, rotationally locking distal capsule 1066 to rod 1168 may be facilitated by extending a portion of accessory 240 through hole 1180 such that the portion occupies a recess 1178 defined by a ring 1174 that is fixedly coupled to the rod.

Notwithstanding similarities between delivery tools 100 and 1020, the description below of delivery tool 1020 focuses upon features that are particular to delivery tool 1020. A difference between delivery tools 100 and 1020 lies in distal portion 1024 being configured to be transluminally advanced to the heart while in a delivery state (FIGS. 10A and 10C) in which an inter-capsule gap 1071*a* exists between proximal capsule 1064 and distal capsule 1066 (e.g., between respective open ends 1065, 1067).

Figure 10C:
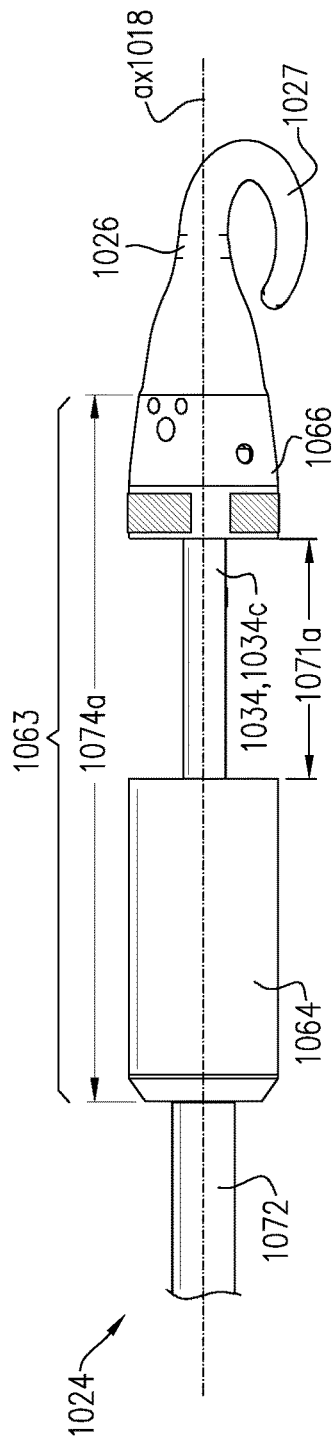
Figure 10D:
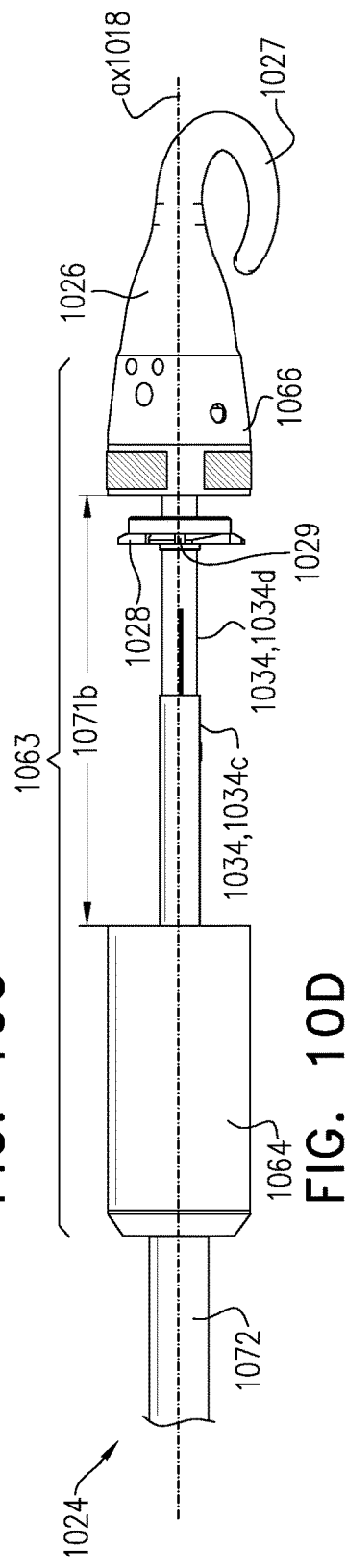

Typically for applications in which capsules 1064, 1066 can be both advanced and retracted, the capsules may be moved axially to a range of positions, relative to mount 1028. For some such applications, and as shown in FIG. 10D, segments 1034*c* and 1034*d* of shaft 1034 may be slidably coupled to each other, thereby facilitating axial movement of capsules 1064, 1066. Thus, and as shown in FIG. 10D, segments 1034*c* and 1034*d* may slide telescopically with respect to each other, such that distal portion 1024 assumes a deployment state in which inter-capsule gap 1071*b* is longer than gap 1071*a* when the distal portion is in the delivery state (FIG. 10C).

Inter-capsule gap 1071*b* is typically at least 50% (e.g., at least 100%) and/or less than 200% (e.g., less than 150%) greater than inter-capsule gap 1071*a*.

For some applications, while distal portion 1024 is in the delivery state, inter-capsule gap 1071*a* is greater than 1 mm (e.g., greater than 5 mm, e.g., greater than 10 mm, e.g., greater than 15 mm, e.g., greater than 20 mm) and/or less than 25 mm in length (e.g., less than 20 mm, e.g., less than 15 mm, e.g., less than 10 mm, e.g., less than 5 mm). For example, inter-capsule gap 1071*a* may be 10-20 mm.

For some such applications, while distal portion 1024 is in the deployment state, inter-capsule gap 1071*b* is greater than 15 mm (e.g., greater than 20 mm, e.g., greater than 25 mm, e.g., greater than 30 mm, e.g., greater than 35 mm) and/or less than 40 mm in length (e.g., less than 35 mm, e.g., less than 30 mm, e.g., less than 25 mm, e.g., less than 20 mm). For example, inter-capsule gap 1071*b* may be 20-35 mm.

Figure 10E:
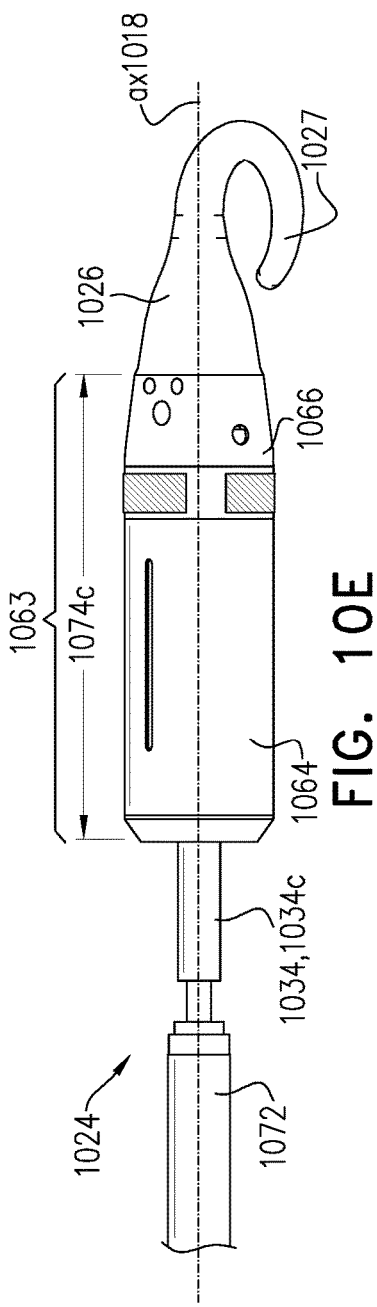

For some applications, proximal capsule 1064 may be further advanced, and/or distal capsule 1066 may be further retracted, such that distal portion 1024 assumes a withdrawal state in which the inter-capsule gap is shorter than when the distal portion is in the delivery state (e.g., such that the gap is closed or nearly-closed, as shown in FIG. 10E). Consequently, for some such applications, a capsule-assembly length 1074*c* from a proximal end of proximal capsule 1064 to a distal end of distal capsule 1066 is lesser while distal portion 1024 is in the withdrawal state (FIG. 10E) than capsule-assembly length 1074*a* while the distal portion is in the delivery state (FIG. 10C).

Although the states (e.g., delivery state, deployment state, withdrawal state) of delivery tool 1020 are described with respect to distal portion 1024, they are typically implemented by controller 1021. For example, controller 1021 may define these states as discrete states by enforcing only certain operations and/or degrees of movement of control elements (e.g., knobs, switches, levers, wheels etc.) of controller 1021, the control elements being operatively coupled to capsules 1064 and 1066, e.g., by wires, rods, and/or cables. Furthermore, for some applications, the orders of operation described hereinbelow are facilitated and/or enforced by controller 1021, e.g., by the controller selectively and/or sequentially locking and/or unlocking locks that selectively and/or sequentially enable and/or disable the control elements of the controller.

Figure 11:
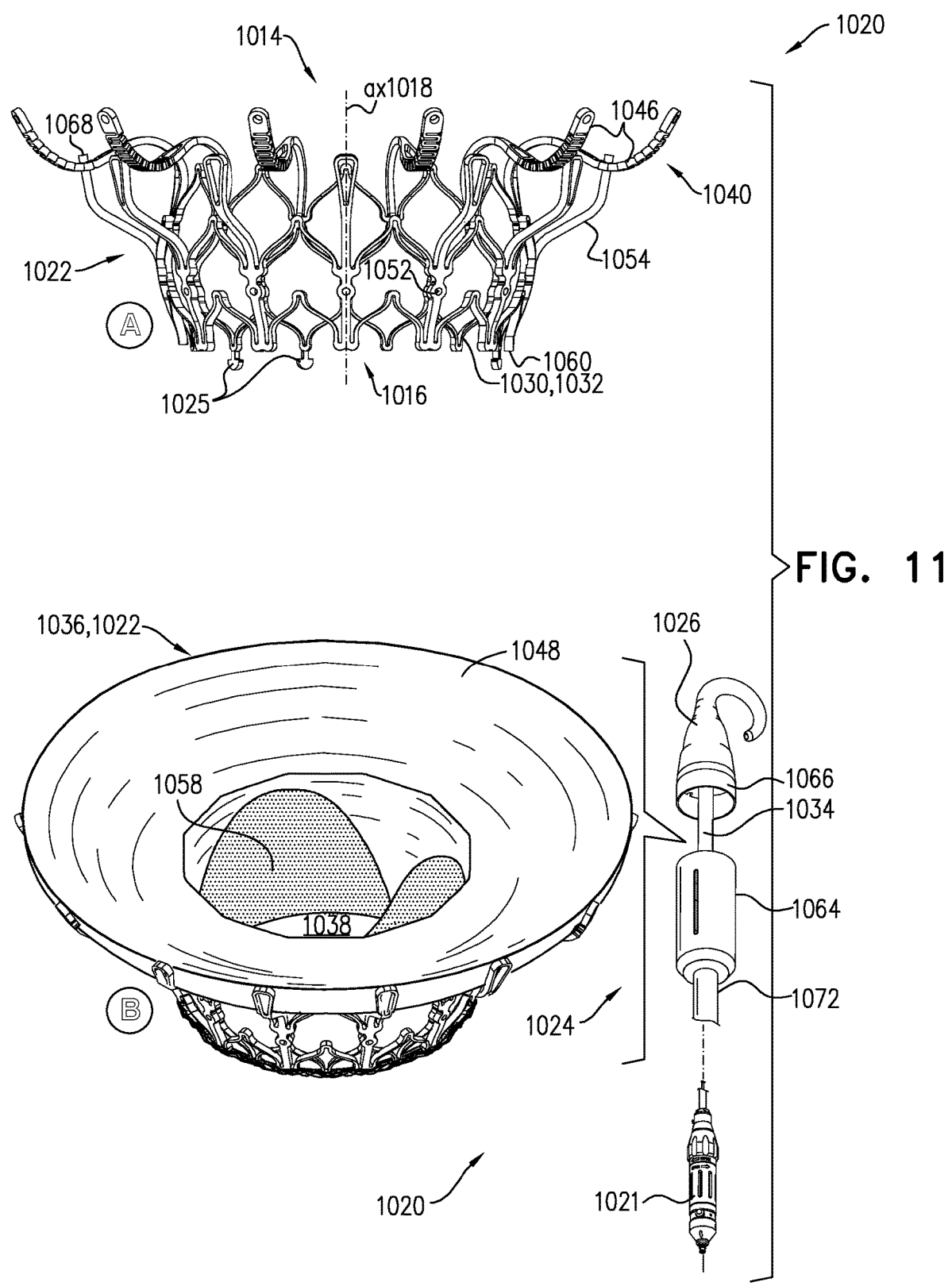
FIG. 11 is a schematic illustration showing the delivery tool while a prosthetic valve has assumed an expanded state, in accordance with some applications of the invention.

Reference is made to FIG. 11, which is a schematic illustration showing delivery tool 1020 while prosthetic valve 1036 has assumed an expanded state, in accordance with some applications of the invention. Prosthetic valve 1036 comprises a frame assembly 1022 (shown in frame A), within which prosthetic leaflets 1058 are disposed (frame B).

Prosthetic valve 1036 is in certain ways similar to that described in WO 2019/026059 to Hariton et al. (e.g., with reference to FIGS. 1, 2, and 18 thereof), which is hereby incorporated by reference. For some applications, delivery tool 1020 may be used to deliver implant (prosthetic valve) 420 of WO 2019/026059 to Hariton et al. Prosthetic valve 1036 is typically self-expanding.

As shown in frame A of FIG. 11, frame assembly 1022 comprises an inner valve frame 1030 nested within an outer frame 1060. Valve frame 1030 is typically shaped to define (i) a tubular portion 1032 that defines a lumen 1038 between an upstream end 1014 and a downstream end 1016, and (ii) a plurality of arms 1046 that collectively form an upstream support portion 1040 that extends upstream from the tubular portion. For some applications, and as shown, valve frame 1030 further defines adaptors 1025, and mount 1028 engages adaptors 1025 (e.g., by receiving adaptors 1025 into slots 1029 defined by the mount).

As shown, outer frame 1060 comprises flanges 1054, which are each coupled to tubular portion 1032 at a respective coupling point 1052 that is disposed downstream of upstream support portion 1040. In this way, each flange 1054 extends upstream from coupling point 1052, to a respective flange end-portion 1068.

Typically, and as shown in frame B, prosthetic valve 1036 comprises a plurality of prosthetic leaflets 1058, which are disposed within lumen 1038 so as to facilitate unidirectional blood flow from upstream end 1014 to downstream end 1016. For some applications, and as shown, prosthetic valve 1036 also comprises an upstream covering 1048, disposed over arms 1046 to define an upstream skirt, in order to reduce a risk of paravalvular leakage.

Reference is made to FIGS. 12 and 13A-B, which are schematic illustrations showing prosthetic valve 1036 being restrained in a compressed state by delivery tool 1020, in accordance with some applications of the invention. FIG. 12 therefore shows delivery system 1010 in a delivery state (described hereinabove in reference to FIGS. 10A and 10C) in which the system is configured to be transluminally advanced to the heart of a subject.

In the delivery state, a distal-implant portion 1100 comprising a distal portion of valve frame 1030 (e.g., downstream end 1016 of tubular portion 1032) is engaged with mount 1028 (e.g., by slots 1029 receiving adaptors 1025), such that the downstream end and the mount are both disposed within distal capsule 1066 (e.g., within a chamber defined by the distal capsule), with the distal capsule restraining the downstream end compressed against the mount, thereby maintaining engagement of the downstream end with the mount.

In the delivery state, a proximal-implant portion 1102 comprising a proximal portion of valve frame 1030 (e.g., upstream support portion 1040) is disposed within (e.g., restrained by) proximal capsule 1064. Additionally, in the delivery state, each flange end-portion 1068 is disposed within (e.g., restrained by) proximal capsule 1064.

Typically, a segment 1056 of prosthetic valve 1036 is disposed at inter-capsule gap 1071a. That is, segment 1056 is exposed by inter-capsule gap 1071a. Typically, segment 1056 includes part of tubular portion 1032, part of each flange 1054, and/or coupling points 1052.

For some applications, and as shown in FIG. 13A, delivery tool 1020 comprises a flexible sheath 1044 (e.g., comprising a polymer and/or a fabric) that covers segment 1056 by circumscribing inter-capsule gap 1071a. For some such applications, a distal end of the sheath may abut, and/or be partially disposed within, distal capsule 1066.

For some such applications, and as shown, sheath 1044 extends proximally from inter-capsule gap 1071a, covering proximal capsule 1064. Sheath 1044 may extend into and through a delivery catheter 1050 that connects distal portion 1024 to extracorporeal controller 1021 (FIGS. 14A-C), e.g., with a proximal end of the sheath remaining outside of the subject.

For some applications, distal portion 1024 of delivery tool 1020 comprises a nosecone 1026 having a flexible distal end-portion 1027. For some such applications, and as shown in FIG. 13A, distal end-portion 1027 has a resting shape (e.g., in the absence of a straightening force that may be provided by a more rigid element such as a guidewire 1023) that is curled. FIG. 13B shows distal end-portion 1027 having been straightened by guidewire 1023 having been extended through capsule catheter 1072 and shaft 1034, and into the distal end-portion. Typically for such applications, an axial length d1025, d1025b of nosecone 1026 is greater when guidewire 1023 is disposed within the distal end-portion (FIG. 13B), than in the absence of the guidewire (e.g., length d1025, d1025a in FIG. 13A). For some such applications, shape-memory of distal end-portion 1027 tends to maintain the distal end-portion in the resting (e.g., curled) shape. That is, even after having been straightened by guidewire 1023, distal end-portion 1027 automatically assumes the curled shape when the guidewire is removed from the distal end-portion. It is hypothesized by the inventors that this curling of nosecone 1026 advantageously allows the nosecone to be longer (and therefore have a shallower taper-angle) than a similar nosecone that does not curl, because it is possible to allow the nosecone to curl during steps in which a long axial length of a nosecone would otherwise be disadvantageous—e.g., as described hereinbelow with respect to FIGS. 14A-B.

Reference is made to FIGS. 14A-J, which are schematic illustrations showing delivery tool 1020 being used to deploy prosthetic valve 1036 at a tricuspid valve 1096 of a heart 1090 of a subject, in accordance with some applications of the invention.

Figure 14A:
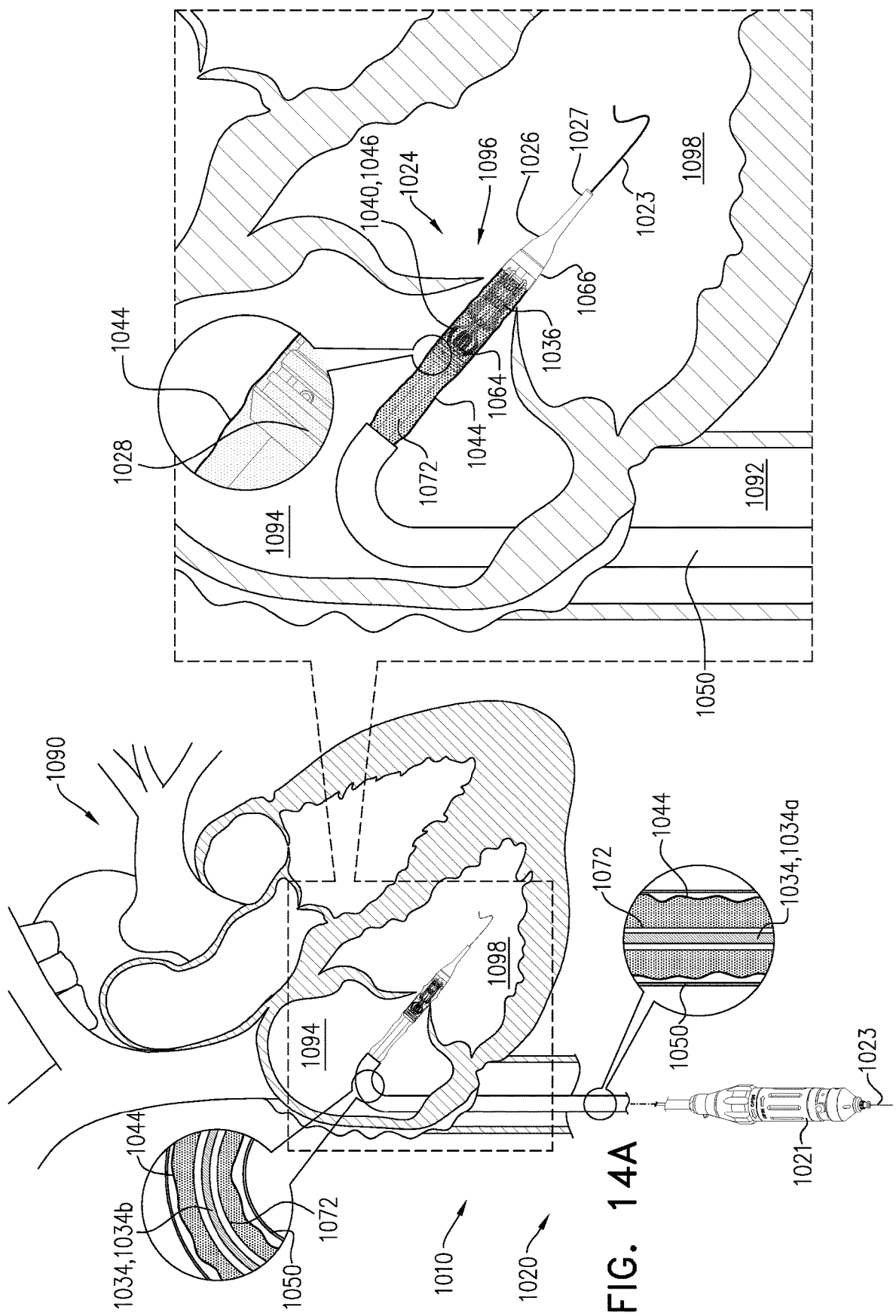
FIGS. 14A-J are schematic illustrations showing the delivery tool being used to deploy the prosthetic valve at a tricuspid valve of a heart of a subject, in accordance with some applications of the invention.

FIG. 14A shows distal portion 1024 of delivery tool 1020 having been transluminally advanced, through inferior vena cava 1092 and right atrium 1094 of heart 1090, such that nosecone 1026 and distal capsule 1066 have passed through tricuspid valve 1096 to enter right ventricle 1098.

For some applications, delivery tool 1020 is transluminally advanced along guidewire 1023 (e.g., after the guidewire is advanced to heart 1090). In this way, guidewire 1023 extends from extracorporeal controller 1021 to delivery catheter 1050. For some applications, controller 1021 is used to manipulate guidewire 1023 (e.g., to steer the guidewire while the guidewire advances to the heart). Alternatively or in addition, steering of distal portion 1024 may be facilitated by delivery tool 1020 comprising at least one pull-wire operatively connecting distal portion 1024 to controller 1021. For example, delivery catheter 1050 may be implemented using catheter system 110 described hereinabove with reference to FIGS. 1C and 2B, such that capsule catheter 1072 and shaft 1034 extend through the catheter system, mutatis mutandis.

For some applications, steering of distal portion 1024 may be further facilitated by shaft 1034 having segments distinguished by their relative rigidity. Typically for such applications, shaft 1034 extends distally from a proximal portion (e.g., from extracorporeal controller 1021) of delivery tool 1020 (e.g., within delivery catheter 1050 and capsule catheter 1072, as shown in the insets on the left side of FIG. 14A). For some such applications, a rigid proximal shaft segment 1034a (lower left inset of FIG. 14A) extends distally from extracorporeal controller 1021. Typically for such applications, rigid proximal shaft segment 1034a is greater than 50 cm (e.g., e.g., greater than 60 cm, e.g., greater than 70 cm, e.g., greater than 80 cm, e.g., greater than 90 cm) and/or less than 100 cm (e.g., e.g., less than 90 cm, e.g., less than 80 cm, e.g., less than 70 cm, e.g., less than 60 cm) in length. It is hypothesized by the inventors that rigidity of rigid proximal shaft segment 1034a facilitates transfer of force from the proximal portion of delivery tool 1020 (e.g., from extracorporeal controller 1021).

For some applications, as described hereinabove, a distal shaft segment 1034b is relatively less rigid than proximal shaft segment 1034a, and is configured to be sufficiently flexible to turn from the vena cava toward tricuspid 1096 (as shown in FIG. 14A). Flexible shaft segment 1034b of shaft 1034 extends distally from rigid proximal shaft segment 1034a (upper left inset of FIG. 14A). For some such applications, flexible shaft segment 1034b is greater than 5 cm (e.g., greater than 6 cm, e.g., greater than 8 cm) and/or less than 10 cm (e.g., less than 8 cm, e.g., less than 6 cm) in length.

For some applications, a rigid distal shaft segment extends distally from flexible shaft segment 1034b, such that the rigid distal shaft segment reaches distal portion 1024 of delivery tool 1020. That is, as shown in FIGS. 10C-D, rigid distal shaft segments 1034c and/or 1034d extend through at least part of capsules 1064, 1066. For example, rigid distal shaft segments 1034c and/or 1034d may extend distally out of proximal capsule 1064. It is hypothesized by the inventors that rigidity of rigid distal shaft segments 1034c and/or 1034d may ensure alignment of capsules 1064, 1066 along distal portion axis ax1018, thereby facilitating axial movement of capsules 1064, 1066 along the distal portion axis.

For some such applications, mount 1028 is attached to the rigid distal shaft segment (e.g., rigid distal shaft segment 1034*d*, as shown). Typically for such applications, prosthetic valve 1036 is compressed upon rigid distal shaft segments 1034*c* and/or 1034*d*.

For some such applications, rigid distal shaft segments 1034*c*, 1034*d* may slide telescopically with respect to each other, as described hereinabove in reference to FIG. 10D. Therefore, while distal portion 1024 is in the delivery state, rigid distal shaft segments 1034*c*, 1034*d* may together be greater than 2 cm (e.g., greater than 3 cm, e.g., greater than 5 cm, e.g., greater than 8 cm) and/or less than 10 cm (e.g., less than 6 cm, e.g., e.g., less than 4 cm) in length.

Figure 14B:
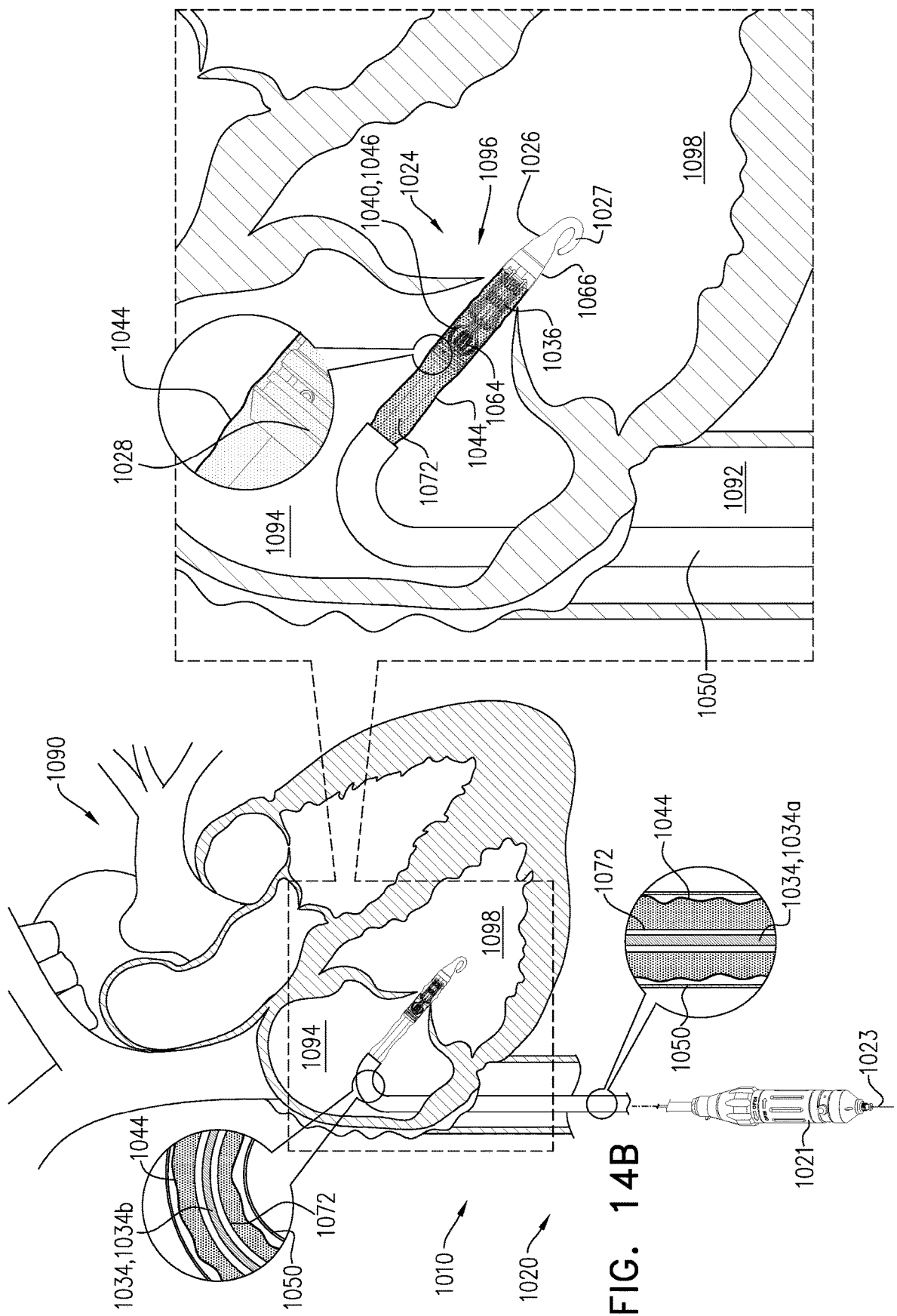
Figure 14C:
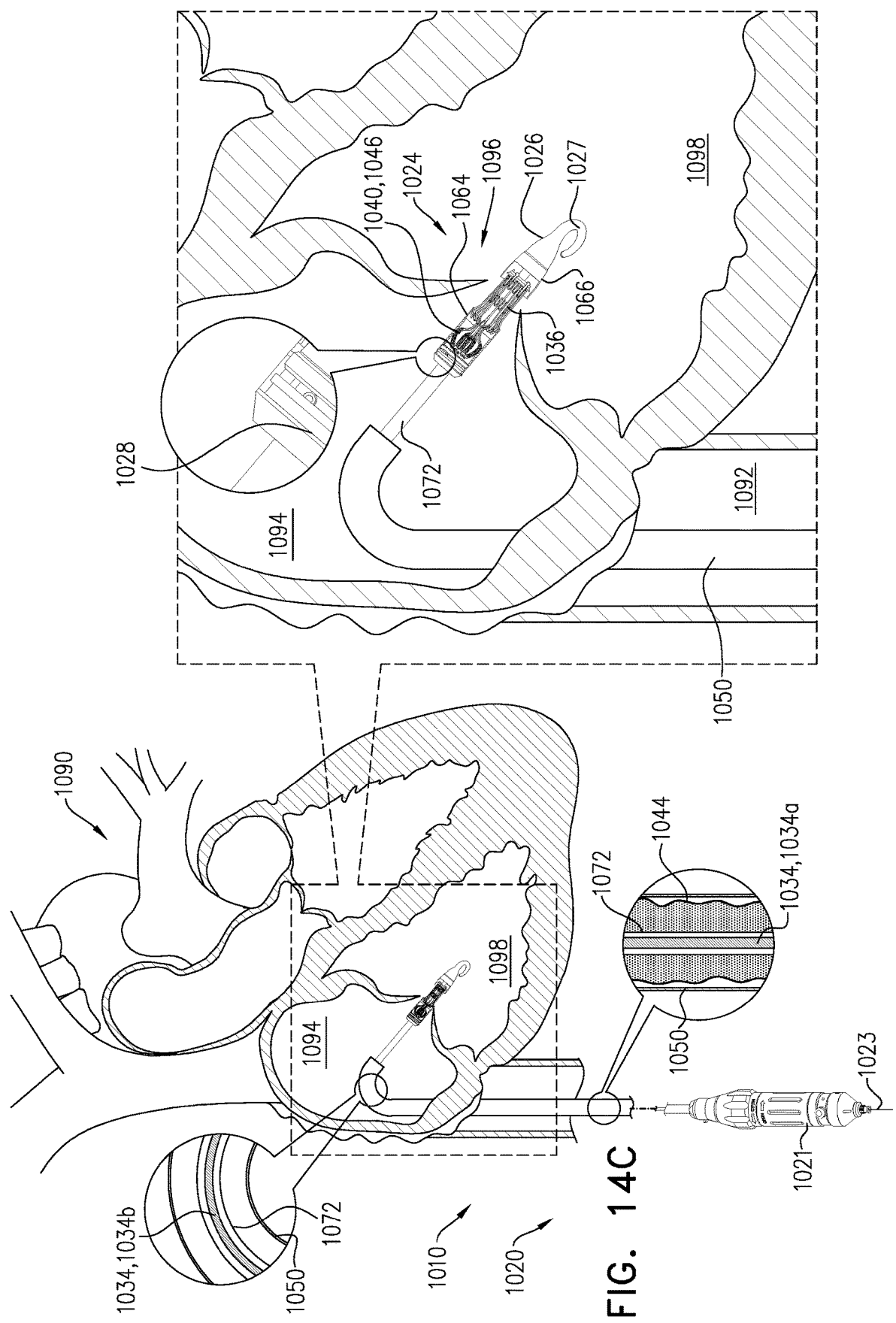

For some such applications, rigid proximal shaft segment 1034*a* (bottom left inset of FIGS. 14A-C), as well as rigid distal shaft segments 1034*c* and 1034*d*, may each be more rigid than flexible shaft segment 1034*b* (upper left inset of FIGS. 14A-C).

It is hypothesized by the inventors that the relative flexibility of flexible shaft segment 1034, 1034*b* facilitates steering of distal portion 1024, particularly from inferior vena cava 1092 to right ventricle 1098. It is further hypothesized by the inventors that the relative rigidity of rigid proximal shaft segment 1034, 1034*a* provides support (e.g., a resistance force) that facilitates steering of distal portion 1024. Additionally, the relative rigidity of rigid distal shaft segments 1034, 1034*c*, 1034*d* is further hypothesized by the inventors to facilitate maintenance of the alignment of the capsules along linear distal portion axis ax1018, e.g., while distal portion 1024 transitions between delivery state, deployment state and withdrawal state, as described hereinabove.

FIG. 14A shows distal end-portion 1027 as it is straightened by guidewire 1023, as described hereinabove. For some applications, it may be desirable to reduce axial length d1025 of nosecone 1026 (FIGS. 13A-B), prior to deploying prosthetic valve 1036 at the native valve. Typically for such applications, and as shown in FIG. 14B, guidewire 1023 is withdrawn from at least distal end-portion 1027, thereby reducing axial length d1025 of nosecone 1026 (as described hereinabove with reference to FIGS. 13A-B). It is hypothesized by the inventors that reducing length d1025 by withdrawing guidewire 1023 may facilitate deployment of prosthetic valve 1036 by reducing an amount of space within right ventricle 1098 required to maneuver distal portion 1024 (e.g., distal capsule 1066 thereof).

FIG. 14B shows distal portion 1024 of delivery tool 1020 after guidewire 1023 has been proximally withdrawn from distal end-portion 1027 of nosecone 1026.

FIG. 14C shows flexible sheath 1044 having been subsequently retracted, exposing segment 1056 and proximal capsule 1064. For the sake of clarity, and similarly to as in FIG. 12, distal portion 1024 is shown as if proximal capsule 1064 and distal capsule 1066 were transparent, in order to visualize the orientation of prosthetic valve 1036 within the respective capsules. As shown, mount 1028 and the downstream end of tubular portion 1032 are disposed within distal capsule 1066, whereas upstream support portion 1040 and flange end-portions 1068 are disposed within proximal capsule 1064, as described hereinabove in reference to FIG. 12.

Figure 14D:
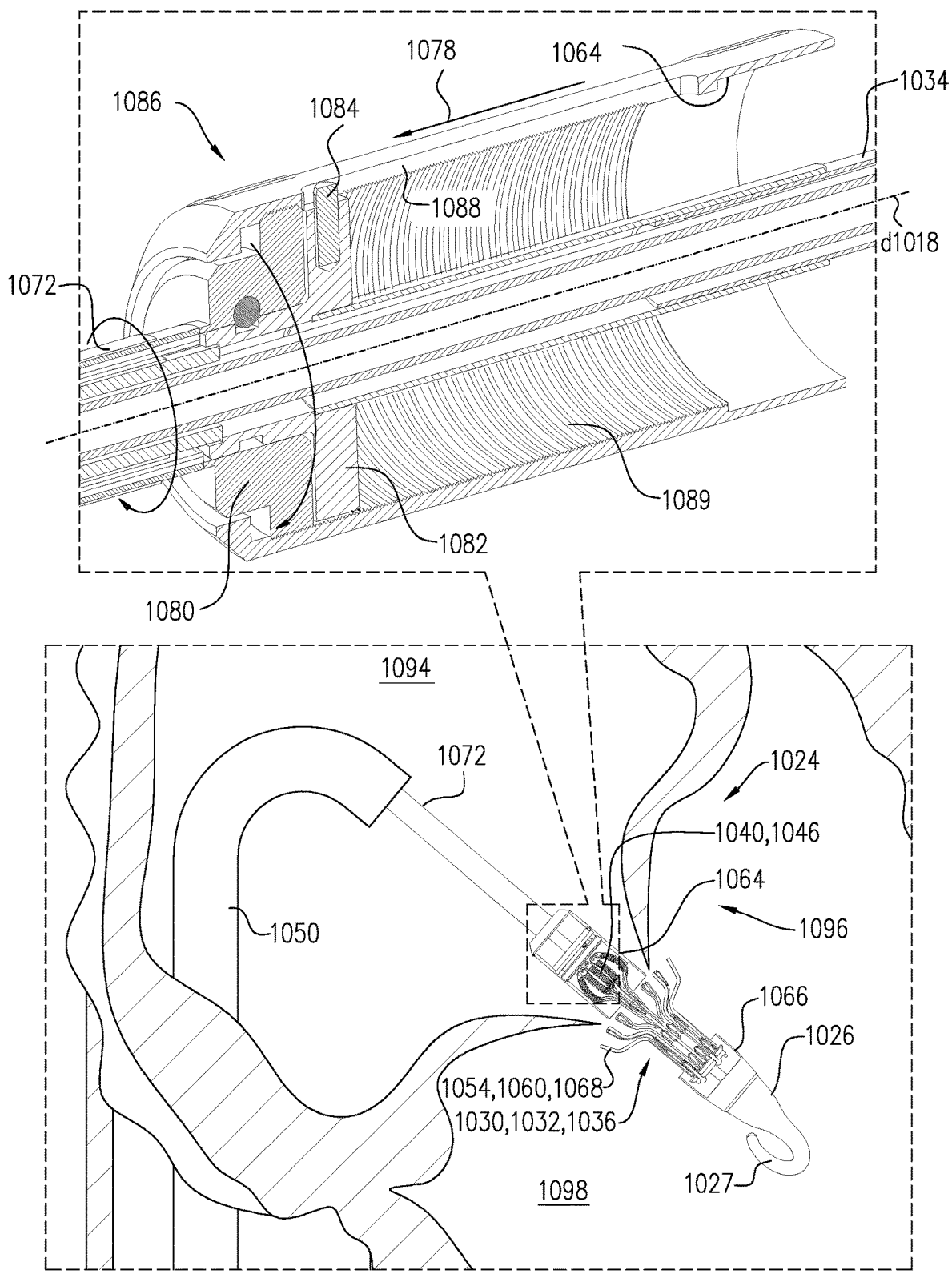

Subsequently, proximal capsule 1064 is partially retracted with respect to mount 1028, such that flange end-portions 1068 are released from the proximal capsule (FIG. 14D). Since outer frame 1060 typically comprises a shape-memory elastic material (e.g., Nitinol), flanges 1054 (e.g., end-portions 1068 thereof) automatically expand radially outward from coupling points 1052 (FIG. 11), upon release from proximal capsule 1064. However, since the distal end of tubular portion 1032 is still restrained by distal capsule 1066, and upstream support portion 1040 is still restrained by proximal capsule 1064, valve frame 1030 remains in the compressed state.

The inset of FIG. 14D shows a mechanism by which, for some applications, proximal capsule 1064 is retracted. (The proximal capsule is shown in the inset without the prosthetic valve, for the sake of simplicity.)

For some applications, and as shown, delivery tool 1020 (e.g., controller 1021 thereof) is configured to retract and/or advance proximal capsule 1064 by translating rotational motion of capsule catheter 1072 into longitudinal motion of the proximal capsule along axis ax1018. For this purpose, a disc-assembly 1086, comprising a proximal disc 1080 that is rotationally coupled to and rotationally movable with respect to a distal disc 1082, is typically fitted within proximal capsule 1064. Further typically, the exterior of proximal disc 1080 defines external screw threading that is complementary to internal screw threading 1089 defined by the interior of proximal capsule 1064. Further typically for such applications, and as shown, the proximal capsule 1064 is shaped to define a longitudinal track 1088 that traverses internal threading 1089.

Since proximal disc 1080 is fixedly coupled to capsule catheter 1072, rotation of capsule catheter 1072 with respect to shaft 1034 (e.g., via controller 1021) screws the proximal disc along internal threading 1089 of proximal capsule 1064. At the same time, distal disc 1082 is inhibited from rotating because distal disc 1082: (i) is fixedly coupled to shaft 1034, and (2) engages track 1088 of proximal capsule 1064 (e.g., by locking pin 1084 having been fitted into the track). Thus, screwing of proximal disc 1080 pushes distal disc 1082 along track 1088, thereby translating rotational movement of the proximal disc into axial movement 1078 (e.g., retraction) of proximal capsule 1064 with respect to disc-assembly 1086, as well as to mount 1028.

Figure 14E:
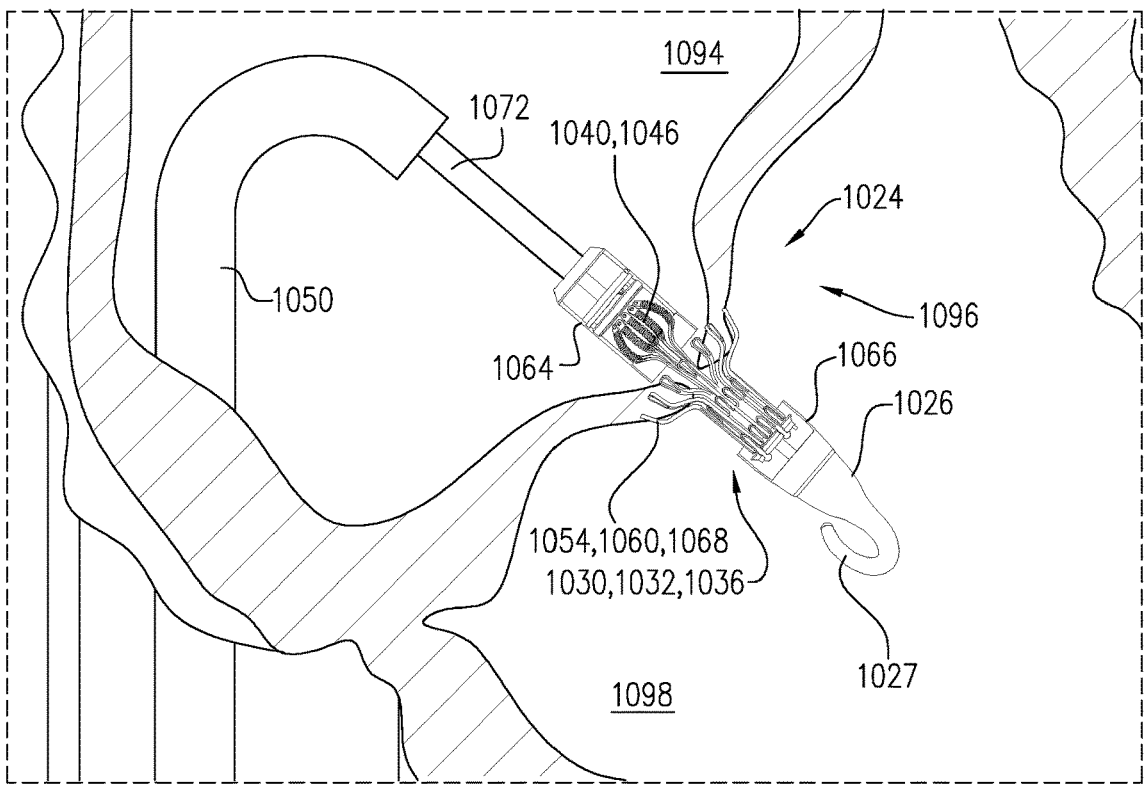

FIG. 14E shows continued deployment of prosthetic valve 1036 at tricuspid valve 1096. Distal portion 1024 has been retracted as a whole, relative to tissue of heart 1090, and to delivery catheter 1050. In this way, flanges 1054 (e.g., end-portions 1068 thereof) now engage tissue (e.g., leaflets) of tricuspid valve 1096.

Figure 14F:
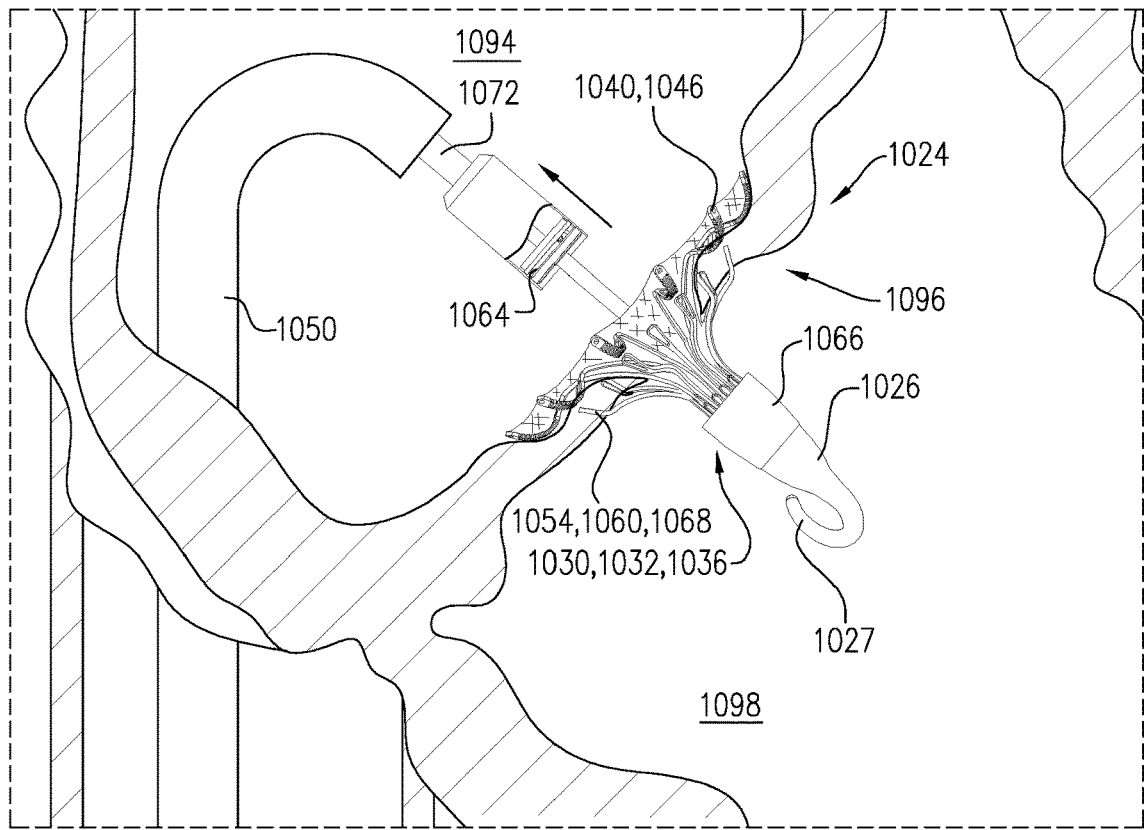

In the following deployment step shown in FIG. 14F, proximal capsule 1064 has been further retracted, thereby releasing upstream support portion 1040 from the proximal capsule, such that the upstream support portion expands radially outward. Similarly to outer frame 1060, valve frame 1030 also typically comprises a shape-memory material, such that upstream support portion 1040 expands automatically upon release from proximal capsule 1064. In this way, tissue of tricuspid valve 1096 is squeezed between upstream support portion 1040 and the flanges 1054.

Figure 14G:
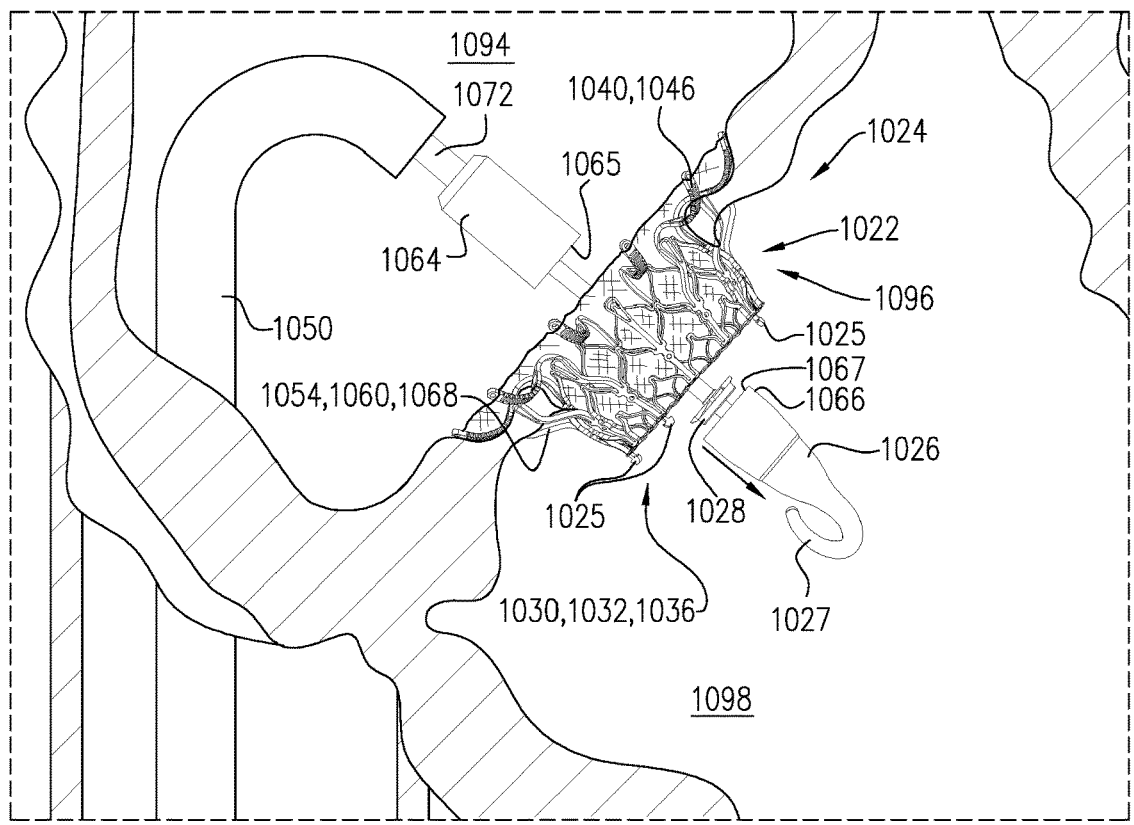

FIG. 14G shows distal capsule 1066 having been advanced with respect to mount 1028, such that distal portion 1024 assumes the deployment state described hereinabove in reference to FIG. 10D. Release of mount 1028 and tubular portion 1032 from the distal capsule allows tubular portion 1032 to automatically expanded radially outward, such that frame assembly 1022 (and therefore prosthetic valve 1036 as a whole) has assumed its expanded state.

Figure 14H:
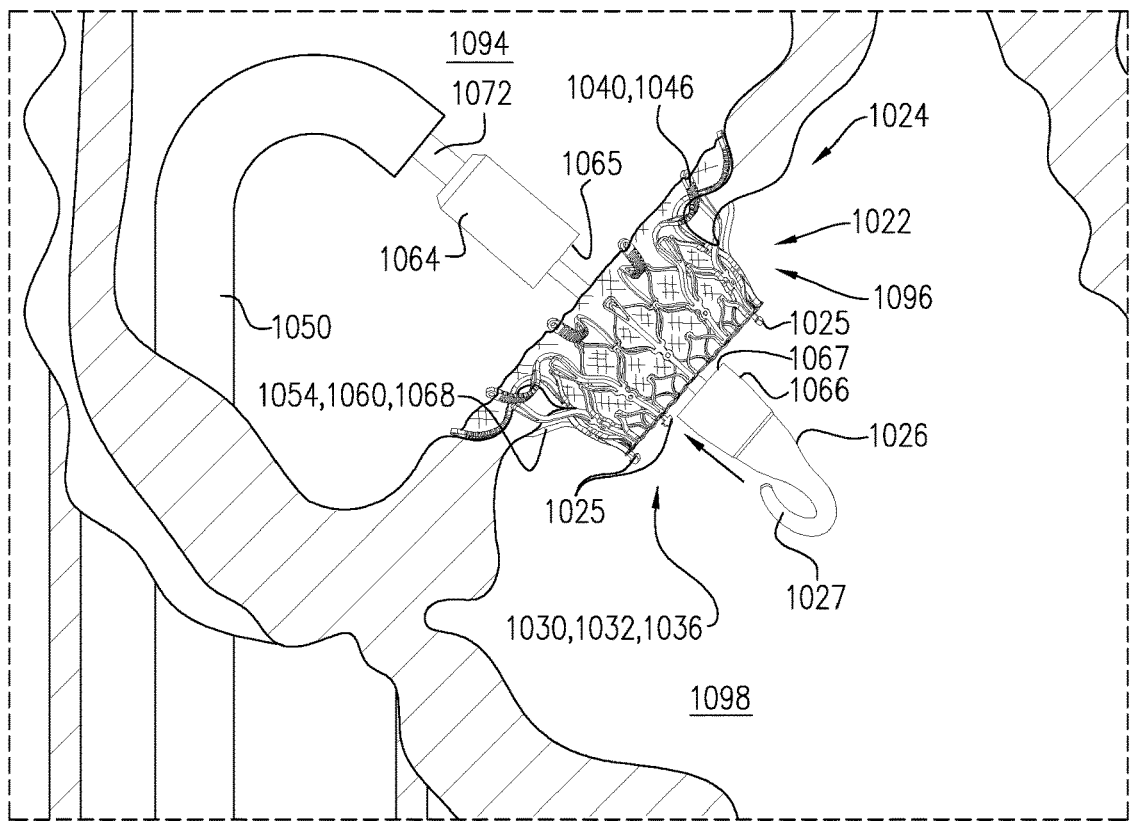
Figure 14I:
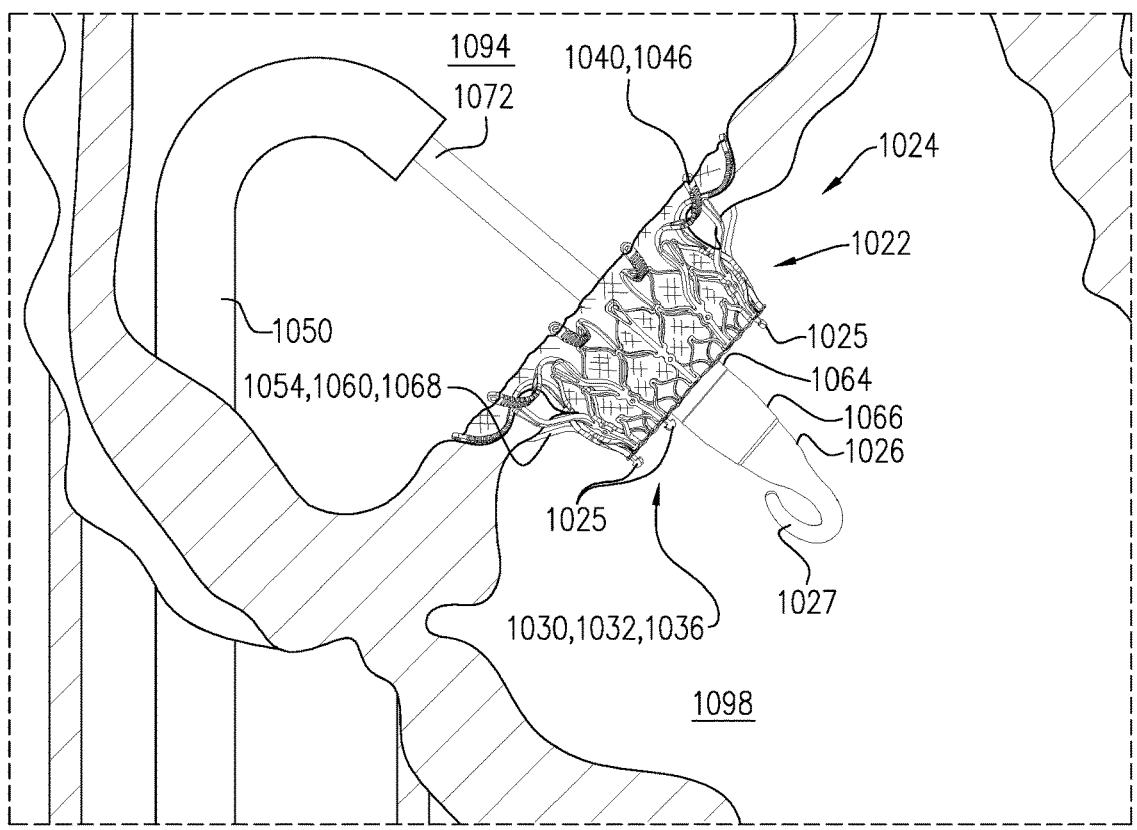

Once prosthetic valve 1036 is fully expanded at tricuspid valve 1096, it is desirable to withdraw distal portion 1024 from heart 1090. In order to reduce a likelihood of distal capsule 1066 (e.g., open end 1067 thereof) undesirably engaging valve 1036 (e.g., leaflets thereof) during upstream retraction through lumen 1038, proximal capsule 1064 is first advanced downstream through lumen 1038, thereby closing inter-capsule gap 1071*b* (e.g., such that open end 1065 of the proximal capsule abuts open end 1067 of the distal capsule), as shown in FIGS. 10E and 14I. As described hereinabove in reference to FIG. 10D, slidable coupling of segments 1034*c* and 1034*d* facilitates closure of gap 1071*b*. For some applications, and as shown in FIG. 14H, distal capsule 1066 is partially retracted (e.g., such that the distal capsule again houses mount 1028), to facilitate closure of inter-capsule gap 1071*b*.

Alternatively or in addition to closing inter-capsule gap 1071*b*, withdrawal of distal portion 1024 from heart 1090 may be facilitated by guidewire 1073 being re-advanced into distal end-portion 1027 of nosecone 1026, either prior to or during retraction of distal portion 1024 through lumen 1038 of tubular portion 1032. Readvancing guidewire 1073 into distal end-portion 1027 typically straightens the distal end-portion, as described hereinabove in reference to FIGS. 13B and 14A. It is hypothesized by the inventors that the straightening of nosecone 1026 may facilitate withdrawal of distal portion 1024 in a retrograde direction through prosthetic valve 1036 (i.e., against the direction for which prosthetic leaflets 1058 are configured to allow blood flow through prosthetic valve 1036), e.g., by reducing a likelihood of the nosecone ensnaring the prosthetic valve compared to when the nosecone is curled.

Figure 14J:
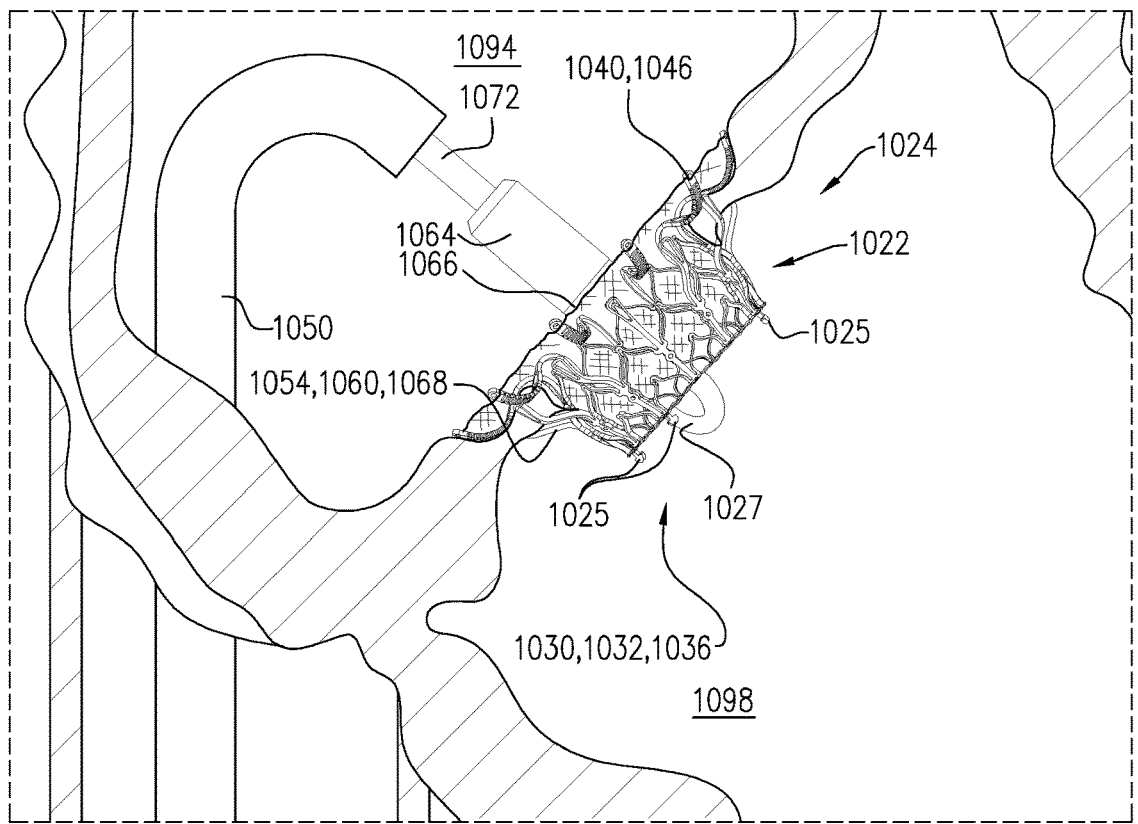

FIG. 14J shows the subsequent retraction of distal portion 1024 through lumen 1038 of tubular portion 1032. It is again noted that capsule assembly-length 1074*c* (FIG. 10E), while distal portion 1024 assumes the withdrawal state, is less than capsule assembly-length 1074*a* of the distal portion in the delivery state (FIG. 10C). It is therefore hypothesized by the inventors that closing the inter-capsule gap 1071*b* facilitates transluminal removal of delivery tool 1020 from the heart.

Reference is made to FIGS. 15A-B, which are schematic illustrations showing a delivery tool 2020, in accordance with some applications of the invention.

Except where noted, delivery tool 2020 is typically identical to delivery tool 1020 described hereinabove with reference to FIGS. 10A-B, and is used similarly to the use of delivery tool 1020, mutatis mutandis. Components that are identically named between the systems typically share similar features and serve similar functions as each other. As such, the description below of delivery tool 2020 focuses upon features that are particular to delivery tool 2020.

FIG. 15A shows delivery tool 2020 assembled, and FIG. 15B shows an exploded view of a distal portion 2024 of the delivery tool. As shown, delivery tool 2020 comprises an extracorporeal controller 2021 and a distal portion 2024 that is dimensioned for transluminal (e.g., transfemoral) delivery to a subject.

As shown, distal portion 2024 comprises a tubular shaft 2034 (e.g., extending distally from within a capsule catheter 2072) to which a proximal capsule 2064 and a distal capsule 2066 (collectively defining a capsule assembly 2063) are coupled. For some applications, and in contrast to shaft 1034, shaft 2034 does not necessarily comprise segments that are distinguishable by their relative rigidity.

As shown, each capsule 2064, 2066 has a respective open end 2065, 2067, such that open end 2065 of proximal capsule 2064 faces open end 2067 of distal capsule 2066. Typically, capsules 2064, 2066 are axially moveable with respect to the shaft (e.g., along a central longitudinal axis ax2018), via extracorporeal controller 2021. For some applications, proximal capsule 2064 and/or distal capsule 2066 can be moved both distally ("advanced") and proximally ("retracted"), with respect to shaft 2034.

For some applications, and as shown, distal portion 2024 further comprises a mount 2028 that surrounds shaft 2034 and that is dimensioned (e.g., defining slots 2029) to engage an implant. For some applications, distal capsule 2066 is shaped to define an opening (e.g., a window) 2110 that facilitates use of delivery capsule assembly 2063 with an implant (e.g., by allowing a user to visualize mount 2028 and/or a portion of the implant), as described hereinbelow with reference to FIGS. 16E-G.

Typically, and as shown in FIG. 15B, distal portion 2024 comprises a rod 2168 having a distal portion that extends out of a distal end of shaft 2034. Similarly to as described hereinabove with reference to delivery tool 1020, delivery tool 2020 is configured to distally advance distal capsule 2066 with respect to mount 2028 by screwing the rod through shaft 2034.

For some applications, and further similarly to delivery tool 1020, distal capsule 2066 is rotationally movable with respect to rod 2168, such that rotation of rod 2168 does not necessarily rotate distal capsule 2066. Typically for such applications, and as shown, pins 2170 are fitted within distal capsule 2066, into a recess 2169 defined by rod 2168, so as to axially fix the distal capsule with relation to the rod, while allowing rotation of the rod with respect to the pins, as described hereinabove.

In contrast to delivery tool 1020, and as shown, delivery tool 2020 comprises a delivery stent 2200 that is fixedly coupled to shaft 2034. Typically, delivery stent 2200 comprises a shape-memory material, such that when an implant is crimped over the delivery stent and shaft 2034 (as described hereinbelow with reference to FIGS. 16E-1), the delivery stent assumes a compressed state within the implant. Delivery stent 2200 is shown in FIGS. 15A-B in an expanded state, without an implant.

Reference is made to FIGS. 16A-I, which are schematic illustrations showing some steps of loading a prosthetic valve 2036 onto a distal portion 2024 of a delivery tool 600, in accordance with some applications of the invention.

Except where noted, delivery tool 600 is in many ways similar to delivery tool 100 described hereinabove with reference to FIGS. 8A-G, and is used similarly as delivery tool 100, mutatis mutandis. Components that are identically named between the systems typically share similar features and serve similar functions as each other. As such, the description below of delivery tool 600 focuses upon features that are particular to delivery tool 600.

Figure 16A:
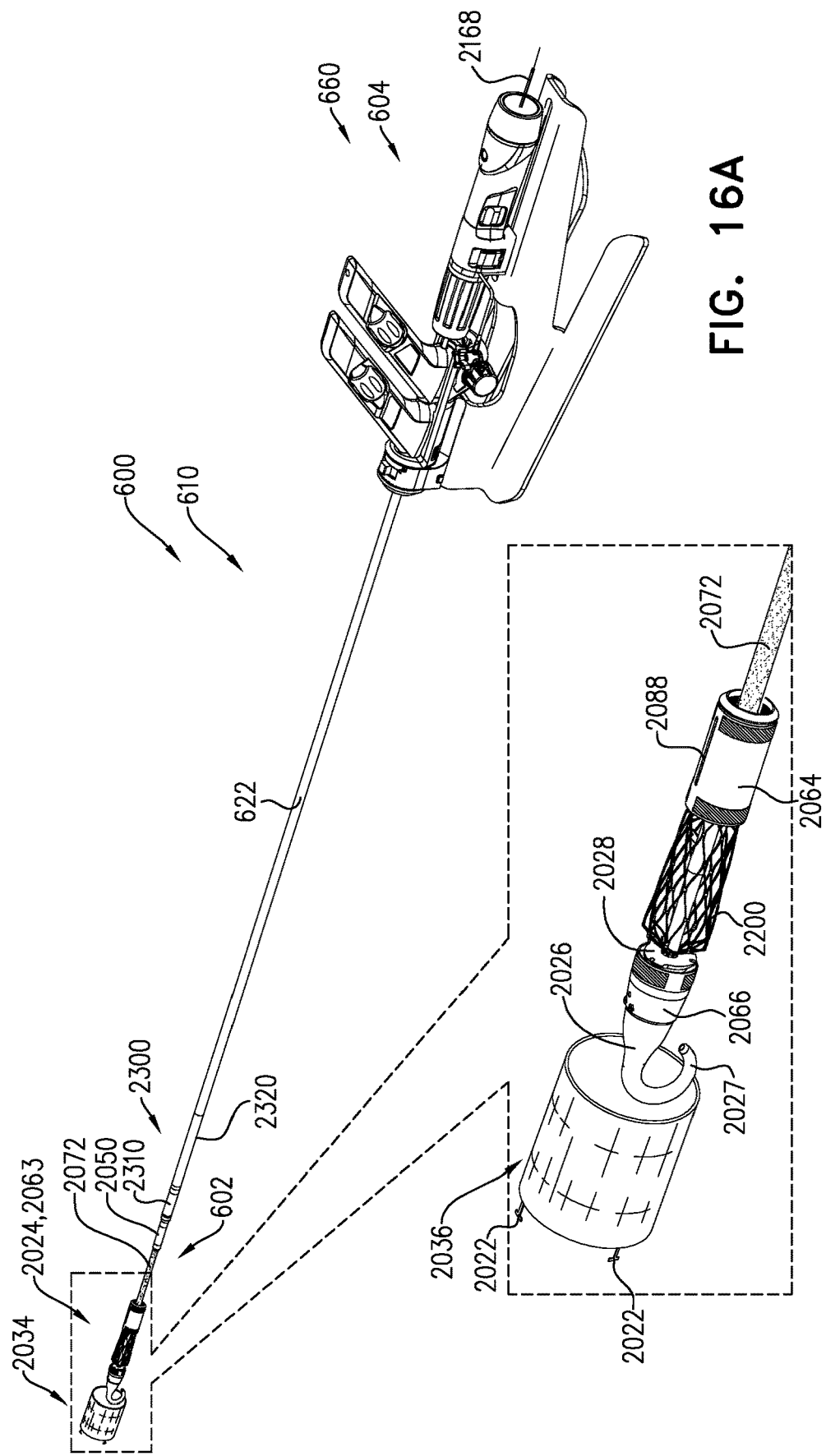

As shown in FIG. 16A, delivery tool 600 is a multi-catheter transluminal (e.g., transfemoral) delivery tool, comprising two primary components: a catheter system 610, and an implantation instrument 660 at a proximal portion 604 of the delivery tool. Similarly to proximal part 104 of delivery tool 100 described hereinabove, implantation instrument 660 may be considered to be an extracorporeal control system of delivery tool 600, and distal portion 663 is configured to be advanced into the subject.

Catheter system 610 comprises an outer catheter 622 coupled at a proximal end thereof to implantation instrument 660. Instrument 660 comprises a plurality of tubular members that extend distally from proximal portion 604, which are coaxial about a central longitudinal axis ax1 of delivery tool 600, and which are discussed in more detail hereinbelow. The outermost of these tubular members is typically a delivery catheter 2050 that extends distally from proximal portion 604, through outer catheter 622, out of an open distal end of catheter 622.

Typically, and as shown, capsule catheter 2072 extends distally through delivery catheter 2050, to proximal capsule 2064 of capsule assembly 2063. As described hereinbelow with reference to FIGS. 17A-B, capsule assembly 2063 is used to encase prosthetic valve 2036 during advancement toward the heart. Catheter system 610 further comprises an alignment mechanism 2300 that is used to align proximal and distal capsules 2064, 2066 during advancement to and/or withdrawal from the heart, as described hereinbelow.

Figure 16B:
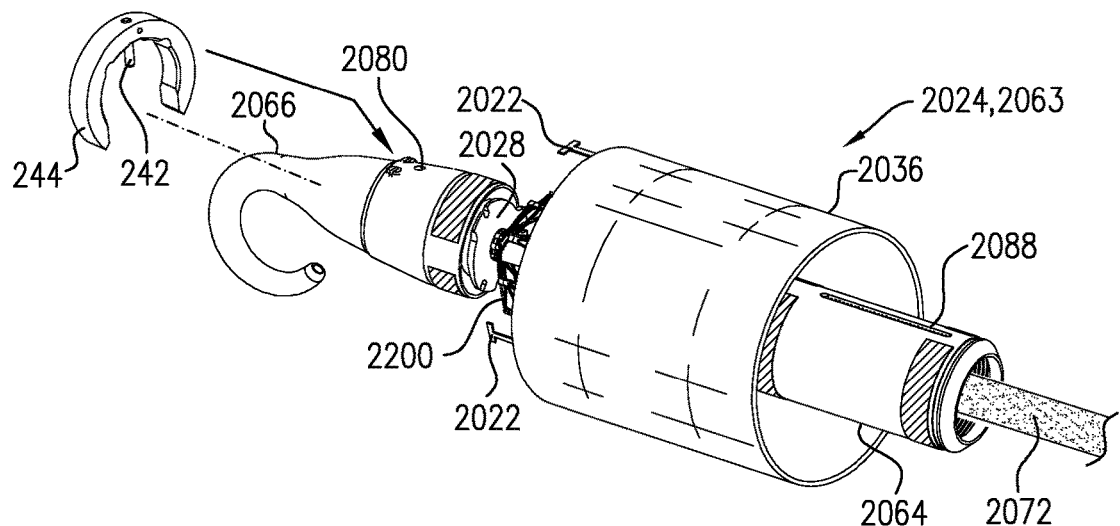
Figure 16C:
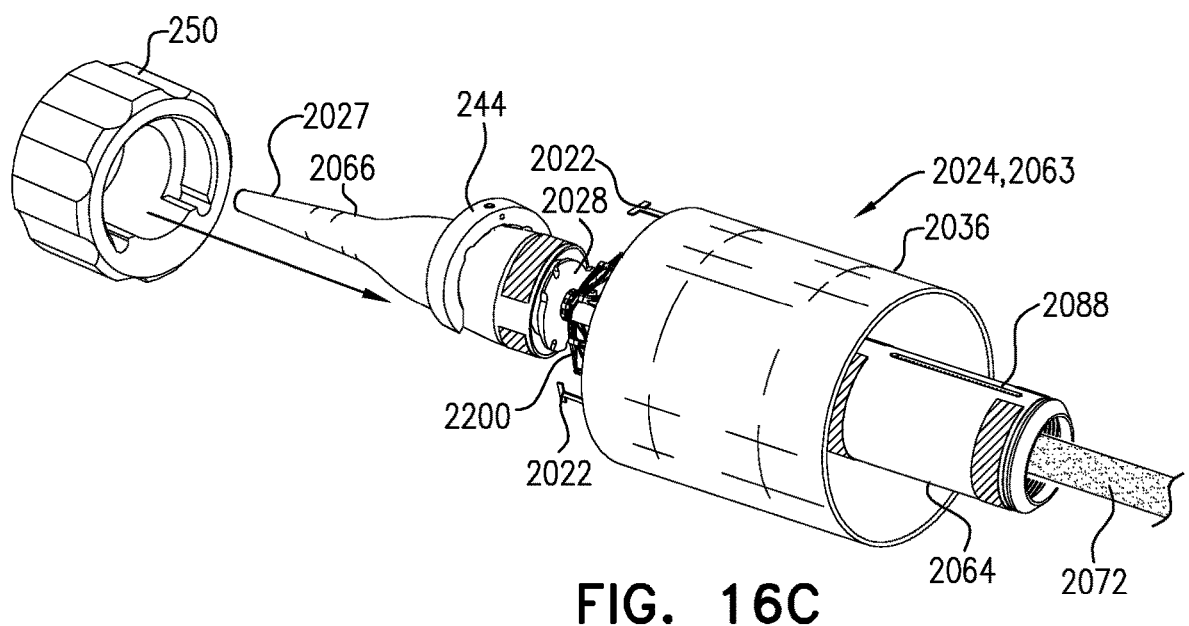
Figure 16D:
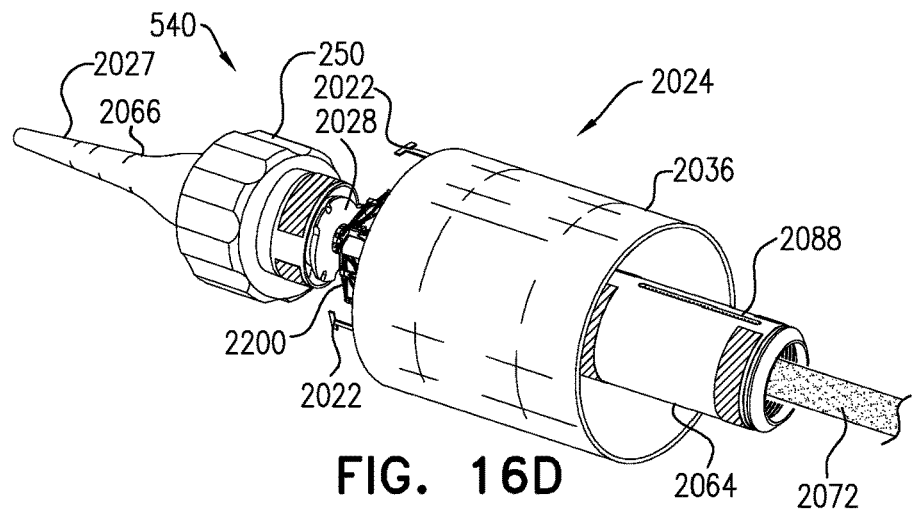

FIGS. 16B-D show attachment of an accessory, e.g., distal-capsule ensheathing tool 540, to ensheathe a downstream end of prosthetic valve 2036 in distal capsule 2066. For example, distal-capsule ensheathing tool 540 comprises a clip 244 and a knob 250. Clip 244 is shaped to define a detent 242, a portion of which is extended within a detent-hole 2080. By extending detent 242 through detent-hole 2080, the detent occupies at least a portion of a recess 2178 defined by a ring 2174 (FIGS. 15A-B) that is fixedly coupled to rod 2168. In this way, distal capsule 2066 is rotationally locked with respect to rod 2168. Knob 250 is typically attached over clip 244, to facilitate manual rotation of the clip, and therefore of distal capsule 2066 and rod 2168, with respect to shaft 2034. As described hereinabove with reference to delivery tool 100, rotation of the rod with respect to the shaft screws the rod into the shaft resulting in linear (e.g., proximal) movement of distal capsule 2066 with respect to the shaft and to prosthetic valve 2036.

Figure 16E:
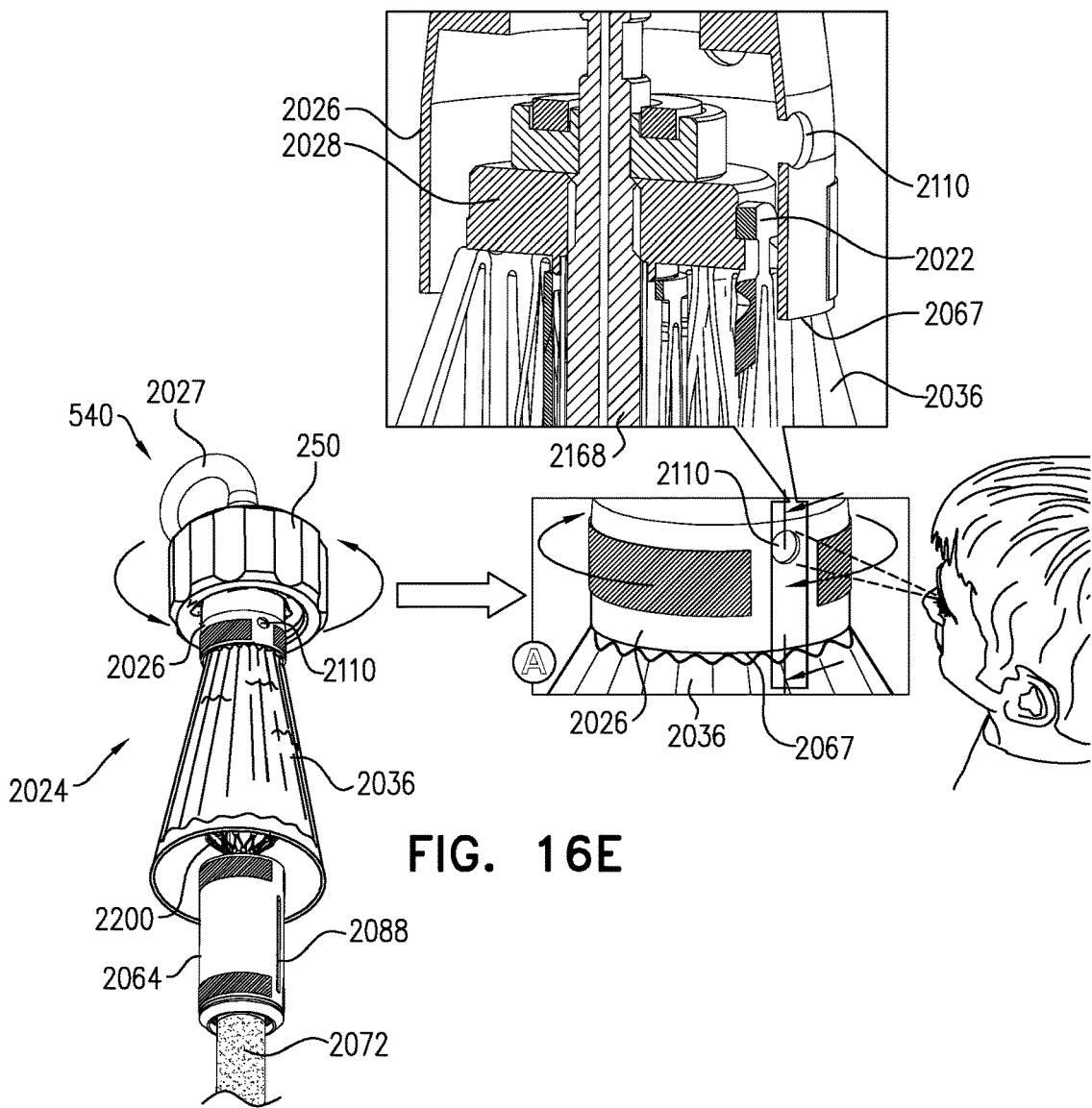

As shown in FIGS. 16E-G, prosthetic valve 2036 is then compressed ("crimped") using a crimping tool, around a distal portion of shaft 2034, such that the downstream end of the prosthetic valve engages mount 2028, e.g., with adaptors 2022 being received by respective slots 2029 (FIG. 16E). As prosthetic valve 2036 is crimped (or subsequently thereto), an ensheathing force is applied to distal-capsule ensheathing tool 540, e.g., by rotating knob 250 that is directly coupled to distal capsule 2066.

Direct application of the ensheathing force to distal capsule 2066 may be desirable over applying the ensheathing force using implantation instrument 660 over the length of catheter system 610, since direct application of the ensheathing force typically avoids resistance that may be encountered over a length of the catheter system.

For some applications, and as shown, distal capsule 2066 defines an opening (e.g., window 2110). As shown in FIGS. 16E-G, a user may use the opening to monitor proximal advancement of distal capsule 2066 over mount 2028 and prosthetic valve 2036. It is hypothesized by the inventors that use of window 2110 to visualize the portion of prosthetic valve 2036 (e.g., a downstream end of the prosthetic valve) that is ensheathed by distal capsule 2066 increases the reliability of delivery tool 600, e.g., by reducing a risk of premature release of the prosthetic valve from the distal capsule that may be caused by the user estimating which portion of the prosthetic valve is ensheathed within the distal capsule. Instead, window 2110 allows the user to monitor the ensheathed portion of prosthetic valve 2036. For example, and as shown, distal capsule 2066 is advanced over prosthetic valve 2036 until a portion of mount 2028 and/or the prosthetic valve (e.g., adaptors 2022 thereof) are visible through window 2110. In this way, ensheathing prosthetic valve 2036 by distal capsule 2066 serves to maintain coupling between the prosthetic valve and mount 2028 by ensuring that: (i) the mount surrounds adaptors 2022, and (ii) each adaptor remains within a respective slot 2029 of the mount.

Figure 16H:
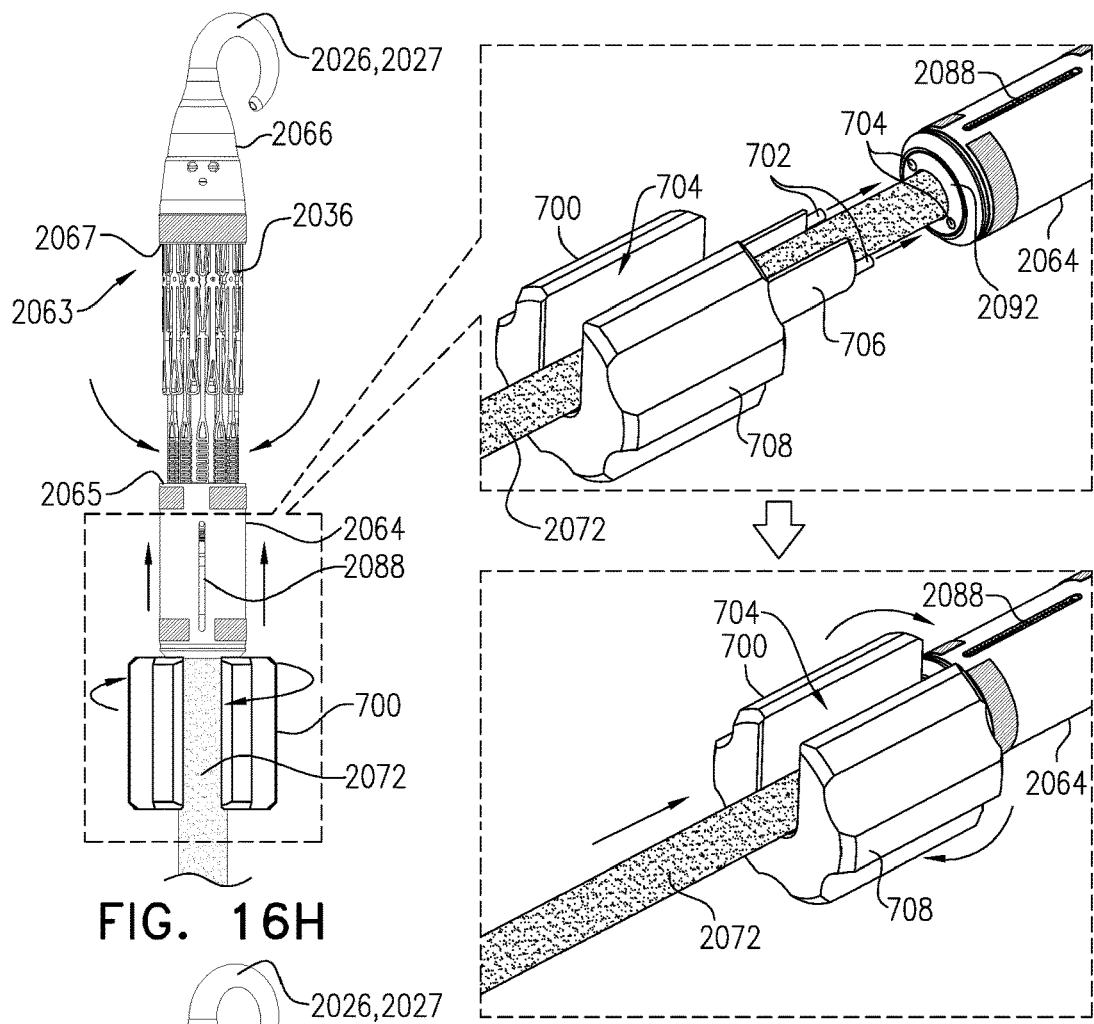

For some applications, and as shown, after ensheathing the downstream end of prosthetic valve 2036 in distal capsule 2066, the upstream end of the prosthetic valve is ensheathed in proximal capsule 2064. The crimping tool is typically used to compress the proximal portion of prosthetic valve 2036, such that the proximal portion assumes the compressed state, as shown in FIG. 16H.

For some applications, a second ensheathing force is applied directly to distal portion 2024 of delivery tool 600. Similarly to as described hereinabove with reference to ensheathing the distal end of prosthetic valve 2036 within distal capsule 2066, application of the ensheathing force directly to distal portion 2024 may be desirable over applying the ensheathing force along the length of catheter system 610, to avoid resistance that may be encountered over the length of the catheter system.

For some applications, a second accessory, e.g., a proximal-capsule ensheathing tool such as cuff 700, is attached to distal portion 2024 (FIG. 16H), for applying the second ensheathing force directly to distal portion 2024. For some applications, and as shown, cuff 700 comprises a user grip 708 that is shaped to facilitate rotation of the cuff with respect to distal portion 2024. For example, and as shown, cuff 700 may be directly coupled to a proximal disc 2092 of a disc assembly 2086 of distal portion 2024, in order to convert rotational movement of cuff 700 into axial motion of proximal capsule 2064 over a proximal portion of prosthetic valve 2036.

Typically for such applications, and as shown, cuff 700 further comprises a distal coupling portion 706 that is configured to reversibly couple the cuff to proximal disc 2092 of disc assembly 2086. For example, and as shown, distal coupling portion 706 comprises one or more pins 702 shaped so as to fit within respective holes 704 defined by the proximal disc 2092. Alternatively or in addition, distal coupling portion 706 is sized to fit within an opening in proximal disc 2092.

Figure 16I:
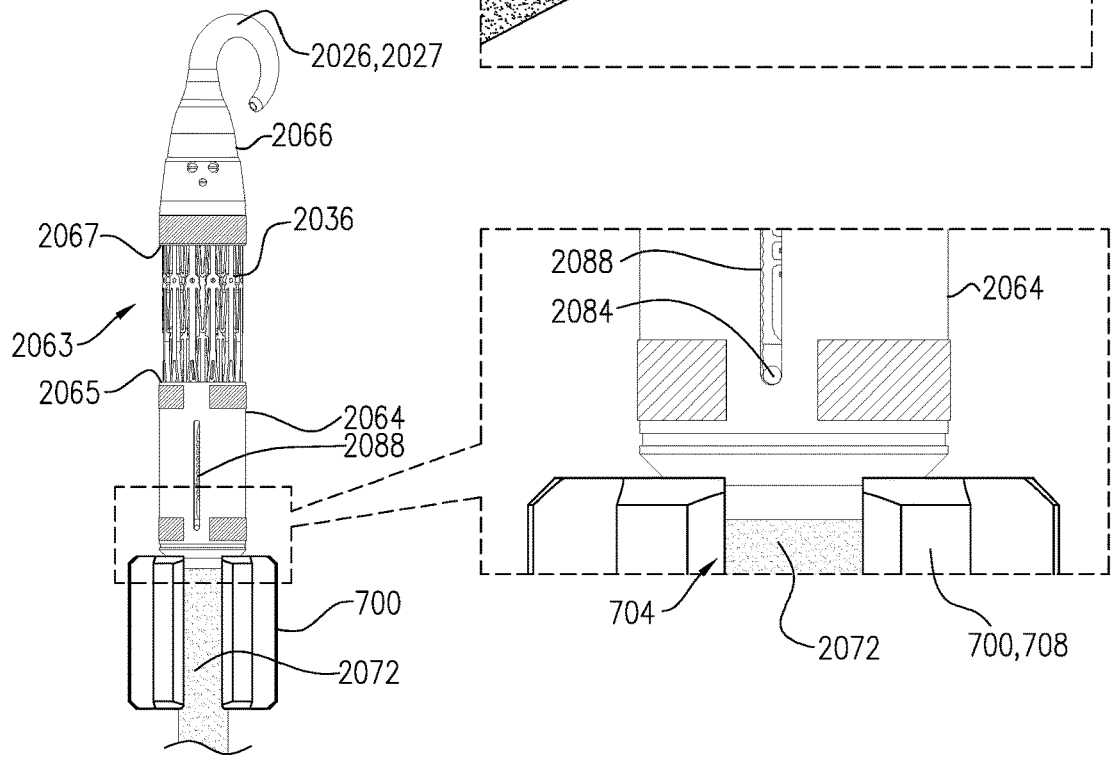

Similarly to disc assembly 1086 (FIG. 14D), disc assembly 2086 (FIG. 15B) comprises (i) proximal disc 2092 that defines external screw threading that is complementary to internal screw threading defined by the interior of proximal capsule 2064, and (ii) a distal disc 2090 that is rotationally coupled to and rotationally movable with respect to the proximal disc. Distal disc 2090 is inhibited from rotating because the distal disc: (i) is fixedly coupled to shaft 2034, and (2) engages track 2088 of proximal capsule 2064 (e.g., by a locking pin 2084 having been fitted into the track). Thus, screwing of proximal disc 2092 using cuff 700 pushes distal disc 2090 and locking pin 2084 along track 2088, translating rotational movement of the proximal disc into advancement of proximal capsule 2064 with respect to shaft 2034 and over the proximal portion of prosthetic valve 2036 (FIGS. 16H-I).

Reference is made to FIGS. 16J-K, which are schematic illustrations showing advancement of an alignment mechanism 2300 over catheter system 610 of delivery tool 600, in accordance with some applications of the invention.

Typically, and as shown, alignment mechanism 2300 comprises a distal supplemental tube 2310 that is coupled to a distal end of an elongate oversheath 2320 at connecting portion 2318. Oversheath 2320 is shaped so as to define an elongate-oversheath lumen, through which catheter system 610 (e.g., capsule catheter 2072 thereof) is slidably passed, and supplemental tube 2310 is shaped so as to define a supplemental-tube lumen that is sized for encasing at least a portion of a housing (e.g., capsule assembly 2063) during transluminal delivery of distal portion 663 of the delivery tool to the heart, and while retracting the housing out of a body of the subject, as described in greater detail hereinbelow.

Reference is made to FIGS. 17A-B, which are schematic illustrations showing use of delivery tool 600 to advance prosthetic valve 2036 toward heart 1090 of a subject, in accordance with some applications of the invention.

FIGS. 17A-B show an operator using implantation instrument 660 to transfemorally advance distal portion 663 of delivery tool 600 to inferior vena cava 1092, toward heart 1090. As shown, supplementary tube 2310 of alignment mechanism 2300 encases a portion of capsule assembly 2063 (e.g., proximal capsule 2064). For example, and as shown, supplementary tube 2310 may abut distal capsule 2066 while distal portion 663 is advanced toward the heart. Alternatively, supplementary tube 2310 may encase a portion of distal capsule 2066 during the advancement.

Typically, while distal portion 2024 is in a delivery state (FIG. 18A), an upstream portion of prosthetic valve 2036 is ensheathed by proximal capsule 2064 and a downstream portion of the prosthetic valve is ensheathed by distal capsule 2066, such that an exposed segment 2056 of prosthetic valve 2036 is disposed at an inter-capsule gap that separates open end 2065 of the proximal capsule from open end 2067 of distal capsule 2066.

The upper inset of FIG. 17A shows distal portion 2024 of delivery tool 600 in a delivery state in which an intermediate alignment tube 2314 of alignment mechanism 2300 is disposed between oversheath 2320 and capsule catheter 2072 of catheter system 610. While distal portion 2024 is in the delivery state, an aligner 2312 of alignment mechanism 2300 is typically disposed between alignment tube 2314 and supplemental tube 2310. For some applications, and as shown, aligner 2312 is shaped to form a ring that fits around alignment tube 2314. Aligner 2312 typically comprises a material that is stiffer than capsule catheter 2072. For example, aligner 2312 may comprise a metal or a polycarbonate.

Typically. and as shown, by occupying a space between capsule catheter 2072 and supplemental tube 2310, aligner 2312 is positioned to align the capsule catheter with respect to the supplemental tube (e.g., the aligner keeps a distal portion of the capsule catheter generally parallel with the supplemental tube). For some applications, and as shown, aligner 2312 is coupled to a distal end of alignment tube 2314.

For some applications, aligner 2312 and a distal portion of alignment tube 2314 are axially slidable along the catheters (e.g., along capsule catheter 2072) of catheter system 610 (e.g., independently of supplemental tube 2310). For some such applications, aligner 2312 and the distal portion of alignment tube 2314 are axially slidable within the elongate-oversheath lumen and within the supplemental-tube lumen. For example, aligner 2312 may be advanced distally to align capsule catheter 2072 with respect to supplemental tube 2310 before capsule assembly 2063 is encased within the supplemental tube.

Elements comprising catheter system 610 and alignment mechanism 2300 are typically dimensioned in order to facilitate sliding aligner 2312 between the capsule catheter 2072 and supplemental tube 2310. Therefore, for some applications, an inner diameter di2312 of aligner 2312 is 0.05-3.0 mm, e.g., 0.15 mm, larger than an outer diameter do2072 of capsule catheter 2072 (i.e., a largest catheter of catheter system 610 that passes through supplemental tube 2310 and through aligner 2312), and/or an alignment-tube outer diameter do2314 of alignment tube 2314 is 1.9-5.5 mm, e.g., 4.9 mm, smaller than a supplemental-tube inner diameter di2310 of supplemental tube 2310. An outer diameter of capsule catheter 2072 is about 6.7 mm and an inner diameter of aligner 2312 is about 6.8 mm by way of illustration and not limitation. A length of aligner 2312 is typically between 1-10 mm, e.g., 8 mm.

Typically, supplemental tube 2310 comprises material that is stiffer than elongate oversheath 2320 of capsule catheter 2072. Alignment-tube outer diameter do2314 of alignment tube 2314 is 1.9-2.4 mm smaller than an inner diameter of elongate oversheath 2320.

Typically for such applications, and as shown, a supplemental-tube outer diameter do2310 is larger than both (i) outer diameter do2072 of capsule catheter 2072, and (ii) an outer diameter do2320 of elongate oversheath 2320.

For some applications, during entry of delivery tool 600 within the body, supplemental tube 2310 surrounds proximal capsule 2064 and at least a proximal portion of distal capsule 2066, as well as exposed segment 2056 of prosthetic valve 2036. Typically for such applications, subsequently to entering the body, proximal capsule 2064 and the proximal portion of distal capsule 2066 are exposed from within supplemental tube 2310 (FIG. 17B) and are advanced toward the heart by distally advancing capsule catheter 2072 with respect to oversheath 2320 (e.g., by pushing capsule catheter 2072 distally while retaining oversheath 2320 in place and/or by retracting the oversheath proximally with respect to capsule catheter 2072.

Figure 18G:
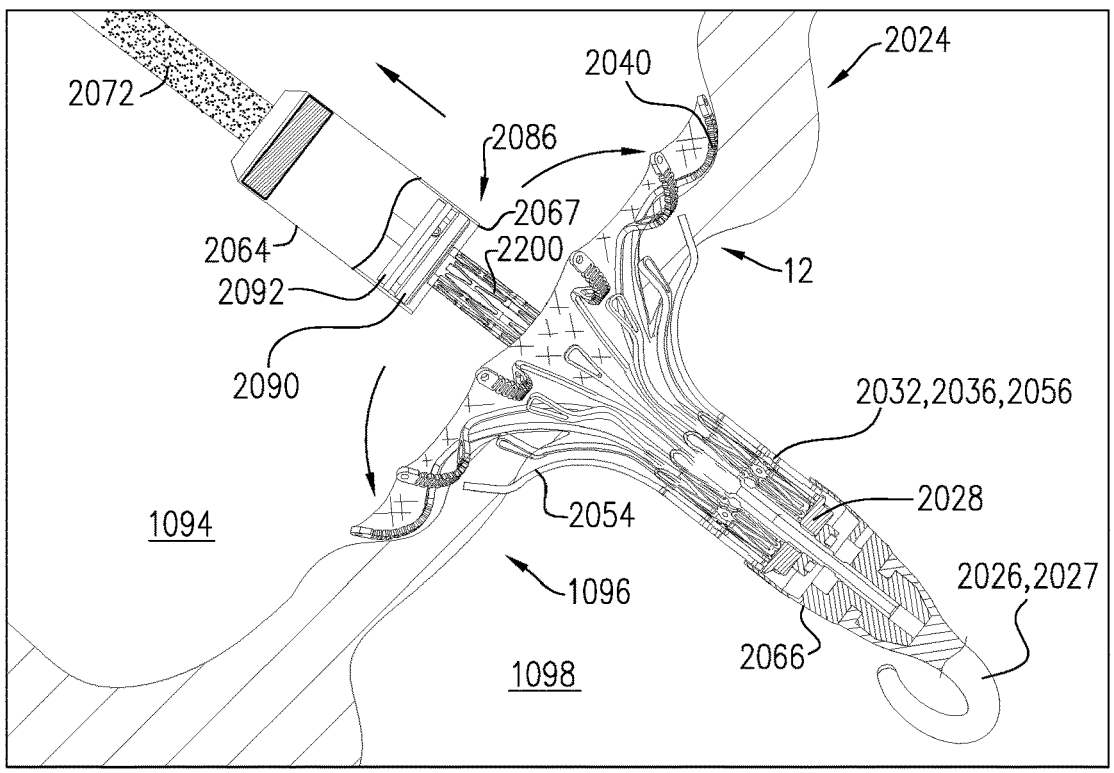
FIGS. 18A-O are schematic illustrations showing use of the delivery tool to deploy the prosthetic valve at the tricuspid valve of the heart, and use of the alignment mechanism to facilitate withdrawal of the delivery tool from the subject, in accordance with some applications of the invention.
Figure 18H:
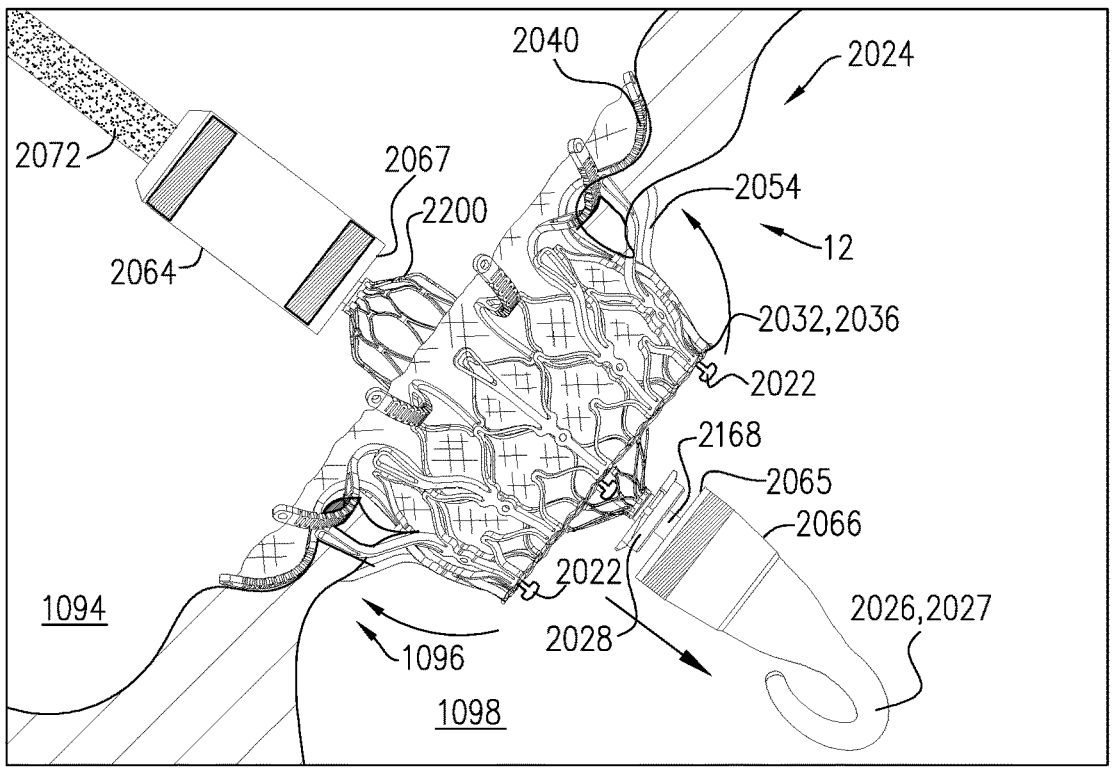
Figure 18I:
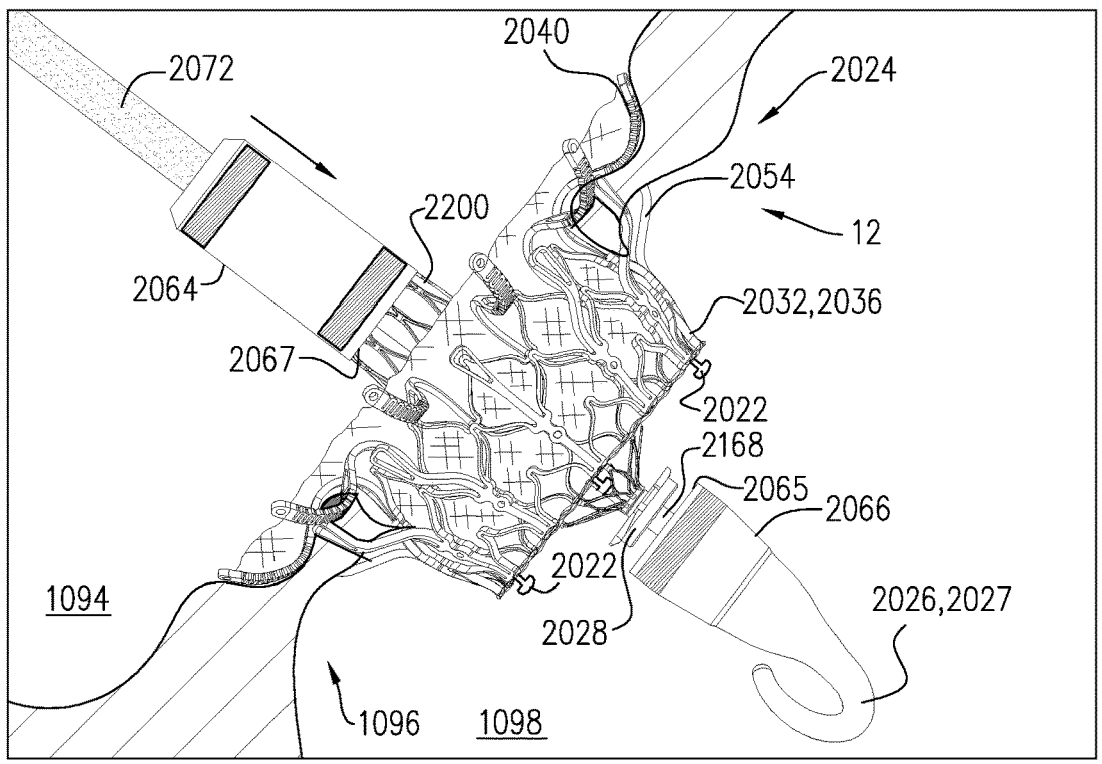
Figure 18J:
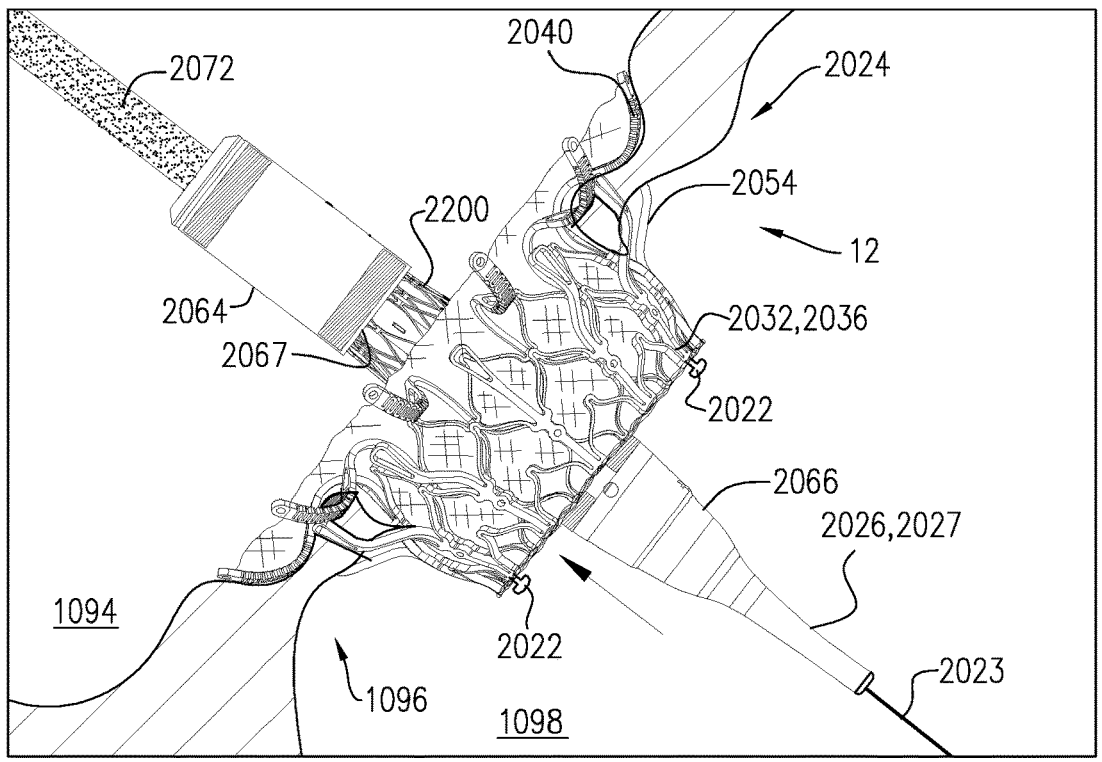
Figure 18K:
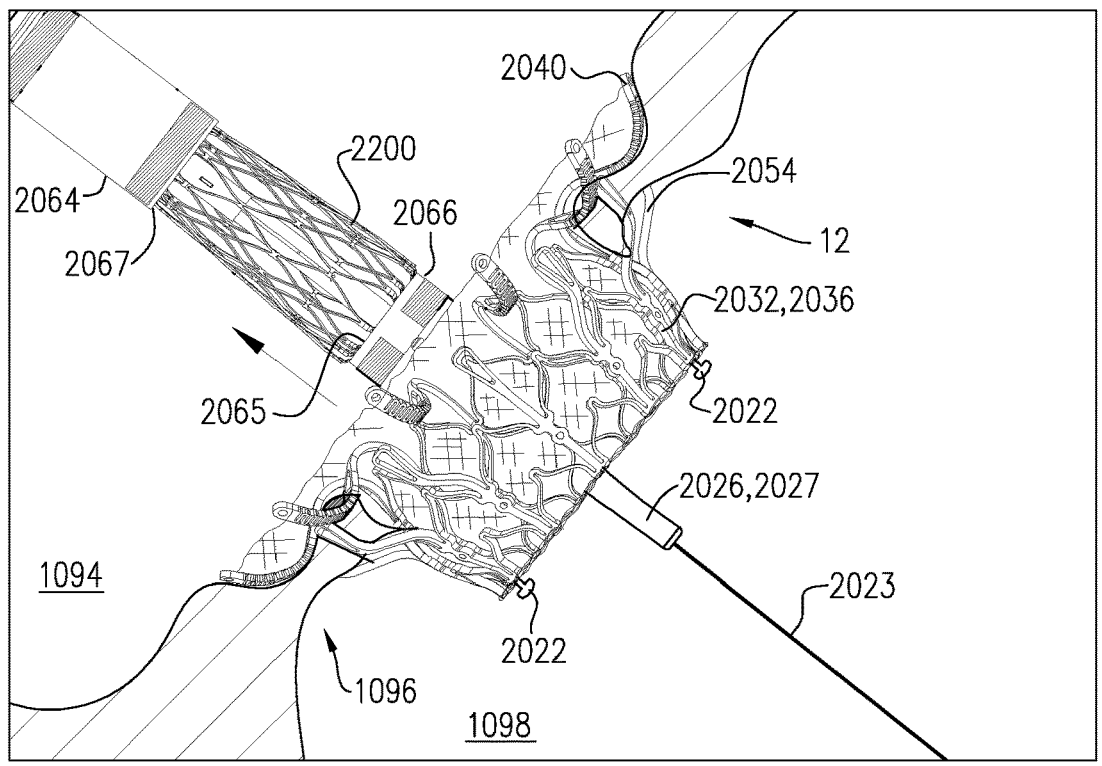
Figure 18L:
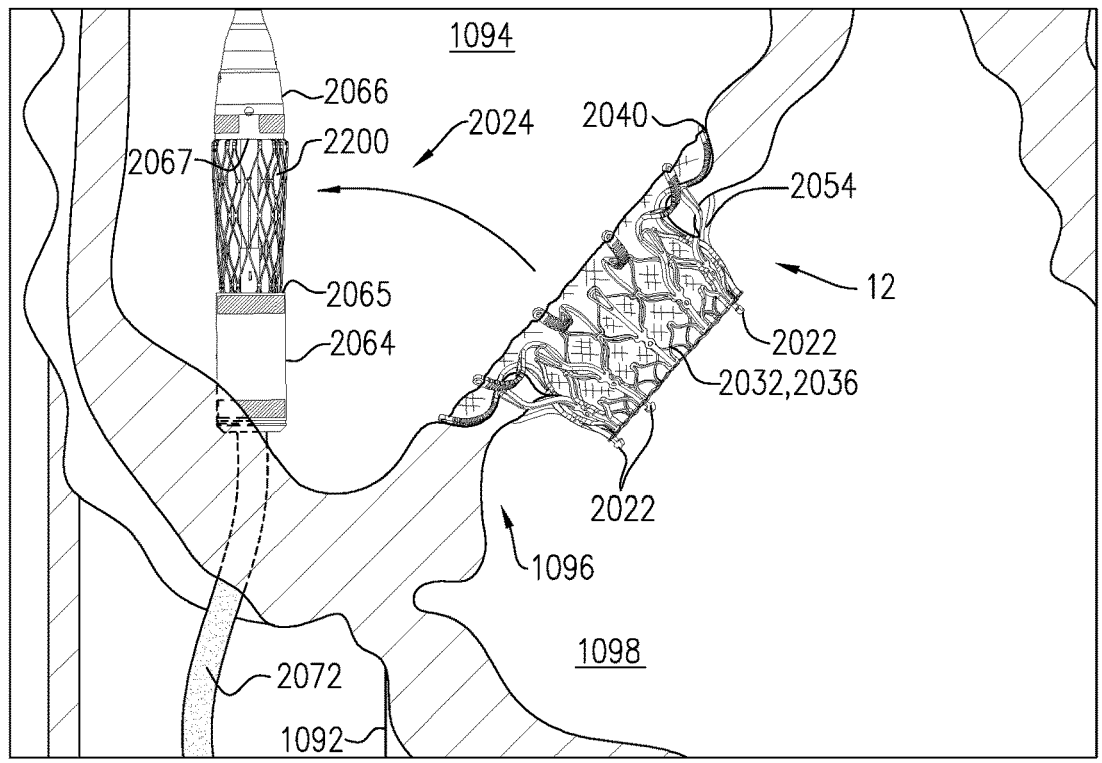
Figure 18M:
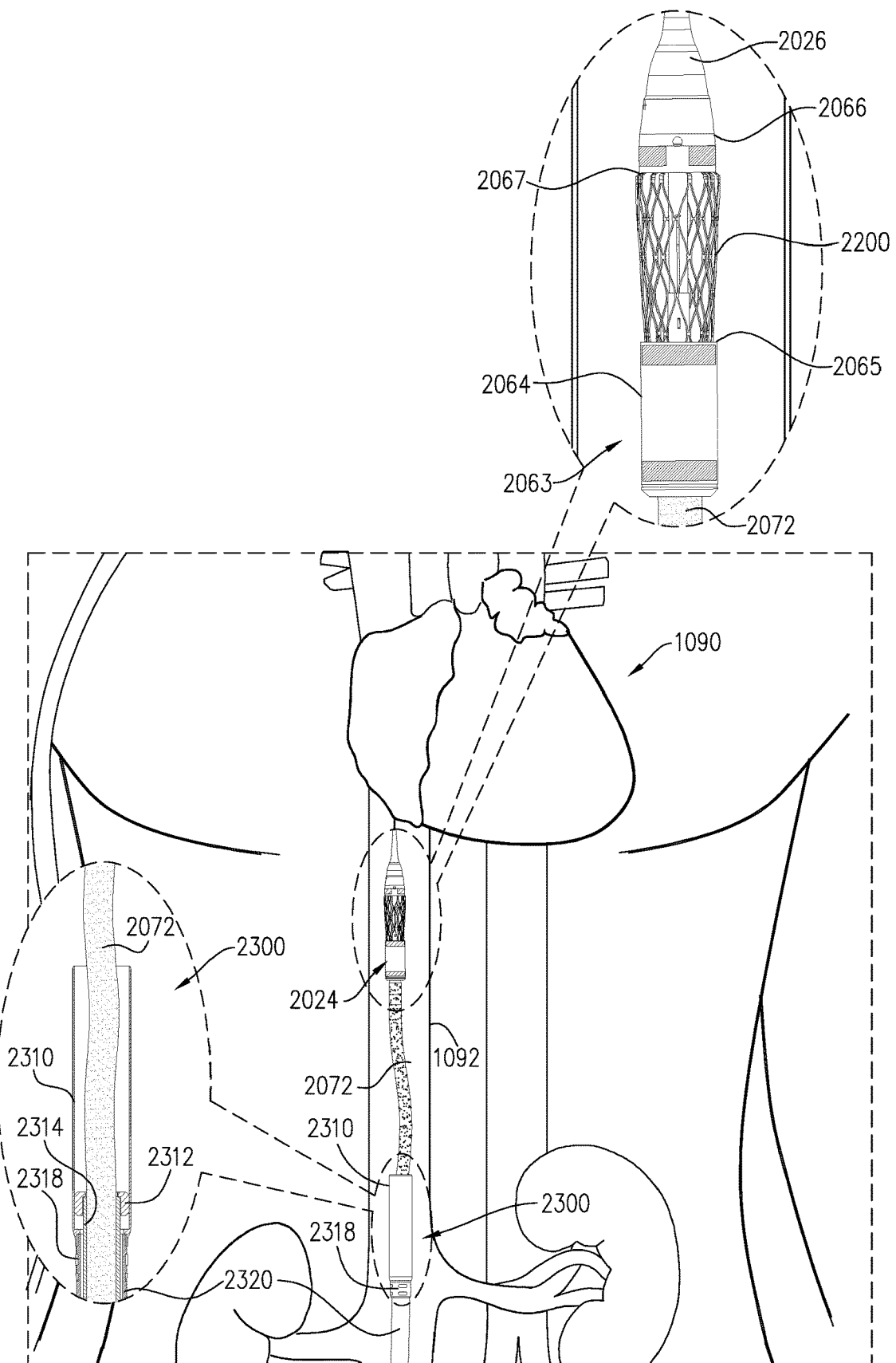
Figure 18N:
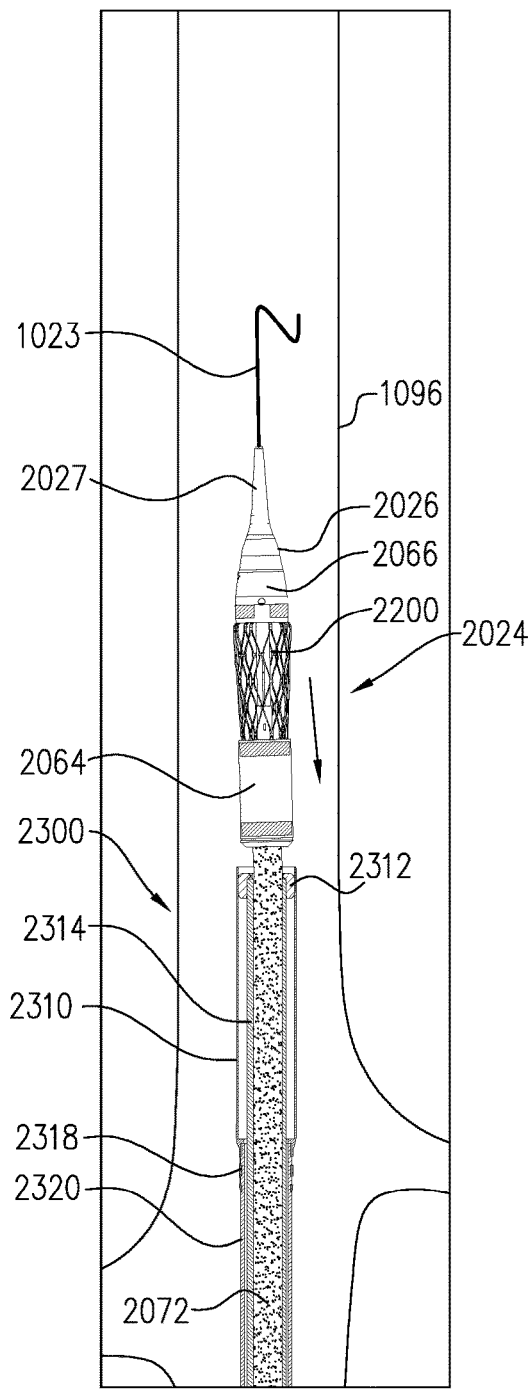
Figure 18O:
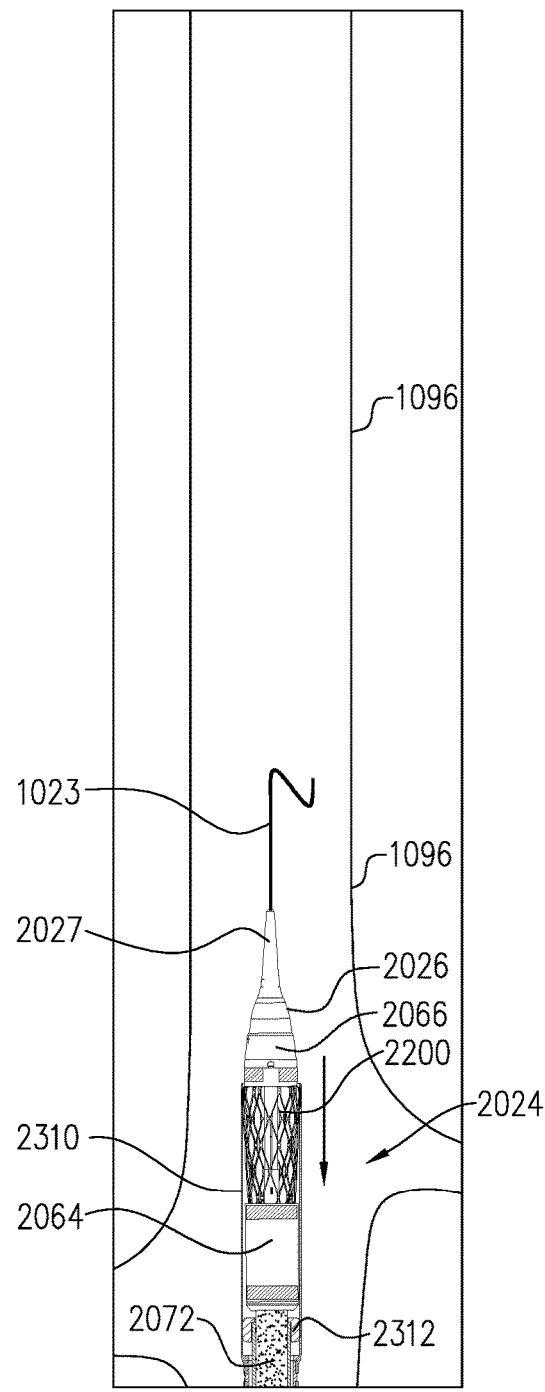

Reference is made to FIGS. 18A-O, which are schematic illustrations showing use of delivery tool 600 to deploy prosthetic valve 2036 at tricuspid valve 1096 of the heart, and use of alignment mechanism 2300 to facilitate withdrawal of the delivery tool from the subject, in accordance with some applications of the invention.

Typically, and as shown, capsule catheter 2072 and capsule assembly 2063 encasing prosthetic valve 2036 are advanced along a guidewire 2023 through inferior vena cava 1092 and into right atrium 1094 of the heart. Further typically, prosthetic valve 1036 remains ensheathed at least until distal capsule 2066 is advanced into right ventricle 1098 of the heart (FIG. 18A).

Similarly to prosthetic valve 1036 described hereinabove with reference to FIG. 11, prosthetic valve 2036 typically comprises a tubular portion 2032 in which a plurality of prosthetic leaflets are disposed, and that defines a lumen between an upstream end and a downstream end. For some applications, and as shown in FIG. 18A, tubular portion 2032 and an upstream support portion 2040 together define a valve frame 2030.

Typically for such applications, and as shown, a plurality of flanges 2054 are coupled to tubular portion 2032 at coupling points that are downstream of the upstream support portion. As shown, prosthetic valve 2036 is engaged with delivery tool 600 such that a downstream end of tubular portion 2032 is disposed within distal capsule 2066, and upstream support portion 2040 and such that end-portions 2068 of flanges 2054 are disposed within proximal capsule 2064.

FIG. 18B shows capsule assembly 2063 having been advanced further distally, such that exposed segment 2056 is partially disposed in right atrium 1094, and partially disposed in right ventricle 1098. Typically, and as shown, at least a portion of flanges 2054 (e.g., end-portions 2068 thereof) are still ensheathed within proximal capsule 2064 at this stage.

FIG. 18C shows capsule assembly 2063 after guidewire 2023 has been proximally withdrawn from distal end-portion 2027 of nosecone 2026. As described hereinabove with reference to FIGS. 13A-B, withdrawal of guidewire 2023 from distal end-portion 2027 reduces an axial length of nosecone 2026, facilitating deployment of prosthetic valve 2036 by reducing an amount of space within right ventricle 1098 required to maneuver capsule assembly 2063 (e.g., distal capsule 2066 thereof).

FIG. 18D shows proximal capsule 2064 having been partially retracted with respect to mount 2028, such that end-portions 2068 of flanges 2054 are released from the proximal capsule. Typically, an unsheathing force is applied extracorporeally to a controller, e.g., a knob or a dial of implantation instrument 660 in order to retract proximal capsule 2064. As shown, flanges 2054 typically automatically expand radially outward from respective coupling points upon release from proximal capsule 2064. However, since the distal end of tubular portion 2032 is still restrained by distal capsule 2066, and upstream support portion 2040 is still restrained by proximal capsule 2064, valve frame 2030 remains in the compressed state.

FIG. 18E shows distal portion 2024 having been advanced distally, such that flanges 2054 enter right ventricle 1098 (e.g., such that the flanges reach a point distal of leaflets 12 of tricuspid valve 1096), and FIG. 18F shows the distal portion having been retracted as a whole, relative to tricuspid valve 1096, such that flanges 2054 (e.g., end-portions 2068 thereof) engage tissue (e.g., the leaflets) of the tricuspid valve.

Subsequently, proximal capsule 2064 is further retracted with respect to mount 2028, such that upstream support portion 2040 is unsheathed from the proximal capsule (FIG. 18G), and distal capsule 2066 is advanced with respect to mount 2028, such that tubular portion 2032 is allowed to expand radially outward, such that prosthetic valve 2036 assumes its expanded state. Typically, the unsheathing force is applied extracorporeally via implantation instrument 660 of delivery tool 600, as described hereinabove with reference to FIG. 14D, mutatis mutandis.

As shown in FIG. 18H, distal movement of distal capsule 2066 with respect to adaptors 2022 and/or mount 2028 (e.g., to a point that is further distal from the mount 2028, or at least to a point that is further distal from slots 2029 thereof) releases the downstream end of tubular portion 2032 from within distal capsule 2066. As shown, tubular portion 2032 radially expands, allowing delivery stent 2200 to expand to the expanded state.

FIG. 18I shows proximal capsule 2064 having advanced distally such that open end 2067 of the proximal capsule meets delivery stent 2200, and FIG. 18J shows distal capsule 2066 having advanced proximally such that open end 2065 of the distal capsule meets delivery stent 2200. Typically, delivery stent 2200 is configured to fit snugly between proximal and distal capsules 2064, 2066, in order to facilitate smooth retraction of capsule assembly 2063 (e.g., the distal capsule thereof) through prosthetic valve 2036 (FIG. 18K), with less risk of damaging the prosthetic leaflets that are disposed within tubular portion 2032. For some applications, delivery stent 2200 comprises a fabric covering (not shown) that further facilitates smooth retraction of capsule assembly 2063 through prosthetic valve 2036.

FIGS. 18L-M show further retraction of distal portion 2024 of delivery tool 600 from within prosthetic valve 2036 and into inferior vena cava 1092. For some applications, distal portion 2024 (e.g., capsule assembly 2063 thereof) is retracted proximally toward supplemental tube 2310 by proximally retracting capsule catheter 2072 and/or delivery catheter 2050.

For some applications, and as shown in FIG. 18M, a distal portion of capsule catheter 2072 is configured (e.g., is sufficiently flexible) to assume a curved orientation while the capsule catheter is retracted through the vasculature. As shown in the lower inset of FIG. 18M, there is sufficient space within the supplemental-tube lumen and capsule catheter 2072 such that a distal portion of the capsule catheter 2072 may assume the curved orientation. That is, supplemental tube 2310 does not necessarily apply an aligning force to the distal portion of capsule catheter 2072. It is hypothesized by the inventors that fully retracting capsule assembly 2063 into supplemental tube 2310 while the distal portion of capsule catheter 2072 is in the curved orientation may result in an imperfect fit of the capsule assembly into supplemental tube 2310, which may complicate withdrawal of distal portion 2024 from the body.

For some applications, to promote better fit of capsule assembly 2063 into supplemental tube 2310, and to facilitate withdrawal of distal portion 2024 from the body, intermediate alignment tube 2314 is positioned to orient aligner 2312 so as to straighten the distal portion of capsule catheter 2072. FIG. 18N shows aligner 2312 having moved distally e.g., by pushing intermediate alignment tube 2314 proximally and/or by distally retracting capsule catheter 2072. As shown in FIG. 18O, aligner 2312 applies the aligning force upon capsule catheter 2072, straightening the distal portion of the capsule catheter. Typically for such applications, straightening the distal portion of capsule catheter 2072 causes capsule assembly 2063 and/or capsule catheter 2072 to be concentrically disposed with respect to supplemental tube 2310 while the capsule assembly is retracted into the supplemental tube, thereby avoiding entry of capsule assembly 2063 into the supplemental tube at an angle.

Typically, distal portion 2024 is then extracted from the body while the distal portion is housed within supplemental tube 2310 (e.g., while supplemental tube 2310 surrounds proximal capsule 2064, and while a distal end of the supplemental tube abuts the distal capsule).

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use at a heart of a subject, the apparatus comprising:
   a delivery tool dimensioned for percutaneous delivery to the heart, the delivery tool having a distal portion that defines a central longitudinal axis at the distal portion and comprises:
   a shaft;
   a supplemental tube; and
   a proximal capsule and a distal capsule, each of the capsules:
      having a respective open end, the open end of the proximal capsule facing the open end of the distal capsule, and
      coupled to the shaft in a manner that allows axial movement of the capsule with respect to the shaft, along the central longitudinal axis at the distal portion; and a prosthetic heart valve comprising:
  a tubular portion that defines a lumen; and
  a plurality of prosthetic leaflets disposed within the lumen,
wherein:
the prosthetic heart valve is restrainable in a compressed state by the delivery tool, such that a downstream end of the tubular portion is disposed within the distal capsule,
the distal capsule is shaped so as to define an opening for visualizing ensheathing of at least a portion of the downstream end of the tubular portion within the distal capsule, and
during a delivery state of the delivery tool:
  an inter-capsule gap separates the open end of the proximal capsule from the open end of the distal capsule,
  a segment of the prosthetic heart valve is disposed at the inter-capsule gap, and
  the supplemental tube surrounds (i) the proximal capsule, (ii) at least a proximal portion of the distal capsule, and (iii) the segment of the prosthetic heart valve disposed at the inter-capsule gap.

2. The apparatus according to claim 1, wherein the opening defines a window.

3. The apparatus according to claim 1, wherein the delivery tool further comprises a mount surrounding the shaft and configured to engage the downstream end of the tubular portion, and wherein the opening is configured to allow visualizing of the mount and the downstream end of the tubular portion.

4. The apparatus according to claim 3, wherein the mount is shaped so as to define one or more slots, and wherein the downstream end of the tubular portion is shaped so as to define one or more adaptors, each one of the adaptors being configured to be received within a respective one of the one or more slots so as to facilitate engaging between the mount and the downstream end of the tubular portion.

5. The apparatus according to claim 4, wherein in the compressed state of the prosthetic heart valve, the distal capsule maintains coupling between the downstream end of the tubular portion and the mount by surrounding the one or more adaptors and maintaining each one of the one or more adaptors within the respective slot of the mount.

6. The apparatus according to claim 1, wherein the prosthetic heart valve comprises:
an upstream support portion that extends from the tubular portion; and
a plurality of flanges, each of the flanges coupled to the tubular portion at a respective coupling point that is downstream of the upstream support portion, and extends from the coupling point to a respective flange end-portion of the flange.

7. The apparatus according to claim 6, wherein the prosthetic heart valve is restrainable in the compressed state by the delivery tool such that the upstream support portion and the flange end-portions are disposed within the proximal capsule.

8. A method for preparing a prosthetic heart valve for implantation, the method comprising:
using a crimping tool, crimping the prosthetic heart valve around a distal portion of a shaft of a delivery tool, the delivery tool:
  being dimensioned for percutaneous delivery to a heart of a subject;
  having a distal portion that defines a central longitudinal axis at the distal portion, and comprising:
  a supplemental tube; and
  a proximal capsule and a distal capsule, each of the capsules;
    having a respective open end, the open end of the proximal capsule facing the open end of the distal capsule, and
    coupled to the shaft in a manner that allows axial movement of the capsule with respect to the shaft, along the central longitudinal axis at the distal portion of the delivery tool; and
the prosthetic heart valve comprising:
  a tubular portion that defines a lumen; and
  a plurality of prosthetic leaflets disposed within the lumen,
wherein:
the prosthetic heart valve is restrainable in a compressed state by the delivery tool, such that a downstream end of the tubular portion is disposed within the distal capsule, and
the distal capsule is shaped so at to define an opening for visualizing ensheathing of at least a portion of the downstream end of the tubular portion within the distal capsule;
subsequently to the crimping, ensheathing the prosthetic heart valve in the proximal and distal capsules by extracorporeally (i) coupling at least one ensheathing tool directly to the distal portion of the delivery tool and (ii) applying a rotational force to the at least one ensheathing tool to effect linear movement of each one of the proximal and distal capsules with respect to the prosthetic heart valve; and
during a delivery state of the delivery tool, delivering the prosthetic valve within the body of the subject in a manner in which:
  an inter-capsule gap separates the open end of the proximal capsule from the open end of the distal capsule,
  a segment of the prosthetic heart valve is disposed at the inter-capsule gap, and
  the supplemental tube surrounds (i) the proximal capsule, (ii) at least a proximal portion of the distal capsule, and (iii) the segment of the prosthetic heart valve disposed at the inter-capsule gap.

9. The method according to claim 8, wherein:
delivering the prosthetic valve within the body of the subject comprises, subsequently to the ensheathing, advancing the ensheathed prosthetic heart valve and the distal portion of the delivery tool into a subject, while retaining a proximal portion of the delivery tool outside of the subject; and
the method further comprises, subsequently, deploying the prosthetic heart valve within the heart of the subject from the proximal and distal capsules by extracorporeally applying an unsheathing force to a controller at the proximal portion of the delivery tool.

10. The method according to claim 8, wherein:
ensheathing the prosthetic heart valve in the proximal and distal capsules comprises:
  ensheathing the downstream end of the tubular portion of the prosthetic heart valve in the distal capsule; and
  subsequently, ensheathing an upstream end of the prosthetic heart valve in the proximal capsule.

11. The method according to claim 10, wherein the ensheathing tool is a distal-capsule ensheathing tool and wherein ensheathing the downstream end of the tubular portion of the prosthetic heart valve comprises applying a first ensheathing force to the distal portion of the delivery tool using the distal-capsule ensheathing tool directly coupled to the distal capsule.

12. The method according to claim 11, further comprising coupling the distal-capsule ensheathing tool directly to the distal capsule.

13. The method according to claim 11, wherein ensheathing the upstream end of the prosthetic heart valve in the proximal capsule comprises applying a second ensheathing force to the distal portion of the delivery tool using a proximal-capsule ensheathing tool directly coupled to the distal portion of the delivery tool.

14. The method according to claim 13, wherein:
   delivering the prosthetic valve within the body of the subject comprises, subsequently to the ensheathing of the upstream end of the prosthetic heart valve, advancing the ensheathed prosthetic heart valve and the distal portion of the delivery tool into a heart of a subject, while retaining a proximal portion of the delivery tool outside of the subject; and
   the method further comprises, subsequently, deploying the prosthetic heart valve within the heart of the subject from the proximal and distal capsules by extracorporeally applying an unsheathing force to a controller at the proximal portion of the delivery tool.

15. The method according to claim 10, further comprising, during the ensheathing of the downstream end of the tubular portion of the prosthetic heart valve in the distal capsule, visualizing the ensheathing of at least a portion of the downstream end of the tubular portion of the prosthetic heart valve within the distal capsule through an opening defined in the distal capsule for visualizing the ensheathing.

16. The method according to claim 15, wherein the delivery tool further includes a mount surrounding the shaft and configured to engage the downstream end of the tubular portion of the prosthetic heart valve, and wherein visualizing the ensheathing of the at least the portion of the downstream end of the tubular portion of the prosthetic heart valve within the distal capsule comprises visualizing the mount and the downstream end of the tubular portion of the prosthetic heart valve.

17. The method according to claim 16, wherein:
   the mount is shaped so as to define one or more slots,
   the downstream end of the tubular portion of the prosthetic heart valve is shaped so as to define one or more adaptors, each one of the adaptors being configured to be received within a respective one of the one or more slots so as to facilitate engaging between the mount and the downstream end of the tubular portion of the prosthetic heart valve, and
   ensheathing the downstream end of the tubular portion of the prosthetic heart valve in the distal capsule comprises ensheathing the downstream end of the tubular portion of the prosthetic heart valve such that the one or more adapters fit within the one or more slots.

18. The method according to claim 17, wherein ensheathing the downstream end of the tubular portion of the prosthetic heart valve in the distal capsule comprises maintaining coupling between the downstream end of the tubular portion of the prosthetic heart valve and the mount by the ensheathing of the downstream end of the tubular portion of the prosthetic heart valve in the distal capsule.

* * * * *